United States Patent
Aldous et al.

(10) Patent No.: US 8,258,130 B2
(45) Date of Patent: Sep. 4, 2012

(54) PYRIMIDINE HYDRAZIDE COMPOUNDS AS PGDS INHIBITORS

(75) Inventors: Suzanne C Aldous, Gillette, NJ (US); Michael W Fennie, East Stroudsburg, PA (US); John Z Jiang, Hillsborough, NJ (US); Stanly John, Basking Ridge, NJ (US); Lan Mu, Basking Ridge, NJ (US); Brian Pedgrift, Flemington, NJ (US); James R Pribish, Piscataway, NJ (US); Barbara S Rauckman, Flemington, NJ (US); Jeffrey S Sabol, Bridgewater, NJ (US); Grzegorz T Stoklosa, Hillsborough, NJ (US); Sukanthini Thurairatnam, Bedminster, NJ (US); Christopher Loren Vandeusen, East Windsor, NJ (US)

(73) Assignee: Sanofi, Paris (FR)

(*) Notice: Subject to any disclaimer, the term of this patent is extended or adjusted under 35 U.S.C. 154(b) by 343 days.

(21) Appl. No.: 12/570,355

(22) Filed: Sep. 30, 2009

(65) Prior Publication Data

US 2010/0048568 A1    Feb. 25, 2010

Related U.S. Application Data

(63) Continuation of application No. PCT/US2008/058347, filed on Mar. 27, 2008.

(60) Provisional application No. 60/909,171, filed on Mar. 30, 2007.

(51) Int. Cl.
    *C07D 239/38* (2006.01)
    *C07D 403/12* (2006.01)
    *A61K 31/506* (2006.01)

(52) U.S. Cl. ............... 514/230.5; 514/235.8; 514/242; 514/252.14; 514/256; 544/105; 544/122; 544/182; 544/295; 544/296; 544/333; 544/335

(58) Field of Classification Search ............ 544/105, 544/122, 182, 295, 296, 333, 335; 514/230.5, 514/235.8, 242, 252.14, 256

See application file for complete search history.

(56) References Cited

U.S. PATENT DOCUMENTS 5,176,132 A    1/1993    Drought et al.

FOREIGN PATENT DOCUMENTS

| WO | WO 2004/026380 |   | 4/2004  |
|----|----------------|---|---------|
| WO | WO 2008/077597 | * | 7/2008  |
| WO | WO 2008/121670 A1 | | 10/2008 |
| WO | WO 2008/121877 | * | 10/2008 |

OTHER PUBLICATIONS

Chi et al., CAPLUS Abstract 52:82614 (1958).*

Mesquita-Santos et al., Cutting Edge: Prostaglandin D2 Enhances Leukotriene C4 Synthesis by Eosinophils during Allergic Inflammation: Synergitic in Vivo Role of Endogenous Eotaxin, J. Immunology, 2006; 176, pp. 1326-1330.*
Ulrich, Chapter 4: Crystallization, Kirk-Othmer Encyclopedia of Chemical Technology, Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Brook, M. A., et. al., A Simple Procedure for the Esterification of Carboxylic Acids, Synthesis, (1983), vol. 3, pp. 201-204.
Brown, D. J., et. al., Unfused Heterocbicycles as Amplifiers of Phleomycin. VII. Some Triazolyl-, Thiadiazolyl- and Oxadiazolylpyridines, and Related Pyrimidines, Aust. J. Chem., vol. 36, No. 7, pp. 1469-1475, (1983), abstract.
Fujitani, Y., et. al., Pronounced Eosinophilic Lung Inflammation and Th2 Cytokine Release in Human Lipocalin-Type Prostaglandin D Synthase Transgenic Mice, Journal of Immunology, vol. 168, pp. 443-449, (2002).
Hosoya, T., et. al., New Pyrimidine Compounds, Useful as Prostaglandin D Synthetase Inhibitor in Pharmaceutical Compositions for Preventing and Treating Diseases, Such as Allergic Disease and Inflammatory Disease, abstract, JP2007051121, (2007).
Ikai, K., et. al., Inhibitory Effect of Tranilast on Prostaglandin D Synthetase, Biochemical Pharmacology, vol. 38, No. 16, pp. 2673-2676, (1989).
Johnson, C. L., et. al., Quantitative Structure-Activity Studies on Monoamine Oxidase Inhibitors, Journal of Medicinal Chemistry, vol. 19, No. 5, pp. 600-605, (1976).
Lewis R. A., et. al., Prostagladin D2 Generation After Activation of Rat and Human Mast Cells With Anti-IgE, The Journal of Immunology, (1982), vol. 129, No. 4, pp. 1627-1631.
Olsen, R. K., et. al., A Convenient Synthesis of Protected N-Methylamio Acid Derivatives, J. Org. Chem., vol. 55, No. 6, (1970) pp. 1912-1915. Ouellet, M., et. al., Aromatic Hydroxamic Acids and Hydrazides as Inhibitors of the Peroxidase Activity of Prostaglandin H2 Synthase-2, Archives of Biochemistry and Biophysics, vol. 431, pp. 107-118, (2004).
Shenbagamurthi, P., et. al., Synthesis and Biological Properties of Chitin Synthetase Inhibitors Resistant to Cellular Peptidase, J. Med. Chem., (1986), vol. 29, pp. 802-809.

(Continued)

*Primary Examiner* — Deepak Rao
(74) *Attorney, Agent, or Firm* — Ronald G. Ort; Barbara E. Kurys

(57) ABSTRACT

This invention is directed to a compound of formula (I):

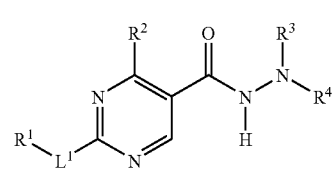

wherein $R^1$, $R^2$, $R^3$, $R^4$ and $L^1$ are as defined herein, a pharmaceutical composition comprising the compound, and the use of the compound to treat allergic and/or inflammatory disorders, particularly disorders such as allergic rhinitis, asthma and/or chronic obstructive pulmonary disease (COPD).

24 Claims, No Drawings

OTHER PUBLICATIONS

Takahata, H., et. al., A Novel C2-Symmetric 2,6-Diallylpiperidine Carboxylic Acid Methyl Ester as a Promising Chiral Building Block for Piperidine-Related Alkaloids, Organic Letters, vol. 4, No. 20, pp. 3459-2462, (2002).

Zhong, Y., et. al., Efficient and Facile Glycol Cleavage Oxidation Using Improved Silica Gel-Supported Sodium Metaperiodate, J. Org. Chem., vol. 62, pp. 2622-2624, (1997).

Brightling C. E., et. al., New Insights Into the Role of the Mast Cell in Asthma, Clin. Exp. Allergy, (2003). vol. 33, pp. 550-556.

Berge, S.M., et. al., Pharmaceutical Salts, J. Pharmaceutical Sciences, (1977), vol. 66, No. 1, pp. 1-18.

Chau, F., et. al., Synthesis of 3,5-Disubstituted 1-Amino-1,3,5-Triazine-2,4,6-Triones (or 1-Aminocyanurates) By Cyclic Transformation of 1,3,4-Oxadiazol-2(3H)-One Derivatives, J. Heterocyclic Chem., vol. 34, pp. 1603-1606, (1997).

Murray, J. J., et. al., Release of Prostaglandin D2 into Human Airways During Acute Antigen Challenge, The New England Journal of Medicine, (1986), vol. 315, No. 13, p. 800-804.

* cited by examiner

PYRIMIDINE HYDRAZIDE COMPOUNDS AS PGDS INHIBITORS

This application is a continuation of PCT/US2008/058347 filed Mar. 27, 2008 which claims priority benefit from U.S. Provisional Application Ser. No. 60/909,171 filed Mar. 30, 2007.

FIELD OF THE INVENTION

The present invention is directed to pyrimidine hydrazide compounds, their preparation, pharmaceutical compositions containing these compounds, and their pharmaceutical use in the treatment of disease states capable of being modulated by the inhibition of the prostaglandin D synthase.

BACKGROUND OF THE INVENTION

Allergic rhinitis, the most common atopic disease, has an estimated prevalence ranging from about 5 to about 22 percent of the general human population and is characterized by the symptoms of sneezing, nasal discharge, and nasal congestion. These symptoms are believed to be triggered by multiple mediators released from mast cells and other inflammatory cells. Current therapies, such as antihistamines, deal effectively with the sneezing and nasal discharge, but have little effect on congestion, which is a key symptom affecting the quality of life of patients.

Local allergen challenge in patients with allergic rhinitis, bronchial asthma, allergic conjunctivitis and atopic dermatitis has been shown to result in rapid elevation of prostaglandin D2 "(PGD2)" levels in nasal and bronchial lavage fluids, tears and skin chamber fluids. PGD2 has many inflammatory actions, such as increasing vascular permeability in the conjunctiva and skin, increasing nasal airway resistance, airway narrowing and eosinophil infiltration into the conjunctiva and trachea. PGD2 is the major cyclooxygenase product of arachidonic acid produced from mast cells on immunological challenge [Lewis, R A, Soter N A, Diamond P T, Austen K F, Oates J A, Roberts L J II, Prostaglandin D2 generation after activation of rat and human mast cells with anti-IgE, *J. Immunol.* 129, 1627-1631, 1982]. Activated mast cells, a major source of PGD2, are one of the key players in driving the allergic response in conditions such as asthma, allergic rhinitis, allergic conjunctivitis, allergic dermatitis and other diseases [Brightling C E, Bradding P, Pavord I D, Wardlaw A J, New Insights into the role of the mast cell in asthma, *Clin. Exp. Allergy* 33, 550-556, 2003].

In the presence of sulfhydryl compounds, PGD2 is formed by the isomerization of PGH2, a common precursor of prostanoids, by catalytic action of prostaglandin D synthase "(PGDS)". There are two isoforms of the PGDS enzyme: L-PGDS; and H-PGDS. H-PGDS is a cytosolic enzyme, which is distributed in the peripheral tissues, and which is localized in the antigen-presenting cells, mast cells, megakaryocytes, and Th2 lymphocytes. The action of the product PGD2 is mediated by G-protein coupled receptors: D prostaglandin "(DP)" and crTH2. See (1) Prostaglandin D Synthase: Structure and Function. T. Urade and O. Hayaishi, *Vitamin and Hormones,* 2000, 58, 89-120, (2) J. J. Murray, *N. Engl J. Med.,* 1986 Sep. 25; 315(13):800, and (3) Urade et. al, *J. Immunology* 168: 443-449, 2002.

We believe that inhibiting the formation of PGD2 should have an effect on nasal congestion and, therefore, be of therapeutic benefit in allergic rhinitis. In addition, we believe that a PGDS inhibitor should be of therapeutic benefit in a number of other indications such as bronchial asthma.

PGDS inhibitors have been reported. The compound, HQL-79, is reported to be a weak PGDS inhibitor, and is antiasthmatic in guinea pig and rat models (Matsusshita, et al., Jpn. J. Pharamcol. 78: 11, 1998). The compound Tranilast is described as a PGDS inhibitor. (Inhibitory Effect of Tranilast on Prostaglandin D Synthesase. K. Ikai, M. Jihara, K. Fujii, and Y. Urade. *Biochemical Pharmacology,* 1989, 28, 2773-2676).

SUMMARY OF THE INVENTION

The present invention is directed to a compound of formula (I):

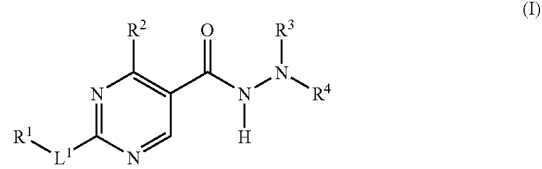

wherein:
$R^1$ is $(C_1-C_6)$-alkyl optionally substituted one or more times independently by halo, hydroxy, $(C_1-C_6)$-alkoxy, or $(C_1-C_4)$-haloalkoxy, or
$(C_3-C_6)$-cycloalkyl, aryl or heteroaryl, each of which is optionally substituted one or more times independently by halo, $(C_1-C_6)$-alkyl, hydroxy, $(C_1-C_6)$-alkoxy, $(C_1-C_4)$-haloalkyl or $(C_1-C_4)$-haloalkoxy;
$R^2$ is hydrogen or $(C_1-C_4)$-alkyl optionally substituted one or more times by halo;
$R^3$ is hydrogen, alkyl, aryl or heteroaryl,
$R^4$ is hydrogen, cycloalkyl, aryl, heteroaryl, heterocyclyl, arylsulfonyl, heteroarylsulfonyl, —C(=O)—NY$^1$Y$^2$, —C(=S)—NY$^1$Y$^2$, $R^5$, —C(=O)—$R^5$ or —C(=S)—$R^5$, wherein the aryl, heteroaryl or heterocyclyl moiety is optionally substituted one or more times independently by $R^6$, or
$R^3$ and $R^4$ together with the nitrogen atom to which they are attached form heterocyclyl, heterocyclenyl, heteroaryl, arylheterocyclyl, arylheterocylenyl, heteroarylheterocyclyl, heteroarylheterocyclenyl, heterocyclylheteroaryl or heterocylenylheteroaryl, each of which is optionally substituted one or more times independently by $R^6$;
$R^5$ is cycloalkyl, cycloalkenyl, aryl, heteroaryl, heterocyclyl, heterocyclenyl, or multicyclic alkaryl, each of which is optionally substituted one or more times independently by $R^6$;
$L^1$ is a bond, —O—, —C(=O)—, —NH—C(=O)—, or $(C_1-C_2)$-alkylene optionally substituted one or more times by halo;
$R^6$ is cyano, nitro, halo, hydroxy, carboxy, $Y^1Y^2N$—, $Y^1Y^2N$—C(=O)—, $Y^1Y^2N$—SO$_2$—,
acyl, acyloxy, alkyl, alkenyl, alkynyl, alkoxy, alkoxycarbonyl, alkylthio, alkylsulfinyl, or alkylsulfonyl, each of which is optionally substituted one or more times independently by:
acyloxy, halo, alkoxy, haloalkoxy, hydroxy, carboxy, alkoxycarbonyl, $Y^1Y^2N$—, $Y^1Y^2N$—C(=O)—, $Y^1Y^2N$—SO$_2$—,
aryl, aryloxy, aroyl, heteroaryl, heteroaryloxy, heteroaroyl, heterocyclyl, heterocyclenyl, cycloalkyl, cycloalkenyl, or multicyclic alkaryl, each of which is optionally substituted one or more times independently by alkyl, halo, haloalkyl, alkoxy, haloalkoxy, hydroxy, amino, alkylamino, dialkylamino, carboxy, or alkoxycarbonyl, or
aryl, heteroaryl, aroyl, heteroaroyl, aryloxy, heteroaryloxy, heterocyclyl, heterocyclenyl, cycloalkyl, cycloalkenyl, or multicyclic alkaryl, each of which is optionally substituted one or more times independently by alkyl, haloalkyl, halo, alkoxy, haloalkoxy, hydroxy, carboxy, alkoxycarbonyl, $Y^1Y^2N$—, or $Y^1Y^2N$—$SO_2$—, wherein the heterocyclyl, heterocyclenyl, cycloalkyl, cycloalkenyl, or multicyclic alkaryl moiety of $R^6$ is also optionally substituted one or more times independently by oxo;

$Y^1$ and $Y^2$ are each independently:

hydrogen, alkylsulfonyl, aroyl, heteroaroyl, or alkyl optionally substituted one or more times independently by hydroxy, carboxy, halo, amino, alkylamino, dialkylamino, alkoxy, heterocyclyl, aryl or heteroaryl, or $Y^1$ and $Y^2$ together with the nitrogen atom to which they are attached form heterocyclyl; or a hydrate, solvate or N-oxide thereof, or a pharmaceutically acceptable salt thereof.

Another aspect of the present invention is a pharmaceutical composition comprising a pharmaceutically effective amount of a compound according to formula (I), or a hydrate, solvate or N-oxide thereof, or a pharmaceutically acceptable salt thereof, in admixture with a pharmaceutically acceptable carrier.

Another aspect of the present invention is directed to a method of treating allergic and/or inflammatory disorders, particularly disorders such as allergic rhinitis, asthma and/or chronic obstructive pulmonary disease (COPD) in a patient in need thereof by administering to the patient a compound according to formula (I), or a hydrate, solvate or N-oxide thereof, or a pharmaceutically acceptable salt thereof.

DETAILED DESCRIPTION OF THE INVENTION

Definition of Terms

As used above, and throughout the description of the invention, the following terms unless otherwise indicated, shall be understood to have the following meanings:

"Acyl" means H—CO— or (aliphatic or cyclyl)-CO—. Particular acyl includes lower alkanoyl that contains a lower alkyl. Exemplary acyl includes formyl, acetyl, propanoyl, 2-methylpropanoyl, butanoyl, palmitoyl, acryloyl, propynoyl, and cyclohexylcarbonyl.

"Acyloxy" means acyl-O—.

"Alkenyl" means a straight or branched aliphatic hydrocarbon group containing a carbon-carbon double bond and having 2 to about 15 carbon atoms. Particular alkenyl has 2 to about 12 carbon atoms. More particular alkenyl has 2 to about 4 carbon atoms. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl includes ethenyl, propenyl, n-butenyl, i-butenyl, 3-methylbut-2-enyl, n-pentenyl, heptenyl, octenyl, cyclohexylbutenyl, and decenyl.

"Alkoxy" means alkyl-O—. Exemplary alkoxy includes methoxy, ethoxy, n-propoxy, i-propoxy, n-butoxy, and heptoxy.

"Alkoxycarbonyl" means alkyl-O—CO—. Exemplary alkoxycarbonyl includes methoxycarbonyl, ethoxycarbonyl, and t-butyloxycarbonyl.

"Alkyl" means straight or branched aliphatic hydrocarbon having 1 to about 20 carbon atoms. Particular alkyl has 1 to about 12 carbon atoms. More particular alkyl is lower alkyl. Branched means that one or more lower alkyl groups such as methyl, ethyl or propyl are attached to a linear alkyl chain. "Lower alkyl" means 1 to about 4 carbon atoms in a linear alkyl chain that may be straight or branched.

"Alkylamino" means alkyl-NH—. Particular alkylamino is $(C_1-C_6)$-alkylamino. Exemplary alkylamino includes methylamino and ethylamino.

"Alkylsulfinyl" means alkyl-SO—. Particular alkylsulfonyl is $(C_1-C_6)$-alkylsulfinyl. Exemplary alkylsulfinyl includes $CH_3$—SO—, and $CH_3CH_2$—SO—.

"Alkylsulfonyl" means alkyl-$SO_2$—. Particular alkylsulfonyl is $(C_1-C_6)$-alkylsulfonyl. Exemplary alkylsulfonyl includes $CH_3$—$SO_2$—, and $CH_3CH_2$—$SO_2$—.

"Alkylthio" means an alkyl-S—. Exemplary alkylthio includes $CH_3$—S—.

"Alkynyl" means straight or branched aliphatic hydrocarbon containing a carbon-carbon triple bond and having 2 to about 15 carbon atoms. Particular alkynyl has 2 to about 12 carbon atoms. More particular alkynyl has 2 to about 6 carbon atoms. Branched means that one or more lower alkyl such as methyl, ethyl or propyl are attached to a linear alkynyl chain.

"Lower alkynyl" means 2 to about 4 carbon atoms in a linear alkynyl chain that may be straight or branched. Exemplary alkynyl includes ethynyl, propynyl, n-butynyl, 2-butynyl, 3-methylbutynyl, n-pentynyl, heptynyl, octynyl, and decynyl.

"Aroyl" means aryl-CO—. Exemplary aroyl includes benzoyl, and 1- and 2-naphthoyl.

"Aryl" means an aromatic monocyclic or multicyclic ring system of about 6 to about 14 carbon atoms. Particular aryl include about 6 to about 10 carbon atoms. Exemplary aryl include phenyl and naphthyl.

"Arylcycloalkenyl" means a fused aryl and cycloalkenyl. Particular arylcycloalkenyl is one wherein the aryl thereof is phenyl and the cycloalkenyl consists of about 5 to about 7 ring atoms. An arylcycloalkenyl is bonded through any atom of the cycloalkenyl moiety thereof capable of such bonding. Exemplary arylcycloalkenyl includes 1,2-dihydronaphthylene and indene.

"Arylcycloalkyl" means a fused aryl and cycloalkyl. Particular arylcycloalkyl is one wherein the aryl thereof is phenyl and the cycloalkyl consists of about 5 to about 6 ring atoms. An arylcycloalkyl is bonded through any atom of the cycloalkyl moiety thereof capable of such bonding. Exemplary arylcycloalkyl includes 1,2,3,4-tetrahydro-naphthylene.

"Arylheterocyclenyl" means a fused aryl and heterocyclenyl. Particular arylheterocyclenyl is one wherein the aryl thereof is phenyl and the heterocyclenyl consists of about 5 to about 6 ring atoms. An arylheterocyclenyl is bonded through any atom of the heterocyclenyl thereof capable of such bonding. The designation of the aza, oxa or thio as a prefix before the heterocyclenyl portion of the arylheterocyclenyl defines that at least a nitrogen, oxygen or sulfur atom is present, respectively, as a ring atom. The nitrogen atom of an arylheterocyclenyl may be a basic nitrogen atom. The nitrogen or sulfur atom of the heterocyclenyl portion of the arylheterocyclenyl may also be optionally oxidized to the corresponding N-oxide, S-oxide or S,S-dioxide. Exemplary arylheterocyclenyl includes 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, and 3,4-dihydroisoquinolinyl.

"Arylheterocyclyl" means a fused aryl and heterocyclyl. Particular heterocyclylaryl is one wherein the aryl thereof is phenyl and the heterocyclyl consists of about 5 to about 6 ring atoms. An arylheterocyclyl is bonded through any atom of the heterocyclyl moiety thereof capable of such bonding. The designation of the aza, oxa or thio as a prefix before heterocyclyl portion of the arylheterocyclyl defines that at least a nitrogen, oxygen or sulfur atom is present, respectively, as a ring atom. The nitrogen atom of an arylheterocyclyl may be a basic nitrogen atom. The nitrogen or sulfur atom of the heterocyclyl portion of the arylheterocyclyl may also be optionally oxidized to the corresponding N-oxide, S-oxide or S,S-dioxide. Exemplary arylheterocyclyl includes indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, and 1,2,3,4-tetrahydrobenz[g]-isoquinolin-2-yl.

"Aryloxy" means an aryl-O—. Exemplary aryloxy includes phenoxy and naphthoxy.

"Compounds of the present invention", and equivalent expressions, are meant to embrace compounds of Formula (I) as hereinbefore described, the hydrates, solvates and N-oxides thereof, and the pharmaceutically acceptable salts thereof, where the context so permits. Similarly, reference to intermediates, whether or not they themselves are claimed, is meant to embrace their salts, N-oxides and solvates, where the context so permits.

"Cycloalkenyl" means a non-aromatic mono- or multicyclic ring system of about 3 to about 10 carbon atoms, particularly of about 5 to about 10 carbon atoms, and which contains at least one carbon-carbon double bond. Particular rings of the ring system include about 5 to about 6 ring atoms; and such particular ring sizes are also referred to as "lower". Exemplary monocyclic cycloalkenyl includes cyclopentenyl, cyclohexenyl, and cycloheptenyl. An exemplary multicyclic cycloalkenyl is norbornylenyl.

"Cycloalkenylaryl" means a fused aryl and cycloalkenyl. Particular cycloalkenylaryl is one wherein the aryl thereof is phenyl and the cycloalkenyl consists of about 5 to about 6 atoms. A cycloalkenylaryl is bonded through any atom of the aryl moiety thereof capable of such bonding. Exemplary cycloalkenylaryl includes 1,2-dihydronaphthylene and indene.

"Cycloalkenylheteroaryl" means a fused heteroaryl and cycloalkenyl. Particular cycloalkenylheteroaryl is one wherein the heteroaryl thereof consists of about 5 to about 6 ring atoms and the cycloalkenyl consists of about 5 to about 6 ring atoms. A cycloalkenylheteroaryl is bonded through any atom of the heteroaryl thereof capable of such bonding. The designation of the aza, oxa or thio as a prefix before heteroaryl portion of the cycloalkenylheteroaryl defines that at least a nitrogen, oxygen or sulfur atom is present, respectively, as a ring atom. The nitrogen atom of a cycloalkenylheteroaryl may be a basic nitrogen atom. The nitrogen atom of the heteroaryl portion of the cycloalkenylheteroaryl may also be optionally oxidized to the corresponding N-oxide. Exemplary cycloalkenylheteroaryl includes 5,6-dihydroquinolyl, 5,6-dihydroisoquinolyl, 5,6-dihydroquinoxalinyl, 5,6-dihydroquinazolinyl, 4,5-dihydro-1H-benzimidazolyl, and 4,5-dihydrobenzoxazolyl.

"Cycloalkyl" means a non-aromatic mono- or multicyclic saturated ring system of about 3 to about 10 carbon atoms, particularly of about 5 to about 10 carbon atoms. Particular ring systems include about 5 to about 7 ring atoms; and such particular ring systems are also referred to as "lower". Exemplary monocyclic cycloalkyl includes cyclopentyl, cyclohexyl, and cycloheptyl. Exemplary multicyclic cycloalkyl includes 1-decalin, norbornyl, and adamant-(1- or 2-)yl.

"Cycloalkylaryl" means a fused aryl and cycloalkyl. Particular cycloalkylaryl is one wherein the aryl thereof is phenyl and the cycloalkyl consists of about 5 to about 6 ring atoms. A cycloalkylaryl is bonded through any atom of the cycloalkyl moiety thereof capable of such bonding. Exemplary cycloalkylaryl includes 1,2,3,4-tetrahydro-naphthylene.

"Cycloalkylheteroaryl" means a fused heteroaryl and cycloalkyl. Particular cycloalkylheteroaryl is one wherein the heteroaryl thereof consists of about 5 to about 6 ring atoms and the cycloalkyl consists of about 5 to about 6 ring atoms. A cycloalkylheteroaryl is bonded through any atom of the heteroaryl thereof capable of such bonding. The designation of the aza, oxa or thio as a prefix before heteroaryl portion of the fused cycloalkylheteroaryl defines that at least a nitrogen, oxygen or sulfur atom is present, respectively, as a ring atom. The nitrogen atom of a cycloalkylheteroaryl may be a basic nitrogen atom. The nitrogen atom of the heteroaryl portion of the cycloalkylheteroaryl may also be optionally oxidized to the corresponding N-oxide. Exemplary cycloalkylheteroaryl includes 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, and 4,5,6,7-tetrahydrobenzoxazolyl.

"Cyclyl" means cycloalkyl, cycloalkenyl, heterocyclyl or heterocyclenyl.

"Dialkylamino" means (alkyl)$_2$-N—. Particular dialkylamino is ($C_1$-$C_6$alkyl)$_2$-N—. Exemplary dialkylamino groups include dimethylamino, diethylamino and methylethylamino.

"Halo" or "halogen" means fluoro, chloro, bromo, or iodo. Particular halo or halogen is fluoro or chloro.

"Haloalkoxy" means alkoxy substituted by one to three halo groups. Particular haloalkoxy are loweralkoxy substituted by one to three halogens. Most particular haloalkoxy are loweralkoxy substituted by one halogen.

"Haloalkyl" means alkyl substituted by one to three halo groups. Particular haloalkyl are loweralkyl substituted by one to three halogens. Most particular haloalkyl are loweralkyl substituted by one halogen.

"Heteroaroyl" means heteroaryl-CO—. Exemplary heteroaroyl includes thiophenoyl, nicotinoyl, pyrrol-2-ylcarbonyl, and pyridinoyl.

"Heteroaryl" means an aromatic monocyclic or multicyclic ring system of about 5 to about 14 carbon atoms, in which one or more of the carbon atoms in the ring system is/are hetero element(s) other than carbon, for example nitrogen, oxygen or sulfur. Particular aromatic ring systems include about 5 to about 10 carbon atoms, and include 1 to 3 heteroatoms. More particular ring sizes of rings of the ring system include about 5 to about 6 ring atoms. The designation of the aza, oxa or thio as a prefix before heteroaryl defines that at least a nitrogen, oxygen or sulfur atom is present, respectively, as a ring atom. A nitrogen atom of a heteroaryl may be a basic nitrogen atom and may also be optionally oxidized to the corresponding N-oxide. When a heteroaryl is substituted by a hydroxy group, it also includes its corresponding tautomer. Exemplary heteroaryl includes pyrazinyl, thienyl, isothiazolyl, oxazolyl, pyrazolyl, furanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofuranyl, azaindolyl, benzimidazolyl, benzothienyl, thienopyridyl, thienopyrimidyl, pyrrolopyridyl, imidazopyridyl, benzoazaindolyl, 1,2,4-triazinyl, benzothiazolyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, and triazolyl.

"Heteroarylalkyl" means heteroaryl-alkyl-. Particular heteroarylalkyl contains a ($C_1$-$C_4$)-alkyl moiety. Exemplary heteroarylalkyl includes tetrazol-5-ylmethyl.

"Heteroarylcycloalkenyl" means a fused heteroaryl and cycloalkenyl. Particular heteroarylcycloalkenyl is one wherein the heteroaryl thereof consists of about 5 to about 6 ring atoms and the cycloalkenyl consists of about 5 to about 6 ring atoms. A heteroarylcycloalkenyl is bonded through any atom of the cycloalkenyl thereof capable of such bonding. The designation of the aza, oxa or thio as a prefix before heteroaryl portion of the heteroarylcycloalkenyl defines that at least a nitrogen, oxygen or sulfur atom is present, respectively, as a ring atom. The nitrogen atom of a heteroarylcycloalkenyl may be a basic nitrogen atom. The nitrogen atom of the heteroaryl portion of the heteroarylcycloalkenyl may also be optionally oxidized to the corresponding N-oxide. Exemplary heteroarylcycloalkenyl includes 5,6-dihydroquinolyl, 5,6-dihydroisoquinolyl, 5,6-dihydroquinoxalinyl, 5,6-dihydroquinazolinyl, 4,5-dihydro-1H-benzimidazolyl, and 4,5-di-hydrobenzoxazolyl.

"Heteroarylcycloalkyl" means a fused heteroaryl and cycloalkyl. Particular heteroarylcycloalkyl is one wherein the heteroaryl thereof consists of about 5 to about 6 ring atoms and the cycloalkyl consists of about 5 to about 6 ring atoms. A heteroarylcycloalkyl is bonded through any atom of the cycloalkyl thereof capable of such bonding. The designation of the aza, oxa or thio as a prefix before heteroaryl portion of the fused heteroarylcycloalkyl defines that at least a nitrogen, oxygen or sulfur atom is present, respectively, as a ring atom. The nitrogen atom of a heteroarylcycloalkyl may be a basic nitrogen atom. The nitrogen atom of the heteroaryl portion of the heteroarylcycloalkyl may also be optionally oxidized to the corresponding N-oxide. Exemplary heteroarylcycloalkyl includes 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, and 4,5,6,7-tetrahydrobenzoxazolyl "Heteroarylheterocyclenyl" means a fused heteroaryl and heterocyclenyl. Particular heteroarylheterocyclenyl is one wherein the heteroaryl thereof consists of about 5 to about 6 ring atoms and the heterocyclenyl consists of about 5 to about 6 ring atoms. A heteroarylheterocyclenyl is bonded through any atom of the heterocyclenyl thereof capable of such bonding. The designation of the aza, oxa or thio as a prefix before the heteroaryl or heterocyclenyl portion of the heteroarylheterocyclenyl defines that at least a nitrogen, oxygen or sulfur atom is present, respectively, as a ring atom. The nitrogen atom of a heteroarylazaheterocyclenyl may be a basic nitrogen atom. The nitrogen or sulfur atom of the heteroaryl or heterocyclenyl portion of the heteroarylheterocyclenyl may also be optionally oxidized to the corresponding N-oxide, S— oxide or S,S-dioxide. Exemplary heteroarylheterocyclenyl includes 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, and 1,2-dihydro-2,6-naphthyridinyl.

"Heteroarylheterocyclyl" means a fused heteroaryl and heterocyclyl. Particular heteroarylheterocyclyl is one wherein the heteroaryl thereof consists of about 5 to about 6 ring atoms and the heterocyclyl consists of about 5 to about 6 ring atoms. A heteroarylheterocyclyl is bonded through any atom of the heterocyclyl thereof capable of such bonding. The designation of the aza, oxa or thio as a prefix before the heteroaryl or heterocyclyl portion of the fused heteroarylheterocyclyl defines that at least a nitrogen, oxygen or sulfur atom is present, respectively, as a ring atom. The nitrogen atom of a fused heteroarylheterocyclyl may be a basic nitrogen atom. The nitrogen or sulfur atom of the heteroaryl or heterocyclyl portion of the heteroarylheterocyclyl may also be optionally oxidized to the corresponding N-oxide, S-oxide or S,S-dioxide. Exemplary heteroarylheterocyclyl includes 2,3-dihydro-1H-pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetra-hydro-9H-pyrido[3,4-b]indol-2-yl, 1,2,3,4-tetrahydro-9H-pyrido[4,3-b]indol-2-yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2 yl, 5,6,7,8-tetra-hydro[1,7]naphthyridyl, 1,2,3,4-tetrhydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, and 1,2,3,4-tetra-hydro[2,6]naphthyridinyl.

"Heteroaryloxy" means heteroaryl-O—. Exemplary heteroaryloxy includes pyridyloxy.

"Heterocyclenyl" means a non-aromatic monocyclic or multicyclic hydrocarbon ring system of about 3 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. A particular non-aromatic ring system includes about 5 to about 10 carbon atoms, and 1 to 3 heteroatoms. More particular ring sizes of rings of the ring system include about 5 to about 6 ring atoms; and such particular ring sizes are also referred to as "lower". The designation of the aza, oxa or thio as a prefix before heterocyclenyl defines that at least a nitrogen, oxygen or sulfur atom is present, respectively, as a ring atom. The nitrogen atom of a heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl includes 1,2,3,4-tetrahydrohydropyridyl, 1,2-dihydropyridyl, 1,4-dihydropyridyl, 1,2,3,6-tetra-hydropyridyl, 1,4,5,6-tetrahydropyrimidine, 2-pyrrolinyl, 3-pyrrolinyl, 2-imidazolinyl, and 2-pyrazolinyl. Exemplary oxaheterocyclenyl includes 3,4-dihydro-2H-pyran, dihydrofuranyl, and fluorodihydro-furanyl. An exemplary multicyclic oxaheterocyclenyl is 7-oxabicyclo[2.2.1]heptenyl. Exemplary monocyclic thioheterocyclenyl includes dihydrothiophenyl and dihydrothiopyranyl.

"Heterocyclenylaryl" means a fused aryl and heterocyclenyl. Particular heterocyclenylaryl is one wherein the aryl thereof is phenyl and the heterocyclenyl consists of about 5 to about 6 ring atoms. A heterocyclenylaryl is bonded through any atom of the aryl thereof capable of such bonding. The designation of the aza, oxa or thio as a prefix before heterocyclenyl portion of the fused heterocyclenylaryl defines that at least a nitrogen, oxygen or sulfur atom is present, respectively, as a ring atom. The nitrogen atom of a heterocyclenylaryl may be a basic nitrogen atom. The nitrogen or sulfur atom of the heterocyclenyl portion of the heterocyclenylaryl may also be optionally oxidized to the corresponding N-oxide, S-oxide or S,S-dioxide. Exemplary heterocyclenylaryl include 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, and 3,4-dihydroisoquinolinyl.

"Heterocyclenylheteroaryl" means a fused heteroaryl and heterocyclenyl. Particular heterocyclenylheteroaryl is one wherein the heteroaryl thereof consists of about 5 to about 6 ring atoms and the heterocyclenyl consists of about 5 to about 6 ring atoms. A heterocyclenylheteroaryl is bonded through any atom of the heteroaryl thereof capable of such bonding. The designation of the aza, oxa or thio as a prefix before the heteroaryl or heterocyclenyl portion of the heterocyclenylheteroaryl define that at least a nitrogen, oxygen or sulfur atom is present, respectively, as a ring atom. The nitrogen atom of an azaheterocyclenylheteroaryl may be a basic nitrogen atom. The nitrogen or sulfur atom of the heteroaryl or heterocyclenyl portion of the heterocyclenylheteroaryl may also be optionally oxidized to the corresponding N-oxide, S-oxide or S,S-dioxide. Exemplary heterocyclenylheteroaryl includes 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl and 1,2-dihydro-2,6-naphthyridinyl.

"Heterocyclyl" means a non-aromatic saturated monocyclic or multicyclic ring system of about 3 to about 10 carbon atoms, in which one or more of the atoms in the ring system is/are hetero element(s) other than carbon, for example nitrogen, oxygen or sulfur. A particular ring system contains about 5 to about 10 carbon atoms, and from 1 to 3 heteroatoms.

Particular ring sizes of the ring system include about 5 to about 6 ring atoms; and such particular ring sizes are also referred to as "lower". The designation of the aza, oxa or thio as a prefix before heterocyclyl define that at least a nitrogen, oxygen or sulfur atom is present respectively as a ring atom. The nitrogen atom of a heterocyclyl may be a basic nitrogen atom. The nitrogen or sulfur atom of the heterocyclyl may also be optionally oxidized to the corresponding N-oxide, S-oxide or S,S-dioxide. Exemplary monocyclic heterocyclyl includes piperidyl, pyrrolidinyl, piperazinyl, morpholinyl, thiomorpholinyl, thiazolidinyl, 1,3-dioxolanyl, 1,4-dioxanyl, THFyl, tetrahydrothiophenyl, and tetrahydrothiopyranyl.

"Heterocyclylaryl" means a fused aryl and heterocyclyl. Particular heterocyclylaryl is one wherein the aryl thereof is phenyl and the heterocyclyl consists of about 5 to about 6 ring atoms. A heterocyclylaryl is bonded through any atom of the aryl moiety thereof capable of such bonding. The designation of the aza, oxa or thio as a prefix before heterocyclyl portion of the heterocyclylaryl defines that at least a nitrogen, oxygen or sulfur atom is present, respectively, as a ring atom. The nitrogen atom of a heterocyclylaryl may be a basic nitrogen atom. The nitrogen or sulfur atom of the heterocyclyl portion of the heterocyclylaryl may also be optionally oxidized to the corresponding N-oxide, S-oxide or S,S-dioxide. Exemplary heterocyclylaryl includes indolinyl, 1,2,3,4-tetrahydroisoquinoline, 1,2,3,4-tetrahydroquinoline, 1H-2,3-dihydroisoindol-2-yl, and 2,3-dihydrobenz[f]isoindol-2-yl, and 1,2,3,4-tetrahydrobenz[g]-isoquinolin-2-yl.

"Heterocyclylheteroaryl" means a fused heteroaryl and heterocyclyl. Particular heterocyclylheteroaryl is one wherein the heteoraryl thereof consists of about 5 to about 6 ring atoms and the heterocyclyl consists of about 5 to about 6 ring atoms. A heterocyclylheteroaryl is bonded through any atom of the heteroaryl thereof capable of such bonding. The designation of the aza, oxa or thio as a prefix before the heteroaryl or heterocyclyl portion of the heterocyclylheteroaryl defines that at least a nitrogen, oxygen or sulfur atom is present, respectively, as a ring atom. The nitrogen atom of a heterocyclylheteroaryl may be a basic nitrogen atom. The nitrogen or sulfur atom of the heteroaryl or heterocyclyl portion of the heterocyclylheteroaryl may also be optionally oxidized to the corresponding N-oxide, S-oxide or S,S-dioxide. Exemplary heterocyclylheteroaryl includes 2,3-dihydro-1H-pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetra-hydro-9H-pyrido[3,4-b]indol-2-yl, 1,2,3,4-tetrahydro-9H-pyrido[4,3-b]indol-2-yl, 2,3-dihydro-1H-pyrrolo[3,4-b]indol-2-yl, 1H-2,3,4,5-tetrahydroazepino[3,4-b]indol-2-yl, 1H-2,3,4,5-tetra-hydroazepino[4,3-b]indol-3-yl, 1H-2,3,4,5-tetrahydroazepino[4,5-b]indol-2-yl, 5,6,7,8-tetra-hydro[1,7]naphthyridyl, 1,2,3,4-tetrhydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, and 1,2,3,4-tetra-hydro[2,6]naphthyridinyl.

"Multicyclic alkaryl" means a multicyclic ring system including at least one aromatic ring fused to at least one non-aromatic ring that may be saturated or unsaturated, and may also contain in the ring system one or more heteroatoms, such as nitrogen, oxygen or sulfur. Exemplary multicyclic alkaryl includes arylcycloalkenyl, arylcycloalkyl, arylheterocyclenyl, arylheterocyclyl, cycloalkenylaryl, cycloalkylaryl, cycloalkenylheteroaryl, cycloalkylheteroaryl, heteroarylcycloalkenyl, heteroarylcycloalkyl, heteroarylheterocyclenyl, heteroarylheterocyclyl, heterocyclenylaryl, heterocyclenylheteroaryl, heterocyclylaryl, and heterocyclylheteroaryl. Particular multicyclic alkaryl groups are bicyclic rings that include one aromatic ring fused to one non-aromatic ring and that also may contain in the ring system one or more heteroatoms, such as nitrogen, oxygen or sulfur.

"Patient" includes human and other mammals.

"Pharmaceutically acceptable salts" refers to the non-toxic, inorganic and organic acid addition salts, and base addition salts, of compounds of the present invention. These salts may be prepared in situ during the final isolation and purification of the compounds or by separately reacting the purified compound in its free base form with a suitable organic or inorganic acid and isolating the salt thus formed. In some cases, the compounds themselves are capable of self-protonating basic sites on the molecule and forming an internal amphoteric salt.

Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts. See, for example S. M. Berge, et al., "Pharmaceutical Salts," *J. Pharm. Sci.* 66, 1-19 (1977) that is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. A particular base addition salt is sodium salt or potassium salt. Suitable inorganic base addition salts are prepared from metal bases which include sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt, and particularly include those amines which are frequently used in medicinal chemistry because of their low toxicity and acceptability for medical use. Exemplary amin includes ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine.

"Solvate" means a physical association of a compound of the present invention with one or more solvent molecules. This physical association includes hydrogen bonding. In certain instances, the solvate will be capable of isolation, for example when one or more solvent molecules are incorporated in the crystal lattice of the crystalline solid. "Solvate" encompasses both solution-phase and insoluble solvates. Particular solvates include hydrates, ethanolates, and methanolates.

"Substituted one or more times independently" means substituted one or more times by same or different substituent groups, particularly substituted one, two or three times by same or different substituent groups.

PARTICULAR EMBODIMENTS OF THE INVENTION

One particular embodiment of the invention is a compound of formula (I) wherein $R^1$ is aryl or heteroaryl, each of which is optionally substituted one or more times independently by halo, $(C_1-C_6)$-alkyl, hydroxy, $(C_1-C_6)$-alkoxy, $(C_1-C_4)$-haloalkyl or $(C_1-C_4)$-haloalkoxy, or a hydrate, solvate or N-oxide thereof, or a pharmaceutically acceptable salt thereof.

Another particular embodiment of the invention is a compound of formula (I) wherein $R^1$ is phenyl or five or six membered heteroaryl, each of which is optionally substituted one or more times independently by halo, $(C_1-C_6)$-alkyl, hydroxy, or $(C_1-C_6)$-alkoxy, or a hydrate, solvate or N-oxide thereof, or a pharmaceutically acceptable salt thereof.

Another particular embodiment of the invention is a compound of formula (I) wherein $R^1$ is phenyl, pyridyl, pyrimidinyl, thiazolyl, or oxodiazolyl, each of which is optionally substituted one or more times independently by halo, $(C_1-C_6)$-alkyl, hydroxy, or $(C_1-C_6)$-alkoxy, or a hydrate, solvate or N-oxide thereof, or a pharmaceutically acceptable salt thereof.

Another particular embodiment of the invention is a compound of formula (I) wherein $R^1$ is phenyl, pyridyl or pyrimidinyl, each of which is optionally substituted independently at the ortho or meta position by halo, $(C_1-C_6)$-alkyl, hydroxy, or $(C_1-C_6)$-alkoxy, or a hydrate, solvate or N-oxide thereof, or a pharmaceutically acceptable salt thereof.

Another particular embodiment of the invention is a compound of formula (I) wherein $R^1$ is phenyl optionally substituted independently at the ortho or meta position by halo, or a hydrate, solvate or N-oxide thereof, or a pharmaceutically acceptable salt thereof.

Another particular embodiment of the invention is a compound of formula (I) wherein $R^1$ is pyridyl, or a hydrate, solvate or N-oxide thereof, or a pharmaceutically acceptable salt thereof.

Another particular embodiment of the invention is a compound of formula (I) wherein $R^2$ is hydrogen, methyl or trifluoromethyl, or a hydrate solvate or N-oxide thereof, or a pharmaceutically acceptable salt thereof.

Another particular embodiment of the invention is a compound of formula (I) wherein $R^2$ is hydrogen, or a hydrate, solvate or N-oxide thereof, or a pharmaceutically acceptable salt thereof.

Another particular embodiment of the invention is a compound of formula (I) wherein $R^2$ is methyl, or a hydrate, solvate or N-oxide thereof, or a pharmaceutically acceptable salt thereof.

Another particular embodiment of the invention is a compound of formula (I) wherein $L^1$ is a bond, —O—, —C(=O)—, or —NH—C(=O)—, or a hydrate, solvate or N-oxide thereof, or a pharmaceutically acceptable salt thereof.

Another particular embodiment of the invention is a compound of formula (I) wherein $L^1$ is a bond, or a hydrate, solvate or N-oxide thereof, or a pharmaceutically acceptable salt thereof.

Another particular embodiment of the invention is a compound of formula (I) wherein:
$R^3$ and $R^4$ together with the nitrogen atom to which they are attached form heterocyclyl, heterocyclenyl, arylheterocyclyl, or heteroaryl, each of which is optionally substituted one or more times independently by $R^6$;
$R^6$ is alkoxy, hydroxyl, cycloalkyl, carboxy, cycloalkyl, halo, cyano, alkylsulfonyl, $Y^1Y^2N$—, $Y^1Y^2N$—$SO_2$—,
  alkyl optionally substituted one or more times independently by acyloxy, hydroxy, alkoxycarbonyl, alkoxy, carboxy, aryl, halo, alkylsulfonyl, cyano, $Y^1Y^2N$—, or $Y^1Y^2N$—C(=O)—,
  acyl or aryl, each of which is optionally substituted one or more times independently by halo,
  alkoxycarbonyl optionally substituted one or more times independently by aryl,
  heteroaroyl optionally substituted one or more times independently by alkyl,
  heterocyclyl optionally substituted one or more times by oxo, or
  aryloxy optionally substituted one or more times independently by haloalkyl; and
$Y^1$ and $Y^2$ are each independently hydrogen, alkylsulfonyl, aroyl, or alkyl optionally substituted by morpholinyl, or
$Y^1$ and $Y^2$ together with the nitrogen atom to which they are attached form morpholinyl;
or a hydrate, solvate or N-oxide thereof, or a pharmaceutically acceptable salt thereof.

Another particular embodiment of the invention is a compound of formula (I) wherein:
$R^3$ and $R^4$ together with the nitrogen atom to which they are attached form [1,2,4]triazolyl, pyrrolyl, indolyl, pyrrolo[2,3-b]pyridyl, pyrrolo[3,2-b]pyridyl, or pyrrolo[2,3-c]pyridyl, each of which is optionally substituted one or more times independently by $R^6$;
$R^6$ is alkoxy, carboxy, cycloalkyl, halo, cyano, alkylsulfonyl, $Y^1Y^2N$—$SO_2$—,
  alkyl optionally substituted one or more times independently by $Y^1Y^2N$—C(=O)—, hydroxy, alkoxycarbonyl, alkoxy, carboxy, aryl, halo, heterocyclyl, cycloalkyl, alkylsulfonyl, cyano, heterocyclylcarbonyl,
  acyl or aryl, each of which is optionally substituted one or more times independently by halo,
  alkoxycarbonyl optionally substituted one or more times independently by aryl,
  heteroaroyl optionally substituted one or more times independently by alkyl,
  heterocyclyl optionally substituted one or more times by oxo, or
  aryloxy optionally substituted one or more times independently by haloalkyl; and
$Y^1$ and $Y^2$ are each independently hydrogen, or alkyl optionally substituted by morpholinyl, or
$Y^1$ and $Y^2$ together with the nitrogen atom to which they are attached form morpholinyl;
or a hydrate, solvate or N-oxide thereof, or a pharmaceutically acceptable salt thereof Another particular embodiment of the invention is a compound of formula (I) wherein:
$R^3$ and $R^4$ together with the nitrogen atom to which they are attached form imidazolidinyl, [1,2,4]thiazinanyl, piperazinyl, morpholinyl, pyrrolidinyl, 1,2,3,4-tetrahydro-pyrimidinyl, piperidinyl, oxazolidinyl, 2,3-dihydro-indolyl, octahydro-cyclopenta[c]pyrrolyl, or 3,4-dihydro-benzo[1,4]oxazine, each of which optionally substituted one or more times independently by $R^6$;
$R^6$ is oxo, alkoxy, carboxy, cycloalkyl, halo, cyano, alkylsulfonyl, $Y^1Y^2N$—$SO_2$—,
  alkyl optionally substituted one or more times independently by hydroxy, alkoxycarbonyl, alkoxy, carboxy, aryl, halo, heterocyclyl, cycloalkyl, alkylsulfonyl, cyano, heterocyclylcarbonyl,
  acyl or aryl, each of which is optionally substituted one or more times independently by halo,
  alkoxycarbonyl optionally substituted one or more times independently by aryl,
  heteroaroyl optionally substituted one or more times independently by alkyl,
  heterocyclyl optionally substituted one or more times by oxo, or
  aryloxy optionally substituted one or more times independently by haloalkyl; and
$Y^1$ and $Y^2$ are each independently hydrogen, or alkyl optionally substituted by morpholinyl, or
$Y^1$ and $Y^2$ together with the nitrogen atom to which they are attached form morpholinyl;

or a hydrate, solvate or N-oxide thereof, or a pharmaceutically acceptable salt thereof.

Another particular embodiment of the invention is a compound of formula (I) wherein:
$R^3$ and $R^4$ together with the nitrogen atom to which they are attached form indolyl, optionally substituted one or more times independently by $R^6$;
$R^6$ is $Y^1Y^2N$—$SO_2$—, alkoxycarbonyl, carboxyalkyl, cyano, halo, alkylsulfonyl, alkoxy, or acyl optionally substituted one or more times independently by halo; and
$Y^1$ and $Y^2$ are each independently hydrogen, or alkyl optionally substituted by morpholinyl, or
$Y^1$ and $Y^2$ together with the nitrogen atom to which they are attached form morpholinyl;
or a hydrate, solvate or N-oxide thereof, or a pharmaceutically acceptable salt thereof.

Another particular embodiment of the invention is a compound of formula (I) wherein:
$R^5$ is phenyl, pyridyl, or benzo[1,3]dioxolyl, each of which is optionally substituted one or more times independently by $R^6$;
$R^6$ is $Y^1Y^2N$—$SO_2$—, hydroxy, alkoxy, halo, alkyl, or haloalkyl; and
$Y^1$ and $Y^2$ are each independently hydrogen or alkyl,
or a hydrate, solvate or N-oxide thereof, or a pharmaceutically acceptable salt thereof.

Another particular embodiment of the invention is a compound of formula (I), which is
2-Pyridin-3-yl-pyrimidine-5-carboxylic acid (5-fluoro-2-methyl-indol-1-yl)-amide,
2-(3-Fluoro-phenyl)-4-methyl-pyrimidine-5-carboxylic acid (5-fluoro-2-methyl-indol-1-yl)amide,
4-Methyl-2-pyridin-2-yl-pyrimidine-5-carboxylic acid (5-fluoro-3-methyl-indol-1-yl)amide,
2-Pyridin-2-yl-pyrimidine-5-carboxylic acid (5-fluoro-3-methyl-indol-1-yl)-amide,
4-Methyl-2-pyridin-3-yl-pyrimidine-5-carboxylic acid (5-fluoro-3-methyl-indol-1-yl)-amide,
2-Pyridin-3-yl-pyrimidine-5-carboxylic acid (5-fluoro-3-methyl-indol-1-yl)-amide,
2-Pyridin-2-yl-pyrimidine-5-carboxylic acid (5-fluoro-2-methyl-indol-1-yl)-amide,
2-(3-Fluoro-phenyl)-pyrimidine-5-carboxylic acid (5-fluoro-3-methyl-indol-1-yl)-amide,
4-Methyl-2-pyridin-3-yl-pyrimidine-5-carboxylic acid (5-fluoro-2-methyl-indol-1-yl)-amide,
2-(3-Fluoro-phenyl)-4-methyl-pyrimidine-5-carboxylic acid (5-fluoro-3-methyl-indol-1-yl)-amide,
2-(3-Fluoro-phenyl)-pyrimidine-5-carboxylic acid (5-fluoro-2-methyl-indol-1-yl)amide,
4-Methyl-2-pyridin-2-yl-pyrimidine-5-carboxylic acid (5-fluoro-2-methyl-indol-1-yl)-amide,
2-(3-Fluoro-phenyl)-4-methyl-pyrimidine-5-carboxylic acid (5-fluoro-3,3-dimethyl-2,3-dihydro-indol-1-yl)-amide,
2-(3-Fluoro-phenyl)-4-methyl-pyrimidine-5-carboxylic acid [3-(2,2,2-trifluoro-acetyl)-indol-1-yl]-amide,
4-Methyl-2-pyridin-2-yl-pyrimidine-5-carboxylic acid (5-fluoro-3,3-dimethyl-2,3-dihydro-indol-1-yl)-amide,
4-Methyl-2-pyridin-3-yl-pyrimidine-5-carboxylic acid (5-fluoro-3,3-dimethyl-2,3-dihydro-indol-1-yl)-amide,
2-(3-Fluoro-phenyl)-4-methyl-pyrimidine-5-carboxylic acid (2,3-dimethyl-indol-1-yl)-amide,
2-(3-Fluoro-phenyl)-4-methyl-pyrimidine-5-carboxylic acid (5-chloro-2-methyl-indol-1-yl)-amide,
2-(3-Fluoro-phenyl)-4-methyl-pyrimidine-5-carboxylic acid (5-bromo-indol-1-yl)-amide,
3-Oxo-4-[(2-phenyl-pyrimidine-5-carbonyl)-amino]-piperazine-1-carboxylic acid benzyl ester,
2-(3-Fluorophenyl)pyrimidine-5-carboxylic acid-(3-dimethylsulfamoyl-5-fluoro-indol-1-yl)amide,
2-(3-Fluorophenyl)-4-methylpyrimidine-5-carboxylic acid-(3-dimethylsulfamoyl-5-fluoroindol-1-yl)amide,
2-(3-Fluorophenyl)pyrimidine-5-carboxylicacid-[5-fluoro-3-(morpholine-4-sulfonyl)indol-1-yl]amide,
2-(3-Fluorophenyl)-4-methylpyrimidine-5-carboxylic acid-[5-fluoro-3-(morpholine-4-sulfonyl) indol-1-yl]amide,
2-(3-Fluorophenyl)pyrimidine-5-carboxylic acid-[5-fluoro-3-sulfamoylindol-1-yl)amide,
2-(3-Fluorophenyl)pyrimidine-5-carboxylic acid-[5-fluoro-3-methylsulfamoyl)indol-1-yl)amide,
2-(3-Fluorophenyl)pyrimidine-5-carboxylic acid-[5-fluoro-3-(2-morpholin-4-ylethylsulfamoyl)indol-1-yl)amide,
2-(3-Fluorophenyl)-4-methylpyrimidine-5-carboxylic acid-[5-fluoro-3-methylsulfamoyl)indol-1-yl)amide,
2-(3-Fluorophenyl)-4-methylpyrimidine-5-carboxylic acid-{5-fluoro-[(3-tetrahydropyran-4-ylmethyl)sulfamoyl]indol-1-yl}amide,
2-(3-Fluorophenyl)-4-methylpyrimidine-5-carboxylic acid-[5-fluoro-3-(2-morpholin-4-ylethylsulfamoyl)indol-1-yl) amide,
2-(3-Fluorophenyl)pyrimidine-5-carboxylic acid-(4-fluoroindol-1-yl)amide,
2-(3-Fluorophenyl)-4-methylpyrimidine-5-carboxylic acid-(4-fluoroindol-1-yl)amide,
2-(Pyridin-2-yl)-pyrimidine-5-carboxylic acid-(4-fluoroindol-1-yl)amide,
2-(Pyridin-2-yl)-4-methylpyrimidine-5-carboxylic acid-(4-fluoroindol-1-yl)amide,
2-Phenyl-pyrimidine-5-carboxylic acid [6-(4-fluoro-phenyl)-3-oxo-2,5-dihydro-3H-1,2,4-triazin-4-yl]-amide,
2-(3-Fluoro-phenyl)-pyrimidine-5-carboxylic acid-[4-(2-hydroxy-ethyl)-piperazin-1-yl]-amide,
2-(3-Fluoro-phenyl)-pyrimidine-5-carboxylic acid (6-methyl-3-oxo-2,5-dihydro-3H-[1,2,4]triazin-4-yl)-amide,
2-(3-Fluoro-phenyl)-pyrimidine-5-carboxylic acid[5-fluoro-3-(2-hydroxy-2-methyl-propyl)-indol-1-yl]-amide,
2-(3-Fluoro-phenyl)-4-methyl-pyrimidine-5-carboxylic acid [5-fluoro-3-(2-hydroxy-2-methyl-propyl)-indol-1-yl]-amide,
4-Methyl-2-pyridin-2-yl-pyrimidine-5-carboxylic acid [5-fluoro-3-(2-hydroxy-2-methyl-propyl)-indol-1-yl]-amide,
2-(3-Fluoro-phenyl)-4-methyl-pyrimidine-5-carboxylic acid (3-cyano-5-fluoro-indol-1-yl)-amide,
2-(3-Fluoro-phenyl)-4-methyl-pyrimidine-5-carboxylic acid [5-fluoro-3-(1H-tetrazol-5-yl)-indol-1-yl]-amide,
2-Phenyl-pyrimidine-5-carboxylic acid [1,2,4]triazol-4-ylamide,
2-phenyl-pyrimidine-5-carboxylic acid piperidin-1-ylamide,
2-Phenyl-pyrimidine-5-carboxylic acid N'-(2-fluoro-phenyl)-hydrazide,
2-Phenyl-pyrimidine-5-carboxylic acid N'-ethyl-N'-tolyl-hydrazide,
2-Phenyl-pyrimidine-5-carboxylic acid (3-oxo-morpholin-4-yl)-amide,
2-(5-Methyl-[1,2,4]oxadiazol-3-yl)-pyrimidine-5-carboxylic acid morpholin-4-ylamide,
2-Benzoyl-pyrimidine-5-carboxylic acid morpholin-4-ylamide,
2-Benzoyl-pyrimidine-5-carboxylic acid [4-(2-hydroxyethyl)-piperazin-1-yl]-amide,
2-Phenyl-pyrimidine-5-carboxylic acid N'-methyl-N'-[5-trifluoromethyl-pyridin-2-yl]-hydrazide,
2-Phenyl-pyrimidine-5-carboxylic acid N'-methyl-N'-[4-trifluoromethyl-pyridin-2-yl]-hydrazide,
2-Phenyl-pyrimidine-5-carboxylic acid N'-pyridin-2-yl-hydrazide,
2-Phenyl-pyrimidine-5-carboxylic acid N'-(2-chloro-phenyl)-hydrazide, 2-Phenyl-pyrimidine-5-carboxylic acid N'-(2-oxo-piperidin-1-yl)-amide,
2-Phenyl-pyrimidine-5-carboxylic acid N'-cyclohexyl-N'-methyl-hydrazide,
2-Phenyoxy-pyrimidine-5-carboxylic acid N'-morpholin-4-yl-amide,
2-Phenyl-pyrimidine-5-carboxylic acid (2,6-dimethyl-3-oxo-2,5-dihydro-3H-1,2,4-triazine-4-yl)-amide,
2-Phenyl-pyrimidine-5-carboxylic acid (6-tert-butyl-3-oxo-2,5-dihydro-3H-1,2,4-triazine-4-yl)-amide,
2-Pyridin-2-yl-pyrimidine-5-carboxylic acid (6-methyl-3-oxo-2,5-dihydro-3H-1,2,4-triazine-4-yl)-amide,
2-(3-Fluoro-phenyl)-pyrimidine-5-carboxylic acid (6-tert-butyl-3-oxo-2,5-dihydro-3H-1,2,4-triazine-4-yl)-amide,
3-{2,4-Dioxo-3-[(2-phenyl-pyrimidine-5-carbonyl)-amino]-1,2,3,4-tetrahydro-pyrimidin-5-yl}-propionic acid methyl ester,
3-{2,4-Dioxo-3-[(2-phenyl-pyrimidine-5-carbonyl)-amino]-1,2,3,4-tetrahydro-pyrimidin-5-yl}-propionic acid,
2-Phenyl-pyrimidine-5-carboxylic acid (4-methyl-piperazin-1-yl)-amide,
2-Phenyl-pyrimidine-5-carboxylic acid morpholin-4-ylamide,
2-Phenyl-pyrimidine-5-carboxylic acid [4-(2-hydroxy-ethyl)-piperazin-1-yl]-amide,
2-Phenyl-pyrimidine-5-carboxylic acid ((s)-2-methoxymethyl)-pyrrolidin-1-yl]-amide,
2-Phenyl-pyrimidine-5-carboxylic acid ((R)-2-methoxymethyl)-pyrrolidin-1-yl]-amide,
2-Phenyl-pyrimidine-5-carboxylic acid (5-bromo-2,4-dioxo-3,4-dihydro-2H-pyrimidin-1-yl)-amide,
2-Phenyl-pyrimidine-5-carboxylic acid (3-isopropyl-5-oxo-1,5-dihydro-[1,2,4]triazol-4-yl)-amide,
2-Phenyl-pyrimidine-5-carboxylic acid pyrrol-1-ylamide,
2-Phenyl-pyrimidine-5-carboxylic acid (5-morpholin-4-yl-methyl-2-oxo-oxazolidin-3-yl)-amide,
2-Phenyl-pyrimidine-5-carboxylic acid (4-cyclopentyl-piperazin-1-yl]-amide,
2-Phenyl-pyrimidine-5-carboxylic acid (2-oxo-oxazolidin-3-yl)-amide,
4-Methyl-2-phenyl-pyrimidine-5-carboxylic acid (6-methyl-3-oxo-2,5-dihydro-3H-[1,2,4]triazin-4-yl]-amide,
[N'-(2-Phenyl-pyrimidine-5-carbonyl)-hydrazino]-acetic acid ethyl ester,
2-[N'-(2-Phenyl-pyrimidine-5-carbonyl)-hydrazino]-acetamide,
4-[3-(4-Morpholino)propyl]-1-(2-phenyl-pyrimidine-5-carbonyl)-3-thiosemicarbazide,
2-Phenyl-pyrimidine-5-carboxylic acid (2,3-dihydro-indol-1-yl)-amide,
{4-[2-Phenyl-pyrimidine-5-carbonyl)-amino]-piperazin-1-yl}-acetic acid methyl ester,
2-Phenyl-pyrimidine-5-carboxylic acid (4-cyanomethyl-piperazin-1-yl)-amide,
Acetic acid 2-{4-[(2-phenyl-pyrimidine-5-carbonyl)-amino]-piperazin-1-yl}-ethyl ester,
2-Phenyl-pyrimidine-5-carboxylic acid (4-acetyl-piperazin-1-yl)-amide,
2-Phenyl-pyrimidine-5-carboxylic acid [4-(2-oxo-tetrahydro-furan-3-yl)-piperazin-1-yl]-amide,
2-Phenyl-pyrimidine-5-carboxylic acid [4-(2,2,2-trifluoro-acetyl)-piperazin-1-yl]-amide,
2-Phenyl-pyrimidine-5-carboxylic acid [4-(2-methoxy-ethyl)-piperazin-1-yl]-amide,
2-Phenyl-pyrimidine-5-carboxylic acid [4-(2-morpholin-4-yl-2-oxo-ethyl)-piperazin-1-yl]-amide,
2-(3-Fluoro-phenyl)-pyrimidine-5-carboxylic acid (2,3-dihydro-indol-1-yl)-amide,
2-(3-Fluoro-phenyl)-pyrimidine-5-carboxylic acid piperadin-1-yl-amide,
2-Phenyl-pyrimidine-5-carboxylic acid piperadin-1-yl-amide,
2-Phenyl-pyrimidine-5-carboxylic acid (hexahydro-cyclopenta[c]pyrrol-2-yl)-amide,
4-Methyl-2-phenyl-pyrimidine-5-carboxylic acid (2,3-dihydro-indol-1-yl)-amide,
2-Phenyl-pyrimidine-5-carboxylic acid pyrrolidin-1-yl-amide,
2-Phenyl-pyrimidine-5-carboxylic acid (2,6-dimethyl-piperadin-1-yl)-amide,
2-(3-Fluoro-phenyl)-pyrimidine-5-carboxylic acid (4-cyclopentyl-piperazin-1-yl)-amide,
2-Phenyl-pyrimidine-5-carboxylic acid (2-methyl-2,3-dihydro-indol-1-yl)-amide,
2-(3-Fluoro-phenyl)-pyrimidine-5-carboxylic acid (2-methyl-2,3-dihydro-indol-1-yl)-amide,
2-Phenyl-pyrimidine-5-carboxylic acid N'-methyl-N'-pyridin-2-yl-hydrazide,
2-Phenyl-pyrimidine-5-carboxylic acid (5-fluoro-indol-1-yl)-amide,
2-Pyridin-2-yl-pyrimidine-5-carboxylic acid (2,3-dihydro-indol-1-yl)-amide,
2-Pyridin-2-yl-pyrimidine-5-carboxylic acid indol-1-yl-amide,
2-(3-Fluoro-phenyl)-pyrimidine-5-carboxylic acid indol-1-yl-amide,
2-(3-Fluoro-phenyl)-4-methyl-pyrimidine-5-carboxylic acid (2,3-dihydro-indol-1-yl)-amide,
2-(3-Fluoro-phenyl)-4-methyl-pyrimidine-5-carboxylic acid (2-methyl-2,3-dihydro-indol-1-yl)-amide,
2-(3-Fluoro-phenyl)-pyrimidine-5-carboxylic acid (2-methyl-indol-1-yl)-amide,
2-(3-Fluoro-phenyl)-4-methyl-pyrimidine-5-carboxylic acid indol-1-ylamide,
4-Methyl-2-pyridin-2-yl-pyrimidine-5-carboxylic acid (2,3-dihydro-indol-1-yl)-amide,
4-Methyl-2-pyridin-2-yl-pyrimidine-5-carboxylic acid indol-1-ylamide,
2-(3-Fluoro-phenyl)-pyrimidine-5-carboxylic acid (5-methanesulfonyl-indol-1-yl)-amide,
2-(3-Fluoro-phenyl)-pyrimidine-5-carboxylic acid (6-methanesulfonyl-indol-1-yl)-amide,
2-Pyridin-2-yl-pyrimidine-5-carboxylic acid (5-methanesulfonyl-indol-1-yl)-amide,
2-Pyridin-3-yl-pyrimidine-5-carboxylic acid (5-methanesulfonyl-indol-1-yl)-amide,
2-(3-Fluoro-phenyl)-4-methyl-pyrimidine-5-carboxylic acid (5-methanesulfonyl-indol-1-yl)-amide,
2-(3-Fluoro-phenyl)-pyrimidine-5-carboxylic acid pyrrolo[2,3-b]pyridin-1-ylamide,
2-(3-Fluoro-phenyl)-pyrimidine-5-carboxylic acid pyrrolo[3,2-b]pyridin-1-ylamide,
2-(3-Fluoro-phenyl)-pyrimidine-5-carboxylic acid (5-fluoro-indol-1-yl)-amide,
2-(3-Fluoro-phenyl-4-methyl)-pyrimidine-5-carboxylic acid (5-fluoro-indol-1-yl)-amide,
2-(3-Fluoro-phenyl)-4-methyl-pyrimidine-5-carboxylic acid pyrrolo[3,2-b]pyridin-1-ylamide,
2-(3-Fluoro-phenyl)-4-methyl-pyrimidine-5-carboxylic acid pyrrolo[2,3-b]pyridin-1-ylamide,
4-Methyl-2-pyridin-2-yl-pyrimidine-5-carboxylic acid (5-fluoro-indol-1-yl)-amide,
2-Pyridin-2-yl-pyrimidine-5-carboxylic acid (5-fluoro-indol-1-yl)-amide,
2-Pyridin-2-yl-pyrimidine-5-carboxylic acid pyrrolo[2,3-b]pyridine-1-ylamide,
4-Methyl-2-pyridin-2-yl-pyrimidine-5-carboxylic acid pyrrolo[2,3-b]pyridin-1-ylamide,
4-Methyl-2-pyridin-2-yl-pyrimidine-5-carboxylic acid pyrrolo[3,2-b]pyridin-1-ylamide, 2-(3-Fluoro-phenyl)-4-methyl-pyrimidine-5-carboxylic acid pyrrolo[2,3-c]pyridin-1-ylamide,
4-Methyl-2-pyridin-2-yl-pyrimidine-5-carboxylic acid pyrrolo[2,3-c]pyridin-1-ylamide,
4-Methyl-2-pyridin-3-yl-pyrimidine-5-carboxylic acid pyrrolo[3,2-b]pyridin-1-ylamide,
4-Methyl-2-pyridin-3-yl-pyrimidine-5-carboxylic acid (5-fluoro-indol-1-yl)-amide,
2-(3-Fluoro-phenyl)-4-methyl-pyrimidine-5-carboxylic acid (5-fluoro-indol-1-yl)-amide,
2-(3-Fluoro-phenyl)-4-methyl-pyrimidine-5-carboxylic acid (5-methoxy-indol-1-yl)-amide,
2-(3-Fluoro-phenyl)-4-methyl-pyrimidine-5-carboxylic acid (5-cyano-indol-1-yl)-amide,
2-(3-Fluoro-phenyl)-4-methyl-pyrimidine-5-carboxylic acid (4-cyano-indol-1-yl)-amide,
2-(3-Fluoro-phenyl)-4-methyl-pyrimidine-5-carboxylic acid [4-(1H-tetrazol-5-yl)-indol-1-yl]-amide,
1-{[2-(3-Fluoro-phenyl)-4-methyl-pyrimidine-5-carbonyl]-amino}-1H-indol-4-carboxylic acid methyl ester,
1-{[2-(3-Fluoro-phenyl)-4-methyl-pyrimidine-5-carbonyl]-amino}-1H-indol-4-carboxylic acid,
2-(3-Fluoro-phenyl)-4-methyl-pyrimidine-5-carboxylic acid (3-cyanomethyl-indol-1-yl)-amide,
4-Methyl-2-pyridin-2-yl-pyrimidine-5-carboxylic acid (5-methoxy-indol-1-yl)-amide,
2-(3-Fluoro-phenyl)-4-methyl-pyrimidine-5-carboxylic acid [3-(1H-tetrazol-5-ylmethyl)-indol-1-yl]-amide,
2-(2-Phenyl-pyrimidine-5-carbonyl)-1-hydrazinecarboxamide,
2-(2-Phenyl-pyrimidine-5-carbonyl)-1-hydrazine-1-carbothioamide,
2-Phenyl-pyrimidine-5-carboxylic acid (2,4-dioxo-imidazolidin-1-yl)-amide,
2-Phenyl-pyrimidine-5-carboxylic acid (6-methyl-3-oxo-2,5-dihydro-3H-[1,2,4]triazin-4-yl)-amide,
2-Phenyl-pyrimidine-5-carboxylic acid N'-phenyl-hydrazide,
Pyridine-2-carboxylic acid N'-(2-phenyl-pyrimidine-5-carbonyl)-hydrazide,
4-[N'-(2-Phenyl-pyrimidine-5-carbonyl)-hydrazino]-benzenesulfonamide,
3-Hydroxy-benzoic acid N'-(2-phenyl-pyrimidine-5-carbonyl)-hydrazide,
Benzo[1,3]dioxo-5-carboxylic acid N'-(phenyl-pyrimidine-5-carbonyl)-hydrazide,
3,4-Dimethoxy-benzoic acid N'-(phenyl-pyrimidine-5-carbonyl)-hydrazide,
2-Phenyl-pyrimidine-5-carboxylic acid N'-methyl-N'-phenyl-hydrazide,
2-(3-Fluoro-phenyl)-4-methyl-pyrimidine-5-carboxylic acid (5-methoxy-3-methyl-indol-1-yl)-amide,
2-(3-Methoxy-phenyl)-pyrimidine-5-carboxylic acid (6-methyl-3-oxo-2,5-dihydro-3H-[1,2,4]triazin-4-yl)-amide,
2-(2-Methoxy-phenyl)-pyrimidine-5-carboxylic acid (6-methyl-3-oxo-2,5-dihydro-3H-[1,2,4]triazin-4-yl)-amide,
2-(4-Methoxy-phenyl)-pyrimidine-5-carboxylic acid (6-methyl-3-oxo-2,5-dihydro-3H-[1,2,4]triazin-4-yl)-amide,
2-(3-Hydroxy-phenyl)-pyrimidine-5-carboxylic acid (6-methyl-3-oxo-2,5-dihydro-3H-[1,2,4]triazin-4-yl)-amide,
2-(2-Hydroxy-phenyl)-pyrimidine-5-carboxylic acid (6-methyl-3-oxo-2,5-dihydro-3H-[1,2,4]triazin-4-yl)-amide,
2-(4-Hydroxy-phenyl)-pyrimidine-5-carboxylic acid (6-methyl-3-oxo-2,5-dihydro-3H-[1,2,4]triazin-4-yl)-amide,
4-Methyl-[2,2']bipyrimidinyl-5-carboxylic acid (5-fluoro-3-methyl-indol-1-yl)-amide,
2-Thiazol-2-yl-pyrimidine-5-carboxylic acid (5-fluoro-3-methyl-indol-1-yl)-amide,
4-Methyl-2-thiazol-2-yl-pyrimidine-5-carboxylic acid (5-fluoro-3-methyl-indol-1-yl)-amide,
[2,2']Bipyrimidinyl-5-carboxylic acid (5-fluoro-3-methyl-indol-1-yl)-amide,
2-(3-Fluoro-phenyl)-4-methyl-pyrimidine-5-carboxylic acid (3-chloro-5-fluoro-indol-1-yl)-amide,
5-Fluoro-1-{[2-(3-fluoro-phenyl)-4-methyl-pyrimidine-5-carbonyl]-amino}-1H-indole-3-carboxylic acid amide,
2-{5-Fluoro-1-[(4-methyl-2-pyridin-2-yl-pyrimidine-5-carbonyl)-amino]-1H-indol-3-yl}-2-methyl-propionic acid,
2-(5-Fluoro-1-{[2-(3-fluoro-phenyl)-4-methyl-pyrimidine-5-carbonyl]-amino}-1H-indol-3-yl)-2-methyl-propionic acid,
2-(3-Fluoro-phenyl)-4-methyl-pyrimidine-5-carboxylic acid [5-fluoro-3-(3-hydroxy-3-methyl-butyl)-indol-1-yl]-amide,
4-Methyl-2-pyridin-2-yl-pyrimidine-5-carboxylic acid [5-fluoro-3-(3-hydroxy-3-methyl-butyl)-indol-1-yl]-amide,
2-(3-Fluoro-phenyl)-4-methyl-pyrimidine-5-carboxylic acid [5-fluoro-3-(2-pyridin-3-yl-ethyl)-indol-1-yl]-amide,
4-Methyl-2-pyridin-2-yl-pyrimidine-5-carboxylic acid (5-fluoro-3-formyl-indol-1-yl)-amide,
5-Fluoro-1-[(4-methyl-2-pyridin-2-yl-pyrimidine-5-carbonyl)-amino]-1H-indole-3-carboxylic acid,
4-Methyl-2-pyridin-2-yl-pyrimidine-5-carboxylic acid (5-fluoro-3-hydroxymethyl-indol-1-yl)-amide,
4-Methyl-[2,2']bipyrimidinyl-5-carboxylic acid [5-fluoro-3-(3-hydroxy-3-methyl-butyl)-indol-1-yl]-amide,
4-Methyl-2-thiazol-2-yl-pyrimidine-5-carboxylic acid [5-fluoro-3-(3-hydroxy-3-methyl-butyl)-indol-1-yl]-amide,
2-(3-Fluoro-phenyl)-4-methyl-pyrimidine-5-carboxylic acid (3-ethyl-5-trifluoromethyl-indol-1-yl)-amide,
4-Methyl-2-pyridin-2-yl-pyrimidine-5-carboxylic acid (3-ethyl-5-trifluoromethyl-indol-1-yl)-amide,
4-Methyl-2-thiazol-2-yl-pyrimidine-5-carboxylic acid (3-ethyl-5-trifluoromethyl-indol-1-yl)-amide,
4-Methyl-[2,2']bipyrimidinyl-5-carboxylic acid (3-ethyl-5-trifluoromethyl-indol-1-yl)-amide,
2-(3-Fluoro-phenyl)-4-methyl-pyrimidine-5-carboxylic acid (3-ethyl-5-trifluoromethoxy-indol-1-yl)-amide,
4-Methyl-2-pyridin-2-yl-pyrimidine-5-carboxylic acid (3-ethyl-5-trifluoromethoxy-indol-1-yl)-amide,
4-Methyl-[2,2']bipyrimidinyl-5-carboxylic acid (3-ethyl-5-trifluoromethoxy-indol-1-yl)-amide,
4-Methyl-2-thiazol-2-yl-pyrimidine-5-carboxylic acid (3-ethyl-5-trifluoromethoxy-indol-1-yl)-amide,
2-(3-Fluoro-phenyl)-4-methyl-pyrimidine-5-carboxylic acid (6-trifluoromethyl-indol-1-yl)-amide,
4-Methyl-2-pyridin-2-yl-pyrimidine-5-carboxylic acid (6-trifluoromethyl-indol-1-yl)-amide,
4-Methyl-2-thiazol-2-yl-pyrimidine-5-carboxylic acid (6-trifluoromethyl-indol-1-yl)-amide,
4-Methyl-[2,2']bipyrimidinyl-5-carboxylic acid (6-trifluoromethyl-indol-1-yl)-amide,
2-(3-Fluoro-phenyl)-4-methyl-pyrimidine-5-carboxylic acid (3-ethyl-5-trifluoromethyl-pyrrolo[3,2-b]pyridin-1-yl)-amide,
4-Methyl-2-pyridin-2-yl-pyrimidine-5-carboxylic acid (3-ethyl-5-trifluoromethyl-pyrrolo[3,2-b]pyridin-1-yl)-amide,
4-Methyl-2-thiazol-2-yl-pyrimidine-5-carboxylic acid (3-ethyl-5-trifluoromethyl-pyrrolo[3,2-b]pyridin-1-yl)-amide,
4-Methyl-[2,2']bipyrimidinyl-5-carboxylic acid (3-ethyl-5-trifluoromethyl-pyrrolo[3,2-b]pyridin-1-yl)-amide,
2-(3-Fluoro-phenyl)-4-methyl-pyrimidine-5-carboxylic acid (5-methoxy-2-methyl-indol-1-yl)-amide,
2-(3-Fluoro-phenyl)-4-methyl-pyrimidine-5-carboxylic acid N',N'-diphenyl-hydrazide 2-(3-Fluoro-phenyl)-4-methyl-pyrimidine-5-carboxylic acid (7-fluoro-3-methyl-indol-1-yl)-amide,
2-(3-Fluoro-phenyl)-4-methyl-pyrimidine-5-carboxylic acid (5-methanesulfonyl-3-methyl-indol-1-yl)-amide,
4-Methyl-2-pyridin-2-yl-pyrimidine-5-carboxylic acid (3-ethyl-pyrrolo[2,3-b]pyridin-1-yl)-amide,
2-(3-Fluoro-phenyl)-4-methyl-pyrimidine-5-carboxylic acid (3-ethyl-pyrrolo[2,3-b]pyridin-1-yl)-amide,
2-(3-Fluoro-phenyl)-4-methyl-pyrimidine-5-carboxylic acid (3-ethyl-pyrrolo[2,3c]pyridin-1-yl)-amide,
4-Methyl-2-pyridin-2-yl-pyrimidine-5-carboxylic acid (3-ethyl-pyrrolo[2,3-c]pyridin-1-yl)-amide,
2-(3-Fluoro-phenyl)-4-methyl-pyrimidine-5-carboxylic acid (3-methyl-pyrrolo[3,2-b]pyridin-1-yl)-amide,
4-Methyl-2-pyridin-2-yl-pyrimidine-5-carboxylic acid (3-methyl-5-trifluoromethyl-indol-1-yl)-amide,
4-Methyl-2-pyridin-2-yl-pyrimidine-5-carboxylic acid (3-methyl-pyrrolo[3,2-b]pyridin-1-yl)-amide,
2-(3-Fluoro-phenyl)-4-methyl-pyrimidine-5-carboxylic acid (3-methyl-pyrrolo[2,3c]pyridin-1-yl)-amide,
4-Methyl-2-pyridin-2-yl-pyrimidine-5-carboxylic acid (3-methyl-pyrrolo[2,3-c]pyridin-1-yl)-amide,
4-Methyl-2-pyridin-2-yl-pyrimidine-5-carboxylic acid (3-methyl-pyrrolo[3,2-c]pyridin-1-yl)-amide,
2-(3-Fluoro-phenyl)-4-methyl-pyrimidine-5-carboxylic acid (3-methyl-pyrrolo[3,2-c]pyridin-1-yl)-amide,
2-(3-Fluoro-phenyl)-4-methyl-pyrimidine-5-carboxylic acid (5-nitro-indol-1-yl)-amide,
2-(3-fluoro-phenyl)-4-methyl-pyrimidine-5-carboxylic acid (5-amino-indol-1-yl)-amide,
2-(3-fluoro-phenyl)-4-methyl-pyrimidine-5-carboxylic acid [5-(dimethanesulfonyl)-amino-indol-1-yl]-amide,
2-(3-Fluoro-phenyl)-4-methyl-pyrimidine-5-carboxylic acid (5-benzoylamino-indol-1-yl)-amide,
4-Methyl-2-pyridin-2-yl-pyrimidine-5-carboxylic acid [5-fluoro-3-(1,2,3,6-tetrahydro-pyridin-4-yl)-indol-1-yl]-amide,
2-Pyridin-2-yl-4-trifluoromethyl-pyrimidine-5-carboxylic acid (5-fluoro-3-methyl-indol-1-yl)-amide,
2-(3-Fluoro-phenyl)-4-methyl-pyrimidine-5-carboxylic acid (2-methyl-indol-1-yl)-amide,
2-(3-Fluoro-phenyl)-pyrimidine-5-carboxylic acid (6-fluoro-2,3-dihydro-1,4-benzoxazin-4-yl)-amide,
2-Phenyl-pyrimidine-5-carboxylic acid (6-fluoro-2,3-dihydro-1,4-benzoxazin-4-yl)-amide,
4-Methyl-2-pyridin-2-yl-pyrimidine-5-carboxylic acid (3-ethyl-5-fluoro-pyrrolo[2,3-b]pyridin-1-yl)-amide,
4-Methyl-2-thiazol-2-yl-pyrimidine-5-carboxylic acid (3-ethyl-5-fluoro-pyrrolo[2,3-b]pyridin-1-yl)-amide,
2-(3-Fluoro-phenyl)-4-methyl-pyrimidine-5-carboxylic acid (5-fluoro-pyrrolo[2,3-b]pyridin-1-yl)-amide,
4-Methyl-2-pyridin-2-yl-pyrimidine-5-carboxylic acid (5-fluoro-pyrrolo[2,3-b]pyridin-1-yl)-amide,
4-Methyl-[2,2']bipyrimidinyl-5-carboxylic acid (2-cyclopropyl-5-fluoro-indol-1-yl)-amide,
4-Methyl-2-thiazol-2-yl-pyrimidine-5-carboxylic acid (2-cyclopropyl-5-fluoro-indol-1-yl)-amide,
2-Pyrimidin-2-yl-4-methyl-pyrimidine-5-carboxylic acid (5-methoxyl-indol-1-yl)-amide,
4-Methyl-[2,2']bipyrimidinyl-5-carboxylic acid (5-fluoro-3-methyl-pyrrolo[3,2-b]pyridin-1-yl)-amide,
4-Methyl-2-pyridin-2-yl-pyrimidine-5-carboxylic acid (5-fluoro-3-methyl-pyrrolo[3,2-b]pyridin-1-yl)-amide,
2-(3-Fluoro-phenyl)-4-methyl-pyrimidine-5-carboxylic acid (5-fluoro-3-methyl-pyrrolo[3,2-b]pyridin-1-yl)-amide,
4-Methyl-2-pyridin-2-yl-pyrimidine-5-carboxylic acid (5-methoxy-3-methyl-pyrrolo[3,2-b]pyridin-1-yl)-amide,
2-(3-Fluoro-phenyl)-4-methyl-pyrimidine-5-carboxylic acid (5-methoxy-3-methyl-pyrrolo[3,2-b]pyridin-1-yl)-amide,
4-Methyl-2-(1-oxy-pyridin-2-yl)-pyrimidin-5-carboxylic acid (5-fluoro-3-methyl-indol-1-yl)-amide,
2-(3-Difluoromethyl-phenyl)-pyrimidine-5-carboxylic acid (5-fluoro-3-methyl-indol-1-yl)-amide, or
2-(3-Trifluoromethyl-phenyl)-pyrimidine-5-carboxylic acid (5-fluoro-3-methyl-indol-1-yl)-amide,
or a hydrate, solvate or N-oxide thereof, or a pharmaceutically acceptable salt thereof.

Another particular embodiment of the invention is a compound of formula (I), which is:
2-Phenyl-pyrimidine-5-carboxylic acid (4-benzyl-piperazin-1-yl)-amide,
2-Phenyl-pyrimidine-5-carboxylic acid piperazin-1-ylamide,
2-Phenyl-pyrimidine-5-carboxylic acid (4-methanesulfonyl-piperazin-1-yl)-amide,
2-(2-Methyl-thiazol-4-yl)-pyrimidine-5-carboxylic acid morpholin-4-ylamide,
2-Phenyl-pyrimidine-5-carboxylic acid [4-(1-methyl-1H-imidazole-2-carbonyl)-piperazin-1-yl]-amide,
2-Phenyl-pyrimidine-5-carboxylic acid [4-(1-methyl-1H-imidazole-4-carbonyl)-piperazin-1-yl]-amide,
4-[(2-Phenyl-pyrimidine-5-carbonyl)-amino]-piperazine-1-carboxylic acid tert-butyl ester,
2-Phenyl-pyrimidine-5-carboxylic acid [4-(4-trifluoromethyl-phenoxy)-piperidin-1-yl]-amide,
2-(3-Fluoro-phenyl)-pyrimidine-5-carboxylic acid [4-(4-trifluoromethyl-phenoxy)-piperidin-1-yl]-amide,
2-(3-Fluoro-phenyl)-pyrimidine-5-carboxylic acid morpholin-4-ylamide,
2-Phenyl-pyrimidine-5-carboxylic acid indol-1-ylamide,
2-Phenyl-pyrimidine-5-carboxylic acid (4-methoxy-piperidin-1-yl)-amide,
2-(3-Fluoro-phenyl)-4-methyl-pyrimidine-5-carboxylic acid (2-methyl-indol-1-yl)-amide,
2-(3-Fluoro-phenyl)-pyrimidine-5-carboxylic acid (6-fluoro-2,3-dihydro-benzo[1,4]oxazin-4-yl)-amide,
2-Phenyl-pyrimidine-5-carboxylic acid (6-fluoro-2,3-dihydro-benzo[1,4]oxazin-4-yl)-amide,
1-{[2-(3-Fluoro-phenyl)-4-methyl-pyrimidine-5-carbonyl]-amino}-3-(2-morpholin-4-yl-ethyl)-1H-indole-6-carboxylic acid methyl ester,
2-(3-Fluoro-phenyl)-4-methyl-pyrimidine-5-carboxylic acid [5-fluoro-3-(tetrahydro-pyran-4-yl)-indol-1-yl]-amide,
N-methyl-N-(5-fluoro)-indol-3-ylsulfonyl N'-[2-(3-fluoro)-phenyl-pyrimidine-5-carbonyl]-hydrazide,
4-Methyl-2-pyridin-2-yl-pyrimidine-5-carboxylic acid [5-fluoro-3-(tetrahydro-pyran-4-yl)-indol-1-yl]-amide,
4-Methyl-2-pyridin-2-yl-pyrimidine-5-carboxylic acid (5-fluoro-3-methyl-indol-1-yl)-amide,
4-Methyl-2-(1-oxy)-pyridin-2-yl-pyrimidine-5-carboxylic acid (5-fluoro-3-methyl-indol-1-yl)-amide,
4-Methyl-2-pyridin-2-yl-pyrimidine-5-carboxylic acid (3-methyl-pyrrolo[3,2-b]pyridin-1-yl)-amide,
4-Methyl-2-(4-methyl-thiazol-2-yl)-pyrimidine-5-carboxylic acid pyrrolo[2,3-b]pyridin-1-ylamide,
4-Methyl-2-(4-methyl-thiazol-2-yl)-pyrimidine-5-carboxylic acid (3-methyl-pyrrolo[2,3-b]pyridin-1-yl)-amide,
4-Methyl-2-(4-methyl-thiazol-2-yl)-pyrimidine-5-carboxylic acid (3-isopropyl-pyrrolo[2,3-b]pyridin-1-yl)-amide,
4-Methyl-2-(4-methyl-thiazol-2-yl)-pyrimidine-5-carboxylic acid (3-difluoromethyl-pyrrolo[2,3-b]pyridin-1-yl)-amide,
4-Methyl-2-(4-methyl-thiazol-2-yl)-pyrimidine-5-carboxylic acid (3-trifluoromethyl-pyrrolo[2,3-b]pyridin-1-yl)-amide,
4-Methyl-2-(4-methyl-thiazol-2-yl)-pyrimidine-5-carboxylic acid (3-methyl-pyrrolo[2,3-c]pyridin-1-yl)-amide,
4-Methyl-2-(4-methyl-thiazol-2-yl)-pyrimidine-5-carboxylic acid pyrrolo[2,3-c]pyridin-1-ylamide, 4-Methyl-2-(4-methyl-thiazol-2-yl)-pyrimidine-5-carboxylic acid (3-isopropyl-pyrrolo[2,3-c]pyridin-1-yl)-amide,
4-Methyl-2-(4-methyl-thiazol-2-yl)-pyrimidine-5-carboxylic acid (3-difluoromethyl-pyrrolo[2,3-c]pyridin-1-yl)-amide,
4-Methyl-2-(4-methyl-thiazol-2-yl)-pyrimidine-5-carboxylic acid (3-trifluoromethyl-pyrrolo[2,3-c]pyridin-1-yl)-amide,
4-Methyl-2-(4-methyl-thiazol-2-yl)-pyrimidine-5-carboxylic acid (3-methyl-pyrrolo[3,2-c]pyridin-1-yl)-amide,
4-Methyl-2-(4-methyl-thiazol-2-yl)-pyrimidine-5-carboxylic acid pyrrolo[3,2-c]pyridin-1-ylamide,
4-Methyl-2-(4-methyl-thiazol-2-yl)-pyrimidine-5-carboxylic acid (3-isopropyl-pyrrolo[3,2-c]pyridin-1-yl)-amide,
4-Methyl-2-(4-methyl-thiazol-2-yl)-pyrimidine-5-carboxylic acid (3-difluoromethyl-pyrrolo[3,2-c]pyridin-1-yl)-amide,
4-Methyl-2-(4-methyl-thiazol-2-yl)-pyrimidine-5-carboxylic acid (3-trifluoromethyl-pyrrolo[3,2-c]pyridin-1-yl)-amide,
4-Methyl-2-thiazol-2-yl-pyrimidine-5-carboxylic acid pyrrolo[2,3-b]pyridin-1-ylamide,
4-Methyl-2-thiazol-2-yl-pyrimidine-5-carboxylic acid (3-methyl-pyrrolo[2,3-b]pyridin-1-yl)-amide,
4-Methyl-2-thiazol-2-yl-pyrimidine-5-carboxylic acid (3-isopropyl-pyrrolo[2,3-b]pyridin-1-yl)-amide,
4-Methyl-2-thiazol-2-yl-pyrimidine-5-carboxylic acid (3-difluoromethyl-pyrrolo[2,3-b]pyridin-1-yl)-amide,
4-Methyl-2-thiazol-2-yl-pyrimidine-5-carboxylic acid (3-trifluoromethyl-pyrrolo[2,3-b]pyridin-1-yl)-amide,
4-Methyl-2-thiazol-2-yl-pyrimidine-5-carboxylic acid pyrrolo[2,3-c]pyridin-1-ylamide,
4-Methyl-2-thiazol-2-yl-pyrimidine-5-carboxylic acid (3-methyl-pyrrolo[2,3-c]pyridin-1-yl)-amide,
4-Methyl-2-thiazol-2-yl-pyrimidine-5-carboxylic acid pyrrolo[2,3-c]pyridin-1-ylamide,
4-Methyl-2-thiazol-2-yl-pyrimidine-5-carboxylic acid (3-isopropyl-pyrrolo[2,3-c]pyridin-1-yl)-amide,
4-Methyl-2-thiazol-2-yl-pyrimidine-5-carboxylic acid (3-difluoromethyl-pyrrolo[2,3-c]pyridin-1-yl)-amide,
4-Methyl-2-thiazol-2-yl-pyrimidine-5-carboxylic acid (3-trifluoromethyl-pyrrolo[2,3-c]pyridin-1-yl)-amide,
4-Methyl-2-thiazol-2-yl-pyrimidine-5-carboxylic acid (3-methyl-pyrrolo[3,2-c]pyridin-1-yl)-amide,
4-Methyl-2-thiazol-2-yl-pyrimidine-5-carboxylic acid pyrrolo[3,2-c]pyridin-1-ylamide,
4-Methyl-2-thiazol-2-yl-pyrimidine-5-carboxylic acid (3-isopropyl-pyrrolo[3,2-c]pyridin-1-yl)-amide,
4-Methyl-2-thiazol-2-yl-pyrimidine-5-carboxylic acid (3-difluoromethyl-pyrrolo[3,2-c]pyridin-1-yl)-amide,
4-Methyl-2-thiazol-2-yl-pyrimidine-5-carboxylic acid (3-trifluoromethyl-pyrrolo[3,2-c]pyridin-1-yl)-amide,
4-Methyl-2-(4-chloro-thiazol-2-yl)-pyrimidine-5-carboxylic acid pyrrolo[2,3-b]pyridin-1-ylamide,
4-Methyl-2-(4-chloro-thiazol-2-yl)-pyrimidine-5-carboxylic acid (3-methyl-pyrrolo[2,3-b]pyridin-1-yl)-amide,
4-Methyl-2-(4-chloro-thiazol-2-yl)-pyrimidine-5-carboxylic acid (3-isopropyl-pyrrolo[2,3-b]pyridin-1-yl)-amide,
4-Methyl-2-(4-chloro-thiazol-2-yl)-pyrimidine-5-carboxylic acid (3-difluoromethyl-pyrrolo[2,3-b]pyridin-1-yl)-amide,
4-Methyl-2-(4-chloro-thiazol-2-yl)-pyrimidine-5-carboxylic acid (3-trifluoromethyl-pyrrolo[2,3-b]pyridin-1-yl)-amide,
4-Methyl-2-(4-chloro-thiazol-2-yl)-pyrimidine-5-carboxylic acid (3-methyl-pyrrolo[2,3-c]pyridin-1-yl)-amide,
4-Methyl-2-(4-chloro-thiazol-2-yl)-pyrimidine-5-carboxylic acid pyrrolo[2,3-c]pyridin-1-ylamide,
4-Methyl-2-(4-chloro-thiazol-2-yl)-pyrimidine-5-carboxylic acid (3-isopropyl-pyrrolo[2,3-c]pyridin-1-yl)-amide,
4-Methyl-2-(4-chloro-thiazol-2-yl)-pyrimidine-5-carboxylic acid (3-difluoromethyl-pyrrolo[2,3-c]pyridin-1-yl)-amide,
4-Methyl-2-(4-chloro-thiazol-2-yl)-pyrimidine-5-carboxylic acid (3-trifluoromethyl-pyrrolo[2,3-c]pyridin-1-yl)-amide,
4-Methyl-2-(4-chloro-thiazol-2-yl)-pyrimidine-5-carboxylic acid (3-methyl-pyrrolo[3,2-c]pyridin-1-yl)-amide,
4-Methyl-2-(4-chloro-thiazol-2-yl)-pyrimidine-5-carboxylic acid pyrrolo[3,2-c]pyridin-1-ylamide,
4-Methyl-2-(4-chloro-thiazol-2-yl)-pyrimidine-5-carboxylic acid (3-isopropyl-pyrrolo[3,2-c]pyridin-1-yl)-amide,
4-Methyl-2-(4-chloro-thiazol-2-yl)-pyrimidine-5-carboxylic acid (3-difluoromethyl-pyrrolo[3,2-c]pyridin-1-yl)-amide,
4-Methyl-2-(4-methyl-thiazol-2-yl)-pyrimidine-5-carboxylic acid (3-trifluoromethyl-pyrrolo[3,2-c]pyridin-1-yl)-amide,
2-(4-Chloro-thiazol-2-yl)-4-methyl-pyrimidine-5-carboxylic acid (5-fluoro-3-methyl-indol-1-yl)-amide,
2-(4-Methyl-thiazol-2-yl)-4-methyl-pyrimidine-5-carboxylic acid (5-fluoro-3-methyl-indol-1-yl)-amide,
2-(3-Fluoro-phenyl)-4-methyl-pyrimidine-5-carboxylic acid (2-methyl-3-oxo-2,3-dihydro-indazol-1-yl)amide,
2-(4-Chloro-thiazol-2-yl)-4-methyl-pyrimidine-5-carboxylic acid (5-fluoro-indol-1-yl)amide)amide,
6-(4-Chloro-thiazol-2-yl)-2-methyl-N-pyrrolo[2,3-c]pyridin-1-yl-nicotinamide,
2-(3-Fluoro-phenyl)-4-methyl-pyrimidine-5-carboxylic acid (5-methyl-4-oxo-4,5-dihydro-pyrrolo[3,2-c]pyridin-1-yl)amide,
4-Methyl-2-(4-methyl-thiazol-2-yl)-pyrimidine-5-carboxylic acid (5-trifluoromethyl-pyrrolo[3,2-b]pyridin-1-yl)-amide,
4-Methyl-2-(4-methyl-thiazol-2-yl)-pyrimidine-5-carboxylic acid (5-difluoromethyl-pyrrolo[3,2-b]pyridin-1-yl)-amide,
4-Methyl-2-(4-methyl-thiazol-2-yl)-pyrimidine-5-carboxylic acid (3-trifluoromethyl-pyrrolo[3,2-b]pyridin-1-yl)-amide,
4-Methyl-2-(4-methyl-thiazol-2-yl)-pyrimidine-5-carboxylic acid (3-difluoromethyl-pyrrolo[3,2-b]pyridin-1-yl)-amide,
4-Methyl-2-(4-methyl-thiazol-2-yl)-pyrimidine-5-carboxylic acid [3-(2,2,2-trifluoro-ethyl)-pyrrolo[3,2-b]pyridin-1-yl]-amide,
4-Methyl-2-(4-methyl-thiazol-2-yl)-pyrimidine-5-carboxylic acid [3-(2,2-difluoro-ethyl)-pyrrolo[3,2-b]pyridin-1-yl]-amide,
4-Methyl-2-(4-methyl-thiazol-2-yl)-pyrimidine-5-carboxylic acid [3-(2,2,2-trifluoro-ethyl)-pyrrolo[3,2-c]pyridin-1-yl]-amide,
4-Methyl-2-(4-methyl-thiazol-2-yl)-pyrimidine-5-carboxylic acid [3-(2,2-difluoro-ethyl)-pyrrolo[3,2-c]pyridin-1-yl]-amide,
4-Methyl-2-(4-methyl-thiazol-2-yl)-pyrimidine-5-carboxylic acid [3-(2,2,2-trifluoro-ethyl)-pyrrolo[2,3-c]pyridin-1-yl]-amide,
4-Methyl-2-(4-methyl-thiazol-2-yl)-pyrimidine-5-carboxylic acid [3-(2,2-difluoro-ethyl)-pyrrolo[2,3-c]pyridin-1-yl]-amide,
4-Methyl-2-(4-methyl-thiazol-2-yl)-pyrimidine-5-carboxylic acid [3-(2,2,2-trifluoro-ethyl)-pyrrolo[2,3-b]pyridin-1-yl]-amide,
4-Methyl-2-(4-methyl-thiazol-2-yl)-pyrimidine-5-carboxylic acid [3-(2,2-difluoro-ethyl)-pyrrolo[2,3-b]pyridin-1-yl]-amide,
4-Methyl-2-thiazol-2-yl-pyrimidine-5-carboxylic acid (5-trifluoromethyl-pyrrolo[3,2-b]pyridin-1-yl)-amide, 4-Methyl-2-thiazol-2-yl-pyrimidine-5-carboxylic acid (5-difluoromethyl-pyrrolo[3,2-b]pyridin-1-yl)-amide,
4-Methyl-2-thiazol-2-yl-pyrimidine-5-carboxylic acid (3-trifluoromethyl-pyrrolo[3,2-b]pyridin-1-yl)-amide,
4-Methyl-2-thiazol-2-yl-pyrimidine-5-carboxylic acid (3-difluoromethyl-pyrrolo[3,2-b]pyridin-1-yl)-amide,
4-Methyl-2-thiazol-2-yl-pyrimidine-5-carboxylic acid [3-(2,2,2-trifluoro-ethyl)-pyrrolo[3,2-b]pyridin-1-yl]-amide,
4-Methyl-2-thiazol-2-yl-pyrimidine-5-carboxylic acid [3-(2,2-difluoro-ethyl)-pyrrolo[3,2-b]pyridin-1-yl]-amide,
4-Methyl-2-thiazol-2-yl-pyrimidine-5-carboxylic acid [3-(2,2,2-trifluoro-ethyl)-pyrrolo[3,2-c]pyridin-1-yl]-amide,
4-Methyl-2-thiazol-2-yl-pyrimidine-5-carboxylic acid [3-(2,2-difluoro-ethyl)-pyrrolo[3,2-c]pyridin-1-yl]-amide,
4-Methyl-2-thiazol-2-yl-pyrimidine-5-carboxylic acid [3-(2,2,2-trifluoro-ethyl)-pyrrolo[2,3-c]pyridin-1-yl]-amide,
4-Methyl-2-thiazol-2-yl-pyrimidine-5-carboxylic acid [3-(2,2-difluoro-ethyl)-pyrrolo[2,3-c]pyridin-1-yl]-amide,
4-Methyl-2-thiazol-2-yl-pyrimidine-5-carboxylic acid [3-(2,2,2-trifluoro-ethyl)-pyrrolo[2,3-b]pyridin-1-yl]-amide,
4-Methyl-2-thiazol-2-yl-pyrimidine-5-carboxylic acid [3-(2,2-difluoro-ethyl)-pyrrolo[2,3-b]pyridin-1-yl]-amide,
2-(4-Chloro-thiazol-2-yl)-4-methyl-pyrimidine-5-carboxylic acid (5-trifluoromethyl-pyrrolo[3,2-b]pyridin-1-yl)-amide,
2-(4-Chloro-thiazol-2-yl)-4-methyl-pyrimidine-5-carboxylic acid (5-trifluoromethyl-pyrrolo[3,2-b]pyridin-1-yl)-amide,
2-(4-Chloro-thiazol-2-yl)-4-methyl-pyrimidine-5-carboxylic acid (3-trifluoromethyl-pyrrolo[3,2-b]pyridin-1-yl)-amide,
4-Methyl-2-(4-methyl-thiazol-2-yl)-pyrimidine-5-carboxylic acid (3-difluoromethyl-pyrrolo[3,2-b]pyridin-1-yl)-amide,
2-(4-Chloro-thiazol-2-yl)-4-methyl-pyrimidine-5-carboxylic acid [3-(2,2,2-trifluoro-ethyl)-pyrrolo[3,2-b]pyridin-1-yl]-amide,
2-(4-Chloro-thiazol-2-yl)-4-methyl-pyrimidine-5-carboxylic acid [3-(2,2-difluoro-ethyl)-pyrrolo[3,2-b]pyridin-1-yl]-amide,
2-(4-Chloro-thiazol-2-yl)-4-methyl-pyrimidine-5-carboxylic acid [3-(2,2,2-trifluoro-ethyl)-pyrrolo[3,2-c]pyridin-1-yl]-amide,
2-(4-Chloro-thiazol-2-yl)-4-methyl-pyrimidine-5-carboxylic acid [3-(2,2-difluoro-ethyl)-pyrrolo[3,2-c]pyridin-1-yl]-amide,
2-(4-Chloro-thiazol-2-yl)-4-methyl-pyrimidine-5-carboxylic acid [3-(2,2,2-trifluoro-ethyl)-pyrrolo[2,3-c]pyridin-1-yl]-amide,
2-(4-Chloro-thiazol-2-yl)-4-methyl-pyrimidine-5-carboxylic acid [3-(2,2-difluoro-ethyl)-pyrrolo[2,3-c]pyridin-1-yl]-amide,
2-(4-Chloro-thiazol-2-yl)-4-methyl-pyrimidine-5-carboxylic acid [3-(2,2,2-trifluoro-ethyl)-pyrrolo[2,3-b]pyridin-1-yl]-amide,
2-(4-Chloro-thiazol-2-yl)-4-methyl-pyrimidine-5-carboxylic acid [3-(2,2-difluoro-ethyl)-pyrrolo[2,3-b]pyridin-1-yl]-amide,
4-Methyl-[2,2']bipyrimidinyl-5-carboxylic acid (5-trifluoromethyl-pyrrolo[3,2-b]pyridin-1-yl)-amide,
4-Methyl-[2,2']bipyrimidinyl-5-carboxylic acid (5-difluoromethyl-pyrrolo[3,2-b]pyridin-1-yl)-amide,
4-Methyl-[2,2']bipyrimidinyl-5-carboxylic acid (3-trifluoromethyl-pyrrolo[3,2-b]pyridin-1-yl)-amide,
4-Methyl-[2,2']bipyrimidinyl-5-carboxylic acid (3-difluoromethyl-pyrrolo[3,2-b]pyridin-1-yl)-amide,
4-Methyl-[2,2']bipyrimidinyl-5-carboxylic acid [3-(2,2,2-trifluoro-ethyl)-pyrrolo[3,2-b]pyridin-1-yl]-amide,
4-Methyl-[2,2']bipyrimidinyl-5-carboxylic acid [3-(2,2-difluoro-ethyl)-pyrrolo[3,2-b]pyridin-1-yl]-amide,
4-Methyl-[2,2']bipyrimidinyl-5-carboxylic acid (3-trifluoromethyl-pyrrolo[3,2-c]pyridin-1-yl)-amide,
4-Methyl-[2,2']bipyrimidinyl-5-carboxylic acid (3-difluoromethyl-pyrrolo[3,2-c]pyridin-1-yl)-amide,
4-Methyl-[2,2']bipyrimidinyl-5-carboxylic acid [3-(2,2,2-trifluoro-ethyl)-pyrrolo[3,2-c]pyridin-1-yl]-amide,
4-Methyl-[2,2']bipyrimidinyl-5-carboxylic acid [3-2,2-difluoro-ethyl)-pyrrolo[3,2-c]pyridin-1-yl]-amide,
4-Methyl-[2,2']bipyrimidinyl-5-carboxylic acid (3-trifluoromethyl-pyrrolo[2,3-c]pyridin-1-yl)-amide,
4-Methyl-[2,2']bipyrimidinyl-5-carboxylic acid (3-difluoromethyl-pyrrolo[2,3-c]pyridin-1-yl)-amide,
4-Methyl-[2,2']bipyrimidinyl-5-carboxylic acid [3-(2,2,2-trifluoro-ethyl)-pyrrolo[2,3-c]pyridin-1-yl]-amide,
4-Methyl-[2,2']bipyrimidinyl-5-carboxylic acid [3-(2,2-difluoro-ethyl)-pyrrolo[2,3-c]pyridin-1-yl]-amide,
4-Methyl-[2,2']bipyrimidinyl-5-carboxylic acid (3-trifluoromethyl-pyrrolo[2,3-b]pyridin-1-yl)-amide,
4-Methyl-[2,2']bipyrimidinyl-5-carboxylic acid (3-difluoromethyl-pyrrolo[2,3-b]pyridin-1-yl)-amide,
4-Methyl-[2,2']bipyrimidinyl-5-carboxylic acid [3-(2,2,2-trifluoro-ethyl)-pyrrolo[2,3-b]pyridin-1-yl]-amide,
4-Methyl-[2,2']bipyrimidinyl-5-carboxylic acid [3-(2,2-difluoro-ethyl)-pyrrolo[2,3-b]pyridin-1-yl]-amide,
2-(3-Fluoro-phenyl)-4-methyl-pyrimidine-5-carboxylic acid (5-trifluoro methyl-pyrrolo[3,2-b]pyridin-1-yl)-amide,
2-(3-Fluoro-phenyl)-4-methyl-pyrimidine-5-carboxylic acid (5-difluoromethyl-pyrrolo[3,2-b]pyridin-1-yl)-amide,
2-(3-Fluoro-phenyl)-4-methyl-pyrimidine-5-carboxylic acid (3-trifluoro methyl-pyrrolo[3,2-b]pyridin-1-yl)-amide,
2-(3-Fluoro-phenyl)-4-methyl-pyrimidine-5-carboxylic acid (3-trifluoro methyl-pyrrolo[3,2-c]pyridin-1-yl)-amide,
2-(3-Fluoro-phenyl)-4-methyl-pyrimidine-5-carboxylic acid (3-trifluoro methyl-pyrrolo[2,3-c]pyridin-1-yl)-amide,
2-(3-Fluoro-phenyl)-4-methyl-pyrimidine-5-carboxylic acid (3-trifluoromethyl-pyrrolo[2,3-b]pyridin-1-yl)-amide,
2-(3-Fluoro-phenyl)-4-methyl-pyrimidine-5-carboxylic acid [3-(2,2-difluoro-ethyl)-pyrrolo[3,2-b]pyridin-1-yl]-amide,
2-(3-Fluoro-phenyl)-4-methyl-pyrimidine-5-carboxylic acid [3-(2,2,2-trifluoro-ethyl)-pyrrolo[3,2-b]pyridin-1-yl]-amide,
2-(3-Fluoro-phenyl)-4-methyl-pyrimidine-5-carboxylic acid [3-(2,2,2-trifluoro-ethyl)-pyrrolo[3,2-c]pyridin-1-yl]-amide,
2-(3-Fluoro-phenyl)-4-methyl-pyrimidine-5-carboxylic acid [3-(2,2,2-trifluoro-ethyl)-pyrrolo[2,3-c]pyridin-1-yl]-amide,
4-Methyl-2-pyridin-2-yl-pyrimidine-5-carboxylic acid (3-difluoromethyl-indol-1-yl)-amide,
2-(4-Chloro-thiazol-2-yl)-4-methyl-pyrimidine-5-carboxylic acid (3-difluoromethyl-indol-1-yl)-amide, or
4-Methyl-2-thiazol-2-yl-pyrimidine-5-carboxylic acid (3-difluoromethyl-indol-1-yl)-amide, or a hydrate, solvate or N-oxide thereof, or a pharmaceutically acceptable salt thereof.

It is to be understood that this invention covers all appropriate combinations of the particular embodiments referred thereto.

The present invention also includes within its scope a pharmaceutical composition comprising a pharmaceutically effective amount of a compound of the invention, in admixture with a pharmaceutically acceptable carrier.

Compounds of the present invention are PGDS inhibitors and thus, are useful for treating allergic and/or inflammatory disorders, particularly disorders such as allergic rhinitis, asthma and/or chronic obstructive pulmonary disease (COPD). Accordingly, another invention herein is directed to a method of treating a patient suffering from allergic rhinitis, asthma, and/or chronic obstructive pulmonary disease (COPD) comprising administering to the patient a pharmaceutically effective amount of compound of formula (I), or a hydrate, solvate or N-oxide thereof, or a pharmaceutically acceptable salt thereof.

References herein directed to treating should be understood to include prophylactic therapy to inhibit PGDS, as well as to treat an established acute or chronic or physiological conditions associated with PGDS to essentially cure a patient suffering therefrom, or ameliorate the physiological conditions associated therewith. Physiological conditions discussed herein include some, but not all, of the possible clinical situations where an anti-allergic rhinitis and/or asthma treatment is warranted. Those experienced in this field are well aware of the circumstances requiring treatment.

In practice, the compound of the present invention may be administered in pharmaceutically acceptable dosage form to humans and other mammals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the particular route may vary with for example the physiological condition of the recipient.

"Pharmaceutically acceptable dosage forms" refers to dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

A particular aspect of the invention provides for the compound of the invention to be administered in the form of a pharmaceutical composition.

Pharmaceutically acceptable carriers include at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

Exemplary suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Exemplary antibacterial and antifungal agents for the prevention of the action of microorganisms include parabens, chlorobutanol, phenol, sorbic acid, and the like.

Exemplary isotonic agents include sugars, sodium chloride, and the like.

Exemplary adsorption delaying agents to prolong absorption include aluminum monostearate and gelatin.

Exemplary adsorption promoting agents to enhance absorption include dimethyl sulfoxide and related analogs.

Exemplary diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethylformamide, Tween® 60, Span® 60, cetostearyl alcohol, myristyl alcohol, glyceryl mono-stearate and sodium lauryl sulfate, fatty acid esters of sorbitan, vegetable oils (such as cottonseed oil, groundnut oil, olive oil, castor oil and sesame oil) and injectable organic esters such as ethyl oleate, and the like, or suitable mixtures of these substances.

Exemplary excipients include lactose, milk sugar, sodium citrate, calcium carbonate and dicalcium phosphate.

Exemplary disintegrating agents include starch, alginic acids and certain complex silicates. Exemplary lubricants include magnesium stearate, sodium lauryl sulfate, talc, as well as high molecular weight polyethylene glycols.

The choice of pharmaceutical acceptable carrier is generally determined in accordance with the chemical properties of the active compound such as solubility, the particular mode of administration and the provisions to be observed in pharmaceutical practice.

Pharmaceutical compositions of the present invention suitable for oral administration may be presented as discrete units such as a solid dosage form, such as capsules, cachets or tablets each containing a predetermined amount of the active ingredient, or as a powder or granules; as a liquid dosage form such as a solution or a suspension in an aqueous liquid or a non-aqueous liquid, or as an oil-in-water liquid emulsion or a water-in-oil liquid emulsion. The active ingredient may also be presented as a bolus, electuary or paste.

"Solid dosage form" means the dosage form of the compound of the invention is solid form, for example capsules, tablets, pills, powders, dragees or granules. In such solid dosage forms, the compound of the invention is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound of the invention in a certain part of the intestinal tract in a delayed manner.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used. A mixture of the powdered compounds moistened with an inert liquid diluent may be molded in a suitable machine to make molded tablets. The tablets may optionally be coated or scored and may be formulated so as to provide slow or controlled release of the active ingredient therein.

Solid compositions may also be employed as fillers in soft and hard-filled gelatin capsules using such excipients as lactose or milk sugar as well as high molecular weight polyethylene glycols, and the like.

If desired, and for more effective distribution, the compound can be microencapsulated in, or attached to, a slow release or targeted delivery systems such as a biocompatible, biodegradable polymer matrices (e.g., poly(d,l-lactide co-glycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria-retaining filter, or by incorporating sterilizing agents in the form of sterile solid compositions that can be dissolved in sterile water, or some other sterile injectable medium immediately before use.

"Liquid dosage form" means the dose of the active compound to be administered to the patient is in liquid form, for example, pharmaceutically acceptable emulsions, solutions, suspensions, syrups and elixirs. In addition to the active compound, the liquid dosage forms may contain inert diluents commonly used in the art, such solvents, solubilizing agents and emulsifiers.

When aqueous suspensions are used they can contain emulsifying agents or agents which facilitate suspension.

Pharmaceutical compositions suitable for topical administration mean formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The oily phase of the emulsion pharmaceutical composition may be constituted from known ingredients, in a known manner. While the phase may comprise merely an emulsifier (otherwise known as an emulgent), it desirably comprises a mixture of at least one emulsifier with a fat or an oil or with both a fat and an oil. In a particular embodiment, a hydrophilic emulsifier is included together with a lipophilic emulsifier that acts as a stabilizer. Together, the emulsifier(s) with, or without, stabilizer(s) make up the emulsifying wax, and together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as, propylene glycol, butane 1,3-diol, mannitol, sorbitol, glycerol and polyethylene glycol (including PEG 400) and mixtures thereof. The topical formulations may desirably include a compound that enhances absorption, or penetration of the active ingredient through the skin, or other affected areas.

The choice of suitable oils or fats for a composition is based on achieving the desired properties. Thus a cream should particularly be a non-greasy, non-staining and washable product with suitable consistency to avoid leakage from tubes or other containers. Straight or branched chain, mono- or dibasic alkyl esters such as di-isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Pharmaceutical compositions suitable for rectal or vaginal administrations mean formulations that are in a form suitable to be administered rectally or vaginally to a patient and containing at least one compound of the invention. Suppositories are a particular form for such formulations that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Pharmaceutical composition administered by injection may be by transmuscular, intravenous, intraperitoneal, and/or subcutaneous injection. The compositions of the present invention are formulated in liquid solutions, in particular in physiologically compatible buffers such as Hank's solution or Ringer's solution. In addition, the compositions may be formulated in solid form and redissolved or suspended immediately prior to use. Lyophilized forms are also included. The formulations are sterile and include emulsions, suspensions, aqueous and non-aqueous injection solutions, which may contain suspending agents and thickening agents and antioxidants, buffers, bacteriostats and solutes which render the formulation isotonic, and have a suitably adjusted pH, with the blood of the intended recipient.

Pharmaceutical composition of the present invention suitable for nasal or inhalational administration means compositions that are in a form suitable to be administered nasally or by inhalation to a patient. The composition may contain a carrier, in a powder form, having a particle size for example in the range 1 to 500 microns (including particle sizes in a range between 20 and 500 microns in increments of 5 microns such as 30 microns, 35 microns, etc.). Suitable compositions wherein the carrier is a liquid, for administration as for example a nasal spray or as nasal drops, include aqueous or oily solutions of the active ingredient. Compositions suitable for aerosol administration may be prepared according to conventional methods and may be delivered with other therapeutic agents. Inhalational therapy is readily administered by metered dose inhalers or any suitable dry powder inhaler, such as the Eclipse, Spinhaler®, or Ultrahaler® as described in patent application WO2004/026380, and U.S. Pat. No. 5,176,132.

Actual dosage levels of active ingredient(s) in the compositions of the invention may be varied so as to obtain an amount of active ingredient(s) that is (are) effective to obtain a desired therapeutic response for a particular composition and method of administration for a patient. A selected dosage level for any particular patient therefore depends upon a variety of factors including the desired therapeutic effect, on the route of administration, on the desired duration of treatment, the etiology and severity of the disease, the patient's condition, weight, sex, diet and age, the type and potency of each active ingredient, rates of absorption, metabolism and/or excretion and other factors.

Total daily dose of the compound of this invention administered to a patient in single or divided doses may be in amounts, for example, of from about 0.001 to about 100 mg/kg body weight daily and particularly 0.01 to 10 mg/kg/day. For example, in an adult, the doses are generally from about 0.01 to about 100, particularly about 0.01 to about 10, mg/kg body weight per day by inhalation, from about 0.01 to about 100, particularly 0.1 to 70, more especially 0.5 to 10, mg/kg body weight per day by oral administration, and from about 0.01 to about 50, particularly 0.01 to 10, mg/kg body weight per day by intravenous administration. The percentage of active ingredient in a composition may be varied, though it should constitute a proportion such that a suitable dosage shall be obtained. Dosage unit compositions may contain such amounts or such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much lower maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day.

The formulations can be prepared in unit dosage form by any of the methods well known in the art of pharmacy. Such methods include the step of bringing into association the pharmaceutically active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds of the invention may be prepared by the application or adaptation of known methods, by which is a meant method used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts, *Protecting Groups in Organic Synthesis*, 3rd edition, John Wiley & Sons, Inc., 1999.

A compound of formula (I), wherein $R^2$ is hydrogen, $L^1$ is a bond, —NH—C(=O)— or $(C_1$-$C_2)$-alkylene optionally substituted one or more times by halo, and $R^1$, $R^3$ and $R^4$ are as defined herein, may be prepared, as shown in Scheme I below, by (i) reacting a corresponding amidine compound of formula (I), with a reagent of formula (2) to provide a compound of formula (3), (ii) hydrolyzing the compound of formula (3) to provide a compound of formula (4), and (iii) coupling the compound of (4) with a corresponding compound of formula (5).

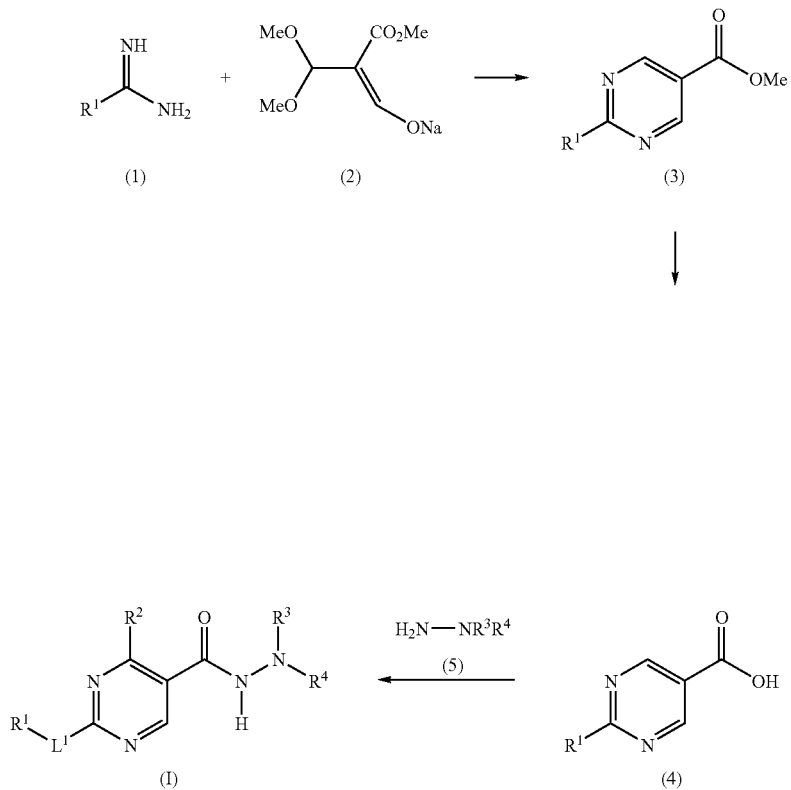

$R^2$ = hydrogen, and $L^1$ is a bond, —NH—C(=O)— or $(C_1$-$C_2)$-alkylene optionally substituted one or more times by halo The first step reaction may conveniently be carried out, for example, at a temperature about 100° C., in an inert solvent, such as DMF. The second step reaction may conveniently be carried out, for example, at room temperature, in the presence of an inorganic base, such as LiOH, KOH or NaOH, in a solvent, such as THF, MeOH, water, or a mixture thereof. The third step reaction may conveniently be carried out, for example, at about a temperature about room temperature to 100° C., in the presence of a coupling agent, such as HCTU, HOTT, PyBrOP, DMTMM, or HATU with HOAt, and a base, such as DIPEA or Et$_3$N, in an inert solvent, such as DMF. The third step reaction may conveniently be carried out, for example, at about a temperature about 0° C. to room temperature, by first reacting the compound of formula (4) with oxalyl chloride, and then adding the compound of formula (5) and a base such as DIPEA, Et$_3$N, K$_2$CO$_3$ or Na$_2$CO$_3$, in an inert solvent, such as DCM or DMF.

A compound of formula (I), wherein R$^2$ is (C$_1$-C$_4$)-alkyl optionally substituted one or more times by halo, L$^1$ is a bond, —NH—C(=O)— or (C$_1$-C$_2$)-alkylene optionally substituted one or more times by halo, and R$^1$, R$^3$ and R$^4$ are as defined herein, may also be prepared, as shown in Scheme II below, by (i) reacting a corresponding amidine compound of formula (1), with a reagent of formula (6) to provide a compound of formula (7), (ii) hydrolyzing the compound of formula (7) to provide a compound of formula (8), and (iii) coupling the compound of formula (8) with a corresponding compound of formula (5).

The first step reaction may conveniently be carried out, for example, at a temperature about 100° C., in the presence of sodium metal, in a solvent, such as EtOH. The second step reaction may conveniently be carried out, for example, at room temperature, in the presence of an inorganic base, such as LiOH, KOH or NaOH, in a solvent, such as THF, MeOH, water, or a mixture thereof. The third step reaction may conveniently be carried out, for example, at about a temperature about room temperature to 100° C., in the presence of a coupling agent, such as HCTU, HOTT, PyBrOP, DMTMM, or HATU with HOAt, and a base, such as DIPEA or Et$_3$N, in an inert solvent, such as DMF. The third step reaction may conveniently be carried out, for example, at about a temperature about 0° C. to room temperature, by first reacting the compound of formula (8) with oxalyl chloride, and then adding the compound of formula (5) and a base such as DIPEA, Et$_3$N, K$_2$CO$_3$ or Na$_2$CO$_3$, in an inert solvent, such as DCM or DMF.

A compound of formula (I), wherein L$^1$ is —C(=O)—, and R$^1$, R$^2$, R$^3$ and R$^4$ are as defined herein, may be prepared, as shown in Scheme III below, by (1) reacting a corresponding compound of formula (9), with a Grignard reagent of formula R$^1$MgBr to provide a compound of formula (10), (2) converting the compound of formula (10) into a compound of formula (11), and (3) hydrolyzing the compound of formula (11) to provide a compound of formula (12), (4) hydrolyzing the compound of formula (12) to provide a compound of formula (13) and (5) coupling the compound of formula (13) with a corresponding compound of formula (5).

Scheme II

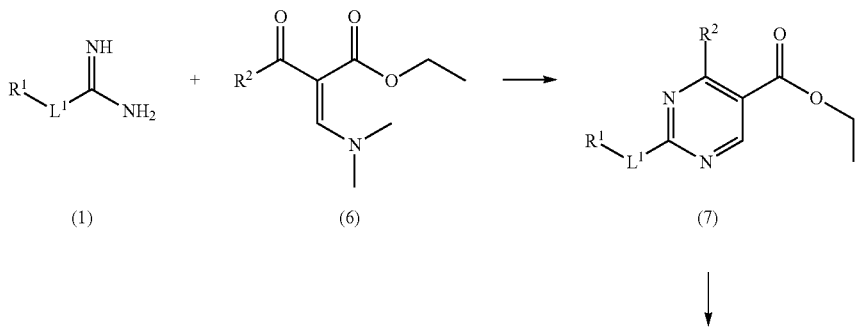

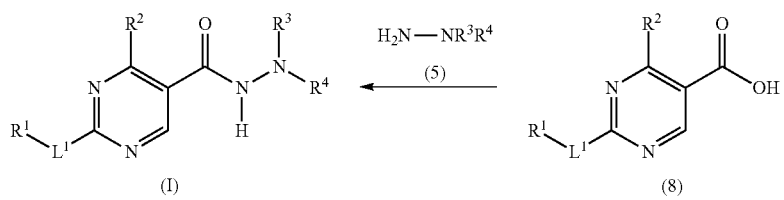

R$^2$ = (C$_1$-C$_4$)-alkyl optionally substituted one or more times by halo, and
L$^1$ is a bond, —NH—C(=O)— or (C$_1$-C$_2$)-alkylene optionally substituted one or more times by halo

Scheme III

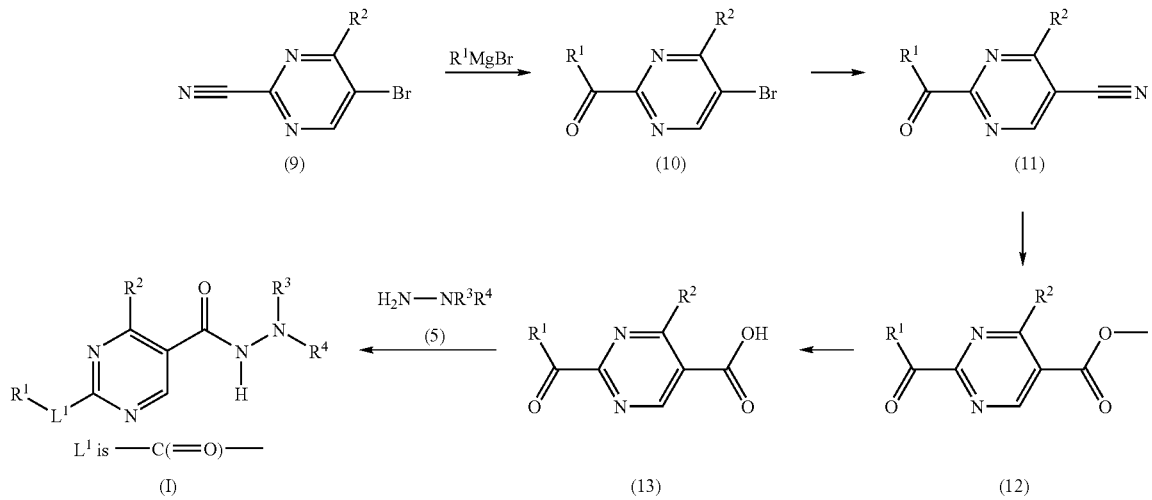

The first step reaction may conveniently be carried out, for example, at a temperature about room temperature to 50° C., in an inert solvent, such as Et₂O. The second step reaction may conveniently be carried out, for example, at a temperature about 150° C., in the presence of potassium hexacyanoferrate(II) trihydrate, palladium (II) acetate and a base such as Na₂CO₃ or K₂CO₃, in an inert solvent, such as dimethylacetamide or DMF. The third step reaction may conveniently be carried out, for example, at about a temperature about 0° C. to room temperature, in the presence of an inorganic base such as KOH, NaOH or LiOH, in a solvent, such as MeOH, or a mixture of MeOH and water. The fourth step reaction may conveniently be carried out, for example, at room temperature, in the presence of an inorganic base, such as LiOH, KOH or NaOH, in a solvent, such as THF, MeOH, water, or a mixture thereof. The fifth step reaction may conveniently be carried out, for example, at about a temperature about room temperature to 100° C., in the presence of a coupling agent, such as HCTU, HOTT, PyBrOP, DMTMM, or HATU with HOAt, and a base, such as DIPEA or Et₃N, in an inert solvent, such as DMF. The third step reaction may conveniently be carried out, for example, at about a temperature about 0° C. to room temperature, by first reacting the compound of formula (4) with oxalyl chloride, and then adding the compound of formula (5) and a base such as DIPEA, Et₃N, K₂CO₃ or Na₂CO₃, in an inert solvent, such as DCM or DMF.

A compound of formula (I), wherein $L^1$ is —O—, and $R^1$, $R^2$, $R^3$ and $R^4$ are as defined herein, may be prepared, as shown in Scheme IV below, by (i) oxidizing a compound of formula (14) to provide a compound of formula (15), (ii) reacting the compound of formula (15) with a corresponding compound having formula $R^1$ONa to provide a compound of formula (16), (iii) hydrolyzing the compound of formula (16) to provide a compound of formula (17), and (iv) coupling the compound of formula (17) with a corresponding compound of formula (5).

Scheme IV

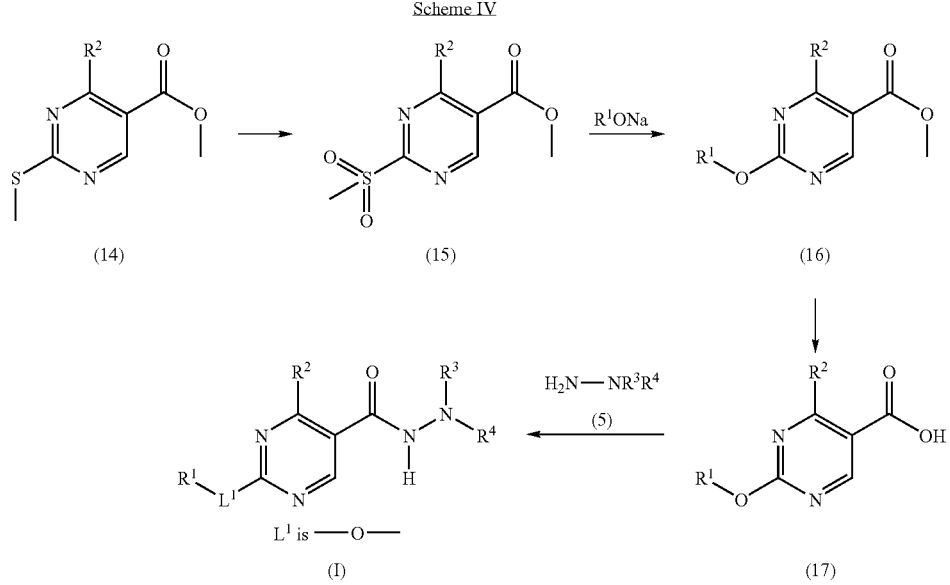

The first step oxidation reaction may conveniently be carried out, for example, at room temperature, in the presence of MCPBA and $Na_2S_2O_3$, in an inert solvent, such as DCM. The second step reaction may conveniently be carried out, for example, in a microwave heated at a temperature about 100° C., in an inert solvent, such as NMP. The third step reaction may conveniently be carried out, for example, at about a temperature about 0° C. to room temperature, in the presence of an inorganic base such as KOH, NaOH or LiOH, in a solvent, such as THF, MeOH, or a mixture thereof. The fourth step reaction may conveniently be carried out, for example, at about a temperature about room temperature to 100° C., in the presence of a coupling agent, such as HCTU, HOTT, PyBrOP, DMTMM, or HATU with HOAt, and a base, such as DIPEA or $Et_3N$, in an inert solvent, such as DMF. The third step reaction may conveniently be carried out, for example, at about a temperature about 0° C. to room temperature, by first reacting the compound of formula (17) with oxalyl chloride, and then adding the compound of formula (5) and a base such as DIPEA, $Et_3N$, $K_2CO_3$ or $Na_2CO_3$, in an inert solvent, such as DCM or DMF.

Compounds of the invention may also be prepared by interconversion of other compounds of the invention.

It will be appreciated that compounds of the present invention may contain asymmetric centers. These asymmetric centers may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods, for example chromatographic techniques and recrystallization techniques, or they are separately prepared from the appropriate isomers of their intermediates.

The compounds of the invention, their methods or preparation and their biological activity will appear more clearly from the examination of the following examples that are presented as an illustration only and are not to be considered as limiting the invention in its scope. Compounds of the invention are identified, for example, by the following analytical methods.

Mass Spectra (MS) are recorded using a Micromass LCT mass spectrometer. The method is positive electrospray ionization, scanning mass m/z from 100 to 1000.

300 MHz $^1$H nuclear magnetic resonance spectra ($^1$H NMR) are recorded at ambient temperature using a Varian Mercury (300 MHz) spectrometer with an ASW 5 mm probe. In the $^1$H NMR chemical shifts (δ) are indicated in parts per million (ppm) with reference to tetramethylsilane (TMS) as the internal standard.

As used in the examples and preparations that follow, as well as the rest of the application, the terms used therein shall have the meanings indicated: "kg"=kilograms, "g"=grams, "mg"=milligrams, "μg"=micrograms, "mol"=moles, "mmol"=millimoles, "M"=molar, "mM"=millimolar, "μM"=micromolar, "nM"=nanomolar, "L"=liters, "mL" or "ml"=milliliters, "μL"=microliters, "OC"=degrees Celsius, "mp" or "m.p."=melting point, "bp" or "b.p."=boiling point, "mm of Hg"=pressure in millimeters of mercury, "cm"=centimeters, "nm"=nanometers, "abs."=absolute, "conc."=concentrated, "c"=concentration in g/mL, "rt"=room temperature, "TLC"=thin layer chromatography, "HPLC"=high performance liquid chromatography, "i.p."=intraperitoneally, "i.v."=intravenously, "s"=singlet, "d"=doublet; "t"=triplet; "q"=quartet; "m"=multiplet, "dd"=doublet of doublets; "br"=broad, "LC"=liquid chromatograph, "MS"=mass spectrograph, "ESI/MS"=electrospray ionization/mass spectrograph, "RT"=retention time, "M"=molecular ion, "PSI"=pounds per square inch, "DMSO"=dimethyl sulfoxide, "DMF"=N,N-dimethylformamide, "DCM"=dichloromethane, "HCl"=hydrochloric acid, "SPA"=Scintillation Proximity Assay, "EtOAc"=ethyl acetate, "PBS"=Phosphate Buffered Saline, "IUPAC"=International Union of Pure and Applied Chemistry, "MHz"=megahertz, "MeOH"=methanol, "N"=normality, "THF"=tetrahydrofuran, "min"=minute(s), "$N_2$"=nitrogen gas, "MeCN" or "$CH_3CN$"=acetonitrile, "$Et_2O$"=ethyl ether, "TFA"=trifluoroacetic acid, "~"=approximately, "$MgSO_4$"=magnesium sulfate, "$Na_2SO_4$"=sodium sulfate, "$NaHCO_3$"=sodium bicarbonate, "$Na_2CO_3$"=sodium carbonate, "MCPBA"=3-Chloroperoxybenzoic acid, "NMP"=N-methylpyrrolidone, "PS-DCC"=polymer supported-dicyclohexylcarbodiimde, "LiOH"=Lithium hydroxide, "PS-trisamine"=polymer supported-trisamine, "PGH2"=prostaglandin H2, "PGD2"=prostaglandin D2; "PGE2"=prostaglandin E2, "hPGDS"=Hematopoietic PGD2 Synthase, "GSH"=glutathione (reduced), "EIA"=Enzyme immunoassay, "$KH_2PO_4$"=potassium phosphate, monobasic, "$K_2HPO_4$"=potassium phosphate, dibasic, "$FeCl_2$"=ferrous chloride, "MOX"=methoxyl amine; "EtOH"=ethanol, "DMSO"=dimethylsulfoxide, "$Ag_2O$"=silver(I) oxide, "HATU"=O-(7-azabenzotriazole-1-yl)-N,N,N',N'-tetramethyluronium hexafluorophosphate, "HOAt"=1-hydroxy-7-azabenzotriazole, "DIPEA"=N,N-diisopropylethylamine, "HOTT"=S-(1-Oxido-2-pyridyl)-N,N,N',N'-tetramethylthiuronium hexafluorophosphate, "HCTU"=N,N',N',N'-tetramethyl-O-(6-chloro-1H-benzotriazol-1-yl)uronium hexafluorophosphate., "PyBrOP"=bromo-tris-pyrrolidinophosphonium hexafluorophosphate, "LiAlH4"=lithium aluminum hydride, "PyAOP"=(7-azabenzotriazol-1-yloxy)-tripyrrolidinophosphonium hexafluorophosphate, "TBTU"=O-benzotriazol-1-yl-N,N,N,N,-tetramethyluronium tetrafluoroborate, "NaHMDS"=sodium bis(trimethylsilyl)amide, "NMP"=N-methyl-2-pyrrolidinone, "HOSA"=hydroxylamine-O-sulfonic acid, "DMTMM"=4-(4,6-dimethoxy-1,3,5-triazin-2-yl)-4-methylmorpholinium chloride, "$TMSN_3$"=trimethylsily azide, "TBAF"=tetrabutylammonium fluoride, "TFAA"=trifluoro acetic anhydride.

EXAMPLES

Example 1

2-Pyridin-3-yl-pyrimidine-5-carboxylic acid (5-fluoro-2-methyl-indol-1-yl)-amide

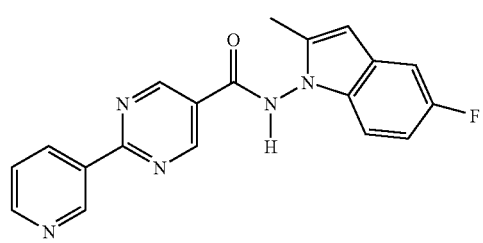

Step 1: A solution of potassium tert-butoxide (1.84 g, 16.43 mmol) and 5-fluoro-2-methylindole (1.21 g, 8.09 mmol) in DMF (20 mL) is stirred under $N_2$ at rt for 60 min. A solution of monochloroamine in ether (65 mL, 9.75 mmol) is added via an addition funnel over 10 min. The resulting mixture is stirred at 23° C. for 2 hours, and then concentrated in vacuo.

The residue is partitioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 10% EtOAc in heptane to afford 5-fluoro-2-methyl-indol-1-ylamine (290 mg, 22%) as a solid. MS: 165 (M+H); $^1$H NMR (300 MHz, CDCl$_3$): δ 7.24-7.19 (m, 1H), 7.12 (dd, 1H), 6.92 (dt, 1H), 6.12 (s, 1H), 4.23 (br s, 2 H), 2.39 (s, 3H).

Step 2: A 250 mL, three-neck, round-bottom flask equipped with a magnetic stirrer and a reflux condenser is purged with N$_2$. The flask is charged sequentially with methyl 3,3-dimethoxypropionate (5.22 g, 35.3 mmol), anhydrous 1,2-dimethoxyethane (25 mL), anhydrous methyl formate (5 mL), 60% sodium hydride (1.7 g, 42.5 mmol), and the mixture warmed to 40-50° C. until evolution of hydrogen gas stops. The reaction mixture is cooled in an ice/water bath and slowly allowed to reach room temperature overnight with stirring. Anhydrous ether (25 mL) is added, and the resulting suspension is filtered under N$_2$, washed with anhydrous ether (10 mL), and vacuum dried for 2 hours to yield sodium salt of 2-dimethoxymethyl-3-hydroxy-acrylicacid methyl ester (3.51 g, 50%) as a powder. $^1$H NMR (CD$_3$OD): δ 3.33 (s, 6H), 3.60 (s, 3H), 5.31 (s, 1H), 8.89 (s, 1H). (see: P. Zhichkin, D. J. Fairfax, S. A. Eisenbeis, Synthesis, 2002, 720-722.)

Step 3: To a solution of nicotinamidine hydrochloride (1 g, 6.35 mmol) in anhydrous DMF (12 mL) is added sodium salt of 2-dimethoxymethyl-3-hydroxy-acrylicacid methyl ester (1.46 g, 7.36 mmol) and the reaction mixture is heated at 100° C. under N$_2$ for 3 hours. After this time the reaction is cooled to room temperature and water (48 mL) is added. The precipitate is collected by filtration, washed with water and vacuum dried to afford 2-pyridin-3-yl-pyrimidine-5-carboxylic acid methyl ester (0.7 g, 51%). MS: 216 (M+H).

Step 4: A solution of 2-pyridin-3-yl-pyrimidine-5-carboxylic acid methyl ester (0.73 g, 3.32 mmol) and 1M aqueous LiOH (3.32 mL) in MeOH (5 mL) is stirred at rt overnight. The MeOH is removed in vacuo, and the aqueous solution is treated with 3 N aqueous HCl to adjust the pH ~2-3. The solid is filtered off and washed with water and dried in vacuum to yield 2-pyridin-3-yl-pyrimidine-5-carboxylic acid (0.2 g, 30%) as a solid. MS: 202 (M+H).

Step 5: A solution of 2-pyridin-3-yl-pyrimidine-5-carboxylic acid (506 mg, 2.13 mmol), HCTU (970 mg, 2.34 mmol), and DIPEA (1 mL, 5.72 mmol) in DMF (10 mL) is stirred at rt under N$_2$ for 10 min. 5-Fluoro-2-methyl-indol-1-ylamine (311 mg, 1.89 mmol) is added. The resulting mixture is stirred at 75° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 45% EtOAc in heptane to afford 2-pyridin-3-yl-pyrimidine-5-carboxylic acid (5-fluoro-2-methyl-indol-1-yl)-amide (300 mg, 46%) as a solid. MS: 348 (M+H). $^1$H NMR (300 MHz, DMSO-d$_6$): δ 12.02 (s, 1H), 9.60 (d, 1H), 9.49 (s, 2H), 8.82-8.76 (m, 2H), 7.64 (dd, 1H), 7.39 (dd, 1H), 7.29 (dd, 1H), 6.94 (dt, 1H), 6.35 (s, 1H), 2.33 (s, 3H).

Example 2

2-(3-Fluoro-phenyl)-4-methyl-pyrimidine-5-carboxylic acid (5-fluoro-2-methyl-indol-1-yl)amide

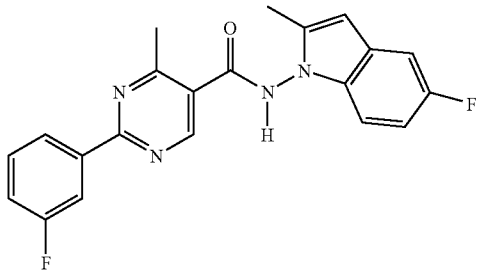

Step 1: Na$^0$ (0.66 g, 28.6 mmol) is added to anhydrous EtOH (100 mL) and stirred at rt for 15 min. 3-Fluorobenzamidine hydrochloride (4.87 g, 27.8 mmol) is added and the solution is stirred for 15 min. 2-Dimethylaminomethylene-3-oxo-butyric acid ethyl ester (5.3 g, 28.6 mmol,) is added and the reaction mixture is heated at reflux under N$_2$ for 1 hours. The reaction is cooled to rt and concentrated in vacuo. The residue is dissolved in EtOAc (300 mL), washed with brine (2×100 mL), dried (Na$_2$SO$_4$), filtered, and concentrated to afford 2-(3-fluoro-phenyl)-4-methyl-pyrimidine-5-carboxylic acid ethyl ester (6.8 g, 99%). MS: 261 (M+H); $^1$H NMR (300 MHz, CDCl$_3$): δ 1.43 (t, J=7.0 Hz, 3H), 2.92 (s, 3H), 4.42 (q, J=7.0 Hz, 2H), 7.24 (m, 1H), 7.45 (m, 1H), 8.27 (m, 1H), 8.37 (m, 1H), 9.21 (s, 1H).

Step 2: A solution of 2-(3-fluoro-phenyl)-4-methyl-pyrimidine-5-carboxylic acid ethyl ester (6.7 g, 27.2 mmol) and NaOH (2.1 g, 54.4 mmol) in a 1:1:1 solution of THF, MeOH and water (300 mL) is heated at reflux for 45 min. The THF/MeOH is evaporated, and the aqueous solution is treated with 3 N HCl to adjust the pH to between 2 and 3. The solid is filtered off, washed with water and dried in vacuo to yield 2-(3-fluoro-phenyl)-4-methyl-pyrimidine-5-carboxylic acid (5.4 g, 91%) as a solid. MS: 233 (M+H); $^1$H NMR (300 MHz, CD$_3$OD): δ 2.85 (s, 3H), 7.24 (m, 1H), 7.50 (m, 1H), 8.17 (m, 1H), 8.32 (m, 1H), 9.20 (s, 1H).

Step 3: A solution of 2-(3-fluoro-phenyl)-4-methyl-pyrimidine-5-carboxylic acid (340 mg, 1.46 mmol, prepared according to the general procedure described in Example 1, steps 3 and 4), HOAt (248 mg, 1.82 mmol), and HATU (645 mg, 1.70 mmol) in DMF (15 mL) is stirred at rt under N$_2$ for 20 min. 5-Fluoro-2-methyl-indol-1-ylamine (237 mg, 1.44 mmol) and DIPEA (380 μL, 2.18 mmol) are added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 20% EtOAc in heptane to afford 2-(3-fluoro-phenyl)-4-methyl-pyrimidine-5-carboxylic acid (5-fluoro-2-methyl-indol-1-yl)amide (300 mg, 55%) as a solid. MS: 379 (M+H). $^1$H NMR (300 MHz, CD$_3$OD): δ 9.14 (s, 1H), 8.38-8.20 (m, 3H), 7.56-7.52 (m, 1H), 7.30-7.27 (m, 2H), 7.19-7.16 (m, 1H), 6.96-6.90 (m, 1H), 6.32 (s, 1H), 2.83 (s, 3H), 2.42 (s, 3H).

Example 3

4-Methyl-2-pyridin-2-yl-pyrimidine-5-carboxylic acid (5-fluoro-3-methyl-indol-1-yl)amide

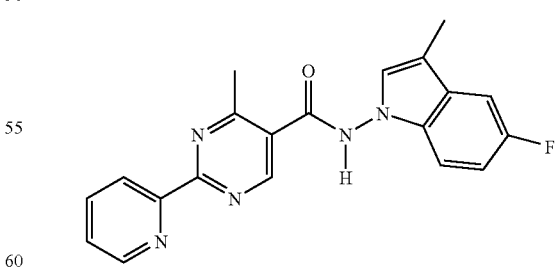

Step 1: A suspension of NaH (2.01 g, 50.3 mmol, 60% in mineral oil) in DMF (45 mL) at 0° C. is treated with 5-fluoro-3-methyl-1H-indole (500 mg, 3.55 mmol), and the mixture is stirred at 0° C. for 1 h. NH$_2$OSO$_3$H (1.9 g, 16.75 mmol) is added portion wise, and the mixture is then warmed to rt and stirred for 2 h. The mixture is quenched with MeOH, diluted with water, extracted with EtOAc, dried (Na$_2$SO$_4$), filtered and concentrated to afford 5-fluoro-3-methyl-indol-1-ylamine. MS: 165 (M+H); $^1$H NMR (300 MHz, CD$_3$OD): δ 2.22 (s, 3H), 6.86 (m, 1H), 6.99 (s, 1H), 7.08 (m, 1H), 7.36 (m, 1H).

Step 2: Na$^0$ (31.7 mmol) is added to anhydrous EtOH (100 mL) and stirred at rt for 15 min. Pyridine-2-carboxamidine hydrochloride (31.7 mmol) is added and the solution is stirred for 15 min. 2-Dimethylaminomethylene-3-oxo-butyric acid ethyl ester (31.7 mmol) is added and the reaction mixture is heated at reflux under N$_2$ for 1 h. The reaction is cooled to rt and concentrated in vacuo. The residue is dissolved in EtOAc (200 mL), washed with brine (2×100 mL), dried (Na$_2$SO$_4$), filtered, and concentrated to afford 4-methyl-2-pyridin-2-yl-pyrimidine-5-carboxylic acid ethyl ester (6.77 g, 88%). MS: 261 (M+H); $^1$H $^1$H NMR (300 MHz, CDCl$_3$): δ 1.44 (t, 3H), 2.97 (s, 3H), 4.44 (q, 2H), 7.44 (m, 1H), 7.91 (m, 1H), 8.60 (m, 1H), 8.90 (m, 1H), 9.31 (s, 1H).

Step 3: A solution of 4-methyl-2-pyridin-2-yl-pyrimidine-5-carboxylic acid ethyl ester (26.7 mmol) and LiOH (53.4 mmol) in a 1:1:1 solution of THF, MeOH and water (200 mL) is stir at rt overnight. The THF/MeOH is evaporated, and the aqueous solution is treated with 10% aqueous HCl to adjust the pH to between 1.5 and 2.5. The solid is filtered off, washed with water and dried in vacuo to yield 4-methyl-2-pyridin-2-yl-pyrimidine-5-carboxylic acid (5.50 g, 96%) as a solid. MS: 233 (M+H); $^1$H $^1$H NMR (300 MHz, CD$_3$OD): δ=2.93(s, 3H), 7.59 (m, 1H), 8.05 (t, 1H), 8.62 (d, 1H), 8.76 (d, 1H), 9.28 (s, 1H).

Step 4, Method A:

A solution of 4-methyl-2-pyridin-2-yl-pyrimidine-5-carboxylic acid (335 mg, 1.56 mmol), HOTT (638 mg, 1.72 mmol), and DIPEA (700 µL, 4.01 mmol in DMF (6 mL) is stirred stirred at rt under N$_2$ for 20 min. 5-Fluoro-3-methyl-indol-1-ylamine (241 mg, 1.47 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 60% EtOAc in heptane to afford 4-methyl-2-pyridin-2-yl-pyrimidine-5-carboxylic acid (5-fluoro-3-methyl-indol-1-yl)amide (193 mg, 36%) as a solid. MS: 362 (M+H). $^1$H NMR (300 MHz, CDCl$_3$): δ 10.41 (s, 1H), 8.84 (s, 1H), 8.55 (s, 1H), 8.48-8.45 (m, 1H), 7.86 (t, 1H), 7.40-7.36 (m, 1H), 7.24-7.20 (m, 2H), 7.05-7.01 (m, 2H), 2.82 (s, 3H), 2.32 (s, 3H).

Step 4, Method B:

5-Fluoro-3-methyl-indol-1-ylamine (10.6 mmol) is treated with 4-methyl-2-pyridin-2-ylpyrimidine-5-carboxylic acid (2.75 g, 12.8 mmol) in DMF (75 mL) and the mixture is stirred at rt for 10 min. The mixture is then treated with 2,4-dimethoxy-6-(4-methylmorpholin-4-yl)-[1,3,5]triazine chloride (3.82 g, 13.85 mmol) and stirred at 60° C. for 1 h. The mixture is concentrated in vacuo. The residue is diluted with Et$_2$O (50 mL) and 10% NaHCO$_3$ (50 mL), and the mixture is stirred at rt for 20 min. The resulting solid is filtered, washed, and dried to afford 4-methyl-2-pyridin-2-yl-pyrimidine-5-carboxylic acid (5-fluoro-3-methyl-indol-1-yl)amide (3.2 g, 83%). The solid is crystallized with MeOH:water (4:1) to afford 4-methyl-2-pyridin-2-yl-pyrimidine-5-carboxylic acid (5-fluoro-3-methyl-indol-1-yl)amide as a crystal. MS: 362 (M+H); $^1$H NMR (300 MHz, DMSO-d$_6$): δ 2.27 (s, 3H), 2.78 (s, 3H), 7.06 (m, 1H), 7.34 (m, 1H), 7.37 (s, 1H), 7.44 (m, 1H), 7.59 (m, 1H), 8.05 (m, 1H), 8.45 (m, 1H), 8.80 (m, 1H), 9.25 (s, 1H). IC$_{50}$=7 nM.

Example 4

2-Pyridin-2-yl-pyrimidine-5-carboxylic acid (5-fluoro-3-methyl-indol-1-yl)-amide

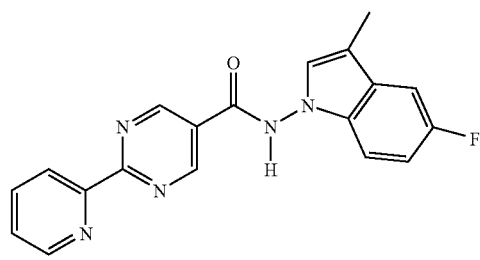

Step 1: Following the procedures similar to those of Example 1, step 3, but substituting pyridine-2-carboxamidine hydrochloride nicotinamidine hydrochloride, there is prepared 2-pyridin-2-yl-pyrimidine-5-carboxylic acid methyl ester.

Step 2: Following the procedures similar to those of Example 2, step 1, but substituting 2-pyridin-2-yl-pyrimidine-5-carboxylic acid methyl ester for 2-pyridin-3-yl-pyrimidine-5-carboxylic acid methyl ester, there is prepared 2-pyridin-2-yl-pyrimidine-5-carboxylic acid.

Step 3: A solution of 2-pyridin-2-yl-pyrimidine-5-carboxylic acid (209 mg, 0.88 mmol), HOTT (435 mg, 1.17 mmol), and DIPEA (400 µL, 2.29 mmol) in DMF (10 mL) is stirred at rt under N$_2$ for 20 min. 5-Fluoro-3-methyl-indol-1-ylamine (125 mg, 0.76 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 70% EtOAc in heptane to afford 2-pyridin-2-yl-pyrimidine-5-carboxylic acid (5-fluoro-3-methyl-indol-1-yl)-amide (180 mg, 68%) as a solid. MS: 348 (M+H). $^1$H NMR (300 MHz, DMSO-d$_6$): δ 12.12 (s, 1H), 9.47 (s, 2H), 8.82 (d, 1H), 8.51 (d, 1H), 8.05 (td, 1H), 7.62 (dd, 1H), 7.42 (dd, 1H), 7.35 (dd, 1H), 7.33 (s, 1H), 7.03 (td, 1H), 2.27 (s, 3H).

Example 5

4-Methyl-2-pyridin-3-yl-pyrimidine-5-carboxylic acid (5-fluoro-3-methyl-indol-1-yl)-amide

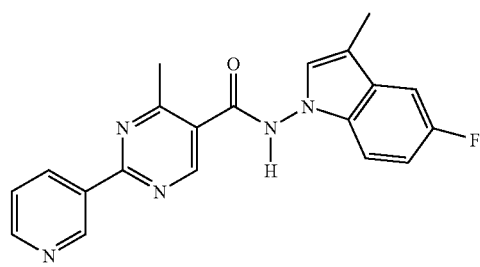

Step 1: Following the procedures similar to those of Example 2, step 1, but substituting nicotinamidine hydrochloride for 3-fluorobenzamidine hydrochloride, there is prepared 2-pyridin-3-yl-4-methyl-pyrimidine-5-carboxylic acid ethyl ester.

Step 2: Following the procedures similar to those of Example 2, step 1, but substituting 2-pyridin-3-yl-4-methyl-pyrimidine-5-carboxylic acid ethyl ester for 2-(3-fluoro-phenyl)-4-methyl-pyrimidine-5-carboxylic acid ethyl ester, there is prepared 4-methyl-2-pyridin-3-yl-pyrimidine-5-carboxylic acid.

Step 3: A solution of 4-methyl-2-pyridin-3-yl-pyrimidine-5-carboxylic acid (502 mg, 2.33 mmol), HCTU (1.054 g, 2.55 mmol), and DIPEA (1.10 mL, 6.30 mmol) in DMF (10 mL) is stirred at rt under $N_2$ for 10 min. 5-Fluoro-3-methyl-indol-1-ylamine (341 mg, 2.08 mmol) is added. The resulting mixture is stirred at rt overnight. The mixture is portioned between EtOAc and water. The organic phase is separated, washed with saturated aqueous $NaHCO_3$, water and brine, dried ($MgSO_4$), filtered and concentrated in vacuo. The residue is triturated in ether (4 times) to afford 4-methyl-2-pyridin-3-yl-pyrimidine-5-carboxylic acid (5-fluoro-3-methyl-indol-1-yl)-amide (160 mg, 21%) as a solid. MS: 362 (M+H). $^1$H NMR (300 MHz, DMSO-$d_6$): δ 11.86 (s, 1H), 9.58 (s, 1H), 9.24 (s, 1H), 8.79-8.78 (m, 1H), 8.74 (td, 1H), 7.62 (dd, 1H), 7.44 (dd, 1H), 7.37-7.36 (m, 2H), 7.06 (td, 1H), 2.78 (s, 3H), 2.27 (s, 3H).

Example 6

2-Pyridin-3-yl-pyrimidine-5-carboxylic acid (5-fluoro-3-methyl-indol-1-yl)-amide

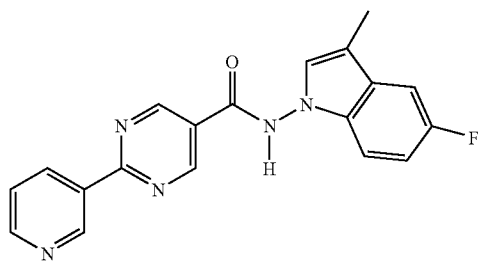

A solution of 2-pyridin-3-yl-pyrimidine-5-carboxylic acid (664 mg, 2.79 mmol), HCTU (1.27 g, 3.07 mmol), and DIPEA (1.4 mL, 8.02 mmol) in DMF (15 mL) is stirred at rt under $N_2$ for 10 min. 5-fluoro-3-methyl-indol-1-ylamine (491 mg, 2.55 mmol) is added. The resulting mixture is stirred at rt overnight. The mixture is portioned between EtOAc and water. The organic phase is separated, washed with saturated aqueous $NaHCO_3$, water and brine, dried ($MgSO_4$), filtered and concentrated in vacuo. The residue is triturated in ether (3 times) and methanol to afford 2-pyridin-3-yl-pyrimidine-5-carboxylic acid (5-fluoro-3-methyl-indol-1-yl)-amide (375 mg, 42%) as a solid. MS: 348 (M+H). $^1$H NMR (300 MHz, DMSO-$d_6$): δ 12.10 (s, 1H), 9.61-9.60 (m, 1H), 9.45 (s, 2H), 8.81-8.80 (m, 1H), 8.77 (dt, 1H), 7.64 (dd, 1H), 7.41 (dd, 1H), 7.35 (dd, 1H), 7.32 (s, 1H), 7.03 (td, 1H), 2.27 (s, 3H). $IC_{50}$=10 nM.

Example 7

2-Pyridin-2-yl-pyrimidine-5-carboxylic acid (5-fluoro-2-methyl-indol-1-yl)-amide

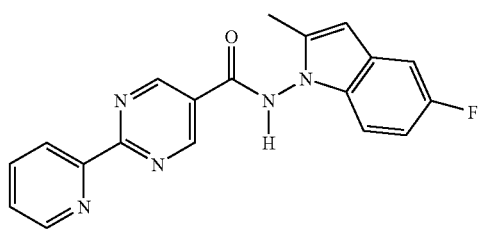

A solution of 2-pyridin-2-yl-pyrimidine-5-carboxylic acid (485 mg, 2.04 mmol), HCTU (909 mg, 2.2 mmol), and DIPEA (1 mL, 5.72 mmol) in DMF (15 mL) is stirred at rt under $N_2$ for 10 min. 5-Fluoro-2-methyl-indol-1-ylamine (299 mg, 1.82 mmol) is added. The resulting mixture is stirred at rt overnight. The mixture is portioned between EtOAc and water. The organic phase is separated, washed with saturated aqueous $NaHCO_3$, water and brine, dried ($MgSO_4$), filtered and concentrated in vacuo. The residue is purified by silica gel chromatography eluting with 70% EtOAc in heptane to afford 2-pyridin-2-yl-pyrimidine-5-carboxylic acid (5-fluoro-2-methyl-indol-1-yl)-amide (112 mg, 18%) as a solid. MS: 348 (M+H). $^1$H NMR (300 MHz, DMSO-$d_6$): δ 12.03 (s, 1H), 9.51 (s, 2H), 8.83 (d, 1H), 8.50 (d, 1H), 8.05 (dt, 1H), 7.62 (dd, 1H), 7.39 (dd, 1H), 7.28 (dd, 1H), 6.94 (dt, 1H), 6.35 (s, 1H), 2.33 (s, 3H).

Example 8

2-(3-Fluoro-phenyl)-pyrimidine-5-carboxylic acid (5-fluoro-3-methyl-indol-1-yl)-amide

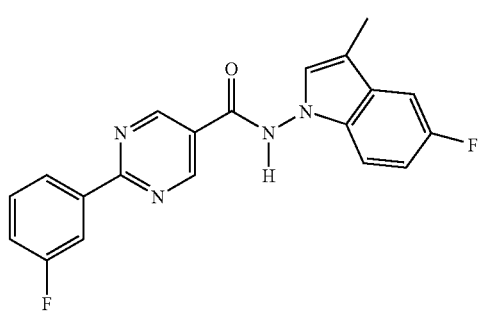

Step 1: To a solution of 3-fluoro-benzamidine hydrochloride (4 g, 22.6 mmol) in anhydrous DMF (35 mL) is added sodium 3,3-dimethoxy-2-carbomethoxyprop-1-en-1-oxide (4.99 g, 25.2 mmol). The reaction mixture is heated at 100° C. under $N_2$ for 3 h and then cooled to rt. Water (150 mL) is added and the mixture is extracted with EtOAc. The organic layer is washed with brine, dried ($MgSO_4$) filtered and concentrated in vacuo to afford 2-(3-fluoro-phenyl)-pyrimidine-5-carboxylic acid methyl ester (1.76 g, 34%). MS: 233 (M+H).

Step 2: To a solution of 2-(3-fluoro-phenyl)-pyrimidine-5-carboxylic acid methyl ester (1.76 g, 7.58 mmol) in anhydrous MeOH (35 mL) is added LiOH (0.38 g, 15.9 mmol) and the reaction mixture is stirred at rt overnight. The mixture is concentrated in vacuo and the residue is partitioned between EtOAc and 3 N aqueous HCl (7.6 mL). The mixture is extracted with EtOAc and the organic layer is washed with brine, dried (MgSO$_4$), filtered and concentrated in vacuo to afford 2-(3-fluoro-phenyl)-pyrimidine-5-carboxylic acid (1.62 g, 98%) as a solid. MS: 219 (M+H).

Step 3: A solution of 2-(3-fluoro-phenyl)-pyrimidine-5-carboxylic acid (372 mg, 1.7 mmol), HCTU (757 mg, 1.83 mmol), and DIPEA (780 µL, 4.47 mmol) in DMF (10 mL) is stirred at rt under N$_2$ for 10 min. 5-Fluoro-3-methyl-indol-1-ylamine (250 mg, 1.52 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is triturated in ether to afford 2-(3-fluoro-phenyl)-pyrimidine-5-carboxylic acid (5-fluoro-3-methyl-indol-1-yl)-amide (332 mg, 60%) as a solid. MS: 365 (M+H). $^1$H NMR (300 MHz, DMSO-d$_6$): δ 12.08 (s, 1H), 9.43 (s, 2H), 8.36 (d, 1H), 8.20 (dt, 1H), 7.70-7.62 (m, 1H), 7.48 (dt, 1H), 7.40 (dd, 1H), 7.35 (dd, 1H), 7.32 (s, 1H), 7.03 (dt, 1H), 2.27 (s, 3H).

Example 9

4-Methyl-2-pyridin-3-yl-pyrimidine-5-carboxylic acid (5-fluoro-2-methyl-indol-1-yl)-amide

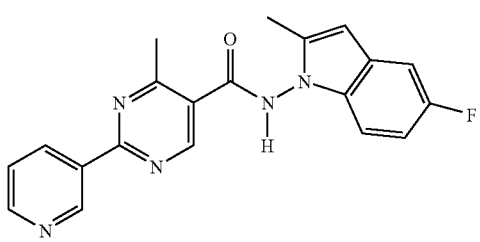

A solution of 4-methyl-2-pyridin-3-yl-pyrimidine-5-carboxylic acid (504 mg, 2.34 mmol), HCTU (1.06 g, 2.55 mmol), and DIPEA (1.11 mL, 6.30 mmol) in DMF (15 mL) is stirred at rt under N$_2$ for 10 min. 5-Fluoro-2-methyl-indol-1-ylamine (346 mg, 2.11 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 70% EtOAc in heptane to afford 4-methyl-2-pyridin-3-yl-pyrimidine-5-carboxylic acid (5-fluoro-2-methyl-indol-1-yl)-amide (82 mg, 11%) as a solid. MS: 362 (M+H). $^1$H NMR (300 MHz, DMSO-d$_6$): δ 11.80 (s, 1H), 9.59 (d, 1H), 9.29 (s, 1H), 8.80-8.73 (m, 2H), 7.63 (dd, 1H), 7.22 (dd, 1H), 7.28 (dd, 1H), 6.97 (dt, 1H), 6.35 (s, 1H), 2.79 (s, 3H), 2.37 (s, 3H).

Example 10

2-(3-Fluoro-phenyl)-4-methyl-pyrimidine-5-carboxylic acid (5-fluoro-3-methyl-indol-1-yl)-amide

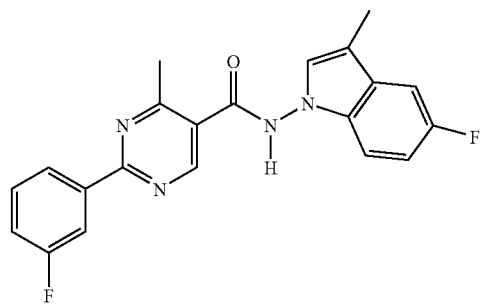

A solution of 2-(3-fluoro-phenyl)-4-methyl-pyrimidine-5-carboxylic acid (645 mg, 2.78 mmol), HCTU (1.25 g, 3.02 mmol), and DIPEA (1.35 mL, 7.73 mmol) in DMF (15 mL) is stirred at rt under N$_2$ for 10 min. 5-Fluoro-3-methyl-indol-1-ylamine (380 mg, 2.31 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is triturated in ether to afford 2-(3-fluoro-phenyl)-4-methyl-pyrimidine-5-carboxylic acid (5-fluoro-3-methyl-indol-1-yl)-amide (533 mg, 61%) as a solid. MS: 379 (M+H). $^1$H NMR (300 MHz, DMSO-d$_6$): δ 11.84 (s, 1H), 9.21 (s, 1H), 8.32 (d, 1H), 8.17-8.15 (m, 1H), 7.66-7.61 (m, 1H), 7.47-41 (m, 2H), 7.36-7.34 (m, 2H), 7.05 (dt, 1H), 2.76 (s, 3H), 2.26 (s, 3H). IC$_{50}$=6 nM.

Example 11

2-(3-Fluoro-phenyl)-pyrimidine-5-carboxylic acid (5-fluoro-2-methyl-indol-1-yl)amide

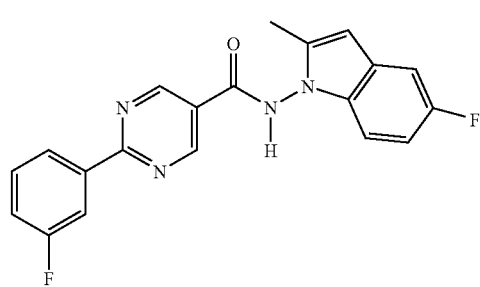

A solution of 2-(3-fluoro-phenyl)-pyrimidine-5-carboxylic acid (389 mg, 1.78 mmol), HOAt (290 mg, 2.13 mmol), and HATU (811 mg, 2.13 mmol) in DMF (20 mL) is stirred at rt under N$_2$ for 20 min. 5-Fluoro-2-methyl-indol-1-ylamine (290 mg, 1.77 mmol) and DIPEA (450 µL, 2.58 mmol) are added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 25% DCM in heptane to afford 2-(3-fluoro-phenyl)-pyrimidine-5-carboxylic acid (5-fluoro-2-methyl-indol-1-yl)amide (300 mg, 47%) as a solid. MS: 365 (M+H). $^1$H NMR (300 MHz, CDCl$_3$): δ 9.23 (s, 1H), 8.76 (s, 1H), 8.35-8.22 (m, 2H), 7.54-7.45 (m, 1H), 7.19-6.86 (m, 5H), 6.25 (s, 1H), 2.29 (s, 3H).

Example 12

4-Methyl-2-pyridin-2-yl-pyrimidine-5-carboxylic acid (5-fluoro-2-methyl-indol-1-yl)-amide

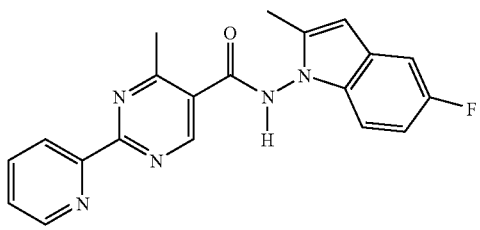

A solution of 4-methyl-2-pyridin-2-yl-pyrimidine-5-carboxylic acid (810 mg, 3.76 mmol), PyBrOP (1.76 g, 3.78 mmol), and DIPEA (1.9 mL, 10.89 mmol) in DMF (15 mL) is stirred at rt under N$_2$ for 10 min. 5-Fluoro-2-methyl-indol-1-ylamine (560 mg, 3.41 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 3% MeOH in DCM to afford 4-methyl-2-pyridin-2-yl-pyrimidine-5-carboxylic acid (5-fluoro-2-methyl-indol-1-yl)-amide (174 mg, 14%) as a solid. MS: 362 (M+H). $^1$H NMR (300 MHz, DMSO-d$_6$): δ 11.82 (s, 1H), 9.30 (d, 1H), 8.81 (d, 1H), 8.46 (d, 1H), 8.03 (dt, 1H), 7.59 (dd, 1H), 7.43 (dd, 1H), 7.29 (dd, 1H), 6.98 (dt, 1H), 6.35 (s, 1H), 2.79 (s, 3H), 2.38 (s, 3H). IC$_{50}$=8 nM.

Example 13

2-(3-Fluoro-phenyl)-4-methyl-pyrimidine-5-carboxylic acid (5-fluoro-3,3-dimethyl-2,3-dihydro-indol-1-yl)-amide

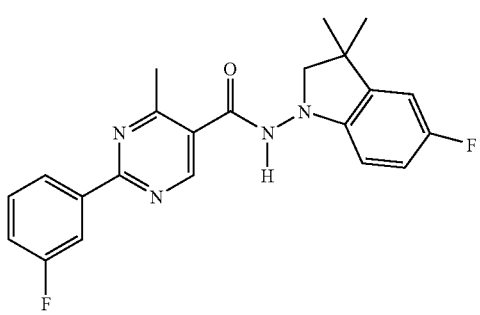

Step 1: Isoamyl nitrite (3.4 mL, 25.42 mmol) is added to a solution of 5-fluoro-3,3-dimethyl-2,3-dihydro-1H-indole (3.75 g, 22.69 mmol) in DCM. The mixture is refluxed overnight. The mixture is cooled and portioned between DCM and water. The organic phase is separated, washed with saturated aqueous NaHCO$_3$, water and brine, dried (MgSO$_4$), filtered and concentrated in vacuo to afford 5-fluoro-3,3-dimethyl-1-nitroso-2,3-dihydro-1H-indole (4.23 g, 96%) as a solid. MS: 195 (M+H). $^1$H NMR (300 MHz, CD$_3$Cl)): δ 7.77 (dd, 1H), 7.08-6.98 (m, 2H), 3.94 (s, 2H), 1.39 (s, 6H).

Step 2: To a solution of 5-fluoro-3,3-dimethyl-1-nitroso-2,3-dihydro-1H-indole (4.03 g, 20.75 mmol) in THF (70 mL) at 0° C. is added a solution of LiAlH$_4$ (40 mL, 40 mmol) in THF dropwise. The mixture is allowed to warm to rt and stirred overnight. The mixture is quenched with a saturated aqueous solution of Rochelle's Salt. The resulting mixture is stirred until a slurry is obtained. The organic phase is separated, washed with 10% aqueous HCl, saturated aqueous NaHCO$_3$, water and brine, dried (MgSO$_4$), filtered and concentrated in vacuo. The residue is purified by silica gel chromatography eluting with 25% EtOAc in heptane to afford 5-fluoro-3,3-dimethyl-2,3-dihydro-indol-1-ylamine (3.51 g, 94%) as an oil. MS: 181 (M+H). $^1$H NMR (300 MHz, CD$_3$Cl)): δ 6.85-6.78 (m, 1H), 6.75-6.68 (m, 2H), 3.44 (br s, 2H), 3.14 (s, 2H), 1.28 (s, 6H).

Step 3: A solution of 2-(3-fluoro-phenyl)-4-methyl-pyrimidine-5-carboxylic acid (348 mg, 1.5 mmol), HOTT (618 mg, 1.66 mmol), and DIPEA (700 μL, 4.01 mmol) in DMF (10 mL) is stirred at rt under N$_2$ for 10 min. 5-Fluoro-3,3-dimethyl-2,3-dihydro-indol-1-ylamine (239 mg, 1.33 mmol) is added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 15% EtOAc in heptane to afford 2-(3-fluoro-phenyl)-4-methyl-pyrimidine-5-carboxylic acid (5-fluoro-3,3-dimethyl-2,3-dihydro-indol-1-yl)-amide (416 mg, 80%) as a solid. MS: 395 (M+H). $^1$H NMR (300 MHz, DMSO-d$_6$): δ 10.43 (s, 1H), 8.99 (s, 1H), 8.28 (d, 1H), 8.15-8.11 (m, 1H), 7.66-7.58 (m, 1H), 7.46-7.39 (m, 1H), 7.06 (dd, 1H), 6.95-6.88 (m, 1H), 6.75-6.71 (m, 1H), 3.51 (s, 2H), 2.68 (s, 3H), 1.33 (s, 6H).

Example 14

2-(3-Fluoro-phenyl)-4-methyl-pyrimidine-5-carboxylic acid [3-(2,2,2-trifluoro-acetyl)-indol-1-yl]-amide

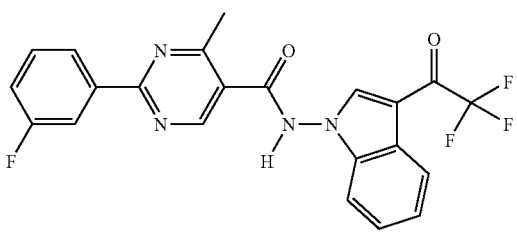

Step 1: Following procedures similar to those of Example 1, step 1, but substituting 3-(2,2,2-trifluoro-acetyl)indole for 5-fluoro-2-methylindole, 1-(1-amino-1H-indol-3-yl)-2,2,2-trifluoro-ethanone is prepared.

Step 2: A solution of 2-(3-fluoro-phenyl)-4-methyl-pyrimidine-5-carboxylic acid (360 mg, 1.55 mmol), HOTT (628 mg, 1.69 mmol), and DIPEA (740 μL, 4.24 mmol) in DMF (10 mL) is stirred at rt under N$_2$ for 10 min. 1-(1-Amino-1H-indol-3-yl)-2,2,2-trifluoro-ethanone (322 mg, 1.4 mmol) is added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by HPLC reverse phase column chromatography eluting with a mobile phase of 0.1% TFA/water through 100% MeCN in a 30 min. ramp to afford 2-(3-fluoro-phenyl)-4-methyl-pyrimidine-5-carboxylic acid [3-(2,2,2-trifluoro-acetyl)-indol-1-yl]-amide (71 mg, 11%) as a solid. MS: 443 (M+H). $^1$H NMR (300 MHz, DMSO-$d_6$): δ 12.56 (s, 1H), 9.32 (s, 1H), 8.90 (d, 1H), 8.35 (d, 1H), 8.30-8.27 (m, 1H), 8.22-8.17 (m, 1H), 7.75-72 (m, 1H), 7.69-7.62 (m, 1H), 7.52-7.44 (m, 3H), 2.81 (s, 3H).

Example 15

4-Methyl-2-pyridin-2-yl-pyrimidine-5-carboxylic acid (5-fluoro-3,3-dimethyl-2,3-dihydro-indol-1-yl)-amide

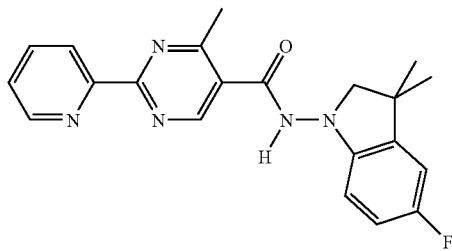

A solution of 4-methyl-2-pyridin-2-yl-pyrimidine-5-carboxylic acid (685 mg, 3.18 mmol), HOTT (1.29 g, 3.48 mmol), and DIPEA (1.6 mL, 9.16 mmol) in DMF (15 mL) is stirred at rt under N$_2$ for 10 min. 5-Fluoro-3,3-dimethyl-2,3-dihydro-indol-1-ylamine (542 mg, 3.01 mmol) is added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 2% MeOH in DCM to afford 4-methyl-2-pyridin-2-yl-pyrimidine-5-carboxylic acid (5-fluoro-3,3-dimethyl-2,3-dihydro-indol-1-yl)-amide (585 mg, 52%) as a solid. MS: 378 (M+H). $^1$H NMR (300 MHz, DMSO-$d_6$): δ 10.46 (s, 1H), 9.02 (s, 1H), 8.78 (d, 1H), 8.42 (d, 1H), 8.00 (dt, 1H), 7.56 (dd, 1H), 7.06 (dd, 1H), 6.92 (dt, 1H), 6.76-6.72 (m, 1H), 3.32 (s, 2H), 2.70 (s, 3H), 1.33 (s, 6H).

Example 16

4-Methyl-2-pyridin-3-yl-pyrimidine-5-carboxylic acid (5-fluoro-3,3-dimethyl-2,3-dihydro-indol-1-yl)-amide

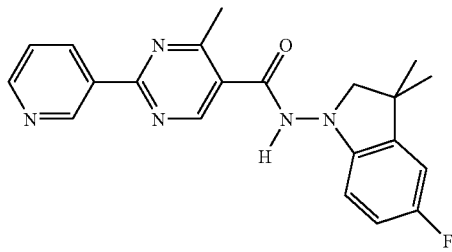

A solution of 4-methyl-2-pyridin-3-yl-pyrimidine-5-carboxylic acid (706 mg, 3.28 mmol), HOTT (1.34 g, 3.6 mmol), and DIPEA (1.65 mL, 9.45 mmol) in DMF (15 mL) is stirred at rt under N$_2$ for 10 min. 5-Fluoro-3,3-dimethyl-2,3-dihydro-indol-1-ylamine (560 mg, 3.11 mmol) is added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 35% EtOAc in heptane to afford 4-methyl-2-pyridin-3-yl-pyrimidine-5-carboxylic acid (5-fluoro-3,3-dimethyl-2,3-dihydro-indol-1-yl)-amide (617 mg, 53%) as a solid. MS: 378 (M+H). $^1$H NMR (300 MHz, DMSO-$d_6$): δ 10.44 (s, 1H), 9.55-9.54 (m, 1H), 9.01 (s, 1H), 8.77-8.75 (m, 1H), 8.72-8.68 (m, 1H), 7.60 (dd, 1H), 7.06 (dd, 1H), 6.96-6.88 (m, 1H), 6.76-6.72 (m, 1H), 3.51 (s, 2H), 2.70 (s, 3H), 1.33 (s, 6H).

Example 17

2-(3-Fluoro-phenyl)-4-methyl-pyrimidine-5-carboxylic acid (2,3-dimethyl-indol-1-yl)-amide

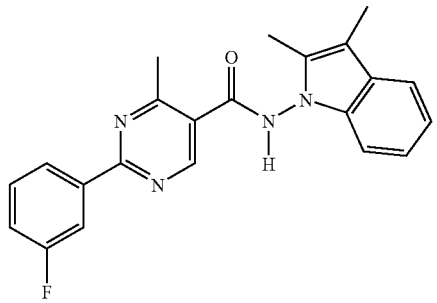

Step 1: Following procedures similar to those of Example 1, step 1, but substituting 2,3-dimethylindole for 5-fluoro-2-methylindole, there is prepared 2,3-dimethyl-indol-1-ylamine as a solid. MS: 161 (M+H). $^1$H NMR (300 MHz, CDCl$_3$): δ 7.48-7.45 (m, 1H), 7.33-7.30 (m, 1H), 7.19-7.13 (m, 1H), 7.10-7.05 (m, 1H), 4.40 (br s, 2H), 2.37 (s, 3H), 2.23 (s, 3H).

Step 2: A solution of 2-(3-fluoro-phenyl)-4-methyl-pyrimidine-5-carboxylic acid (764 mg, 3.29 mmol), HOTT (1.33 g, 3.58 mmol), and DIPEA (1.65 mL, 9.45 mmol) in DMF (15 mL) is stirred at rt under N$_2$ for 10 min. 2,3-Dimethyl-indol-1-ylamine (497 mg, 3.1 mmol) is added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 20% EtOAc in heptane to afford 2-(3-fluoro-phenyl)-4-methyl-pyrimidine-5-carboxylic acid (2,3-dimethyl-indol-1-yl)-amide (568 mg, 49%) as a solid. MS: 375 (M+H). $^1$H NMR (300 MHz, DMSO-$d_6$): δ 11.68 (s, 1H), 9.24 (s, 1H), 8.33 (d, 1H), 8.20-8.15 (m, 1H), 7.69-7.61 (m, 1H), 7.50-7.43 (m, 2H), 7.37 (d, 1H), 7.17-7.05 (m, 2H), 2.78 (s, 3H), 2.30 (s, 3H), 2.24 (s, 3H).

Example 18

2-(3-Fluoro-phenyl)-4-methyl-pyrimidine-5-carboxylic acid (5-chloro-2-methyl-indol-1-yl)-amide

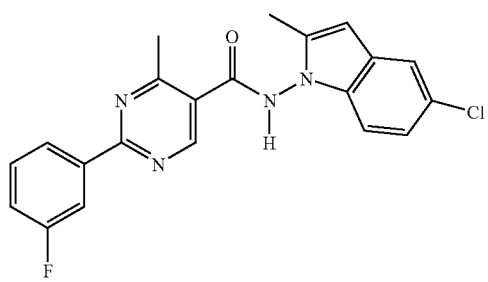

Step 1: Following procedures similar to those of Example 1, step 1, but substituting 5-chloro-2-methylindole for 5-fluoro-2-methylindole, there is prepared 5-chloro-2-methyl-indol-1-ylamine as a solid. MS: 181 (M+H). $^1$H NMR (300 MHz, CDCl$_3$): δ 7.46-7.43 (m, 1H), 7.27-7.24 (m, 1H), 7.12-7.09 (m, 1H), 6.10 (s, 1H), 4.44 (br s, 2H), 2.44-2.43 (m, 3H).

Step 2: A solution of 2-(3-fluoro-phenyl)-4-methyl-pyrimidine-5-carboxylic acid (379 mg, 1.63 mmol), HOTT (662 mg, 1.78 mmol), and DIPEA (800 μL, 4.58 mmol) in DMF (10 mL) is stirred at rt under N$_2$ for 10 min. 5-Chloro-2-methyl-indol-1-ylamine (274 mg, 1.52 mmol) is added. The resulting mixture is stirred at 80° C. overnight. The mixture is cooled and portioned between EtOAc and water. The organic phase is separated, washed with saturated aqueous NaHCO$_3$, water and brine, dried (MgSO$_4$), filtered and concentrated in vacuo. The residue is triturated in ether to afford 2-(3-fluoro-phenyl)-4-methyl-pyrimidine-5-carboxylic acid (5-chloro-2-methyl-indol-1-yl)-amide (93 mg, 16%) as a solid. MS: 395 (M+H). $^1$H NMR (300 MHz, DMSO-d$_6$): δ 11.83 (s, 1H), 9.27 (s, 1H), 8.33 (d, 1H), 8.20-8.15 (m, 1H), 7.69-7.61 (m, 1H), 7.56 (d, 1H), 7.50-7.43 (m, 2H), 6.36 (s, 1H), 2.78 (s, 3H), 2.37 (s, 3H).

Example 19

2-(3-Fluoro-phenyl)-4-methyl-pyrimidine-5-carboxylic acid (5-bromo-indol-1-yl)-amide

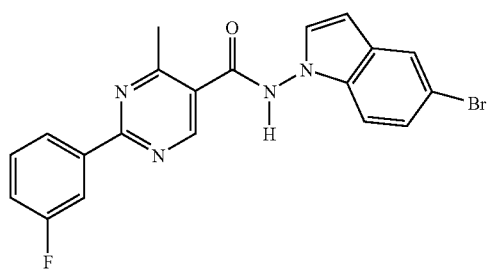

Step 1: Following procedures similar to those of Example 1, step 1, but substituting 5-bromoindole for 5-fluoro-2-methylindole, there is prepared 5-bromoindol-1-ylamine as a solid. MS: 211 (M+H). $^1$H NMR (300 MHz, CDCl$_3$): δ 7.71-7.70 (m, 1H), 7.29-7.28 (m, 2H), 7.13 (d, 1H), 6.32-6.31 (m, 1H), 4.73 (br s, 2H).

Step 2: A solution of 2-(3-fluoro-phenyl)-4-methyl-pyrimidine-5-carboxylic acid (596 mg, 2.57 mmol), PyAOP (2.63 mmol), and DIPEA (830 μL, 4.75 mmol) in DCM (20 mL) is stirred at rt under N$_2$ for 10 min. 5-Bromoindol-1-ylamine (500 mg, 2.37 mmol) is added. The resulting mixture is stirred at rt overnight. The mixture is portioned between EtOAc and water. The organic phase is separated, washed with saturated aqueous NaHCO$_3$, water and brine, dried (MgSO$_4$), filtered and concentrated in vacuo. The residue is purified by silica gel chromatography eluting with 2% MeOH in DCM to afford 2-(3-fluoro-phenyl)-4-methyl-pyrimidine-5-carboxylic acid (5-bromo-indol-1-yl)-amide (246 mg, 24%) as a solid. MS: 425 (M) & 427 (M+2). $^1$H NMR (300 MHz, DMSO-d$_6$): δ 12.02 (s, 1H), 9.24 (s, 1H), 8.34 (d, 1H), 8.20-8.15 (m, 1H), 7.84 (d, 1H), 7.68-7.61 (m, 1H), 7.59 (d, 1H), 7.50-7.43 (m, 2H), 7.35 (dd, 1H), 6.57 (dd, 1H), 2.78 (s, 3H).

Example 20

3-Oxo-4-[(2-phenyl-pyrimidine-5-carbonyl)-amino]-piperazine-1-carboxylic acid benzyl ester

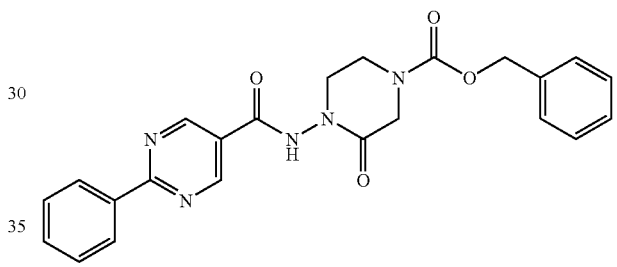

Step 1: Following the procedures described in M. A. Brook, T. H. Chan Synthesis 1983, (3), 201-204, there is prepared benzyloxycarbonylamino-acetic acid ethyl ester (95%). MS: 238 (M+H); $^1$H NMR (300 MHz, CDCl$_3$) δ 7.24-7.41 (m, 5H), 5.20-5.37 (br s, 1H), 5.13 (s, 2H), 4.21 (q, J=7.0 Hz, 2H), 3.96 (br d, J=5.3 Hz, 2H), 1.27 (t, J=7.1 Hz, 3H).

Step 2: Following the procedures described in P. Shenbagamurthi, H. A. Smith, J. M. Becker, F. Naider *J. Med. Chem.* 1986, 29 (5), 802-809; R. K. Olsen *J. Org. Chem.* 1970, 35 (6), 1912-1915, there is prepared (allyl-benzyloxycarbonyl-amino)-acetic acid ethyl ester as a liquid (92%): MS: 278 (M+H); $^1$H NMR (300 MHz, CDCl$_3$) δ 7.17-7.41 (m, 5H), 5.70-5.88 (m, 1H), 5.06-5.25 (m, 4H), 4.02-4.23 (m, 2H), 3.81-4.02 (m, 4H), 1.10-1.30 (m, 3H).

Step 3: To a 0° C. solution of AD-mix-β (2.54 g) in a mixture of t-butanol (10 mL) and water (12 mL) is added a solution of (allyl-benzyloxycarbonyl-amino)-acetic acid ethyl ester (0.52 g, 1.91 mmol) in t-butanol (2.00 mL). The reaction mixture is allowed to gradually warm to ambient temperature over 2 h, and stirred at rt for 20 h. Excess oxidant is quenched by the addition of Na$_2$SO$_3$ (2.58 g, 20.44 mmol) and the mixture is stirred vigorously for 4 h. The mixture is extracted with EtOAc (50 mL) and the organic phase is washed with saturated aqueous NaCl (2×30 mL). The organic solution is dried (MgSO$_4$), filtered, and concentrated in vacuo. The residue is purified by silica gel chromatography (1:1:1 of EtOAc:DCM:heptane to 50:50 DCM:EtOAc gradient elution) to afford [benzyloxycarbonyl-(2,3-dihydroxy-propyl)-amino]-acetic acid ethyl ester as an oil (0.276 g, 46%). MS: 312 (M+H); $^1$H NMR (300 MHz, CDCl$_3$) δ 7.20-7.40 (m, 5H), 5.05-5.18 (m, 2H), 3.95-4.25 (m, 4H), 3.80-

3.95 (m, 1H), 3.20-3.80 (m, 11H), 1.11-1.35 (m, 3H). (See H. Takahata, H. Ouchi, M. Ichinose, H. Nemoto *Org. Lett.* 2002, 4 (20), 3459-3462 and supplementary material; J. Gonzalez, C. Aurigemma, L. Truesdale Org. Synth. 2002, 79, 93-102).

Step 4: To a solution of [benzyloxycarbonyl-(2,3-dihydroxy-propyl)-amino]-acetic acid ethyl ester (1.98 g, 6.37 mmol) in DCM (30 mL) is added NaIO$_4$-impregnated silica (13.04 g). The slurry is stirred rapidly for 4.5 h, and then filtered through a coarse porosity sintered glass funnel. The filtrate is concentrated to afford [benzyloxycarbonyl-(2-oxo-ethyl)-amino]-acetic acid ethyl ester (1.65 g, 92%). MS: 280 (M+H); $^1$H NMR (300 MHz, CDCl$_3$) δ 9.60-9.68 (m, 1H), 7.26-7.40 (m, 5H), 510-5.19 (m, 2H), 4.00-4.22 (m, 6H), 1.18-1.30 (m, 3H). (see Y.-L. Zhong, T. K. M. Shing *J. Org. Chem.* 1997, 62 (8), 2622-2624).

Step 5: N-Aminophthalimide (0.55 g, 3.4 mmol) is added to a solution of benzyloxycarbonyl-(2-oxo-ethyl)-amino]-acetic acid ethyl ester (0.72, 2.6 mmol) in 1,4-dioxane (10 mL), and the mixture is heated to reflux under N$_2$ for 15 h. The reaction mixture is cooled to rt and filtered through diatomaceous earth. The filtrate is concentrated. The residue is redissolved in CHCl$_3$ (30 mL) and filtered again through diatomaceous earth. This filtrate is concentrated to afford (benzyloxycarbonyl-[2-[(E)-1,3-dioxo-1,3-dihydro-isoindol-2-ylimino]ethyl]-amino)-acetic acid ethyl ester (~100%). MS: 424 (M+H); $^1$H NMR (300 MHz, CDCl$_3$) δ 8.77-8.88 (m, 1H), 7.80-7.93 (m, 2H), 7.67-7.80 (m, 2H), 7.23-7.40 (m, 5H), 5.09-5.21 (m, 2H), 4.25-4.45 (m, 2H), 3.97-4.25 (m, 4H), 1.12-1.32 (m, 3H).

Step 6: A solution of (benzyloxycarbonyl-{2-[(E)-1,3-dioxo-1,3-dihydro-isoindol-2-ylimino]ethyl}-amino)-acetic acid ethyl ester (7.7 mmol) in CH$_3$CN (65 mL) is treated with sodium cyanoborohydride (1.92 g, 30.5 mmol), and acetic acid (6.8 mL, 118.8 mmol) is added with stirring under N$_2$. After 5.5 h, the reaction solution is diluted with EtOAc (150 mL) and washed with saturated aqueous KHCO$_3$ (3×50 mL) and saturated aqueous NaCl (50 mL). The organic phase is dried (MgSO$_4$), filtered, and concentrated in vacuo. The residue is purified by silica gel chromatography (75:25 to 50:50 heptane:ethyl acetate gradient elution) to afford {benzyloxycarbonyl-[2-(1,3-dioxo-1,3-dihydro-isoindol-2-ylamino)-ethyl]-amino}-acetic acid ethyl ester as an oil (2.66 g, 81%). MS: 426 (M+H); $^1$H NMR (300 MHz, CDCl$_3$) δ 7.79-7.91 (m, 2H), 7.69-7.79 (m, 2H), 7.17-7.39 (m, 5H), 5.04-5.21 (m, 2H), 4.87-5.04 (m, 1H), 4.04-4.23 (m, 4H), 3.48-3.59 (m, 2H), 3.18-3.38 (m, 2H), 1.10-1.30 (m, 3H).

Step 7: A solution of {benzyloxycarbonyl-[2-(1,3-dioxo-1,3-dihydro-isoindol-2-ylamino)-ethyl]-amino}-acetic acid ethyl ester (0.22 g, 0.52 mmol) in diphenyl ether (3 mL) is heated to reflux for 2 h. Diphenyl ether is removed by vacuum distillation and the residue is purified by flash silica gel chromatography (2:1:1 to 1:1:1 heptane:DCM:EtOAc gradient elution) to afford 4-(1,3-dioxo-1,3-dihydro-isoindol-2-yl)-3-oxo-piperazine-1-carboxylic acid benzyl ester as a solid (0.126 g, 64%). MS: 380 (M+H); $^1$H NMR (300 MHz, CDCl$_3$) δ 7.86-7.95 (m, 2H), 7.75-7.86 (m, 2H), 7.24-7.42 (m, 5H), 5.20 (s, 2H), 4.42 (s, 2H), 3.90-4.05 (m, 2H), 3.65-3.87 (m, 2H).

Step 8: To a solution of benzamidine hydrochloride hydrate (2 mmol) in anhydrous DMF (4 mL) is added sodium salt of 2-dimethoxymethyl-3-hydroxy-acrylicacid methyl ester (0.46 g, 2.32 mmol) and the reaction mixture heated at 100° C. under N2 for 1 hour. The reaction is cooled to rt and water (15 mL) is added. After addition of water, immediate precipitation of the product is observed. The solids are collected by filtration, washed with water (2.5 mL) and vacuum dried to yield 2-phenyl-pyrimidine-5-carboxylic acid methyl ester (0.32 g, 74%). (see: P. Zhichkin, D. J. Fairfax, S. A. Eisenbeis, Synthesis, 2002, 720-722.)

Step 9: A solution of 2-phenyl-pyrimidine-5-carboxylic acid methyl ester (3.15 g) and LiOH (0.71 g) in a mixture of MeOH, THF and water (1:1:1 in volume, 120 mL) is stirred at rt overnight. MeOH and THF are evaporated off to give an aqueous solution. The aqueous solution is acidified with 5% hydrochloric acid to adjust pH to between 2.5 and 3. The precipitate is filtered off and washed with water, dried in vacuo to yield 2.94 g (~100%) of 2-phenyl-pyrimidine-5-carboxylic acid as a solid. MS: 201 (M+H).

Step 10: A solution of 4-(1,3-dioxo-1,3-dihydro-isoindol-2-yl)-3-oxo-piperazine-1-carboxylic acid benzyl ester (53 mg, 0.14 mmol) in MeOH (10 mL) is treated with anhydrous hydrazine (0.3 mL, 9.56 mmol). The reaction mixture is stirred at reflux under N$_2$ for 3.5 h. The reaction mixture is concentrated. The residue is dissolved in a mixture of DMF (2 mL) and DCM (2 mL), and treated with 2-phenyl-pyrimidine-5-carbonyl chloride (32 mg, 0.15 mmol). The mixture is stirred under N$_2$ for 16 h, and then diluted with EtOAc (35 mL). The mixture is washed successively with saturated aqueous KHCO$_3$, (15 mL), water (2×15 mL), and saturated aqueous NaCl (15 mL), dried (MgSO$_4$), filtered, and concentrated in vacuo. The residue is purified by flash silica gel chromatography (80:20 to 0:100 heptane:EtOAc gradient elution) to afford 3-oxo-4-[(2-phenyl-pyrimidine-5-carbonyl)-amino]-piperazine-1-carboxylic acid benzyl ester as an oil (111 mg, 18%). MS: 432 (M+H); $^1$H NMR (300 MHz, CDCl$_3$) δ 9.70-10.10 (br, 1H), 9.06 (s, 2H), 8.46 (dd, J=7.8, 1.7 Hz, 2H), 7.44-7.60 (m, 3H), 7.25-7.40 (m, 5H), 5.18 (s, 2H), 4.36 (s, 2H), 3.93 (t, J=5.1 Hz, 2H), 3.69-3.81 (br s, 2H). IC$_{50}$=103.5 nM.

Example 21

2-(3-Fluorophenyl)pyrimidine-5-carboxylic acid-(3-dimethylsulfamoyl-5-fluoro-indol-1-yl)amide

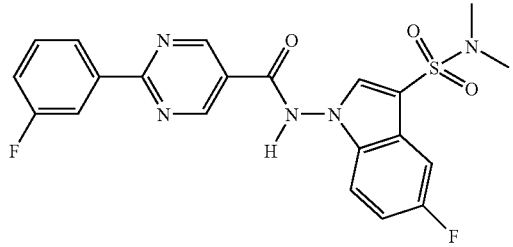

Step 1: A solution of 5-fluoroindole (5.4 g) and toluene-4-sulphonyl chloride (9.12 g) in toluene (300 mL) is treated with a cooled solution of sodium hydroxide pellets (23.2 g) in water (200 mL) followed by the tetrabutylammonium hydrogen sulfate catalyst (400 mg). The mixture is stirred at rt for 24 h. The organic phase is separated, washed with water and brine, dried (MgSO$_4$) and concentrated in vacuo to afford 5-fluoro-1-(toluene-4-sulfonyl)-1H-indole (10.7 g, 78%). MS: 290 (M+H)

Step 2: A solution of 5-fluoro-1-(toluene-4-sulfonyl)indole (5.2 g) in dry CH$_3$CN (80 mL) is cooled in an ice-bath and treated drop wise with chlorosulfonic acid (12 mL). The reaction mixture is allowed to warm to rt and stirred for 24 h. The reaction mixture is carefully poured onto ice/water (300 mL). The precipitate is collected by filtration and washed with water to afford 5-fluoro-3-chlorosulfonyl-1-(toluene-4-sulfonyl)-1H-indole (6.8 g, 98%) as a solid. MS: 386 (M−H).

Step 3: A solution of 5-fluoro-3-chlorosulfonyl-1-(toluene-4-sulfonyl)indole (2.52 g) in DCM (75 mL) is added to an aqueous solution of dimethylamine (40%, 20 mL) in water (50 mL) and stirred at rt for 20 h. The organic phase is separated, washed with water, brine, dried (MgSO$_4$), filtered and concentrated in vacuo to afford 5-fluoro-1-(toluene-4-sulfonyl)-1H-indole-3-sulphonic acid dimethylamide (2.55 g, 99%) as a solid. MS: 397 (M+H).

Step 4: A mixture of 5-fluoro-1-(touene-4-sulfonyl)indole-3-sulfonic acid dimethylamide (2.55 g) in MeOH (100 mL) and 5 N KOH (15 mL) is heated to reflux for 1.5 hours. The reaction mixture is concentrated in vacuo. The residue is diluted with water (50 mL) and acidified to pH 3 with 10 N aqueous HCl. The mixture is extracted with EtOAc. The organic layer is separated, washed with water, brine, dried (MgSO$_4$), filtered and concentrated in vacuo to afford 5-fluoro-1H-indole-3-sulfonic acid dimethylamide (1.35 g, 87%) as a solid. MS: 241 (M−H).

Step 5: A solution of 5-fluoro-1H-indole-3-sulfonic acid dimethylamide (1.24 g) in dry DMF (50 mL) is cooled to 0° C. and treated portion wise with 60% MaH oil dispersion (3.07 g). The mixture is stirred at 0° C. for 30 min. Hydroxylamine-O-sulfonic acid (2.9 g) is added portion wise and the mixture is warmed to rt and stirred for 5 h. The reaction mixture is poured onto ice/water and extracted with EtOAc. The organic layer is separated, washed water and brine, dried (MgSO$_4$) filtered and concentrated in vacuo. The residue is triturated with ether. The solid is collected by filteration to afford 1-amino-5-fluoro-1H-indole-3-sulfonic acid dimethylamide (0.53 g, 41%). MS: 258 (M+H).

Step 6: A suspension of 2-(3-fluorophenyl)-pyrimidine-5-carboxylic acid (76 mg) in dry DCM (25 mL)/dry DMF (2 drops) is treated with oxalyl chloride (0.15 mL) and stirred at rt for 3.5 hours. The reaction mixture is concentrated in vacuo. The residue is dissolved in toluene (15 mL) and then concentrated in vacuo. The residue is dried on high vacuum pump, and then dissolved in EtOAc (7 mL). The solution is added to a mixture of 1-amino-5-fluoro-1H-indole-3-sulfonic acid dimethylamide (100 mg) and Na$_2$CO$_3$ (106 mg) in EtOAc (5 mL)/water (5 mL). The mixture is stirred at rt for 24 h. The organic phase is separated, washed water and brine, dried (MgSO$_4$), filtered and concentrated in vacuo. The residue is purified by silica gel chromatography eluting with 50% EtOAc in heptane to afford 2-(3-fluorophenyl)pyrimidine-5-carboxylic acid-(3-dimethylsulfamoyl-5-fluoroindol-1-yl)amide (100 mg, 62%) as a solid. MS: 458 (M+H); $^1$H NMR (300 MHz, DMSO-d$_6$): δ 2.67 (s, 6H), 7.20-7.3 (m, 1H), 7.45-7.55 (m, 1H), 7.57-7.6 (dd, 1H), 7.65-7.75 (m, 2H), 8.2 (d, 1H), 8.38-8.4 (d, 2H), 9.45 (s, 2H), 12.6 (s, 1H).

Example 22

2-(3-Fluorophenyl)-4-methylpyrimidine-5-carboxylic acid-(3-dimethylsulfamoyl-5-fluoroindol-1-yl)amide

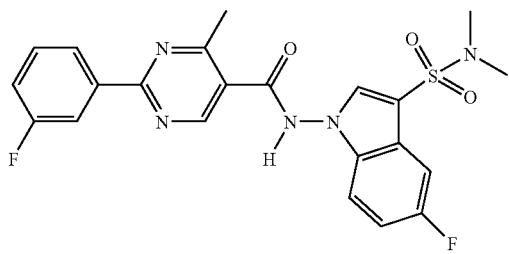

A solution of 2-(3-fluorophenyl)-4-methylpyrimidine-5-carboxylic acid (116 mg) and HATU (190 mg) in dry DMF is treated with DIPEA (0.09 mL) and stirred at rt for 40 min. 1-Amino-5-fluoro-1H-indole-3-sulfonic acid dimethylamide (192 mg) is added and the mixture is stirred at rt for 24 h. The mixture is concentrated in vacuo. The residue is dissolved in EtOAc, washed with 2 N aqueous NaOH, water and brine, dried (MgSO$_4$) and concentrated in vacuo. The residue is purified by silica gel chromatography eluting with 30% EtOAc/heptane to afford 2-(3-fluorophenyl)-4-methylpyrimidine-5-carboxylic acid-(3-dimethylsulfamoyl-5-fluoroindol-1-yl)amide (85 mg, 40%) as a solid. MS: 472 (M+H); $^1$H NMR (300 MHz, DMSO-d$_6$): δ 2.68 (s, 6H), 2.79 (s, 3H), 7.25-7.35 (m, 1H), 7.45-7.55 (m, 1H), 7.57-7.80 (m, 3H), 8.20 (d, 1H), 8.35 (s, 1H), 8.47 (s, 2H), 9.28 (s, 1H), 12.40 (s, 1H).

Example 23

2-(3-Fluorophenyl)pyrimidine-5-carboxylicacid-[5-fluoro-3-(morpholine-4-sulfonyl)indol-1-yl]amide

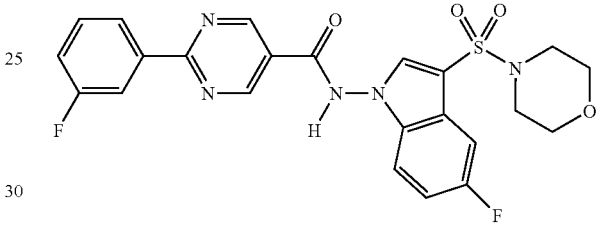

Step 1: A solution of 5-fluoro-3-chlorosulfonyl-1-(toluene-4-sulfonyl)-1H-indole (1 g) in DCM is added to a solution of morpholine (2.26 mL) in water (50 mL) and stirred at rt for 5 h. The organic phase is separated and washed water, brine and dried (MgSO$_4$), filtered and concentrated in vacuo to afford 5-fluoro-3-(morpholine-4-sulfonyl)-1-(toluene-4-sulfonyl)-1H-indole (1.3 g, 100%). MS: 439 (M+H).

Step 2: A solution of 5-fluoro-3-(morpholine-4-sulfonyl)-1-(toluene-4-sulfonyl)-1H-indole (1.3 g) in MeOH (50 mL)/5 N KOH (3 mL) is heated to reflux for 1 h. The reaction mixture is concentrated in vacuo. The residue is diluted with water (30 mL) and acidified with 10 N aqueous HCl to pH 4. The mixture is extracted with EtOAc. The organic layer washed with water, brine and dried (MgSO$_4$), filtered and concentrated in vacuo to afford 5-fluoro-3-(morpholine-4-sulfonyl)-1H-indole (0.8 g, 95%) as a solid. MS: 285 (M+H).

Step 3: Following procedures similar to those of Example 21, step 5, but substituting 5-fluoro-3-(morpholine-4-sulfonyl)-1H-indole for 5-fluoro-1H-indole-3-sulfonic acid dimethylamide, and the product is purified by silica gel chromatography eluting with 20% EtOAc, there is prepared 1-amino-5-fluoro-3-(morpholine-4-sulfonyl)-1H-indole (16%) as a solid. MS: 300 (M+H).

Step 4: Following procedures similar to those of Example 21, step 6, but substituting 1-amino-5-fluoro-3-(morpholine-4-sulfonyl)-1H-indole for 1-amino-5-fluoro-1H-indole-3-sulfonic acid dimethylamide, there is prepared 2-(3-fluorophenyl)pyrimidine-5-carboxylicacid-[5-fluoro-3-(morpholine-4-sulfonyl)indol-1-yl]amide (27%) as a solid. MS: 500 (M+H). $^1$H NMR (300 MHz, DMSO-d$_6$): δ 2.95 (m, 4H), 3.67 (m, 4H), 7.25-7.35 (m, 1H), 7.45-7.55 (m, 1H), 7.57-7.60 (dd, 1H), 7.62-7.72 (q, 1H), 7.75-7.80 (q, 1H), 8.20 (d, 1H), 8.35-8.40 (d, 1H), 8.41 (s, 1H), 9.45 (s, 2H), 12.6 (s, 1H).

Example 24

2-(3-Fluorophenyl)-4-methylpyrimidine-5-carboxylic acid-[5-fluoro-3-(morpholine-4-sulfonyl) indol-1-yl]amide

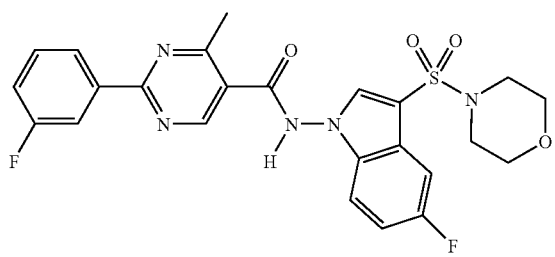

Following procedures similar to those of Example 22, but substituting 1-amino-5-fluoro-3-(morpholine-4-sulfonyl)-1H-indole for 1-amino-5-fluoro-1H-indole-3-sulfonic acid dimethylamide, there is prepared 2-(3-fluorophenyl)-4-methylpyrimidine-5-carboxylic acid-[5-fluoro-3-(morpholine-4-sulfonyl)indol-1-yl]amide (48%) as a solid. MS: 512 (M−H). $^1$H NMR (300 MHz, DMSO-d$_6$): δ 2.80 (s, 3H), 2.95 (m, 4H), 3.67 (m, 4H), 7.25-7.35 (m, 1H), 7.45-7.55 (m, 1H), 7.57-7.60 (m, 1H), 7.62-7.72 (m, 1H), 7.75-7.80 (m, 1H), 8.15-8.20 (d, 1H), 8.30-8.35 (d, 1H), 8.45 (s, 1H), 9.30 (s, 1H), 12.4 (s, 1H).

Example 25

2-(3-Fluorophenyl)pyrimidine-5-carboxylic acid-[5-fluoro-3-sulfamoylindol-1-yl)amide

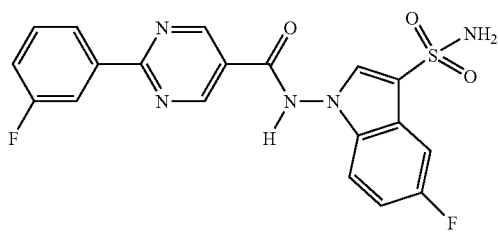

Step 1: A solution of 2-(3-fluorophenyl)pyrimidine-5-carboxylic acid-(5-fluoroindol-1-yl)amide (0.35 g,) in dry CH$_3$CN (20 mL) is treated with chlorosulfonic acid (0.5 mL) and stirred at rt for 24 h. The reaction mixture is poured onto ice/water (150 mL) and extracted with EtOAc. The organic layer is washed with water, brine and dried (MgSO$_4$), filtered and concentrated in vacuo to afford 5-fluoro-1-{[2-(3-fluorophenyl)pyrimidine-5-carbonyl]amino}-1H-indole-3-sulfonyl chloride (0.43 g, 95%). MS: 449 (M+H).

Step 2: A solution of 5-fluoro-1-{[2-(3-fluorophenyl)pyrimidine-5-carbonyl]amino}-1H-indole-3-sulfonyl chloride (0.14 g) in DCM (20 mL) is treated with a solution of aqueous ammonia solution (28%-5 mL) in water (15 mL) and stirred at rt for 24 h. The reaction mixture is acidified with 10 N aqueous HCl to pH ~3 and extracted with DCM. The organic layer is washed with water and brine, dried (MgSO$_4$), filtered and concentrated in vacuo. The residue is purified by silica gel chromatography eluting with 50% EtOAc in heptane to afford 2-(3-fluorophenyl)pyrimidine-5-carboxylic acid-[5-fluoro-3-sulfamoylindol-1-yl)amide (10 mg, 8%) as a solid. MS: 430 (M+H). $^1$H NMR (300 MHz, DMSO-d$_6$): δ 7.20-7.30 (m, 1H), 7.40-7.50 (m, 2H), 7.60-7.72 (m, 2H), 8.10 (s, 1H), 8.19-8.22 (d, 1H), 8.33-8.37 (d, 1H), 9.44 (s, 1H), 12.45 (s, 1H).

Example 26

2-(3-Fluorophenyl)pyrimidine-5-carboxylic acid-[5-fluoro-3-methylsulfamoyl)indol-1-yl)amide

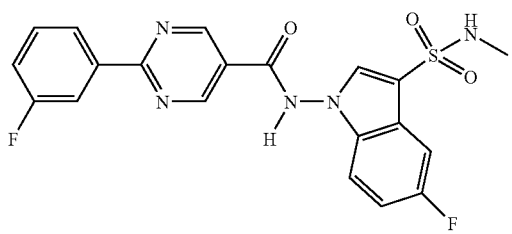

Following procedures similar to those of Example 25, but substituting 40% aqueous methylamine for aqueous ammonia solution, there is prepared 2-(3-fluorophenyl)pyrimidine-5-carboxylic acid-[5-fluoro-3-methylsulfamoyl)indol-1-yl)amide (60%) as a solid. MS: 444 (M+H). $^1$H NMR (300 MHz, DMSO-d$_6$): δ 2.45 (d, 3H), 7.20-7.30 (m, 1H), 7.40-7.50 (m, 2H), 7.60-7.70 (m, 3H), 8.19-8.22 (d, 1H), 8.24 (s, 1H), 8.34-8.37 (d, 1H), 9.44 (s, 1H), 12.50 (s, 1H).

Example 27

2-(3-Fluorophenyl)pyrimidine-5-carboxylic acid-[5-fluoro-3-(2-morpholin-4-ylethylsulfamoyl)indol-1-yl)amide

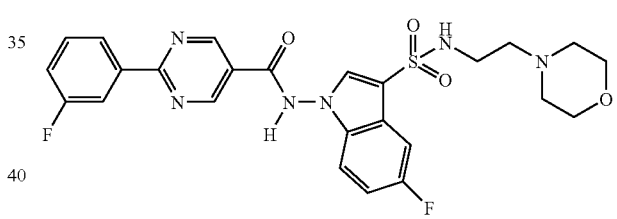

Following procedures similar to those of Example 25, but substituting an aqueous solution of 2-(morpholin-4-yl)ethylamine for the aqueous ammonia solution, there is prepared 2-(3-fluorophenylpyrimidine-5-carboxylic acid-[5-fluoro-3-(2-morpholin-4-ylethylsulfamoyl)indol-1-yl)amide (35%). MS: 543 (M+H). $^1$H NMR (300 MHz, DMSO-d$_6$): δ 2.20-2.38 (m, 6H), 2.89-2.95 (q, 2H), 3.40-3.50 (s, 4H), 7.20-7.30 (m, 1H), 7.42-7.55 (m, 2H), 7.63-7.70 (m, 3H), 8.19-8.22 (d, 1H), 8.26 (s, 1H), 8.34-8.37 (d, 1H), 9.44 (s, 2H), 12.40-12.60 (s, 1H).

Example 28

2-(3-Fluorophenyl)-4-methylpyrimidine-5-carboxylic acid-[5-fluoro-3-methylsulfamoyl)indol-1-yl) amide

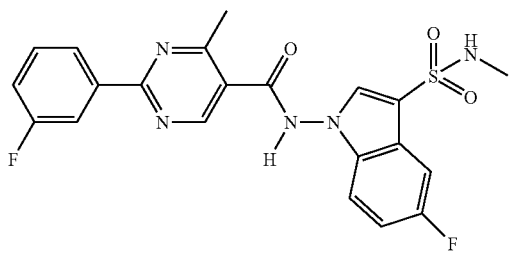

Step 1: A solution 2-(3-fluorophenyl)-4-methylpyrimidine-5-carboxylic acid-(5-fluoroindol-1-yl)amide (1 g, 2.75 mmol) in dry CH$_3$CN is cooled to 0° C. and treated drop wise with chlorosulfonic acid (0.55 mL) and stirred for 2 hours. The precipitated solid is filtered off and washed with ether to afford 5-fluoro-1-{[2-(3-fluorophenyl)-4-methylperimidine-5-carbonyl]amino}-1H-indole-3-sulfonic acid (1.06 g, 87%) as an off-white solid. MS: 443 (MH−).

Step 2: To a suspension of 5-fluoro-1-{[2-(3-fluorophenyl)-4-methylpyrimidine-5-carbonyl]amino}-1H-indole-3-sulfonic acid (1.06 g) in DCM (60 mL) at 0° C. is added dry DMF (10 drops). Oxalyl chloride (1.05 mL) is added drop wise and the mixture is stirred at 0° C. for 3 h. The mixture is filtered and the collected solid is washed with ether to afford 5-fluoro-1-{[2-(3-fluorophenyl)-4-methylpyrimidine-5-carbonyl]amino}-1H-indole-3-sulfonyl chloride (0.94 g). MS: 461 (M−H)

Step 3: Following procedures similar to those of Example 25, step 2, but substituting 40% aqueous methylamine for the aqueous ammonia solution, and substituting 5-fluoro-1-{[2-(3-fluorophenyl)-4-methylpyrimidine-5-carbonyl]amino}-1H-indole-3-sulfonyl chloride for 5-fluoro-1-{[2-(3-fluorophenyl)pyrimidine-5-carbonyl]amino}-1H-indole-3-sulfonyl chloride, there is prepared 2-(3-fluorophenyl)-4-methylpyrimidine-5-carboxylic acid-[5-fluoro-3-methylsulfamoyl)indol-1-yl)amide (40 mg, 35%) as a solid. MS: 456 (M−H); $^1$H NMR (300 MHz, DMSO-d$_6$): δ 2.45 (d, 3H), 2.80 (s, 3H), 7.20-7.30 (m, 1H), 7.40-7.50 (m, 2H), 7.60-7.70 (m, 3H), 8.17-8.20 (d, 1H), 8.30-8.35 (d, 2H), 9.28 (s, 1H), 12.30 (s, 1H).

Example 29

2-(3-Fluorophenyl)-4-methylpyrimidine-5-carboxylic acid-{5-fluoro-[(3-tetrahydropyran-4-ylmethyl)sulfamoyl]indol-1-yl}amide

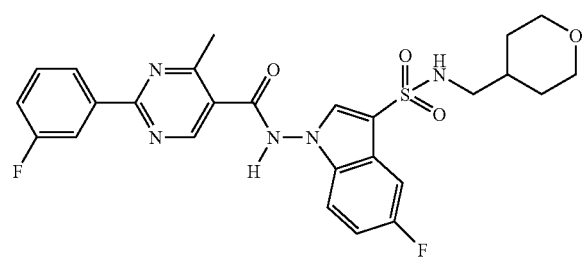

Following procedures similar to those of Example 25, step 2, but substituting an aqueous solution of 4-aminomethyltetrahydropyran for the aqueous ammonia solution, and substituting 5-fluoro-1-{[2-(3-fluorophenyl)-4-methylpyrimidine-5-carbonyl]amino}-1H-indole-3-sulfonyl chloride for 5-fluoro-1-{[2-(3-fluorophenyl)pyrimidine-5-carbonyl]amino}-1H-indole-3-sulfonyl chloride, there is prepared 2-(3-fluorophenyl)-4-methylpyrimidine-5-carboxylic acid-{5-fluoro-[(3-tetrahydropyran-4-ylmethyl)sulfamoyl]indol-1-yl}amide as a solid. MS: 542 (M+H); $^1$H NMR (300 MHz, DMSO-d$_6$): δ 1.00-1.15, (m, 2H), 1.50-1.70, (m, 3H), 2.60-2.70, (t, 2H), 2.80, (s, 1H), 3.1-3.2, (t, 2H), 3.70-3.80, (dd, 2H), 7.20-7.30, (m, 1H), 7.40-7.50, (m, 1H), 7.60-7.70, (m, 4H), 8.16-8.20, (d, 1H), 8.28-8.34 (d, 2H), 9.28, (s, 1H), 12.25, (s, 1H).

Example 30

2-(3-Fluorophenyl)-4-methylpyrimidine-5-carboxylic acid-[5-fluoro-3-(2-morpholin-4-ylethylsulfamoyl)indol-1-yl)amide

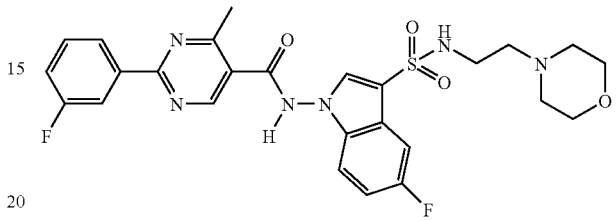

Following procedures similar to those of Example 25, step 2, but substituting an aqueous solution of 2-(morpholin-4-yl)ethylamine for the aqueous ammonia solution, and substituting 5-fluoro-1-{[2-(3-fluorophenyl)-4-methylpyrimidine-5-carbonyl]amino}-1H-indole-3-sulfonyl chloride for 5-fluoro-1-{[2-(3-fluorophenyl)pyrimidine-5-carbonyl]amino}-1H-indole-3-sulfonyl chloride, there is prepared 2-(3-fluorophenyl)-4-methylpyrimidine-5-carboxylic acid-[5-fluoro-3-(2-morpholin-4-ylethylsulfamoyl)indol-1-yl)amide (58%) MS: 557 (M+H); $^1$H NMR (300 MHz, DMSO-d$_6$): δ 2.20-2.30 (s, 4H), 2.30-2.40 (t, 2H), 2.80 (s, 3H), 2.89-2.95 (q, 2H), 3.40-3.50 (s, 4H), 7.20-7.30 (m, 1H), 7.42-7.55 (m, 2H), 7.63-7.70 (m, 3H), 8.17-8.20 (d, 1H), 8.32-8.35 (d, 2H), 9.28 (s, 2H), 12.25-12.30 (s, 1H).

Example 31

2-(3-Fluorophenyl)pyrimidine-5-carboxylic acid-(4-fluoroindol-1-yl)amide

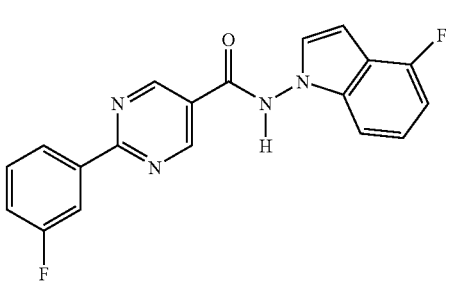

Step 1: The crude product of 1-amino-4-fluoroindole is prepared according to the procedures described in J. Hymes et al., J.O.C., (2004), 69, 1368-1371. The crude product is then purified by silica gel chromatography eluting with 30% DCM in heptane to afford 1-amino-4-fluoroindole (43%). MS: 151 (M+H).

Step 2: A solution of 2-(3-fluorophenyl)-pyrimidine-5-carboxylic acid (0.33 g), HATU (0.67 g) and hydroxyazabenzotriazole (0.26 g) in dry DMF (15 mL) is stirred at rt for 30 min under N$_2$. A solution of 1-amino-4-fluoroindole (0.24 g) in dry DMF (5 mL) is added followed by the addition of DIPEA (0.39 mL). The mixture is stirred at 80° C. for 24 h, cooled to rt, and then concentrated in vacuo. The residue is dissolved in EtOAc and washed with water, brine and dried (MgSO₄), filtered and concentrated in vacuo. The residue is purified by silica gel chromatography eluting with 60% DCM/heptane to afford 2-(3-fluorophenyl)pyrimidine-5-carboxylic acid-(4-fluoroindol-1-yl)amide (0.24 g, 53%) as a solid. MS: 351 (M+H); ¹H NMR (300 MHz, DMSO-d₆): δ 6.64 (d, 1H), 6.89-6.92 (q, 1H), 7.15-7.22 (m, 1H), 7.31-7.33 (d, 1H), 7.46-7.52 (m, 1H), 7.56 (d, 1H), 7.63-7.70 (q, 1H), 8.18-8.23 (d, 1H), 8.34-8.37 (d, 1H), 9.45 (s, 2H), 12.30 (s, 1H). IC₅₀=11 nM.

Example 32

2-(3-Fluorophenyl)-4-methylpyrimidine-5-carboxylic acid-(4-fluoroindol-1-yl)amide

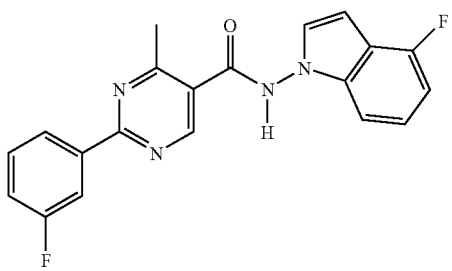

Following procedures similar to those of Example 31, step 2, but substituting 2-(3-fluorophenyl)-4-methylpyrimidine-5-carboxylic acid for 2-(3-fluorophenyl)-pyrimidine-5-carboxylic acid, there is prepared 2-(3-fluorophenyl)-4-methylpyrimidine-5-carboxylic acid-(4-fluoroindol-1-yl)amide (63%) as a solid. MS: 365 (M−H); ¹H NMR (300 MHz, DMSO-d₆): δ 2.75 (σ, 3H), 6.61 (d, 1H), 6.86-6.92 (q, 1H), 7.15-7.22 (m, 1H), 7.30-7.32 (d, 1H), 7.40-7.46 (m, 1H), 7.56-7.65 (m, 2H), 8.13-8.16 (d, 1H), 8.28-8.31 (d, 1H), 9.21 (s, 1H), 12.05 (s, 1H).

Example 33

2-(Pyridin-2-yl)-pyrimidine-5-carboxylic acid-(4-fluoroindol-1-yl)amide

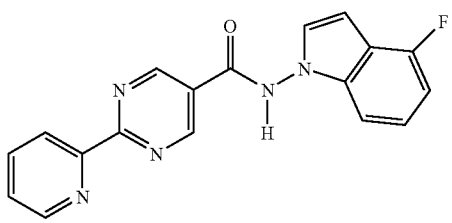

A suspension of 2-(pyridine-2-yl)-pyrimidine-5-carbonyl chloride (0.44 g) in EtOAc (20 mL) is added portion wise to a mixture of 1-amino-4-fluoroindole (0.30 g) and K₂CO₃ (0.276 g) in EtOAc (10 mL)/water (20 mL) and the resulting mixture is stirred at rt for 24 h. The aqueous phase is separated and extracted twice with EtOAc. The combined organic layer is washed with water and brine, dried (MgSO₄), filtered and concentration in vacuo. The residue is purified by silica gel chromatography eluting with EtOAc to afford 2-(pyridin-2-yl)pyrimidine-5-carboxylic acid-(4-fluoroindol-1-yl)amide (0.115 g, 17%) as a solid. MS: 334 (M+H); ¹H NMR (300 MHz, DMSO-d₆): δ 6.65 (d, 1H), 6.89-6.95 (q, 1H), 7.16- 7.23 (m, 1H), 7.32-7.35 (d, 1H), 7.57 (d, 1H), 7.57-7.64 (m, 1H), 8.02-8.08 (t, 1H), 8.50-8.52 (d, 1H), 8.82-8.83 (d, 1H), 9.49 (s, 2H), 12.30 (s, 1H).

Example 34

2-(Pyridin-2-yl)-4-methylpyrimidine-5-carboxylic acid-(4-fluoroindol-1-yl)amide

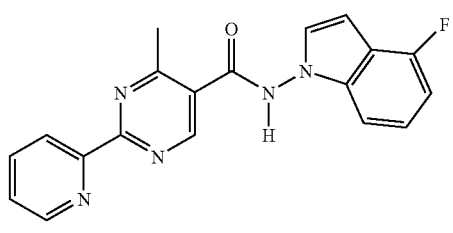

A solution of 2-(pyridine-2-yl)-4-methylpyrimidine-5-carboxylic acid (0.11 g) and HATU (0.19 g) in dry DMF (7 mL) is treated with DIPEA (0.09 mL) and stirred at rt under N₂ for 30 min. 1-Amino-4-fluoroindole (0.112 g) is added and the mixture is stirred at rt for 24 h. The mixture is concentrated in vacuo. The residue is dissolved in EtOAc, washed with water and brine and dried (MgSO₄), filtered, and concentration in vacuo. The residue is purified by silica gel chromatography eluting with 75% EtOAc to afford 2-(pyridin-2-yl)-4-methylpyrimidine-5-carboxylic acid-(4-fluoroindol-1-yl)amide (0.085 gms, 50%). MS: 348 (M+H); ¹H NMR (300 MHz, DMSO-d₆): δ 2.82 (s, 3H), 6.65 (d, 1H), 6.93-6.97 (q, 1H), 7.19-7.26 (m, 1H), 7.35-7.38 (d, 1H), 7.62 (d, 1H), 7.74-7.78 (m, 1H), 8.20-8.25 (t, 1H), 8.58-8.61 (d, 1H), 8.85-8.86 (d, 1H), 9.33 (s, 1H), 12.15 (s, 1H).

Example 35

2-Phenyl-pyrimidine-5-carboxylic acid [6-(4-fluorophenyl)-3-oxo-2,5-dihydro-3H-1,2,4-triazin-4-yl]-amide

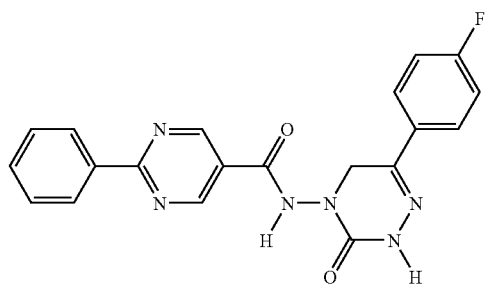

Step 1: Following procedures described in F. Chau, J.-C. Malanda, and R. Milcent J. Heterocyclic Chem. 1997, 34, 1603-1606, there is prepared 5-methyl-3H-1,3,4-oxadiazol-2-one (24%). MS: 101 (M+H); ¹H NMR (300 MHz, CDCl₃) δ 9.76 (br s, 1H), 2.28 (s, 3H).

Step 2: To a solution of 5-methyl-3H-1,3,4-oxadiazol-2-one (2.77 g, 27.7 mmol) in MeOH (25 mL) is added 25 wt % NaOMe solution in methanol (6.4 mL, 27.9 mmol) and the mixture is stirred at rt for 10 min. The mixture is concentrated in vacuo and the residue is added to a solution of 2-chloro-4'-fluoroacetophenone (4.71 g, 27.3 mmol) and tetrabutylammonium bromide (0.174 g, 0.54 mmol) in CHCl₃ (16 mL).

The mixture is heated to reflux for 2.5 h under N₂. The reaction mixture is then allowed to cool and stirred overnight at ambient temperature. The resultant slurry is filtered through qualitative filter paper and the filtrate is concentrated to obtain a liquid. This liquid is further filtered through a pad of silica gel, eluting with 1:1 EtOAc/DCM. The filtrate is concentrated in vacuo to afford 3-[2-(4-fluoro-phenyl)-2-oxo-ethyl]-5-methyl-3H-1,3,4-oxadiazol-2-one (~100%). MS: 237 (M+H); ¹H NMR (300 MHz, CDCl₃) δ 7.90-8.10 (m, 2H), 7.10-7.22 (m, 2H), 5.08 (s, 2H), 2.29 (s, 3H).

Step 3: To a solution of 3-[2-(4-fluoro-phenyl)-2-oxo-ethyl]-5-methyl-3H-1,3,4-oxadiazol-2-one (2.3 g, 9.7 mmol) in a mixture of 2-propanol (12 mL) and water (0.3 mL) is added hydrzazine monohydrate (0.71 mL, 14.6 mmol). The reaction mixture is heated to reflux under N₂ for 14.5 h, and then a solution of oxalic acid (0.3 g, 3.3 mmol) in 2-propanol (6 mL) is added. The resulting precipitate is removed by filtration. The filtrate is concentrated to ~35 mL and then chilled to afford N-[6-(4-fluoro-phenyl)-3-oxo-2,5-dihydro-3H-1,2,4-triazin-4-yl]-acetamide as a crystal that is collected by filtration (0.83 g, 34%). MS: 251 (M+H); ¹H NMR (300 MHz, DMSO-d₆) δ 10.37 (s, 1H), 10.16 (s, 1H), 7.65-7.79 (m, 2H), 7.16-7.27 (m, 2H), 4.57 (s, 2H), 1.90 (s, 3H).

Step 4: To a slurry of N-[6-(4-fluoro-phenyl)-3-oxo-2,5-dihydro-3H-1,2,4-triazin-4-yl]-acetamide (0.48 g, 1.9 mmol) in MeOH (5 mL) is added 37% aqueous HCl. The mixture is heated to reflux for 3 h, and then cooled to rt. The mixture is basified with 1 M aqueous NaOH to pH ~12. The resulting precipitate is collected by filtration and dried to afford 4-amino-6-(4-fluoro-phenyl)-4,5-dihydro-2H-1,2,4-triazin-3-one (0.35 g, 88%). MS: 209 (M+H); ¹H NMR (300 MHz, DMSO-d₆) δ 10.17 (s, 1H), 7.67-7.75 (m, 2H), 7.18-7.29 (m, 2H), 4.75 (s, 2H), 4.45 (s, 2H).

Step 5: To a slurry of 4-amino-6-(4-fluoro-phenyl)-4,5-dihydro-2H-1,2,4-triazin-3-one (0.26 g, 1.23 mmol), 2-phenyl-pyrimidine-5-carboxylic acid (0.25 g, 1.23 mmol), and 1-(3-dimethylaminopropyl)-3-ethylcarbodiimide hydrochloride (0.37 g, 1.94 mmol) in DMF (12 mL) is added Et₃N (0.2 mL, 1.435 mmol) under N₂ and the reaction mixture is stirred at rt for 49 h. The mixture is diluted with EtOAc (120 mL), and washed successively with saturated aqueous NH₄Cl (2×50 mL), water (2×50 mL), and saturated aqueous NaCl (50 mL). The organic phase is dried (MgSO₄), filtered, and concentrated in vacuo. The residue is triturated with EtOH (30 mL) to afford 2-phenyl-pyrimidine-5-carboxylic acid [6-(4-fluoro-phenyl)-3-oxo-2,5-dihydro-3H-1,2,4-triazin-4-yl]-amide (0.12 g, 25%). MS: 391 (M+H); ¹H NMR (300 MHz, DMSO-d₆) δ 11.25 (s, 1H), 10.58 (s, 1H), 9.31 (s, 2H), 8.47 (dd, J=7.7, 1.8 Hz, 2 H), 7.70-7.86 (m, 2 H), 7.49-7.67 (m, 3H), 7.18-7.34 (m, 2H), 4.77.

Example 36

2-(3-Fluoro-phenyl)-pyrimidine-5-carboxylic acid-[4-(2-hydroxy-ethyl)-piperazin-1-yl]-amide

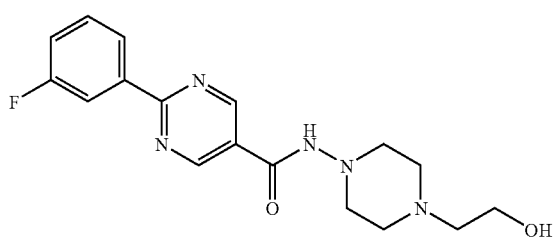

To a solution of 2-(3-fluoro-phenyl)-pyrimidine-5-carboxylic acid (0.28 g, 1.4 mmol) in anhydrous DCM (10 mL) at 0° C. is added the oxalyl chloride (0.18 mL, 1.4 mmol) followed by the addition of DMF (0.11 mL). The mixture is stirred at 0° C. for 30 min, and then allowed to warm up to rt and stirred for 30 min. The mixture is concentrated in vacuo. The residue is dissolved in anhydrous DCM (10 mL). 2-(4-Amino-piperazin-1-yl)-ethanol (0.145 g, 1 mmol) is added at rt followed by the addition of NMP (0.19 mL, 2 mmol). The mixture is stirred at rt for 2 h and the mixture is then concentrated in vacuo. The residue is triturated in Et₂O and the resulting solid is collected by filtration to afford 2-(3-fluoro-phenyl)-pyrimidine-5-carboxylic acid-[4-(2-hydroxy-ethyl)-piperazin-1-yl]-amide (0.16 g). MS: 346 (M+H).

Example 37

2-(3-Fluoro-phenyl)-pyrimidine-5-carboxylic acid (6-methyl-3-oxo-2,5-dihydro-3H-[1,2,4]triazin-4-yl)-amide

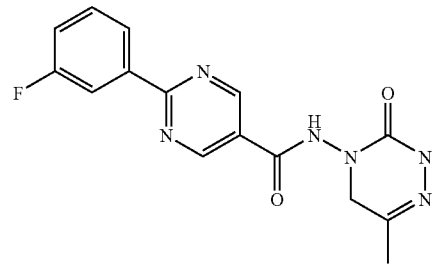

To a solution of 2-(3-fluoro-phenyl)-pyrimidine-5-carboxylic acid (0.317 g, 1.45 mmol) in anhydrous DMF (5 mL) is added 4-amino-6-methyl-4,5-dihydro-2H-[1,2,4]triazin-3-one (0.206 g, 1.45 mmol) followed by the addition of DMTMM (0.421 g, 1.52 mmol). The mixture is stirred at rt overnight. The mixture is partitioned between a saturated aqueous NaHCO₃ solution and EtOAc. The organic phase is separated, dried (MgSO₄), filtered and concentrated in vacuo to afford 2-(3-Fluoro-phenyl)-pyrimidine-5-carboxylic acid (6-methyl-3-oxo-2,5-dihydro-3H-[1,2,4]triazin-4-yl)-amide (0.306 g) as a solid. MS: 329 (M+H).

Example 38

2-(3-Fluoro-phenyl)-pyrimidine-5-carboxylic acid[5-fluoro-3-(2-hydroxy-2-methyl-propyl)-indol-1-yl]-amide

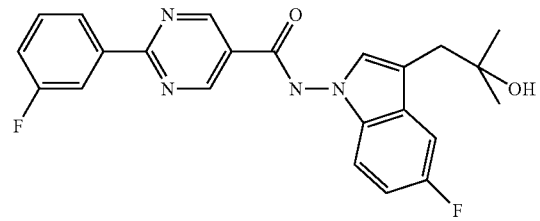

Step 1: A solution of (5-fluoro-1H-indol-3-yl)-acetic acid (1 g, 5.2 mmol) in MeOH (20 mL) is treated with sulfuric acid (20 µL) and stirred at rt for 1 h. This mixture is treated with 10% aqueous NaHCO₃ (200 µL) and then concentrated in vacuo to afford (5-fluoro-1H-indol-3-yl)-acetic acid methyl ester, which is used in the next step without further purification. MS: 208 (M+H); ¹H NMR (300 MHz, CD₃OD): δ 3.68 (s, 3H), 3.72 (s, 2H), 6.86 (m, 1H), 7.16 (m, 1H), 7.21 (s, 1H), 7.28 (m, 1H).

Step 2: The above (5-fluoro-1H-indol-3-yl)-acetic acid methyl ester is dissolved in THF (40 mL), cooled to 0° C., and treated with MeMgBr (18.5 mL, 26 mmol, 1.4 M in PhMe/THF (3:1)). The mixture is stirred at rt for 12 h. Additional MeMgBr (5 mL, 7 mmol) is added and the mixture is stirred at rt for 6 h. The mixture is poured onto ice/water, extracted with EtOAc (100 mL), dried (Na₂SO₄), filtered and concentrated in vacuo. The residue is purified by silica gel chromatography eluting with 20%-70% EtOAc in heptane to afford 1-(5-fluoro-1H-indol-3-yl)-2-methyl-propan-2-ol (0.65 g, 60%). MS: 208 (M+H); ¹H NMR (300 MHz, CDCl₃): δ 1.28 (s, 6H), 2.87 (s, 2H), 6.94 (m, 1H), 7.14 (m, 1H), 7.26-7.30 (m, 2H).

Step 3: A solution of 1-(5-fluoro-1H-indol-3-yl)-2-methyl-propan-2-ol (207 mg, 1 mmol) in DMF (10 mL) is cooled to 0° C., treated with NaH (600 mg, 15 mmol, 60% in mineral oil) and stirred for 30 min. H₂NOSO₃H (565 mg, 5 mmol) is added portion wise, and the mixture is warmed to rt over 2 h. The mixture is diluted with EtOAc (100 mL), quenched with water, extracted with EtOAc, dried (Na₂SO₄), filtered and concentrated in vacuo to afford 1-(1-amino-5-fluoroindol-3-yl)-2-methyl-propan-2-ol, which is used in the next step without further purification.

Step 4: A solution of 2-(3-fluoro-phenyl)-pyrimidine-5-carboxylic acid (175 mg, 0.8 mmol) in DCM (5 mL) is treated with DMF (20 μL) and ClCOCOCl (348 μL, 4 mmol), and stirred at rt for 3 h. Toluene (10 mL) is added and the mixture is concentrated in vacuo. The residue is added to a solution of the above 1-(1-amino-5-fluoroindol-3-yl)-2-methyl-propan-2-ol and Na₂CO₃ (1 g) in EtOAc/H₂O (20 mL, 1:1). The mixture is stirred at rt for 12 h. The mixture is then diluted with saturated aqueous Na₂CO₃, extracted with EtOAc. The organic layer is separated, dried (Na₂SO₄), filtered and concentrated in vacuo. The residue is purified by silica gel chromatography eluting with 30%-50% EtOAc in heptane to afford 2-(3-fluoro-phenyl)-pyrimidine-5-carboxylic acid[5-fluoro-3-(2-hydroxy-2-methyl-propyl)-indol-1-yl]-amide (160 mg, 50%). MS: 423 (M+H); ¹H NMR (300 MHz, DMSO-d₆): δ 1.14 (s, 6H), 2.77 (s, 2H), 7.03 (m, 1H), 7.33 (s, 1H), 7.35-7.55 (m, 3H), 7.65 (m, 1H), 8.21 (m, 1H), 8.36 (m, 1H), 9.43 (s, 2H).

Example 39

2-(3-Fluoro-phenyl)-4-methyl-pyrimidine-5-carboxylic acid [5-fluoro-3-(2-hydroxy-2-methyl-propyl)-indol-1-yl]-amide

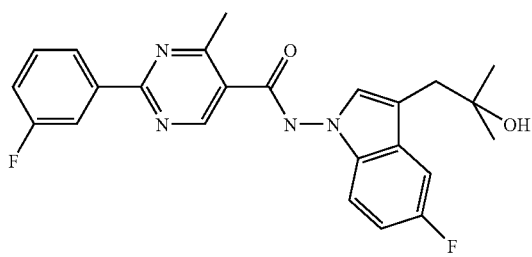

A solution of 2-(3-fluoro-phenyl)-4-methyl-pyrimidine-5-carboxylic acid (250 mg, 1.07 mmol) in DCM (10 mL) is cooled to 0° C., treated with DMF (20 μL) and ClCOCOCl (280 μL, 3.21 mmol), and stirred for 20 min. Toluene (10 mL) is added and the mixture is concentrated in vacuo. The residue is dissolved in pyridine (10 mL) and treated with DMAP (5 mg) and 1-(1-amino-5-fluoroindol-3-yl)-2-methyl-propan-2-ol (0.72 mmol). The mixture is stirred at rt for 12 h. The mixture is diluted with saturated aqueous Na₂CO₃, extracted with EtOAc. The organic layer is separated, dried (Na₂SO₄), filtered and concentrated in vacuo. The residue is purified by silica gel chromatography eluting with 20%-60% EtOAc in heptane to afford 2-(3-fluoro-phenyl)-4-methyl-pyrimidine-5-carboxylic acid [5-fluoro-3-(2-hydroxy-2-methyl-propyl)-indol-1-yl]-amide (218 mg, 70%). MS: 437 (M+H); ¹H NMR (300 MHz, DMSO-d₆): δ 1.14 (s, 6H), 2.77 (s, 2H), 3.29 (s, 3H), 7.03 (m, 1H), 7.37 (s, 1H), 7.35-7.55 (m, 3H), 7.65 (m, 1H), 8.19 (m, 1H), 8.34 (m, 1H), 9.22 (s, 1H).

Example 40

4-Methyl-2-pyridin-2-yl-pyrimidine-5-carboxylic acid [5-fluoro-3-(2-hydroxy-2-methyl-propyl)-indol-1-yl]-amide

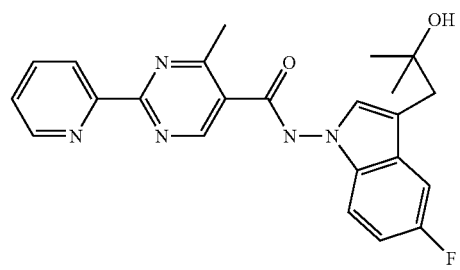

A solution of 4-methyl-2-pyridin-2-yl-pyrimidine-5-carboxylic acid (748 mg, 3.48 mmol) in DMF (30 mL) is treated with HATU (1.3 g, 3.48 mmol) and DIPEA (1.2 mL, 6.96 mmol), and the mixture is stirred at rt for 30 min. 1-(1-Amino-5-fluoroindol-3-yl)-2-methyl-propan-2-ol (2.9 mmol) is added and the mixture is stirred at 80° C. for 12 h. The mixture is diluted with EtOAc, washed with saturated aqueous NH₄Cl and saturated aqueous Na₂CO₃, dried (Na₂SO₄), filtered and concentrated in vacuo to afford 4-methyl-2-pyridin-2-yl-pyrimidine-5-carboxylic acid [5-fluoro-3-(2-hydroxy-2-methyl-propyl)-indol-1-yl]-amide (990 mg, 81%). MS: 420 (M+H); ¹H NMR (300 MHz, DMSO-d₆): δ 1.13 (s, 6H), 2.75 (s, 2H), 2.85 (s, 3H), 6.84 (m, 1H), 7.24 (m, 1H), 7.37 (m, 1H), 7.53 (m, 1H), 7.95 (s, 1H), 7.98 (m, 1H), 8.44 (m, 1H), 8.76 (m, 1H), 9.15 (s, 1H).

Example 41

2-(3-Fluoro-phenyl)-4-methyl-pyrimidine-5-carboxylic acid (3-cyano-5-fluoro-indol-1-yl)-amide

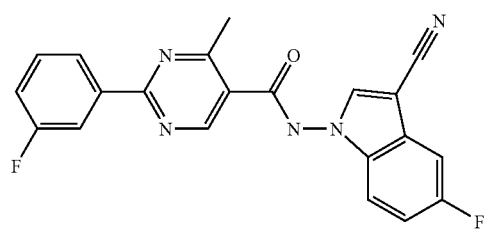

A solution of 2-(3-fluoro-phenyl)-4-methyl-pyrimidine-5-carboxylic acid (5-fluoro-indol-1-yl)-amide (300 mg, 0.82 mmol) in THF (8 mL) is cooled to 0° C., treated with chlorosulfonyl isocyanate (86 μL, 0.99 mmol) and the mixture is stirred at rt for 1 h. The mixture is treated with Et$_3$N (138 μL, 0.99 mmol) and stirred for 1 h. The mixture is diluted with brine, extracted with EtOAc. The organic layer is separated, dried (Na$_2$SO$_4$), filtered and concentrated in vacuo. The residue is purified by silica gel chromatography eluting with 25%-35% EtOAc in heptane to afford 2-(3-fluoro-phenyl)-4-methyl-pyrimidine-5-carboxylic acid (3-cyano-5-fluoro-indol-1-yl)-amide (120 mg, 38%). MS: 390 (M+H); $^1$H NMR (300 MHz, DMSO-d$_6$): δ 2.78 (s, 3H), 7.32 (m, 1H), 7.46 (m, 1H), 7.55 (m, 1H), 7.66 (m, 1H), 7.77 (m, 1H), 8.20 (m, 1H), 8.35 (m, 1H), 8.65 (s, 1H), 9.28 (s, 1H).

Example 42

2-(3-Fluoro-phenyl)-4-methyl-pyrimidine-5-carboxylic acid [5-fluoro-3-(1H-tetrazol-5-yl)-indol-1-yl]-amide

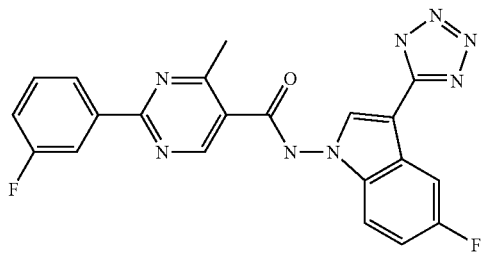

A solution of 2-(3-fluoro-phenyl)-4-methyl-pyrimidine-5-carboxylic acid (3-cyano-5-fluoro-indol-1-yl)-amide (120 mg, 0.31 mmol), TMSN$_3$ (62 μL, 0.465 mmol), and TBAF (0.155 μL, 0.155 mmol, 1 M in THF) in toluene (3 mL) is heated at 80° C. for 18 h. The mixture is cooled, diluted with EtOAc, and washed with 1 M HCl. The organic layer is extracted with Na$_2$CO$_3$. The aqueous layer is acidified to pH ~3 with 3 N aqueous HCl, extracted with EtOAc The organic layer is separated, dried (Na$_2$SO$_4$), filtered and concentrated in vacuo to afford 2-(3-fluoro-phenyl)-4-methyl-pyrimidine-5-carboxylic acid [5-fluoro-3-(1H-tetrazol-5-yl)-indol-1-yl]-amide (100 mg, 75%). MS: 433 (M+H); $^1$H NMR (300 MHz, DMSO-d$_6$): δ 2.81 (s, 3H), 7.28 (m, 1H), 7.47 (m, 1H), 7.67 (m, 1H), 7.73 (m, 1H), 8.01 (m, 1H), 8.21 (m, 1H), 8.33 (m, 1H), 8.36 (s, 1H), 9.33 (s, 1H). IC$_{50}$=5 nM.

Example 43

2-Phenyl-pyrimidine-5-carboxylic acid [1,2,4]triazol-4-ylamide

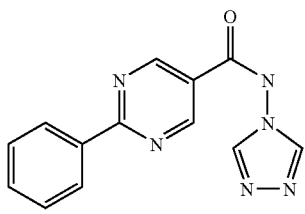

To a solution of 2-phenyl-pyrimidine-5-carboxylic acid (300 mg, 1.5 mmol) in DCM (10 mL) is added 1-[3-(dimethylamino)propyl-3-ethylcarbodiimide (316 mg, 1.65 mmol) and N-hydroxybenzotriazole (223 mg, 1.65 mmol) at rt and the mixture is stirred for 10 min. 4-Amino-4H-1,2,4-triazole (252 mg, 3 mmol) is added and the mixture is stirred at rt for 3 days. The resulting precipitate is filtered, washed with DCM and water, and dried in vacuum oven at 40° C. overnight to afford 2-phenyl-pyrimidine-5-carboxylic acid [1,2,4]triazol-4-ylamide (270 mg) as a solid. MS: 267 (M+H); $^1$H NMR (300 MHz, DMSO): δ=7.59 (m, 3H), 8.50 (d, 2H), 8.84 (s, 2H), 9.36 (s, 2H). IC$_{50}$=262.5 nM.

Example 44

2-phenyl-pyrimidine-5-carboxylic acid piperidin-1-Ylamide

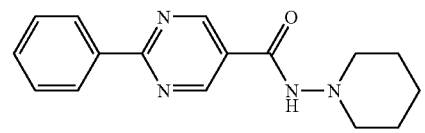

Method A: To a solution of 2-phenyl-pyrimidine-5-carboxylic acid (150 mg, 075 mmol) in DCM (10 mL) is added 1-[3-(dimethylamino)propyl-3-ethylcarbodiimide (158 mg, 0.83 mmol) and N-hydroxybenzotriazole (112 mg, 0.83 mmol) at rt and the mixture is stirred for 10 min. 1-Aminopiperidine (150 mg, 1.5 mmol) is added. The mixture is stirred at rt overnight. The mixture is washed with 2 N aqueous HCl (5 mL), saturated aqueous NaHCO$_3$, (5 mL), and water (5 mL), dried (Na$_2$SO$_4$), filtered and concentrated in vacuo. The residue is purified by silica gel chromatography eluting with 10% EtOAc in heptane to afford 2-phenyl-pyrimidine-5-carboxylic acid piperidin-1-ylamide (125 mg) as a solid. MS: 290 (M+H).

Method B: Following procedures similar to those of Example 127 but substituting piperadin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid piperadin-1-yl-amide (72%) as a solid. MS: 283 (M+H); $^1$H NMR (300 MHz, CDCl$_3$): δ 1.35-1.98 (m, 6H), 2.20-3.60 (m, 4H), 6.60-7.17 (d, N—H), 7.52 (s, 3H), 8.52 (s, 2H), 9.07-9.39 (d, 2H).

Example 45

2-Phenyl-pyrimidine-5-carboxylic acid N'-(2-fluoro-phenyl)-hydrazide

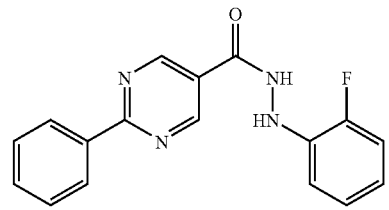

Following procedures similar to those of Example 44, but substituting (2-fluoro-phenyl)-hydrazine for 1-aminopiperidine, there is prepared 2-phenyl-pyrimidine-5-carboxylic acid N'-(2-fluoro-phenyl)-hydrazide as a solid. MS: 309

(M+H); ¹H NMR (300 MHz, CDCl₃): δ 6.68 (broad, 1H), 6.87 (m, 1H), 7.04 (m, 3H), 7.51 (m, 3H), 8.51 (m, 2H), 9.36 (s, 2H), 10.65 (broad, 1H). IC$_{50}$=12 nM.

Example 46

2-Phenyl-pyrimidine-5-carboxylic acid N'-ethyl-N'-tolyl-hydrazide

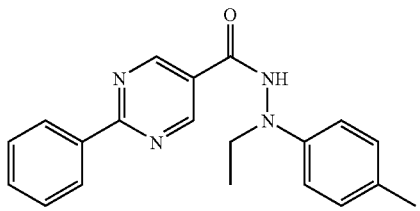

Following procedures similar to those of Example 44, but substituting N-ethyl-N-para-tolyl-hydrazine for 1-aminopiperidine, there is prepared 2-phenyl-pyrimidine-5-carboxylic acid N'-ethyl-N'-tolyl-hydrazide as a solid. MS: 333 (M+H); ¹H NMR (300 MHz, CDCl₃): δ=0.87 (t, 1H), 1.11 (t, 2H), 1.28 (t, 3H), 2.28 (d, 3H), 3.46 (q, 1H), 3.65(q, 1H), 6.84 (d, 1H), 6.94(d, 1H), 7.10(t, 2H), 7.52 (m, 3H), 8.47 (m, 2H), 9.12 (s, 1H0, 9.23 (s, 1H).

Example 47

2-Phenyl-pyrimidine-5-carboxylic acid (3-oxo-morpholin-4-yl)-amide

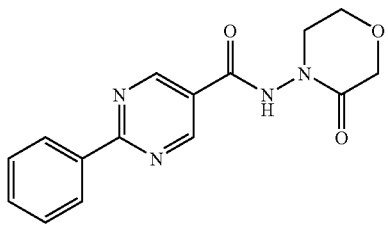

Following procedures similar to those of Example 44, but substituting 4-amino-morpholin-3-one for 1-aminopiperidine, there is prepared 2-phenyl-pyrimidine-5-carboxylic acid (3-oxo-morpholin-4-yl)-amide as a solid. MS: 299 (M+H); ¹H NMR (300 MHz, DMSO): δ=3.66 (m, 2H), 4.00 (m, 2H), 4.26 (s, 2H), 7.60 (m, 3H), 8.47 (m, 2H), 9.29(s, 2H), 11.27 (s, 1H). IC$_{50}$=55 nM.

Example 48

2-(5-Methyl-[1,2,4]oxadiazol-3-yl)-pyrimidine-5-carboxylic acid [4-(2-hydroxy-ethyl)-piperazin-1-yl]-amide

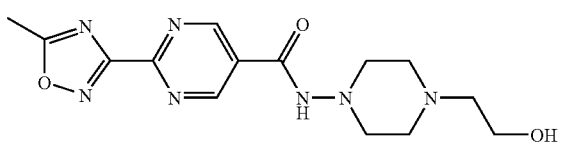

Step 1: To a solution of 2-methylsulfanyl-pyrimidine-5-carboxylic acid methyl ester 1 (1 g, 5.43 mmol) in DCM (60 mL) is added MCPBA (2.81 g, 16.29 mmol) portion wise at rt. The resulting solution is stirred at rt overnight. A solution of Na₂S₂O₃ (1.6 g) in water (60 mL) is added. The mixture is stirred at rt for 20 min. The layer is separated, and the water layer is extracted with DCM (2×20 mL). The combined DCM layer is washed with saturated NaHCO₃ (3×20 mL), dried (Na₂SO₄), filtered and concentrated in vacuo to afford 2-methanesulfonyl-pyrimidine-5-carboxylic acid methyl ester as a solid (1.05 g, 90%). MS: 217 (M+H); ¹H NMR (300 MHz, CDCl₃): δ 3.41 (s, 3H), 4.06 (s, 3H), 9.44 (s, 2H).

Step 2: To a solution of 2-methanesulfonyl-pyrimidine-5-carboxylic acid methyl ester 2 (2.5 g, 11.56 mmol) in DCM (30 mL) is added a solution of tetrabutylammonium cyanide (3.1 g, 11.56 mmol) in water (30 mL) slowly at rt. The mixture is stirred for 80 min. The mixture is washed with water (2×20 mL), dried (Na₂SO₄), filtered and concentrated in vacuo. The residue is purified by column chromatography eluting with 5-60% EtOAc in heptane to afford 2-cyano-pyrimidine-5-carboxylic acid methyl ester (1.16 g, 61%) as a solid. MS: 164 (M+H); ¹H NMR (300 MHz, CDCl₃): δ 4.05 (s, 3H), 9.37 (s, 2H).

Step 3: To a solution of 2-cyano-pyrimidine-5-carboxylic acid methyl ester 3 (1 g, 6.13 mmol) in MeOH (20 mL) at rt is added hydroxylamine hydrochloride (0.64 g, 9.2 mmol) and sodium acetate (0.76 g, 9.2 mmol). The resulting mixture is heated to reflux for 2 hours. The mixture is cooled to rt and concentrated in vacuo. Water (30 mL) is added to the residue, and the solid is filtered, and washed with water twice. The solid is dried in vacuum oven overnight to afford 2-(N-hydroxycarbamimidoyl)-pyrimidine-5-carboxylic acid methyl ester (1.09 g, 91%) as a solid. MS: 197 (M+H).

Step 4: To a solution of 2-(N-hydroxycarbamimidoyl)-pyrimidine-5-carboxylic acid methyl ester (900 mg, 4.59 mmol) in pyridine (15 mL) is added acetyl chloride (432 mg, 5.5 mmol) dropwise. The resulting solution is stirred at rt for 1 hour, and heated to reflux for 3 h. The solution is cooled to rt and concentrated in vacuo. Water (30 mL) is added to the residue, and the mixture is extracted with EtOAc (3×20 mL). The combined organic layer is washed with saturated NaHCO₃, dried (Na₂SO₄), filtered and concentrated in vacuo to afford 2-(5-methyl-[1,2,3]oxadiazo-3-yl)-pyrimidine-5-carboxylic acid methyl ester (900 mg, 89%) as a solid. MS: 221 (M+H).

Step 5: To a solution of 2-(5-methyl-[1,2,3]oxadiazo-3-yl)-pyrimidine-5-carboxylic acid methyl ester (900 mg) in MeOH (20 mL) is added a solution of LiOH (100 mg) in water (20 mL) at 0° C. The ice-bath is removed, and the mixture is stirred for another 10 min. The solvent is evaporated, and water (20 mL) is added. The water solution is washed with ether (2×20 mL), and acidified with 2 N HCl to pH 3. The resulting precipitate is filtered, washed with water and dried in vacuum oven overnight to afford 2-(5-methyl-[1, 2,4]oxadiazol-3-yl)-pyrimidine-5-carboxylic acid (350 mg, 37%) as a solid. MS: 207 (M+H); ¹H NMR (300 MHz, DMSO-d₆): δ 2.73 (s, 3H), 9.39 (s, 2H).

Step 6: Following procedures similar to those of Example 44, but substituting 2-(5-methyl-[1,2,4]oxadiazol-3-yl)-pyrimidine-5-carboxylic acid for 2-phenyl-pyriminde-5-carboxylic acid, and substituting 2-(4-amino-piperazin-1-yl)-ethanol for 1-aminopiperidine, there is prepared 2-(5-methyl-

[1,2,4]oxadiazol-3-yl)-pyrimidine-5-carboxylic acid [4-(2-hydroxy-ethyl)-piperazin-1-yl]-amide as a solid. MS: 334 (M+H). IC$_{50}$=461 nM.

Example 49

2-(5-Methyl-[1,2,4]oxadiazol-3-yl)-pyrimidine-5-carboxylic acid morpholin-4-ylamide

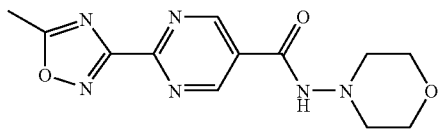

Following procedures similar to those of Example 44, but substituting 2-(5-methyl-[1,2,4]oxadiazol-3-yl)-pyrimidine-5-carboxylic acid for 2-phenyl-pyriminde-5-carboxylic acid, and substituting morpholine-4-ylamine for 1-aminopiperidine, there is prepared 2-(5-methyl-[1,2,4]oxadiazol-3-yl)-pyrimidine-5-carboxylic acid morpholin-4-ylamide as a solid. MS: 291 (M+H).

Example 50

2-Benzoyl-pyrimidine-5-carboxylic acid morpholin-4-ylamide

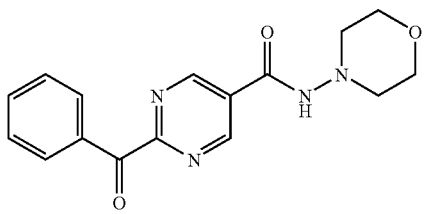

Step 1: 5-Bromo-2-chloropyrimidine (7.51 g, 38.83 mmol) is dissolved in DMSO (20 mL) is added to a mixture of NaCN (1.9 g, 38.83 mmol) and 1,4-diazabicyclo[2,2,2]octane (0.87 g, 7.77 mmol) in DMSO (10 mL) and water (20 mL). The mixture is stirred at rt overnight, and then water (100 mL) is added. The mixture is extracted with ether (3×100 mL). The combined organic layer is dried (Na$_2$SO$_4$), filtered and concentrated in vacuo to afford 5-bromo-pyrimidine-2-carbonitrile (6.28 g, 88%) as a solid. MS: 184 (M+H).

Step 2: 5-Bromo-pyrimidine-2-carbonitrile (2.5 g, 13.59 mmol) is dissolved ether (30 mL), and PhMgBr (3 ether solution, 13.59 mmol, 4.53 mL) is added dropwise at rt. The mixture is heated to reflux for 3 h under N$_2$, and then cooled to rt. THF (30 mL) is added followed by the addition of 2 N aqueous HCl (10 mL). The resulting solution is stirred at rt for 30 min, and water (30 mL) is added. The aqueous layer is extracted with EtOAc (3×20 mL). The combined organic layer is washed with saturated aqueous NaHCO$_3$ (15 mL), dried (Na$_2$SO$_4$), filtered and concentrated in vacuo. The residue is purified by silica gel chromatography eluting 70% EtOAc in heptane to afford (5-bromo-pyrimidine-2-yl)-phenyl-methanone (3.01 g, 84%) as a solid. MS: 264 (M+H).

Step 3: (5-Bromo-pyrimidine-2-yl)-phenyl-methanone (1.6 g, 6.08 mmol) is dissolved in dimethylacetamide (20 mL), and potassium hexacyanoferrate(II) trihydrate (0.57 g, 1.34 mmol) is added, followed by Na$_2$CO$_3$ (0.64 g, 6.08 mmol), and palladium (II) acetate (68 mg, 0.3 mmol). The mixture is heated to 150° C. under N$_2$ for 3 h, and then cooled to rt. EtOAc (30 mL) is added and the mixture is filtered. The filtrate is washed with water (2×15 mL) and 5% aqueous NH$_4$OH (15 mL), dried (Na$_2$SO$_4$), filtered and concentrated in vacuo. The residue is purified by silica gel chromatography eluting with 70% EtOAc in heptane to afford 2-benzoyl-pyrimidine-5-carbonitrile (0.53 g, 42%) as a solid. MS: 210 (M+H).

Step 4: 2-Benzoyl-pyrimidine-5-carbonitrile (500 mg, 2.39 mmol) is suspended in MeOH (5 mL), a solution of KOH (148 mg, 2.63 mmol) in water (5 mL) is added in one portion at 0° C. The mixture is stirred at 0° C. for 25 min, and then acidified with 2 N aqueous HCl to pH ~3. MeOH is evaporated in vacuo and the residue is extracted with DCM (2×5 mL). The combined organic layer is dried (Na$_2$SO$_4$), filtered and concentrated in vacuo to afford 2-benzoyl-pyrimidine-5-carboxylic acid methyl ester (500 mg, 86%) as an oil. MS: 243 (M+H); $^1$H NMR (300 MHz, CDCl$_3$): δ 4.05 (s, 3H), 7.50 (m, 2H), 7.65 (m, 1H), 8.01 (m, 2H), 9.46 (s, 2H).

Step 5: 2-Benzoyl-pyrimidine-5-carboxylic acid methyl ester (420 mg, 1.73 mmol) is dissolved in THF (5 mL), and a solution of LiOH (46 mg, 1.91 mmol) in water (5 mL) is added in one portion at 0° C. The mixture is stirred at 0° C. for 60 min. THF is evaporated in vacuo, and the residue is diluted with water (5 mL) and washed with ether (10 mL). The aqueous layer is acidified with 2 N aqueous HCl to pH ~3. The resulting precipitate is collected by filtration, washed with water three times, and dried in vacuum oven overnight to afford 2-benzoyl-pyrimidine-5-carboxylic acid (260 mg, 66%). MS: 229 (M+H); $^1$H NMR (300 MHz, DMSO): δ 7.60 (m, 3H), 7.73 (m, 1H), 7.85 (m, 2H), 9.4 (s, 1H).

Step 6: 2-Benzoyl-pyrimidine-5-carboxylic acid (50 mg, 0.22 mmol) is dissolved in anhydrous DCM (5 mL), and a 2 M oxalyl chloride (0.26 mmol, 0.13 mL) solution in DCM is added at rt followed by one drop of DMF. The mixture is stirred at rt for 2 h, and then concentrated in vacuo. The residue is dissolved in DCM (5 mL), and morpholine-4-ylamine (0.24 mmol, 25 mg) is added, followed by DIPEA (0.44 mmol, 57 mg). The reaction mixture is stirred at rt overnight, and then concentrated in vacuo. The residue is purified by silica gel column chromatography eluting with 10% MeOH in DCM to afford 2-benzoyl-pyrimidine-5-carboxylic acid morpholin-4-ylamide (42 mg) as a solid. MS: 313 (M+H). IC$_{50}$=342 nM.

Example 51

2-Benzoyl-pyrimidine-5-carboxylic acid [4-(2-hydroxy-ethyl)-piperazin-1-yl]-amide

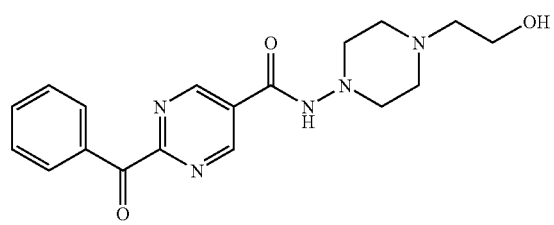

Following procedures similar to those of Example 49, step 6, but substituting 2-(4-amino-piperazin-1-yl)-ethanol for morpholine-4-ylamine, there is prepared 2-benzoyl-pyrimidine-5-carboxylic acid [4-(2-hydroxy-ethyl)-piperazin-1-yl]-amide as a solid. MS: 356 (M+H). IC$_{50}$=665 nM.

Example 52

2-Phenyl-pyrimidine-5-carboxylic acid N'-methyl-N'-[5-trifluoromethyl-pyridin-2-yl]-hydrazide

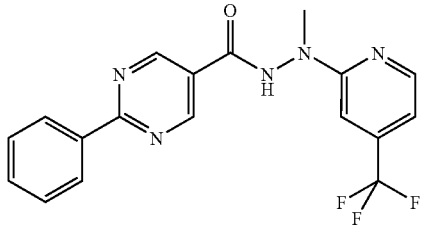

To a solution of 2-phenyl-pyrimidine-5-carboxylic acid (100 mg, 0.52 mmol), 1-hydroxybenzotriazole (77 mg, 0.57 mmol), 1-[3-(dimethylamino)propyl-3-ethylcarbodiimide (111 mg, 0.57 mmol) and DIPEA (0.57 mmol) in DCM (5 mL) is added N-methyl-N-(5-trifluoromethyl-pyridin-2-yl)-hydrazine (109 mg, 0.57 mmol). The reaction mixture is stirred at rt for 18 hours and then concentrated. The residue is purified by silica gel chromatography eluting with 10-75% EtOAc in heptane to afford 2-phenyl-pyrimidine-5-carboxylic acid N'-methyl-N'-[5-trifluoromethyl-pyridin-2-yl]-hydrazide as a solid (189 mg). MS: 374 (M+H); $^1$H NMR (300 MHz, CDCl$_3$): δ 3.54 (s, 3H), 6.82 (d, 1H), 7.53-7.59 (m, 3H), 7.74 (d, 1H), 8.45 (d, 2H), 8.53 (d, 2H), 9.25 (s, 2H). IC$_{50}$=100 nM.

Example 53

2-Phenyl-pyrimidine-5-carboxylic acid N'-methyl-N'-[4-trifluoromethyl-pyridin-2-yl]-hydrazide

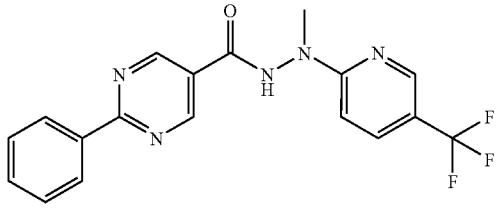

Following procedures similar to those of Example 52, but substituting N-methyl-N-(4-trifluoromethyl-pyridin-2-yl)-hydrazine (109 mg, 0.57 mmol) for N-methyl-N-(5-trifluoromethyl-pyridin-2-yl)-hydrazine, there is prepared 2-phenyl-pyrimidine-5-carboxylic acid N'-methyl-N'-[4-trifluoromethyl-pyridin-2-yl]-hydrazide as a solid. MS: 374 (M+H); $^1$H NMR (300 MHz, CDCl$_3$): δ 3.54 (s, 3H), 6.95 (m, 2H), 7.50-7.68 (m, 3H), 8.35 (d, 1H), 8.4 (s, 1H), 8.52 (d, 2H), 9.26 (s, 2H).

Example 54

2-Phenyl-pyrimidine-5-carboxylic acid N'-pyridin-2-yl-hydrazide

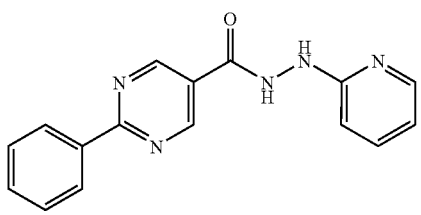

Following procedures similar to those of Example 52, but substituting 2-hydrazinopyridine (54 mg, 0.52 mmol) for N-methyl-N-(5-trifluoromethyl-pyridin-2-yl)-hydrazine, there is prepared 2-phenyl-pyrimidine-5-carboxylic acid N'-pyridin-2-yl-hydrazide as a solid (56 mg). MS: 292 (M+H); $^1$H NMR (300 MHz, DMSO-d$_6$): δ 6.72-6.8 (m, 2H), 7.53-7.62 (m, 4H), 8.09 (m, 2H), 8.48 (d, 2H), 8.62 (s, 1H), 9.34 (s, 2H).

Example 55

2-Phenyl-pyrimidine-5-carboxylic acid N'-(2-chlorophenyl)-hydrazide

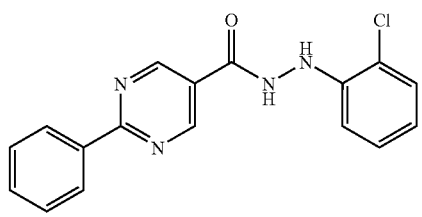

Following procedures similar to those of Example 52, but substituting 2-chlorophenylhydrazine hydrochloride (93 mg, 0.52 mmol) for N-methyl-N-(5-trifluoromethyl-pyridin-2-yl)-hydrazine, and using 1.14 mmol of DIPEA, there is prepared 2-phenyl-pyrimidine-5-carboxylic acid N'-(2-chlorophenyl)-hydrazide as a solid (65 mg). MS: 325 (M+H); $^1$H NMR (300 MHz, CDCl$_3$): δ 6.65-6.75 (m, 2H), 6.90-7.05 (m, 2H), 7.25 (t, 1H), 7.39 (d, 1H), 7.58 (m, 3H), 8 (s, 1H), 8.55 (d, 2H), 9.25 (s, 2H).

Example 56

2-Phenyl-pyrimidine-5-carboxylic acid N'-(2-oxo-piperidin-1-yl)-amide

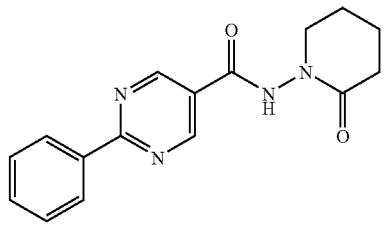

Step 1: A mixture of Methyl-5-bromovalerate (3 g, 15.4 mmol) and hydrazine hydrate (55%, 15.4 mmol) in MeOH (50 mL) is stirred at rt for 18 h. A solution of NaOMe (15.4 mmol) in MeOH (10 mL) is added and the reaction mixture is stirred at rt for 18 h. The reaction mixture is concentrated in vacuo. The residue is triturated with cold MeOH and then filtered. The filtrate is concentrated in vacuo. The residue is placed on a SCX column (10 g) and the column is washed with MeOH (3×20 mL). The product is eluted with 7 M ammonia in MeOH to afford 1-amino-piperidin-2-one as an oil. MS: 137 (M+Na).

Step 2: To a solution of 2-phenyl-pyrimidine-5-carboxylic acid (100 mg, 0.52 mmol), 1-hydroxybenzotriazole (77 mg, 0.57 mmol), 1-[3-(dimethylamino)propyl-3-ethylcarbodiimide (111 mg, 0.57 mmol) and DIPEA (0.57 mmol) in DCM (5 mL) is added 1-amino-piperidin-2-one (64 mg, 0.57 mmol), and the mixture is stirred at rt for 18 h. DCM (15 mL) is added and the mixture is washed with 0.5 N aqueous HCl (25 mL) and brine, and dried (Na$_2$SO$_4$.), filtered and concentrated in vacuo. The residue is purified by silica gel chromatography through eluting with 50-100% EtOAc in heptane to afford 2-phenyl-pyrimidine-5-carboxylic acid N'-(2-oxo-piperidin-1-yl)-amide (20 mg) as a solid. MS: 297 (M+H); $^1$H NMR (300 MHz, CDCl$_3$): δ 1.96-2.10 (m, 4H), 2.60 (t, 2H), 3.77 (t, 2H), 7.51-7.56 (m, 3H), 8.51 (d, 2H), 9.02 (bs, 1H), 9.16 (s, 2H). IC$_{50}$=55 nM.

Example 57

2-Phenyl-pyrimidine-5-carboxylic acid N'-cyclohexyl-N'-methyl-hydrazide

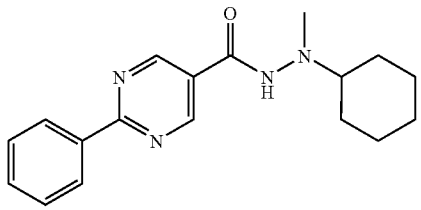

Following procedures similar to those of Example 52, but substituting N-methyl-N-cyclohexyl-hydrazine hydrochloride (72 mg, 0.44 mmol) for N-methyl-N-(5-trifluoromethyl-pyridin-2-yl)-hydrazine, and using 0.88 mmol of DIPEA, there is prepared 2-phenyl-pyrimidine-5-carboxylic acid N'-cyclohexyl-N'-methyl-hydrazide as a solid (40 mg). MS: 311 (M+H); $^1$H NMR (300 MHz, DMSO-d$_6$): δ 0.9-1.35 (m, 5H), 1.60-1.95 (m, 6H), 3.25 (s, 3H) 7.53-7.62 (m, 3H), 8.09 (m, 2H), 9.09 (s, 2H). IC$_{50}$=146.5 nM.

Example 58

2-Phenyoxy-pyrimidine-5-carboxylic acid N'-morpholin-4-yl-amide

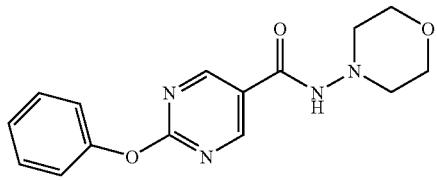

Step 1: To a solution of 2-methylsulfanyl-pyrimidine-5-carboxylic acid methyl ester (1 g, 5.43 mmol) in DCM (60 mL) is added MCPBA (2.81 g, 16.29 mmol) portion wise at rt. The resulting solution is stirred at rt overnight. A solution of Na$_2$S$_2$O$_3$ (1.6 g) in water (60 mL) is added. The mixture is stirred at rt for 20 min. The organic layer and aqueous layer are separated, and the aqueous layer is extracted with DCM (2×20 mL). The combined organic layer is washed with saturated aqueous NaHCO$_3$ (3×20 mL), dried (Na$_2$SO$_4$), filtered and concentrated in vacuo to afford 2-methanesulfonyl-pyrimidine-5-carboxylic acid methyl ester (1.05 g, 90%) as a solid. MS: 217 (M+H); $^1$H NMR (300 MHz, CDCl$_3$): δ 3.41 (s, 3H), 4.06 (s, 3H), 9.44 (s, 2H).

Step 2: To a solution of 2-methanesulfonyl-pyrimidine-5-carboxylic acid methyl ester (0.8 g, 3.7 mmol) in NMP (3 mL) is added sodium phenoxide trihydrate (0.68 g, 4 mmol). The mixture is heated at 100° C. in Biotage Microwave for 60 sec. The reaction is poured into water and the precipitate is collated by filtration and dried to afford 2-phenoxy-pyrimidine-5-carboxylic acid methyl ester (0.56 g, 66%) as a solid. MS: 231 (M+H); $^1$H NMR (300 MHz, CDCl$_3$): δ 4.75 (s, 3H), 7.19-7.33 (m, 3H), 7.46 (t, 2H) 9.10 (s, 2H).

Step 3: To a solution of 2-phenoxy-pyrimidine-5-carboxylic acid methyl ester (0.5 g, 2.17 mmol) in THF (10 mL) and water (5 mL) is added LiOH (105 mg, 4.35 mmol). The reaction is stirred at 0° C. for 1 h. The THF is evaporated and the aqueous reissue is washed with ether, acidified with 2 M aqueous HCl. The resulting precipitate is filtered and dried to afford 2-phenoxy-pyrimidine-5-carboxylic acid (0.34 g, 73%) as a solid. MS: 217 (M+H); $^1$H NMR (300 MHz, CDCl$_3$): δ 7.20-7.35 (m, 3H), 7.47 (t, 2H) 9.16 (s, 2H).

Step 4: To a solution of 2-phenoxy-pyrimidine-5-carboxylic acid (60 mg, 0.28 mmol) in DCM (5 mL) is added oxalyl chloride (2M in DCM, 0.15 mL, 0.29 mmol) and 1 drop of DMF. The reaction is stirred at rt for 1 h and concentrated in vacuo. The residue is dissolved in DCM (3 mL), and DIPEA (53 μL, 0.3 mmol) and 4-amino-morpholine (30 μL, 0.3 mmol) is added. The reaction is stirred at rt for 18 h and then water and DCM are added. The organic layer is separated, dried (Na$_2$SO$_4$), filtered and concentrated in vacuo. The residue is purified by silica gel chromatography eluting with 20-100% EtOAc in heptane to afford 2-phenyloxy-pyrimidine-5-carboxylic acid N'-morpholin-4-yl-amide (20 mg) as a solid. MS: 301 (M+H); $^1$H NMR (300 MHz, CDCl$_3$): δ 2.85-3.05 (m, 4H), 3.75-3.95 (m, 4H), 7.18-7.35 (m, 3H), 7.45 (t, 2H), 8.95 (s, 2H). IC$_{50}$=227 nM.

Example 59

2-(3-Methoxy-phenyl)-pyrimidine-5-carboxylic acid (6-methyl-3-oxo-2,5-dihydro-3H-[1,2,4]triazin-4-yl)-amide

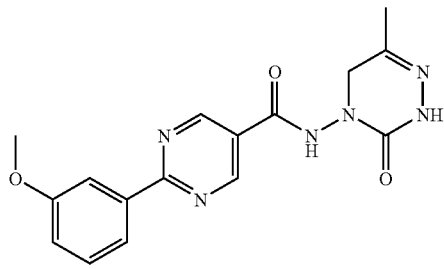

Step 1: 2-Methylsulfanyl-pyrimidine-5-carboxylicacid methyl ester (323 mg, 1.75 mmol), Copper(I) thiophene-2-carboxylate (501 mg, 2.63 mmol), tetrakis(triphenylphosphine) palladium(0) (202 mg, 0.175 mmol) and 3-methoxyphenylboronic acid (400 mg, 2.63 mmol) are taken in a glass tube, evacuated, refilled with N$_2$, added anhydrous THF (6 mL) and is heated overnight at 85° C. after closing with a cap. The reaction is cooled to rt, diluted with EtOAc and ammonium hydroxide is added. The organic layer is seperated, dried (MgSO$_4$), filtered and concentrated in vacuo. The residue is purified by flash silica gel chromatography to afford 2-(3-methoxy-phenyl)-pyrimidine-5-carboxylic acid methyl ester (152 mg) as a powder. MS: 245 (M+H); $^1$H NMR (CDCl₃): δ 4.00 (s, 3H), 4.82 (d, 2H), 7.55 (m, 2H), 8.46 (m, 1H), 8.53 (s, 1H), 9.33 (s, 2H).

Step 2: A mixture of 2-(3-methoxy-phenyl)-pyrimidine-5-carboxylic acid methyl ester (145 mg, 0.59 mmol), lithium hydroxide monohydrate (49.5 mg, 1.18 mmol), MeOH (1.5 mL), water (1.5 mL) and THF (1.5 ml) is stirred at rt for 3.5 hrs. The reaction mixture is concentrated, and water (1 mL) and 1 N aqueous HCl (1.2 mL) are added. The precipitated product is filtered and dried to afford 2-(3-methoxy-phenyl)-pyrimidine-5-carboxylic acid (140 mg). MS: 231 (M+H); ¹H NMR (DMSO-d₆): δ 4.62 (s, 3H), 7.54 (m, 2H), 8.14 (s, 1H), 8.34 (m, 1H), 8.46 (s, 1H), 9.30 (s, 2H).

Step 3: A mixture of 2-(3-methoxy-phenyl)-pyrimidine-5-carboxylic acid (135 mg, 0.58 mmol), 4-amino-6-methyl-4,5-dihydro-2H-[1,2,4]triazin-3-one (76 mg, 0.58 mmol), DMTMM (171 mg, 0.6 mmol) and DMF (3 mL) is stirred at rt for 2 days. Water (3 ml) is added, and the precipitated product is filtered, washed with water and dried to afford 2-(3-methoxy-phenyl)-pyrimidine-5-carboxylic acid (6-methyl-3-oxo-2,5-dihydro-3H-[1,2,4]triazin-4-yl)-amide (127 mg). MS: 341 (M+H); ¹H NMR (DMSO-d₆): δ 1.91 (s, 3H), 4.23 (s, 3H), 4.62 (s, 2H), 7.53 (m, 2H), 8.34 (m, 1H), 8.46 (s, 1H), 9.27 (s, 2H), 9.97 (s, 1H), 11.08 (s, 1H). IC₅₀=174.5 nM.

Example 60

2-Phenyl-pyrimidine-5-carboxylic acid (2,6-dimethyl-3-oxo-2,5-dihydro-3H-1,2,4-triazine-4-yl)-amide

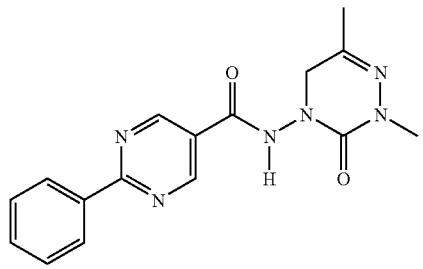

Step 1: To a solution of 5-methyl-3H-1,3,4-oxadiazol-2-one (5.509 g, 55.0 mmol) in MeOH (40 mL) is added 25 wt % NaOMe solution in methanol (12.7 mL, 58.8 mmol). The mixture is stirred at rt for 15 min and then concentrated in vacuo. The residue is added to a solution of tetrabutylammonium bromide (0.358 g, 1.08 mmol) and chloro-acetone (4.6 ml, 54.9 mmol) in CHCl₃ (33 mL), and the mixture is heated to reflux for 5 h under N₂. The mixture is cooled to rt and stirred overnight. The resulting slurry is filtered, and the filtrate is concentrated in vacuo. The residue is purified on a pad of silica gel, eluting with 2:1:1/heptane:EtOAc:DCM to afford 5-methyl-3-(2-oxo-propyl)-3H-1,3,4-oxadiazol-2-one (7.32 g, 86%) as a crystalline solid. MS: 157 (M+H); ¹H NMR (300 MHz, CDCl₃) δ 4.46 (s, 2H), 2.27 (s, 3H), 2.21 (s, 3H).

Step 2: To a solution of 5-methyl-3-(2-oxo-propyl)-3H-1,3,4-oxadiazol-2-one (1.518 g, 9.72 mmol) in a mixture of 2-propanol (8.8 mL) and water (0.22 mL) is added methyl hydrazine (0.79 mL, 14.6 mmol). The reaction mixture is heated to reflux under N₂ for 4 h, and then a solution of oxalic acid (0.273 g, 2.92 mmol) in 2-propanol (4 mL) is added. The resulting precipitate is removed by filtration. The filtrate is concentrated in vacuo and the residue dissolved in 2-propanol (25 mL). The solution is chilled and Et₂O is added. The precipitate is collected by filtration and dried to afford N-(2,6-dimethyl-3-oxo-2,5-dihydro-3H-1,2,4-triazin-4-yl)-acetamide (0.96 g, 54%) as a crystalline solid. MS: 185 (M+H); ¹H NMR (300 MHz, DMSO-d₆) δ 8.28 (s, 1H), 4.18 (s, 2H), 3.28 (s, 3H), 2.02 (s, 3H), 1.95 (s, 2H).

Step 3: To a slurry of N-(2,6-dimethyl-3-oxo-2,5-dihydro-3H-1,2,4-triazin-4-yl)-acetamide (0.34 g, 1.846 mmol) in MeOH (3 mL) is added concentrated HCl (0.25 mL, 2.9 mmol). The mixture is heated to reflux for 3 h. The mixture is then chilled to 0° C., adjusted to pH 12 with 1 M aqueous NaOH (2.9 mL) and concentrated in vacuo. CH₃CN is added to the residue with stirring and the mixture is filtered. The filtrate is concentrated in vacuo. CH₃CN is added to the residue with stirring and the mixture is filtered. The filtrate is concentrated in vacuo to afford 4-amino-2,6-dimethyl-4,5-dihydro-2H-1,2,4-triazin-3-one (~100%)). MS: 143 (M+H); ¹H NMR (300 MHz, DMSO-d₆) δ 4.6-3.6 (broad peak, 2H), 4.02 (s, 2H), 3.29 (s, 3H), 1.95 (s, 3H).

Step 4: To a solution of 4-amino-2,6-dimethyl-4,5-dihydro-2H-1,2,4-triazin-3-one (0.219 g, 1.58 mmol) and 2-phenyl-pyrimidine-5-carboxylic acid (0.317 g, 1.58 mmol) in dry DMF (10 mL) under N₂ is added DMTMM (0.46 g, 1.66 mmol). The mixture is stirred at rt for 22 h, then diluted with EtOAc (70 mL), and washed successively with saturated aqueous NaHCO₃ solution (2×10 mL) and brine (10 mL). The organic phase is dried (MgSO₄), filtered and concentrated in vacuo. The residue is purified by silica gel chromatography eluting with heptane:EtOAc gradient to afford 2-phenyl-pyrimidine-5-carboxylic acid (2,6-dimethyl-3-oxo-2,5-dihydro-3H-1,2,4-triazin-4-yl)-amide as a solid (0.28 g, 55%). MS: 325 (M+H); ¹H NMR (300 MHz, DMSO-d₆) δ 9.24 (s, 2H), 8.45 (dd, J=7.7, 2.0 Hz, 2 H), 7.52-7.62 (m, 3H), 4.25 (s, 2H), 3.18 (s, 3H), 1.95 (s, 3H).

Example 61

2-Phenyl-pyrimidine-5-carboxylic acid (6-tert-butyl-3-oxo-2,5-dihydro-3H-1,2,4-triazin-4-yl)-amide

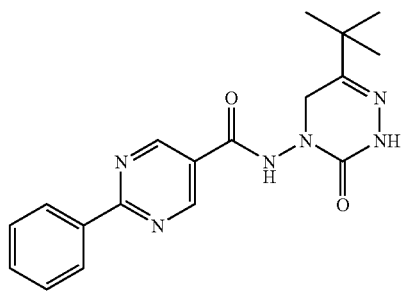

Step 1: To a solution of 5-methyl-3H-1,3,4-oxadiazol-2-one (1.01 g, 10.09 mmol) in MeOH (8 mL) is added 25 wt % NaOMe solution in methanol (2.32 mL, 10.8 mmol). The mixture is stirred at rt for 15 min and then concentrated in vacuo. The residue is added to a solution of tetrabutylammonium bromide (0.07 g, 0.22 mmol) and 1-chloropinacolone (1.35 mL, 10.07 mmol). in CHCl₃ (7 mL), and the mixture is heated to reflux for 5 h under N₂. The mixture is cooled to rt and stirred over the weekend at rt. The resulting slurry is filtered, and the filtrate is concentrated in vacuo to afford 3-(3,3-dimethyl-2-oxo-butyl)-3H-1,314-oxadiazol-2-one (1.876 g, 94%) as an oil. MS: 199 (M+H); ¹H NMR (300 MHz, CDCl₃) δ 4.62 (s, 2H), 2.26 (s, 3H), 1.23 (s, 9H).

Step 2: To a solution of 3-(3,3-dimethyl-2-oxo-butyl)-3H-1,3,4-oxadiazol-2-one (0.91 g, 4.59 mmol) in a mixture of 2-propanol (4 mL) and water (0.11 mL) is added hydrazine monohydrate (0.34 mL, 6.89 mmol). The reaction mixture is heated to reflux under nitrogen for 5 h, then a solution of oxalic acid (0.13 g, 1.38 mmol) in 2-propanol (5 mL) is added to the hot solution. The resulting precipitate is removed hot by filtration. The filtrate is concentrated in vacuo and the residue is purified on a pad of silica gel, eluting with heptane:EtOAc gradient to afford N-(6-tert-butyl-3-oxo-2,5-dihydro-3H-1,2,4-triazin-4-yl)-acetamide (0.546 g, 56%) as a solid. MS: 213 (M+H); $^1$H NMR (300 MHz, DMSO-d$_6$) δ 8.29 (s, 1H), 7.64 (s, 1H), 4.22 (s, 2H), 2.04 (s, 3H), 1.15 (s, 9H).

Step 3: To a slurry of N-(6-tert-butyl-3-oxo-2,5-dihydro-3H-1,2,4-triazin-4-yl)-acetamide (0.51 g, 2.40 mmol) in MeOH (5 mL) is added concentrated HCl (0.33 mL, 3.84 mmol). The mixture is heated to reflux for 3 h. The mixture is then chilled to 0° C. and basified with 1 M aqueous NaOH (2.9 mL) to pH 12, and concentrated in vacuo. EtOH is added to the residue with stirring and the mixture is filtered. The filtrate is concentrated in vacuo. CH$_3$CN is added to the residue with stirring and the mixture is filtered. The filtrate is concentrated in vacuo to afford 4-amino-6-tert-butyl-4,5-dihydro-2H-1,2,4-triazin-3-one (0.354 g, 84%) as a solid. MS: 171 (M+H); $^1$H NMR (300 MHz, DMSO-d$_6$) δ 7.49 (br s, 1H), 4.22 (br s, 2H), 4.06 (s, 2H), 1.15 (s, 9H).

Step 4: Following the procedure similar to those of Example 60, step 4, but substituting 4-amino-6-tert-butyl-4,5-dihydro-2H-1,2,4-triazin-3-one for 4-amino-2,6-dimethyl-4,5-dihydro-2H-1,2,4-triazin-3-one, there is prepared 2-phenyl-pyrimidine-5-carboxylic acid (6-tert-butyl-3-oxo-2,5-dihydro-3H-1,2,4-triazin-4-yl)-amide (74%) as a solid. MS: 353 (M+H); $^1$H NMR (300 MHz, DMSO-d$_6$) δ 11.09 (s, 1H), 10.03 (s, 1H), 9.27 (s, 2H), 8.45 (dd, J=7.7, 2.0 Hz, 2H), 7.52-7.60 (m, 3H), 4.29 (s, 2H), 1.13 (s, 9H).

Example 62

2-Pyridin-2-yl-pyrimidine-5-carboxylic acid (6-methyl-3-oxo-2,5-dihydro-3H-1,2,4-triazine-4-yl)-amide

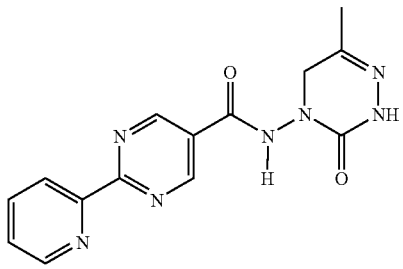

Step 1: To a solution of 5-methyl-3-(2-oxo-propyl)-3H-1,3,4-oxadiazol-2-one (2.052 g, 13.14 mmol) in a mixture of 2-propanol (12 mL) and water (0.3 mL) is added hydrazine monohydrate (0.96 mL, 19.8 mmol). The mixture is stirred at rt under N$_2$ for 15 h, and then heated to reflux for 7 h. A solution of oxalic acid (0.363 g, 4.032 mmol) in 2-propanol (6 mL) is added to the warm reaction solution. The resulting precipitate is removed by filtration through a coarse porosity sintered glass funnel, and the filtrate is concentrated in vacuo to approximately 10 mL in total volume. The concentrated solution is chilled to −12° C., and the resulting crystals are collected by filtration and dried to afford N-(6-methyl-3-oxo-2,5-dihydro-3H-1,2,4-triazin-4-yl)-acetamide (1.562 g, 70%). MS: 171 (M+H); $^1$H NMR (300 MHz, CDCl$_3$) δ 8.10 (br s, 1H), 7.57 (br s, 1H), 4.20 (s, 2H), 2.04 (s, 3H), 1.95 (s, 3H); $^1$H NMR (300 MHz, DMSO-d$_6$) δ 9.98 (s, 1), 9.74 (s, 1), 4.04 (s, 2), 1.84 (s, 6).

Step 2: Following the procedure similar to those of Example 35, step 4, but substituting N-(6-methyl-3-oxo-2,5-dihydro-3H-1,2,4-triazin-4-yl)-acetamide for N-[6-(4-fluoro-phenyl)-3-oxo-2,5-dihydro-3H-1,2,4-triazin-4-yl]-acetamide, there is prepared 4-amino-6-methyl-4,5-dihydro-2H-1,2,4-triazin-3-one (92%) as a solid. MS: 129 (M+H); $^1$H NMR (300 MHz, CD$_3$CN) δ 8.25 (br s, 1H), 4.26 (br s, 2H), 3.96 (s, 2H), 1.85 (s, 3H).

Step 3: To a solution of 2-pyridin-2-yl-pyrimidine-5-carboxylic acid (0.152 g, 0.75 mmol), in dry DCM (3 mL) and DMF (0.9 µL) in a dry flask under N$_2$ is added oxalyl chloride (74 µL, 0.86 mmol). The reaction mixture is stirred at rt for 1 h. The solvent is evaporated and toluene is added and evaporated three times. The residue is dissolved in dry DCM (3 mL), and a solution of 4-amino-6-methyl-4,5-dihydro-2H-1,2,4-triazin-3-one (0.77 g, 0.6 mmol) in DCM (5 mL) is added followed by the addition of DIPEA (0.14 mL, 0.79 mmol). The mixture is stirred at rt overnight, and then concentrated in vacuo. The residue is diluted with water and adjusted to pH ~8.5 with saturated aqueous NaHCO$_3$ solution. The resulting precipitate is filtered to afford 2-pyridin-2-yl-pyrimidine-5-carboxylic acid (6-methyl-3-oxo-2,5-dihydro-3H-1,2,4-triazine-4-yl)amide (0.043 g, 23%). MS: 312 (M+H); $^1$H NMR (300 MHz, DMSO-d$_6$) δ 11.11 (s, 1H), 9.95 (s, 1H), 9.31 (s, 2H), 8.78 (d, 1H), 8.45 (d, 1H), 8.01 (tr, 1H), 7.58 (dd, 1H), 4.22 (2, 2H), 1.91 (s, 3H).

Example 63

2-(3-Fluoro-phenyl)-pyrimidine-5-carboxylic acid (6-tert-butyl-3-oxo-2,5-dihydro-3H-1,2,4-triazine-4-yl)-amide

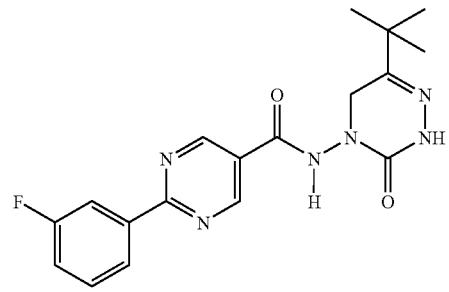

Following the procedure similar to those of Example 62, step 3, but substituting 2-(3-Fluoro-phenyl)-pyrimidine-5-carbonyl chloride for 2-pyridin-2-yl-pyrimidine-5-carbonyl chloride, substituting 4-amino-6-tert-butyl-4,5-dihydro-2H-1,2,4-triazin-3-one for 4-amino-6-methyl-4,5-dihydro-2H-1,2,4-triazin-3-one, and substituting Et$_3$N for DIPEA, there is prepared 2-(3-fluoro-phenyl)-pyrimidine-5-carboxylic acid (6-tert-butyl-3-oxo-2,5-dihydro-3H-1,2,4-triazine-4-yl)-amide (0.067 g, 61%). MS: 371 (M+H); $^1$H NMR (300 MHz, CD$_3$OD) δ 9.26 (s, 2H), 8.35 (d, J=8.1 Hz, 1H), 8.21 (d, J=10.3 Hz), 7.55 (q, J=10.3 Hz, 1 H), 7.30 (tr, J=8.2 Hz, 1H), 4.37 (s, 2H), 1.19 (s, 9H).

Example 64

3-{2,4-Dioxo-3-[(2-phenyl-pyrimidine-5-carbonyl)-amino]-1,2,3,4-tetrahydro-pyrimidin-5-yl}-propionic acid methyl ester

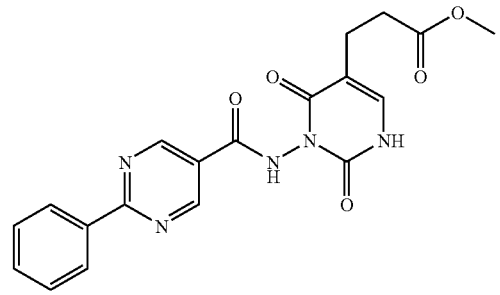

A mixture of 2-phenyl-pyrimidine-5-carboxylic acid (1.17 mmol), 1-hydroxybenzotriazole (1.99 mmol), and PS-DCC (1.21 mmol/g, 2.34 mmol in DMF (8 mL) is shaken at rt for 60 min. 3-{3-Amino-2,4-dioxo-1,2,3,4-tetrahydro-pyrimidin-5-propionic acid methyl ester (1.17 mmol) is added and the mixture is shaken at rt for 2-4 days. Polymer supported-trisamine (PS-trisamine) (4.08 mmol/g, 3.51 mmol) is added and the mixture is continually shaken at rt for 18 hours. The solid is filtered and washed with MeOH. The filtrate is concentrated. The residue is purified by silica gel chromatography eluting with 10-60% EtOAc in hexanes to afford 3-{2,4-dioxo-3-[(2-pheyl-pyrimidine-5-carbonyl)-amino]-1,2,3,4-tetrahydro-pyrimidin-5-yl-propionic acid methyl ester (115 mg, 25%) as a solid. MS: 397 (M+H) 397; $^1$H NMR (300 MHz, CDCl$_3$): δ 2.57-2.76 (m, 2H), 2.80-3.00 (m, 2H), 3.64 (s, 3H), 5.30 (br. N—H), 7.37-7.55 (m, 3H), 8.35 (d, 2H), 9.26 (s, 2H).

Example 65

3-{2,4-Dioxo-3-[(2-pheyl-pyrimidine-5-carbonyl)-amino]-1,2,3,4-tetrahydro-pyrimidin-5-yl}-propionic acid

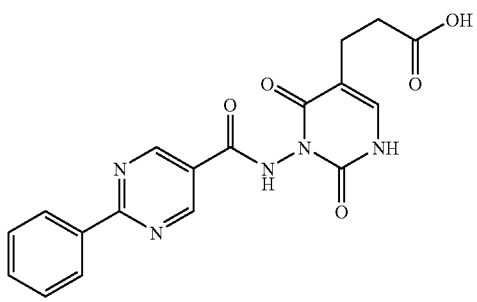

3-{2,4-Dioxo-3-[(2-pheyl-pyrimidine-5-carbonyl)-amino]-1,2,3,4-tetrahydro-pyrimidin-5-yl}-propionic acid methyl ester (0.22 mol) is hydrolyzed by LiOH (0.88 mol) in MeOH/water/THF (1:1:1) at rt overnight. MeOH and THF are evaporated in vacuo. The residue is acidified by 5% aqueous HCl. The resulting precipitate is collected and dried to afford 3-{2,4-dioxo-3-[(2-pheyl-pyrimidine-5-carbonyl)-amino]-1,2,3,4-tetrahydro-pyrimidin-5-yl}-propionic acid (40 mg, 48%). MS: 383 (M+H); $^1$H NMR (300 MHz, CD$_3$OD): δ 2.68-2.77 (m, 2H), 2.98-2.90 (m, 2H), 5.49 (s. N—H), 7.48-7.60 (m, 3H), 8.41-8.56 (m, 2H), 9.32 (s, 2H).

Example 66

2-Phenyl-pyrimidine-5-carboxylic acid (4-methyl-piperazin-1-yl)-amide

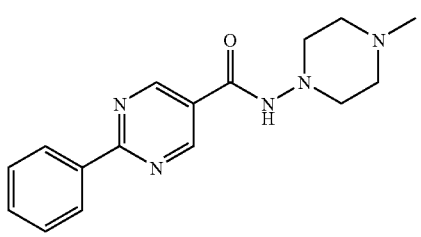

Following procedures similar to those of Example 64 but substituting 4-methyl-piperazin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid (4-methyl-piperazin-1-yl)-amide.

Example 67

2-Phenyl-pyrimidine-5-carboxylic acid (4-methyl-piperazin-1-yl)-amide dihydrochloride

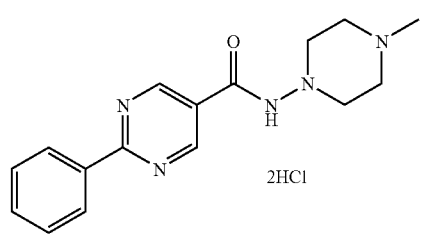

2-Phenyl-pyrimidine-5-carboxylic acid (4-methyl-piperazin-1-yl)-amide is dissolved in HCl methanol solution and evaporated methanol to dryness to afford 2-phenyl-pyrimidine-5-carboxylic acid (4-methyl-piperazin-1-yl)-amide dihydrochloride as a solid. MS: 298 (M+H).

Example 68

2-Phenyl-pyrimidine-5-carboxylic acid morpholin-4-ylamide

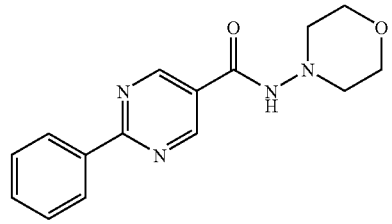

Following procedures similar to those of Example 64 but substituting 4-aminomorpholine for 3-{3-amino-2,4-dioxo-1,2,3,4-tetrahydro-pyrimidin-5-propionic acid methyl ester, there is prepared 2-phenyl-pyrimidine-5-carboxylic acid morpholin-4-ylamide (71%) as a solid. MS: 285 (M+H); $^1$H NMR (300 MHz, CD$_3$OD): δ 2.90-3.00 (m, 2H), 3.80-3.85 (m, 2H), 7.44-7.58 (m, 3H), 8.45-8.53 (m, 2H), 9.18 (s, 2H).

Example 69

2-Phenyl-pyrimidine-5-carboxylic acid [4-(2-hydroxy-ethyl)-piperazin-1-yl]-amide

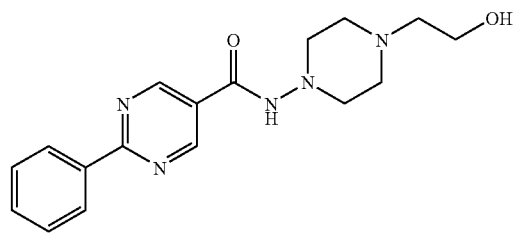

Following procedures similar to those of Example 64 but substituting 2-(4-amino-piperazin-1-yl)-ethanol for 3-{3-amino-2,4-dioxo-1,2,3,4-tetrahydro-pyrimidin-5-propionic acid methyl ester, there is prepared 2-phenyl-pyrimidine-5-carboxylic[4-(2-hydroxy-ethyl)-piperazin-1-y]-amide (25%) as a solid. MS: 328 (M+H); $^1$H NMR (300 MHz, CD$_3$OD): δ 2.65 (t, 2H), 2.80 (br, 2H), 3.04 (br, 2H), 3.73 (t, 2H), 7.24-7.34 (m, H), 7.47-7.57 (m, 3H), 7.62-7.73 (m, H), 8.43-8.52 (m, 2H), 9.18 (s, 2H).

Example 70

2-Phenyl-pyrimidine-5-carboxylic acid ((s)-2-methoxymethyl)-pyrrolidin-1-yl]-amide

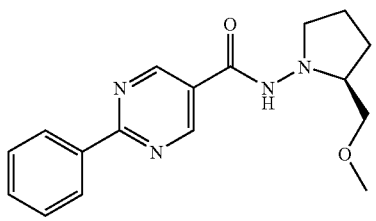

Following procedures similar to those of Example 64 but substituting (S)-2-methoxymethyl-pyrrolidin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid ((s)-2-methoxymethyl)-pyrrolidin-1-yl]-amide (63%) as a solid. MS: 313 (M+H); $^1$H NMR (300 MHz, CDCl$_3$): δ 1.57-2.15 (m, 4H), 2.70-3.70 (m, 8H), 6.93 (br, 0.4N—H), 7.81 (br, 0.6N—H), 7.50 (m, 3H), 8.48 (m, 2H), 9.10-9.38 (d, 2H).

Example 71

2-Phenyl-pyrimidine-5-carboxylic acid ((R)-2-methoxymethyl)-pyrrolidin-1-yl]-amide

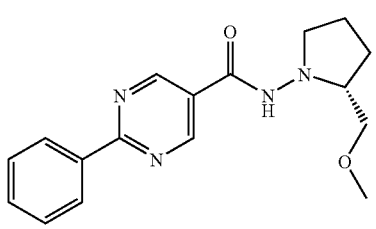

Following procedures similar to those of Example 64 but substituting (R)-2-methoxymethyl-pyrrolidin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid ((R)-2-methoxymethyl)-pyrrolidin-1-yl]-amide (66%) as a solid. MS: 313 (M+H); $^1$H NMR (300 MHz, CDCl$_3$): δ 1.57-2.15 (m, 4H), 2.71-3.63 (m, 8H), 6.93 (br, 0.4N—H), 7.71 (br, 0.6N—H), 7.50 (m, 3H), 8.50 (m, 2H), 9.10-9.38 (d, 2H).

Example 72

2-Phenyl-pyrimidine-5-carboxylic acid (5-bromo-2,4-dioxo-3,4-dihydro-2H-pyrimidin-1-yl)-amide

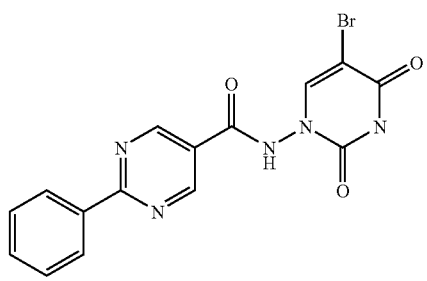

Following procedures similar to those of Example 64 but substituting 5-bromo-2,4-dioxo-3,4-dihydro-2H-pyrimidin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid (5-bromo-2,4-dioxo-3,4-dihydro-2H-pyrimidin-1-yl)-amide (34%) as a solid. MS: 389 (M+H); $^1$H NMR (300 MHz, CD$_3$OD): δ 7.49-7.62 (m, 3H), 7.98 (br, 3H), 8.23 (s, H), 8.54 (d, 2H), 9.29 (s, 2H). IC$_{50}$=107.5 nM.

Example 73

2-Phenyl-pyrimidine-5-carboxylic acid (3-isopropyl-5-oxo-1,5-dihydro-[1,2,4]triazol-4-yl)-amide

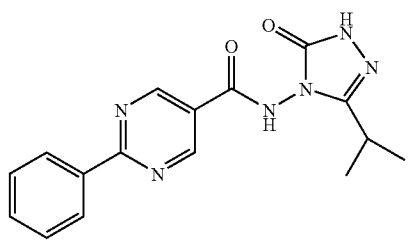

Following procedures similar to those of Example 64 but substituting 3-isopropyl-5-oxo-1,5-dihydro(1,2,4)-triazol-4-ylamine for 3-{3-amino-2,4-dioxo-1,2,3,4-tetrahydro-pyrimidin-5-propionic acid methyl ester, there is prepared 2-phenyl-pyrimidine-5-carboxylic acid (3-isopropyl-5-oxo-1,5-dihydro-[1,2,4]triazol-4-yl)-amide (25%) as a solid. MS: 325 (M+H).

Example 74

2-Phenyl-pyrimidine-5-carboxylic acid pyarrol-1-ylamide

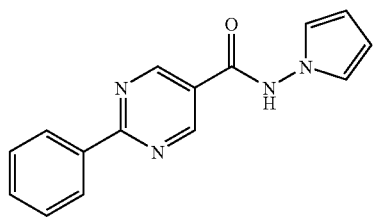

Following procedures similar to those of Example 64 but substituting pyrrol-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid pyrrol-1-ylamide (62%) as a solid. MS: 265 (M+H); $^1$H NMR (300 MHz, CDCl$_3$): δ 6.25 (d, 2H), 6.76 (d, 2H), 7.48-7.63 (m, 3H), 8.52 (d, 2H), 8.95-9.60 (br, 2H).

Example 75

2-Phenyl-pyrimidine-5-carboxylic acid (5-morpholin-4-ylmethyl-2-oxo-oxazolidin-3-yl)-amide

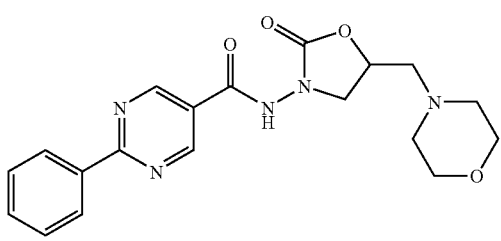

Following procedures similar to those of Example 64 but substituting 5-morpholin-4-ylmethyl-2-oxo-oxazolidin-3-ylamine for 3-{3-amino-2,4-dioxo-1,2,3,4-tetrahydro-pyrimidin-5-propionic acid methyl ester, there is prepared 2-phenyl-pyrimidine-5-carboxylic acid (5-morpholin-4-ylmethyl-2-oxo-oxazolidin-3-yl)-amide (51%) as a solid. MS: 384 (M+H); $^1$H NMR (300 MHz, CD$_3$OD): δ 2.50-2.95 (m, 6H), 3.64-3.85 (m, 5H), 3.98 (t, H), 4.88 (m, H), 7.48-7.60 (m, 3H), 8.49 (d, 2H), 9.16 (s, 2H), 9.37 (br. N—H). IC$_{50}$=20 nM.

Example 76

2-Phenyl-pyrimidine-5-carboxylic acid (4-cyclopentyl-piperazin-1-yl]-amide

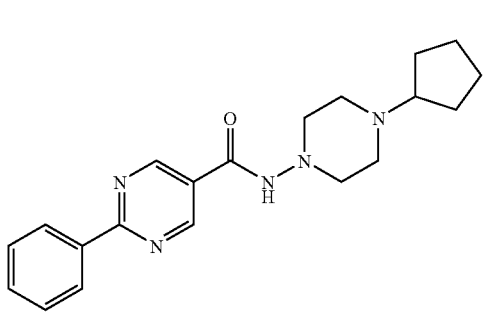

Following procedures similar to those of Example 64 but substituting 4-cyclopentyl-piperazin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid (4-cyclopentyl-piperazin-1-yl]-amide (67%) as a solid. MS: 352 (M+H); $^1$H NMR (300 MHz, CDCl$_3$): δ 1.25-2.00 (m, 8H), 2.00-3.35 (m, 9H), 6.70-7.40 (m, N—H), 7.40-7.60 (m, 3H), 8.50 (s, 2H), 8.86-9.38 (m, 2H).

Example 77

2-Phenyl-pyrimidine-5-carboxylic acid (2-oxo-oxazolidin-3-yl)-amide

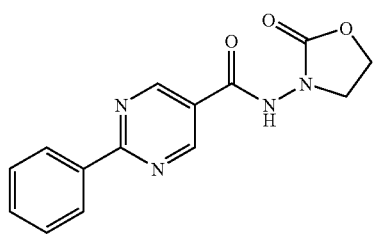

Following procedures similar to those of Example 64 but substituting 2-oxo-oxazolidin-3-ylamine hydrochloride for 3-{3-amino-2,4-dioxo-1,2,3,4-tetrahydro-pyrimidin-5-propionic acid methyl ester, there is prepared 2-phenyl-pyrimidine-5-carboxylic acid (2-oxo-oxazolidin-3-yl)-amide (18%) as a solid. MS: 285 (M+H); $^1$H NMR (300 MHz, CD$_3$OD): δ 3.94 (t, 2H), 4.55 (t, 2H), 7.46-7.62 (m, 3H), 8.53 (d, 2H), 9.30 (d, 2H). IC$_{50}$=49 nM.

Example 78

4-Methyl-2-phenyl-pyrimidine-5-carboxylic acid (6-methyl-3-oxo-2,5-dihydro-3H-[1,2,4]triazin-4-yl]-amide

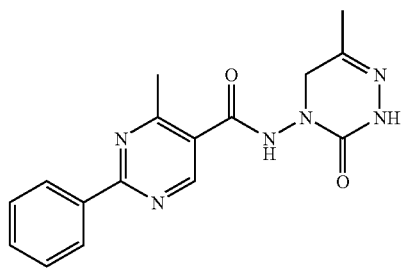

Following procedures similar to those of Example 64 but substituting 6-methyl-3-oxo-2,5-dihydro-3H-[1,2,4]triazin-4-ylamine for 3-{3-amino-2,4-dioxo-1,2,3,4-tetrahydro-pyrimidin-5-propionic acid methyl ester, there is prepared 4-methyl-2-phenyl-pyrimidine-5-carboxylic acid (6-methyl-3-oxo-2,5-dihydro-3H-[1,2,4]triazin-4-yl]-amide (87%) as a solid. MS: 325 (M+H); $^1$H NMR (300 MHz, CDCl$_3$): δ 1.95

(s, 3H), 3.72 (s, 3H), 4.30 (s, 2H), 7.34-7.58 (m, 4H), 7.72 (br, H), 8.92 (br, H), 8.43 (d, 2H), 8.87 (s, H), 9.46 (br, H).

Example 79

[N'-(2-Phenyl-pyrimidine-5-carbonyl)-hydrazino]-acetic acid ethyl ester

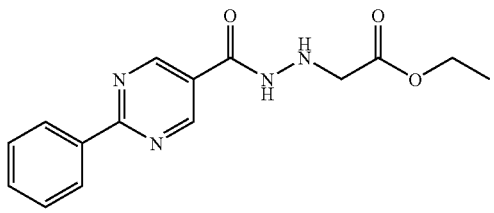

Et₃N (13.15 mmol) is added to a stirred solution of 2-phenyl-pyrimidine-5-carboxylic acid chloride (5.26 mmol) and hydrazine-acetic acid ethyl ester hydrochloride (5 mmol) in DCM (30 mL) at rt, and the mixture is stirred at rt for 5 h. The mixture is quenched with water and extracted with EtOAc (60 mL). The organic layer is washed with water (20 mL) and brine (15 mL), dried, filtered and concentrated in vacuo. The residue is purified by silical gel chromatography eluting with 5-50% EtOAc in heptane to afford [N'-(2-phenyl-pyrimidine-5-carbonyl)-hydrazino]-acetic acid ethyl ester (256 mg, 16%) as a solid. MS: 301 (M+H); $^1$H NMR (300 MHz, CDCl₃): δ 1.35 (s, 3H), 4.20-4.40 (m, 4H), 4.56 (s, 2H), 7.54 (m, 3H), 8.53 (m, 2H), 9.24 (s, 2H).

Example 80

2-[N'-(2-Phenyl-pyrimidine-5-carbonyl)-hydrazino]-acetamide

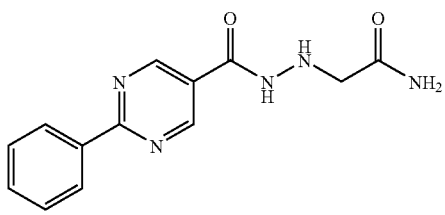

A mixture of [N'-(2-phenyl-pyrimidine-5-carbonyl)-hydrazino]-acetic acid ethyl ester (0.37 mmol) in 25% ammonia solution (25 mL) is stirred at rt over night. The solid is collected by filtration and dried to afford 2-[N'-(2-phenyl-pyrimidine-5-carbonyl)-hydrazino]-acetamide (46%). MS: 272 (M+H); $^1$H NMR (300 MHz, CD₃OD): δ 4.45 (s, 2H), 7.45-7.56 (m, 3H), 8.40-8.50 (m, 2H), 9.18 (s, 2H).

Example 81

4-[3-(4-Morpholino)propyl]-1-(2-phenyl-pyrimidine-5-carbonyl)-3-thiosemicarbazide

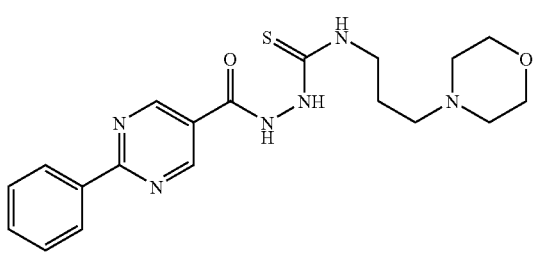

Following procedures similar to those of Example 64 but substituting 4-[3-(4-morpholino)-propyl]-3-thiosemicarbazide for 3-{3-amino-2,4-dioxo-1,2,3,4-tetrahydro-pyrimidin-5-propionic acid methyl ester, there is prepared 4-[3-(4-morpholino)propyl](2-phenyl-pyrimidine-5-carbonyl)-3-thiosemicarbazide (32%) as a solid. MS: 401 (M+H); $^1$H NMR (300 MHz, CD₃OD): δ 1.67-1.97 (m, 2H), 2.27-2.84 (m, 6H), 3.40-3.86 (m, 6H), 7.34-7.59 (m, 3H), 8.33-8.57 (m, 2H), 9.24 (s, 2H).

Example 82

2-Phenyl-pyrimidine-5-carboxylic acid (2,3-dihydro-indol-1-yl)-amide

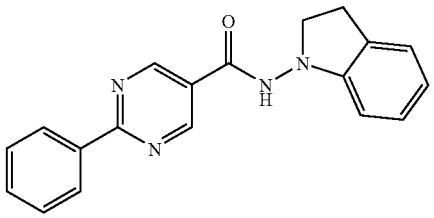

Oxalyl chloride in DCM (2 M, 1.5 mL) is added to a solution of 2-phenyl-pyrimidine-5-carboxylic acid (200 mg, 2 mmol) in DCM (20 mL) and stirred at rt for 2 h. The reaction solution is concentrated in vacuo. The residue is dissolved in DCM (20 mL). N-amino-indoline (268 mg, 2 mmol) and triethylamine (404 mg, 4 mmol) are added and stirred at rt overnight. The mixture is concentrated in vacuo and the residue is purified by silica gel column chromatography eluting with 0-40% EtOAc in heptane to afford 2-phenyl-pyrimidine-5-carboxylic acid (2,3-dihydro-indol-1-yl)-amide (195 mg, 31%) as a solid. MS: 317 (M+H); $^1$H NMR (300 MHz, CD₃OD): δ 3.07 (t, 2H), 3.77 (t, 2H), 6.76 (m, H), 6.82-6.95 (m, H) 7.09-7.24 (m, 2H), 7.54-7.63 (m, 3H), 8.52 (d, 2H), 9.28 (s, 2H) and 2-phenyl-pyrimidine-5-carboxylic acid (indol-1-yl)-amide (10 mg, 2%). MS: 315 (M+H). IC₅₀=2 nM.

Example 83

{4-[2-Phenyl-pyrimidine-5-carbonyl)-amino]-piperazin-1-yl}-acetic acid methyl ester

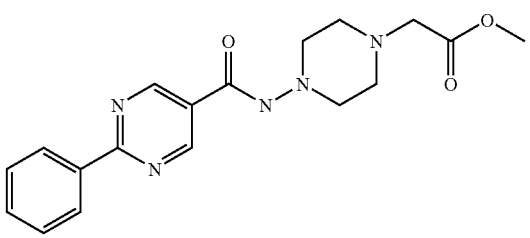

Step 1: Following procedures similar to those of Example 64 but substituting piperazin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid piperazin-1-yl-amide.

Step 2: Phenyl-pyrimidine-5-carboxylic acid piperazin-1-yl-amide is dissolved in HCl methanol solution and evaporated methanol to dryness to afford 2-phenyl-pyrimidine-5-carboxylic acid piperazin-1-yl)-amide dihydrochloride as a solid.

Step 3: A suspended solution of 2-phenyl-pyrimidine-5-carboxylic acid piperazin-1-ylamide dihydrochloride (0.5 mmol), methyl bromoacetate (0.5 mmol) and Na$_2$CO$_3$ (2.5 mmol) in wet THF (20 mL) is stirred at rt for 20 h. The mixture is concentrated in vacuo. The residue is purified by silica gel chromatography eluting with 1-5% methanol in DCM to afford {4-[2-phenyl-pyrimidine-5-carbonyl)-amino]-piperazin-1-yl}-acetic acid methyl ester (135 mg, 76%) as a solid. MS: 356 (M+H); $^1$H NMR (300 MHz, CDCl$_3$): δ 2.60-3.18 (m, 8H), 3.18-3.35 (d, 2H), 3.74 (s, 3H), 6.67 (br, 0.5 N—H) 7.03 (br, 0.5 N—H), 7.46-7.60 (m, 3H), 8.50 (d, 2H), 9.21 (d, 2H).

Example 84

2-Phenyl-pyrimidine-5-carboxylic acid (4-cyanomethyl-piperazin-1-yl)-amide

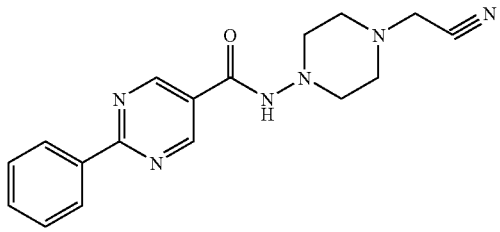

A solution of 2-phenyl-pyrimidine-5-carboxylic acid piperazin-1-ylamide dihydrochloride (0.29 mmol), bromoacetonitrile (0.29 mmol) and Na$_2$CO$_3$ (1.46 mmol) in wet THF (8 mL) is stirred at rt overnight. The reaction mixture is filtered and the filtrate is concentrated in vacuo. The residue is purified by silica gel chromatography eluting with 1-2% methanol in DCM to afford 2-phenyl-pyrimidine-5-carboxylic acid (4-cyanomethyl-piperazin-1-yl)-amide (38 mg, 40%) as a solid. MS: 323 (M+H); $^1$H NMR (300 MHz, CDCl$_3$): δ 2.60-3.30 (m, 8H), 3.55 (s, 2H), 6.63 (br, 0.5 N—H), 7.14 (br, 0.5 N—H), 7.52 (s, 3H), 8.53 (d, 2H), 9.06-9.38 (m, 2H).

Example 85

Acetic acid 2-{4-[(2-phenyl-pyrimidine-5-carbonyl)-amino]-piperazin-1-yl}-ethyl ester

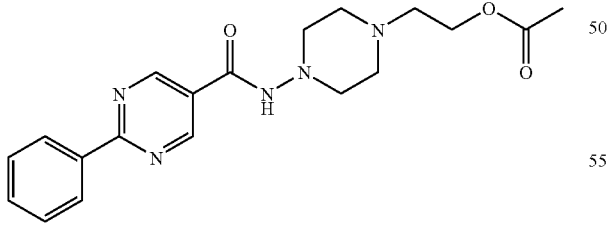

A solution of 2-phenyl-pyrimidine-5-carboxylic[4-(2-hydroxy-ethyl)-piperazin-1-y]-amide (0.21 mmol), acetyl chloride (1.06 mmol) in pyridine (4 mL) is stirred at 80° C. overnight. The reaction mixture is filtered and the filtrate is concentrated in vacuo. The residue is dissolved in EtOAc (10 mL), washed with water (10 mL), 10% Na$_2$CO$_3$ (10 mL) and brine (10 mL), dried (Na$_2$SO$_4$), filtered and concentrated in vacuo. The residue is purified by silica gel chromatography eluting with 0-5% methanol in DCM to afford 2-{4-[(2-phenyl-pyrimidine-5-carbonyl)-amino]-piperazin-1-yl)-ethyl ester (12 mg, 15%) as a solid. MS: 370 (M+H); $^1$H NMR (300 MHz, CDCl$_3$): δ 2.08 (s, 3H), 2.42-3.20 (m, 8H), 3.20-3.80 (m, 3H), 4.10-4.52 (m, 2H) 7.42-7.65 (m, 3H), 8.52 (m, 2H), 9.07-9.38 (d, 2H).

Example 86

2-Phenyl-pyrimidine-5-carboxylic acid (4-acetyl-piperazin-1-yl)-amide

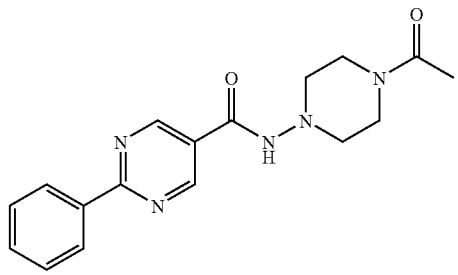

A solution of 2-phenyl-pyrimidine-5-carboxylic acid piperazin-1-ylamide dihydrochloride (0.43 mmol), acetyl chloride (1.28 mmol) and Et$_3$N (1.72 mmol) in DMF (8 mL) is stirred at rt overnight. mixture is concentrated in vacuo. The residue is dissolved in EtOAc (15 mL), washed with water and brine, dried (Na$_2$SO$_4$), filtered and concentrated in vacuo. The residue is triturated with ether to afford 2-phenyl-pyrimidine-5-carboxylic acid (4-acetyl-piperazin-1-yl)-amide (98 mg, 71%) as a solid. MS: 326 (M+H); $^1$H NMR (300 MHz, CDCl$_3$): δ 2.12 (s, 3H), 2.92-3.10 (m, 4H), 3.40-4.10 (m, 4H), 7.43-7.60 (m, 3H), 7.75 (br, N—H), 8.52 (m, 2H), 9.11-9.38 (br, 2H).

Example 87

2-Phenyl-pyrimidine-5-carboxylic acid [4-(2-oxo-tetrahydro-furan-3-yl)-piperazin-1-yl]-amide

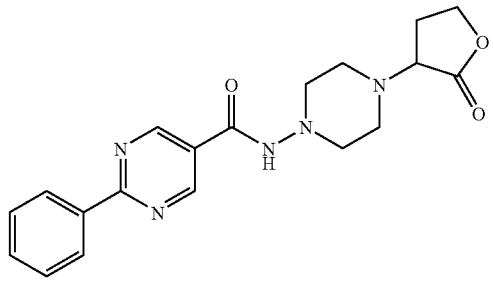

A solution of 2-phenyl-pyrimidine-5-carboxylic acid piperazin-1-ylamide dihydrochloride (0.45 mmol) and bromo-dihydro-furan-2-one (1.8 mmol) in DMF (10 mL) is stirred under N$_2$ at 0° C. for 15 min, then NaH (60%, 1.8 mmol) is added and the mixture is warmed to rt and stirred overnight. The mixture is quenched with water, and extracted with EtOAC. The organic layer is dried (Na$_2$SO$_4$), filtered and concentrated in vacuo. The residue is purified by silica gel chromatography eluting with 0-2% methanol in DCM to afford give 2-phenyl-pyrimidine-5-carboxylic acid [4-(2-oxo-tetrahydro-furan-3-yl)-piperazin-1-yl]-amide (120 mg, 73%) as a solid. MS: 368 (M+H); $^1$H NMR (300 MHz, CDCl$_3$): δ 2.34 (s, 2H), 2.50-3.30 (m, 8H), 3.42-3.70 (m, H), 4.17-4.50 (m, 2H), 7.34-7.68 (m, 3H), 8.50 (d, 2H), 9.06-9.38 (d, 2H). IC$_{50}$=26 nM.

Example 88

2-Phenyl-pyrimidine-5-carboxylic acid [4-(2,2,2-trifluoro-acetyl)-piperazin-1-yl]-amide

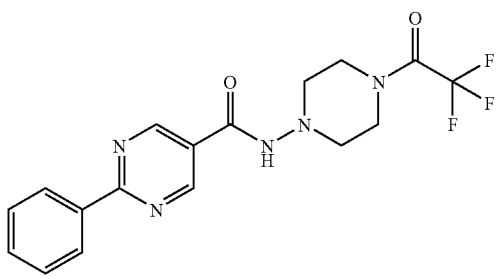

A solution of 2-phenyl-pyrimidine-5-carboxylic acid piperazin-1-ylamide dihydrochloride (0.36 mmol), trifluoroacetic anhydride (1.08 mmol) and Et$_3$N (1.44 mmol) in DMF (8 mL) is stirred under N$_2$ at rt overnight. The reaction mixture is concentrated in vacuo. The residue is dissolved in EtOAc (15 mL), washed with water (10 ml) and brine (15 mL), dried (Na$_2$SO$_4$), filtered and concentrated in vacuo. The residue is triturated with ether to give 2-phenyl-pyrimidine-5-carboxylic acid [4-(2,2,2-trifluoro-acetyl)-piperazin-1-yl]-amide (136 mg, 100%) as a solid. MS: 380 (M+H); $^1$H NMR (300 MHz, CDCl$_3$): δ 2.95-3.40 (s, 4H), 3.60-4.10 (m, 4H), 7.41-7.68 (m, 3H), 8.52 (d, 2H), 9.03-9.40 (br, 2H). IC$_{50}$=57 nM.

Example 89

2-Phenyl-pyrimidine-5-carboxylic acid [4-(2-methoxy-ethyl)-piperazin-1-yl]-amide

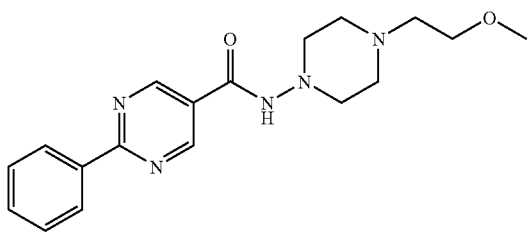

Step 1: To a suspended solution of 2-phenyl-pyrimidine-5-carboxylic acid [4-(2-hydroxy-ethyl)-piperazin-1-yl]-amide (0.83 mmol) in DCM (8 mL) under N$_2$ are added a solution of Et$_3$N (2.67 mmol) in DCM (1 mL), a solution of N,N-dimethyl-4-aminopyridine (0.2 mmol) in DCM (1 mL) and a solution of di-tert-butyl dicarbonate (1.48 mmol) in DCM (1 mL) at rt. The resulting mixture is stirred at rt for 3 h, and then concentrated in vacuo. The residue is purified by silica gel chromatography eluting with 6% ethanol in EtOAc to afford [4-(2-methoxy-ethyl)-piperazin-1-yl]-(2-phenyl-pyrimidine-5-carbonyl)-carbamic acid tert-butyl ester (70 mg, 20%) as a solid. MS: 428 (M+H).

Step 2: A solution of [4-(2-methoxy-ethyl)-piperazin-1-yl]-(2-phenyl-pyrimidine-5-carbonyl)-carbamic acid tert-butyl ester (0.21 mmol), NaH (60%, 0.66 mmol) and iodomethane (0.63 mmol) in DMF (8 mL) is stirred under N$_2$ at rt overnight. The reaction mixture is quenched with water, and extracted with EtOAc. The organic layer is separated, dried (Na$_2$SO$_4$), filtered and concentrated in vacuo. The residue is purified by silica gel chromatography eluting with 0-2% methanol in DCM to afford 2-phenyl-pyrimidine-5-carboxylic acid [4-(2-methoxy-ethyl)-piperazin-1-yl]-amide (32 mg, 44%) as a solid. MS: 342 (M+H).

Example 90

2-Phenyl-pyrimidine-5-carboxylic acid [4-(2-morpholin-4-yl-2-oxo-ethyl)-piperazin-1-yl]-amide

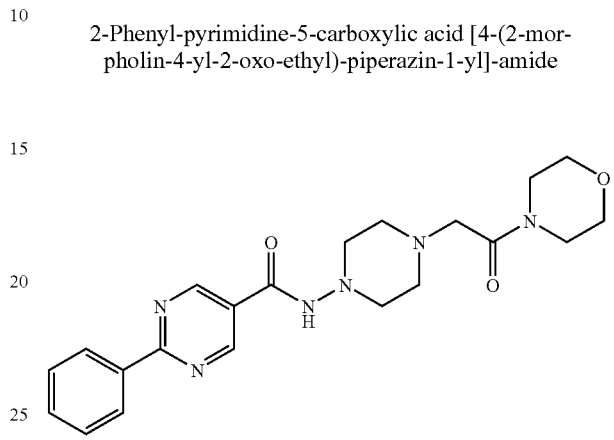

A solution of 2-phenyl-pyrimidine-5-carboxylic acid piperazin-1-ylamide dihydrochloride (0.43 mmol) and NaH (60%, 2.15 mmol) in DMF (10 mL) is stirred under N$_2$ at rt for 20 min. 2-Chloro-1-morpholin-4-yl-ethanone (0.65 mmol)) is added and the reaction mixture is stirred at rt overnight. The reaction mixture is quenched with water, and extracted with EtOAc. The organic layer is separated, dried (Na$_2$SO$_4$), filtered and concentrated in vacuo. The residue is purified by silica gel chromatography eluting with 0-4% methanol in DCM to afford 2-phenyl-pyrimidine-5-carboxylic acid [4-(2-morpholin-4-yl-2-oxo-ethyl)-piperazin-1-yl]-amide (24 mg, 14%) as a solid. MS: 411 (M+H); $^1$H NMR (300 MHz, CDCl$_3$): δ 2.85-3.10 (m, 2H), 3.60-4.00 (m, 12H), 4.46 (d, 2H), 4.84 (s, 2H), 7.44-7.62 (m, 3H), 8.34-8.58 (m, 2H), 9.20-9.38 (d, 2H). IC$_{50}$=831.5 nM.

Example 91

2-(3-Fluoro-phenyl)-pyrimidine-5-carboxylic acid (2,3-dihydro-indol-1-yl)-amide

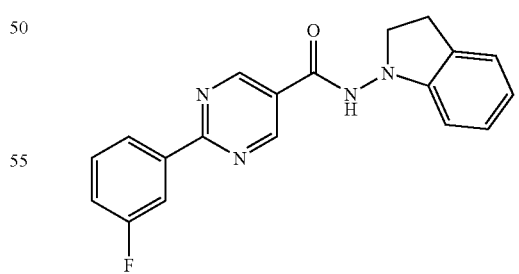

Following procedures similar to those of Example 64 but substituting 2-(3-fluoro-phenyl)-pyrimidine-5-carboxylic acid for 2-phenyl-4-yl-pyrimidine-5-carboxylic acid, and substituting 2,3-dihydro-indol-1-ylamine for 3-{3-amino-2,4-dioxo-1,2,3,4-tetrahydro-pyrimidin-5-propionic acid methyl ester, there is prepared 2-(3-fluoro-phenyl)-pyrimidine-5-carboxylic acid (2,3-dihydro-indol-1-yl)-amide (83%) as a solid. MS: 335 (M+H); $^1$H NMR (300 MHz, CDCl$_3$): δ 3.00 (s, 2H), 3.70 (s, 2H), 6.53-7.34 (m, 5H), 7.45 (s, H), 8.00-8.38 (m, 2H), 9.20 (s, 2H). IC$_{50}$=3 nM.

Example 92

2-(3-Fluoro-phenyl)-pyrimidine-5-carboxylic acid piperadin-1-yl-amide

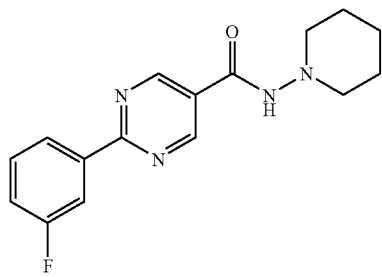

Following procedures similar to those of Example 64 but substituting 2-(3-fluoro-phenyl)-pyrimidine-5-carboxylic acid for 2-phenyl-4-yl-pyrimidine-5-carboxylic acid, and substituting piperadin-1-ylamine for 3-{3-amino-2,4-dioxo-1,2,3,4-tetrahydro-pyrimidin-5-propionic acid methyl ester, there is prepared 2-(3-fluoro-phenyl)-pyrimidine-5-carboxylic acid piperadin-1-yl-amide (71%) as a solid. MS: 301 (M+H); $^1$H NMR (300 MHz, CDCl$_3$): δ 1.20-2.00 (m, 6H), 2.20-3.60 (m, 4H), 6.97-7.30 (m, H), 7.34-7.56 (m, H), 8.06-8.38 (m, 2H), 9.00-9.38 (d, 2H). IC$_{50}$=19.5 nM.

Example 93

2-(4-Methoxy-phenyl)-pyrimidine-5-carboxylic acid (6-methyl-3-oxo-2,5-dihydro-3H-[1,2,4]triazin-4-yl)-amide,

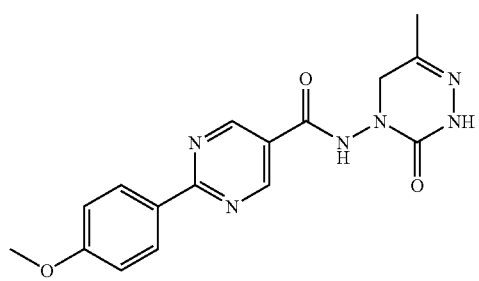

Step 1: Following the procedures similar to those of Example 59, step 1, but substituting 4-methoxyphenylboronic acid for 3-methoxyphenylboronic acid, there is prepared 2-(4-methoxy-phenyl)-pyrimidine-5-carboxylic acid methyl ester.

Step 2: Following the procedures similar to those of Example 59, step 2, but substituting 2-(4-methoxy-phenyl)-pyrimidine-5-carboxylic acid methyl ester for 2-(3-methoxy-phenyl)-pyrimidine-5-carboxylic acid methyl ester, there is prepared 2-(4-methoxy-phenyl)-pyrimidine-5-carboxylic acid.

Step 3: Following the procedures similar to those of Example 59, step 3, but substituting 2-(4-methoxy-phenyl)-pyrimidine-5-carboxylic acid for 2-(3-methoxy-phenyl)-pyrimidine-5-carboxylic acid, there is prepared 2-(4-methoxy-phenyl)-pyrimidine-5-carboxylic acid (6-methyl-3-oxo-2,5-dihydro-3H-[1,2,4]triazin-4-yl)-amide. MS: 341 (M+H); $^1$H NMR (DMSO-d$_6$): δ 1.91 (s, 3H), 3.86 (s, 3H), 4.22 (s, 2H), 7.12 (d, J=8.5 Hz, 1H), 7.95 (s, 1H), 8.42 (d, J=8.6 Hz, 1H), 9.21 (s, 2H), 9.95 (s, 1H), 11.02 (s, 1H).

Example 94

2-Phenyl-pyrimidine-5-carboxylic acid (hexahydro-cyclopenta[c]pyrrol-2-yl)-amide

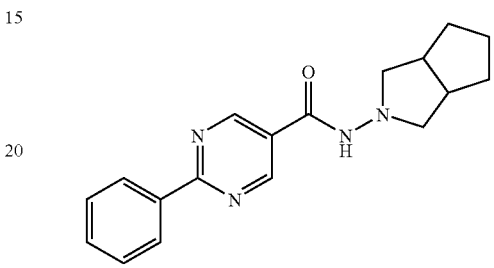

Following procedures similar to those of Example 64 but substituting hexahydro-cyclopenta[c]pyrrol-2-ylamine for 3-{3-amino-2,4-dioxo-1,2,3,4-tetrahydro-pyrimidin-5-propionic acid methyl ester, there is prepared 2-(3-fluoro-phenyl)-pyrimidine-5-carboxylic acid (hexahydro-cyclopenta[c]pyrrol-2-yl)-amide (39%) as a solid. MS: 309 (M+H); $^1$H NMR (300 MHz, CDCl$_3$): δ 1.20-1.90 (m, 6H), 2.40-3.50 (m, 6H), 6.94 (s, N—H), 7.52 (s, 3H), 8.50 (s, 2H), 9.08-9.38 (d, 2H).

Example 95

4-Methyl-2-phenyl-pyrimidine-5-carboxylic acid (2,3-dihydro-indol-1-yl)-amide

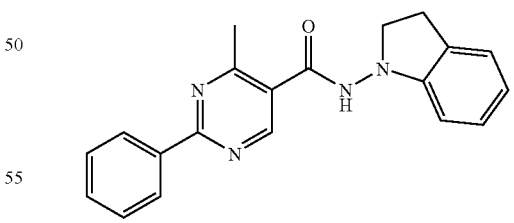

Following procedures similar to those of Example 64 but substituting 4-methyl-2-phenyl-pyrimidine-5-carboxylic acid chloride for 2-phenyl-4-yl-pyrimidine-5-carboxylic acid, and substituting 2,3-dihydro-indol-1-ylamine for 3-{3-amino-2,4-dioxo-1,2,3,4-tetrahydro-pyrimidin-5-propionic acid methyl ester, there is prepared 4-methyl-2-phenyl-pyrimidine-5-carboxylic acid (2,3-dihydro-indol-1-yl)-amide (80%) as a solid. MS: 331 (M+H); $^1$H NMR (300 MHz, CDCl$_3$): δ 2.69 (s, 3H), 2.74-3.10 (m, 2H), 3.64 (t, 2H), 6.58-6.97 (m, 2H), 7.03-7.30 (m, 2H), 7.49 (s, 3H), 7.96 (s, N—H), 8.44 (s, 2H), 8.72 (d, 2H). IC$_{50}$=5.5 nM.

Example 96

2-Phenyl-pyrimidine-5-carboxylic acid pyrrolidin-1-yl-amide

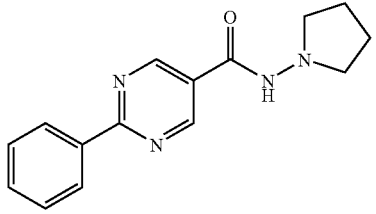

Following procedures similar to those of Example 64 but substituting pyrrolidin-1-ylamine hydrochloride for 3-{3-amino-2,4-dioxo-1,2,3,4-tetrahydro-pyrimidin-5-propionic acid methyl ester, there is prepared 2-(3-fluoro-phenyl)-pyrimidine-5-carboxylic acid pyrrolidin 1-yl-amide (67%) as a solid. MS: 269 (M+H); $^1$H NMR (300 MHz, CDCl$_3$): δ 1.70-2.20 (m, 4H), 2.70-3.46 (m, 4H), 7.55 (s, 3H), 8.42-8.67(m, 2H), 9.14-9.49 (t, 2H).

Example 97

2-Phenyl-pyrimidine-5-carboxylic acid (2,6-dimethyl-piperadin-1-yl)-amide

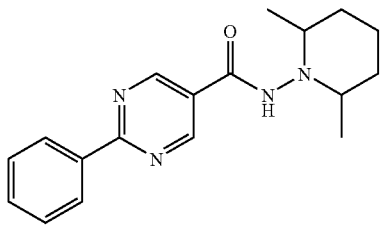

Following procedures similar to those of Example 64 but substituting 2,6-dimethyl-piperadin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid (2,6-dimethyl-piperadin-1-yl)-amide (69%) as a solid. MS: 311 (M+H); $^1$H NMR (300 MHz, CDCl$_3$): δ 0.95-1.24 (m, 6H), 1.24-1.87 (m, 6H), 1.88-3.60 (m, 2H), 6.35 (br, N—H), 7.53 (s, 3H), 8.52 (s, 2H), 9.10-9.73 (m, 2H).

Example 98

2-(3-Fluoro-phenyl)-pyrimidine-5-carboxylic acid (4-cyclopentyl-piperazin-1-yl)-amide

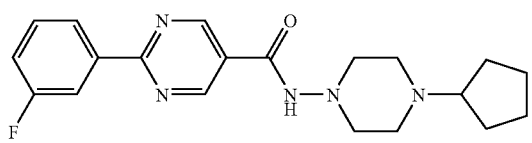

Following procedures similar to those of Example 64 but using substituting 2-(3-fluoro-phenyl)-pyrimidine-5-carboxylic acid for 2-phenyl-4-yl-pyrimidine-5-carboxylic acid, and substituting 4-cyclopentyl-piperazin-1-ylamine for 3-{3-amino-2,4-dioxo-1,2,3,4-tetrahydro-pyrimidin-5-propionic acid methyl ester, there is prepared 2-(3-fluoro-phenyl)-pyrimidine-5-carboxylic acid (4-cyclopentyl-piperazin-1-yl-amide (64%) as a solid. MS: 370 (M+H).

Example 99

2-Phenyl-pyrimidine-5-carboxylic acid (2-methyl-2,3-dihydro-indol-1-yl)-amide

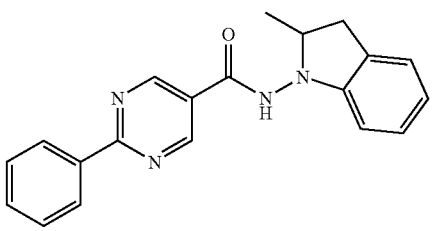

Following procedures similar to those of Example 64 but substituting 2-methyl-2,3-dihydro-indol-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid (2-methyl-2,3-dihydro-indol-1-yl)-amide (32%) as a solid. MS: 331 (M+H); $^1$H NMR (300 MHz, CDCl$_3$): δ 1.05 (m, 3H), 2.50-2.79 (m, H), 3.03-3.24 (m, H), 3.40-3.58 (m, 0.5H), 3.92 (br, 0.5H), 6.67 (d, 0.5N—H), 6.77-7.33 (m, 4H), 7.51 (m, 3H), 7.98 (s, 0.5N—H), 8.52 (m, 2H), 9.23 (d, 2H). IC$_{50}$=4 nM.

Example 100

2-(3-Fluoro-phenyl)-pyrimidine-5-carboxylic acid (2-methyl-2,3-dihydro-indol-1-yl)-amide

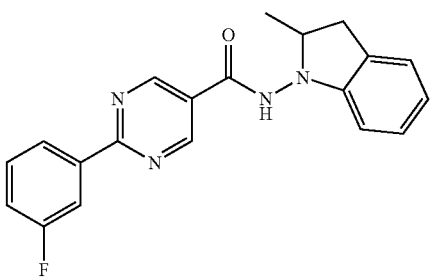

Following procedures similar to those of Example 64 but substituting 2-(3-fluoro-phenyl)-pyrimidine-5-carboxylic acid for 2-phenyl-4-yl-pyrimidine-5-carboxylic acid, and substituting 2-methyl-2,3-dihydro-indol-1-ylamine for 3-{3-amino-2,4-dioxo-1,2,3,4-tetrahydro-pyrimidin-5-propionic acid methyl ester, there is prepared 2-(3-fluoro-phenyl)-pyrimidine-5-carboxylic acid (2-methyl-2,3-dihydro-indol-1-yl)-amide (31%) as a solid. MS: 349 (M+H); $^1$H NMR (300 MHz, CDCl$_3$): δ 1.00-1.48 (m, 3H), 2.43-2.78 (m, 2H), 3.32-

4.06 (m, H), 6.50-6.93 (m, 1.5H), 6.93-7.34 (m, 4H), 7.34-7.54 (d, H), 8.05-8.32 (m, 2H), 8.56 (s, 0.5N—H), 9.17 (d, 2H). IC$_{50}$=4 nM.

Example 101

2-Phenyl-pyrimidine-5-carboxylic acid N'-methyl-N'-pyridin-2-yl-hydrazide

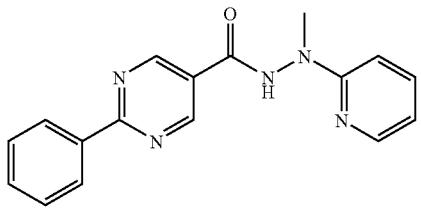

Following procedures similar to those of Example 64 but substituting N'-methyl-N'-pyridin-2-yl-hydrazine for 3-{3-amino-2,4-dioxo-1,2,3,4-tetrahydro-pyrimidin-5-propionic acid methyl ester, there is prepared 2-phenyl-pyrimidine-5-carboxylic acid N'-methyl-N'-pyridin-2-yl-hydrazide (31%) as a solid. MS: 306 (M+H); $^1$H NMR (300 MHz, CDCl$_3$): δ 3.48 (s, 3H), 6.88 (m, 2H), 7.40-7.70 (m, 4H), 8.23 (s, H), 8.52 (m, 2H), 9.13 (br, N—H), 9.28 (s, 2H).

Example 102

2-Phenyl-pyrimidine-5-carboxylic acid (5-fluoro-indol-1-yl)-amide

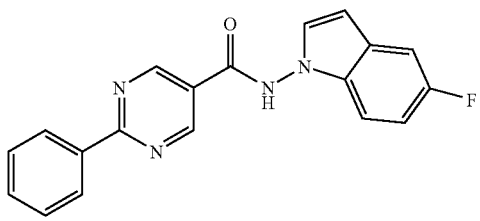

Step 1: A solution of 5-fluoro-1H-indole (16.9 mmol) and potassium tert-butoxide (33.8 mmol) in DMF (76 mL) is stirred at rt under N$_2$ for 2 h. 0.15 M NH$_2$Cl. in ether (169.2 mL) is added drop-wise for 15 minutes at rt. The reaction mixture is stirred at rt for 2 h, then quenched with 10% Na$_2$S$_2$O$_3$ aqueous solution and extracted with ether. The organic layer is separated, dried (Na$_2$SO$_4$), filtered and concentrated in vacuo. The residue is purified by silica gel chromatography eluting with 60-80% EtOAc in heptane to afford 5-fluoro-indole-1-ylamine (751 mg, 30%) as a solid. $^1$H NMR (300 MHz, CDCl$_3$): δ 4.80 (br, 2N—H), 6.38 (d, H), 7.00 (m, H), 7.19-7.43 (m, 3H).

Step 2: Diethyl-iso-propylamine (2.30 mmol) is added to a stirred solution of 2-phenyl-pyrimidine-5-carboxylic acid chloride (1.15 mmol) and 5-fluor-indol-1-ylamine (1.15 mmol) in DCM (20 mL) at rt. The reaction mixture is stirred at rt overnight and concentrated in vacuo. The residue is dissolved in EtOAc (30 mL), then washed with 5% HCl (10 mL), water (10 mL) and brine (10 mL), dried (Na$_2$SO$_4$), filtered and concentrated in vacuo. The residue is purified by silica gel chromatography eluting with 10-40% EtOAc in heptane to afford 2-phenyl-pyrimidine-5-carboxylic acid (5-fluoro-indol-1-yl)-amide (185 mg, 49%) as a solid. MS: 333 (M+H); $^1$H NMR (300 MHz, CDCl$_3$): δ 6.56 (s, H) 7.02 (m, H), 7.10-7.38 (m, 4H), 7.55 (s, 3H), 8.53 (s, 2H), 8.70-9.40 (br, 2H). IC$_{50}$=3 nM.

Example 103

2-Pyridin-2-yl-pyrimidine-5-carboxylic acid (2,3-dihydro-indol-1-yl)-amide

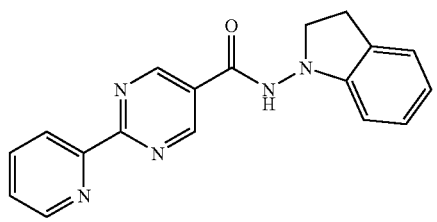

Following procedures similar to those of Example 64 but substituting 2-pyridin-2-yl-pyrimidine-5-carboxylic acid for 2-phenyl-4-yl-pyrimidine-5-carboxylic acid, and substituting 2,3-dihydro-indol-1-ylamine for 3-{3-amino-2,4-dioxo-1,2,3,4-tetrahydro-pyrimidin-5-propionic acid methyl ester, there is prepared 2-pyridin-2-yl-pyrimidine-5-carboxylic acid (2,3-dihydro-indol-1-yl)-amide (98%) as a solid. MS: 318 (M+H); $^1$H NMR (300 MHz, CDCl$_3$): δ 2.85-3.20 (m, 2H), 3.77 (t, 2H), 6.76 (d, 0.5N—H), 6.82-7.49 (m, 4H), 7.46 (d, H), 7.89 (d, H), 8.07 (br, 0.5N—H), 8.57 (m, H), 8.84 (d, H), 9.30 (s, 2H). IC$_{50}$=3 nM.

Example 104

2-Pyridin-2-yl-pyrimidine-5-carboxylic acid indol-1-yl-amide

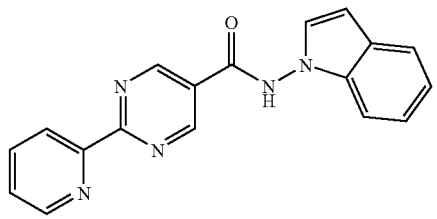

A suspended solution of 2-pyridin-2-yl-pyrimidine-5-carboxylic acid (2,3-dihydro-indol-1-yl)-amide (0.28 mmol) and MnO$_2$ (1.42 mmol) in DCM (8 mL) is stirred at rt for 2 h. The reaction mixture is filtered and the filtrate is concentrated in vacuo. The residue is purified by silica gel chromatography eluting with 0-5% methanol in DCM to afford 2-pyridin-2-yl-pyrimidine-5-carboxylic acid indol-1-yl-amide (45 mg, 50%) as a solid. MS: 316 (M+H); $^1$H NMR (300 MHz, CDCl$_3$): δ 6.48 (s, H), 6.72-7.48 (m, 5H), 7.56 (s, H), 7.88 (s, H), 8.52 (br, 2H), 9.08 (br, 2H), 11.56 (br, N—H). IC$_{50}$=4.5 nM.

Example 105

2-(3-Fluoro-phenyl)-pyrimidine-5-carboxylic acid indol-1-yl-amide

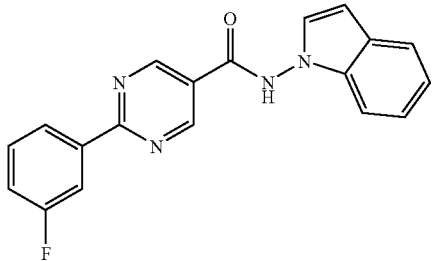

A suspended solution of 2-(3-fluoro-phenyl)-pyrimidine-5-carboxylic acid (2,3-dihydro-indol-1-yl)-amide (0.39 mmol) and MnO$_2$ (1.95 mmol) in DCM (10 mL) is stirred at rt for 40 min. The reaction mixture is filtered and the filtrate is concentrated in vacuo. The residue is purified by silica gel chromatography eluting with 0-40% EtOAc in heptane to afford 2-(3-fluoro-phenyl)-pyrimidine-5-carboxylic indol-1-yl-amide (70 mg, 54%) as a solid. MS: 333 (M+H); $^1$H NMR (300 MHz, CDCl$_3$): δ 6.60 (s, H), 7.10 (d, H), 7.14-7.46 (m, 4H), 7.50 (br, H), 7.64 (d, H), 8.37 (d, 2H), 8.60-9.40 (br, 3H). IC$_{50}$=5 nM.

Example 106

2-(3-Fluoro-phenyl)-4-methyl-pyrimidine-5-carboxylic acid (2,3-dihydro-indol-1-yl)-amide

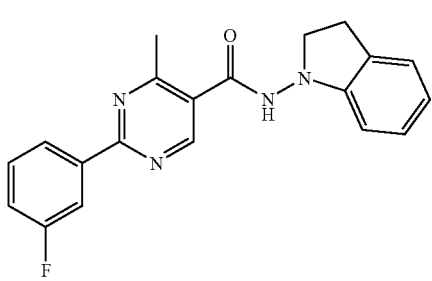

Following procedures similar to those of Example 64 but substituting 2-(3-fluoro-phenyl)-4-methyl-pyrimidine-5-carboxylic acid for 2-phenyl-4-yl-pyrimidine-5-carboxylic acid, and substituting 2,3-dihydro-indol-1-ylamine for 3-{3-amino-2,4-dioxo-1,2,3,4-tetrahydro-pyrimidin-5-propionic acid methyl ester, there is prepared 2-(3-fluoro-phenyl)-4-methyl-pyrimidine-5-carboxylic acid (2,3-dihydro-indol-1-yl)-amide (91%) as a solid. MS: 349 (M+H); $^1$H NMR (300 MHz, CDCl$_3$): δ 2.77-3.08 (m, 2H), 3.09-3.80 (m, 2H), 6.75-7.00 (m, 2H), 7.04-7.32 (m, 3H), 7.44 (q, H), 8.06-8.31 (m, 2H), 8.51 (d, 2H). IC$_{50}$=23 nM.

Example 107

2-(3-Fluoro-phenyl)-4-methyl-pyrimidine-5-carboxylic acid (2-methyl-2,3-dihydro-indol-1-yl)-amide

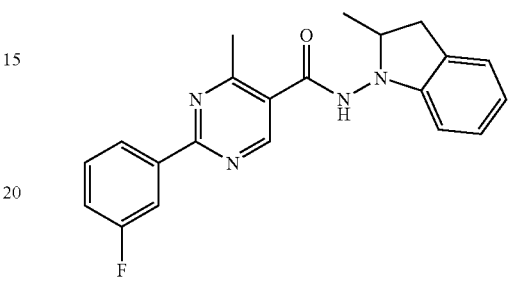

Following procedures similar to those of Example 64 but substituting 2-(3-fluoro-phenyl)-4-methyl-pyrimidine-5-carboxylic acid for 2-phenyl-4-yl-pyrimidine-5-carboxylic acid, and substituting 2-methyl-2,3-dihydro-indol-1-ylamine for 3-{3-amino-2,4-dioxo-1,2,3,4-tetrahydro-pyrimidin-5-propionic acid methyl ester, there is prepared 2-(3-fluoro-phenyl)-4-methyl-pyrimidine-5-carboxylic acid (2-methyl-2,3-dihydro-indol-1-yl)-amide (94%) as a solid. MS: 363 (M+H); $^1$H NMR (300 MHz, CDCl$_3$): δ 1.00-1.50 (d, 3H), 2.30-2.80 (m, 4H), 3.01 (m, H), 3.26-3.96 (m, H), 6.45-7.00 (m, 2H), 7.00-7.30 (m, 3H), 7.41 (q, H), 7.97-8.28 (m, 2H), 8.68 (d, H).

Example 108

2-(3-Fluoro-phenyl)-pyrimidine-5-carboxylic acid (2-methyl-indol-1-yl)-amide

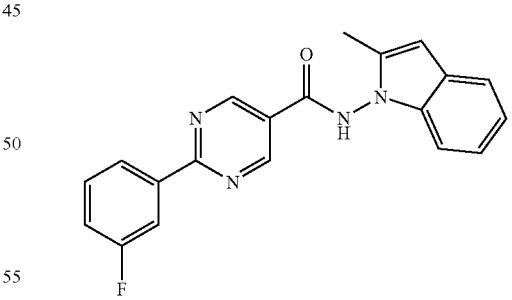

A suspended solution of 2-(3-fluoro-phenyl)-pyrimidine-5-carboxylic acid (2-methyl-2,3-dihydro-indol-1-yl)-amide (0.98 mmol) and MnO2 (4.88 mmol) in DCM (15 mL) is stirred at rt for 2 h. The reaction mixture is filtered and the filtrate is concentrated in vacuo. The residue is purified by silica gel chromatography eluting with 0-40% EtOAc in heptane to afford 2-(3-fluoro-phenyl)-pyrimidine-5-carboxylic acid (2-methyl-indol-1-yl)-amide (230 mg, 97%) as a solid. MS: 347 (M+H); $^1$H NMR (300 MHz, CDCl$_3$): δ 2.08-2.40

(m, 3H), 6.27 (s, H), 6.95-7.35 (m, 4H), 7.36-7.65 (m, 2H), 8.20-8.44 (m, 2H), 8.49-9.20 (d, 2H). IC$_{50}$=6 nM.

Example 109

2-(3-Fluoro-phenyl)-4-methyl-pyrimidine-5-carboxylic acid indol-1-ylamide

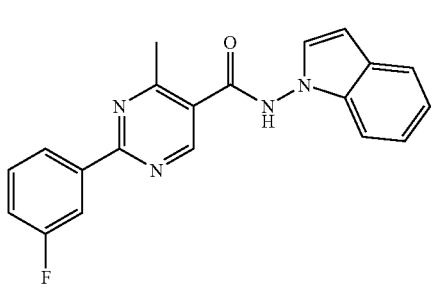

A suspended solution of 2-(3-fluoro-phenyl)-4-methyl-pyrimidine-5-carboxylic acid (2,3-dihydro-indol-1-yl)-amide (0.72 mmol) and MnO2 (3.60 mmol) in DCM (10 mL) is stirred at rt for 40 min. The reaction mixture is filtered and the filtrate is concentrated in vacuo. The residue is purified by silica gel chromatography eluting with 0-40% EtOAc in heptane to afford 2-(3-fluoro-phenyl)-4-methyl-pyrimidine-5-carboxylic acid indol-1-ylamide (185 mg, 75%) as a solid. MS: 347 (M+H); $^1$H NMR (300 MHz, CDCl$_3$): δ 2.73 (s, 3H), 6.53 (s, H), 7.03 (d, H), 7.08-7.36 (m, 4H), 7.37-7.75 (m, 2H), 8.04-8.40 (m, 2H), 8.56 (br, H), 8.81 (br, H). IC$_{50}$=10 nM.

Example 110

4-Methyl-2-pyridin-2-yl-pyrimidine-5-carboxylic acid (2,3-dihydro-indol-1-yl)-amide

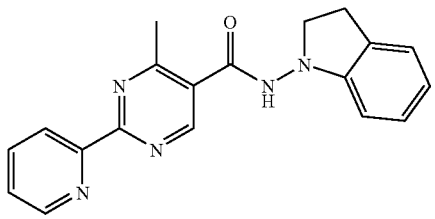

Following procedures similar to those of Example 64 but substituting 4-methyl-2-pyridin-2-yl-pyrimidine-5-carboxylic acid for 2-phenyl-4-yl-pyrimidine-5-carboxylic acid, and substituting 2,3-dihydro-indol-1-ylamine for 3-{3-amino-2,4-dioxo-1,2,3,4-tetrahydro-pyrimidin-5-propionic acid methyl ester, there is prepared 4-methyl-2-pyridin-2-yl-pyrimidine-5-carboxylic acid (2,3-dihydro-indol-1-yl)-amide (96%) as a solid. MS: 332 (M+H); $^1$H NMR (300 MHz, CDCl$_3$): δ 2.78 (s, 3H), 3.09 (t, 2H), 3.77 (t, 2H), 6.70-7.01 (m, 2H), 7.09-7.23 (m, 2H), 7.36-7.46 (m, H), 7.85 (t, H), 8.43-8.64 (m, 2H), 8.80 (d, H). IC$_{50}$=3 nM.

Example 111

4-Methyl-2-pyridin-2-yl-pyrimidine-5-carboxylic acid indol-1-ylamide

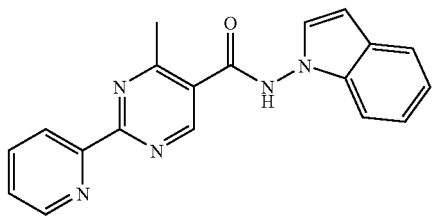

A suspended solution of 4-methyl-2-pyridin-2-yl-pyrimidine-5-carboxylic acid (2,3-dihydro-indol-1-yl)-amide (1.00 mmol) and MnO2 (5.00 mmol) in DCM (10 mL) is stirred at rt for 60 min. The reaction mixture is filtered and the filtrate is concentrated in vacuo. The residue is purified by silica gel chromatography eluting with 0-5% methanol in DCM to afford 4-methyl-2-pyridin-2-yl-pyrimidine-5-carboxylic acid indol-1-ylamide (196 mg, 60%) as a solid. MS: 330 (M+H); $^1$H NMR (300 MHz, CDCl$_3$): δ 2.77 (s, 3H), 6.58 (s, H), 7.15 (s, 2H), 7.26 (m, 3H), 7.84 (d, H), 8.44 (s, 2H), 8.73 (s, H), 10.94 (br, N—H). IC$_{50}$=5 nM.

Example 112

2-(3-Fluoro-phenyl)-pyrimidine-5-carboxylic acid (5-methanesulfonyl-indol-1-yl)-amide

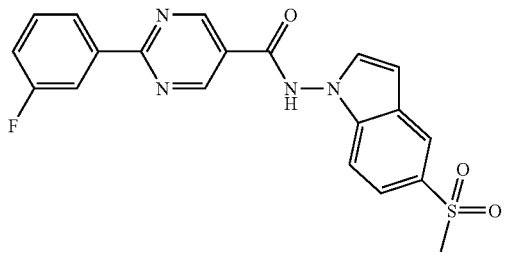

Step 1: A solution of 5-methanesulfonyl-indoline (4.11 mmol) and MnO2 (20.55 mmol) in DCM (20 mL) is stirred at rt overnight. The reaction mixture is filtered and the filtrate is concentrated in vacuo to afford 5-methanesulfonyl-1H-indole (782 mg, 100%) as a solid. MS: 196 (M+H); $^1$H NMR (300 MHz, CDCl$_3$): δ 3.09 (s, 3H), 6.71 (s, H), 7.39 (s, H), 7.53 (d, H), 7.74 (m, H), 8.30 (s, H), 8.66 (br, N—H).

Step 2: A solution of 5-methanesulfonyl-1H-indole (4.1 mmol) and potassium tert-butoxide (8.2 mmol) in DMF (20 mL) is stirred at rt under N$_2$ for 2 h. 0.15 M NH$_2$Cl in ether (41 mL) is added drop-wise for 15 min at rt and the reaction mixture is stirred at rt for 2 h. The reaction mixture is quenched with 10% Na$_2$S$_2$O$_3$ aqueous solution, and extracted with ether (3×40 mL). The combined organic layer is washed with water (2×30 mL) and brine (20 mL), dried (Na$_2$SO$_4$), filtered and concentrated in vacuo. The residue is purified by silica gel chromatography eluting with EtOAc and heptane to afford 5-methanesulfonyl-indole-1-ylamine (230 mg, 32%) as a solid. MS: 211 (M+H); $^1$H NMR (300 MHz, CDCl$_3$): δ

3.08 (s, 3H), 4.94 (br, 2N—H), 6.55 (d, H), 7.34 (m, H), 7.57 (d, H), 7.73 (m, H), 8.21 (m, H).

Step 3: A solution of 2-(3-fluoro-phenyl)-pyrimidine-5-carboxylic acid chloride (0.62 mmol) in EtOAc (10 mL) is added to a stirred solution of 5-methanesulfonyl-indole-1-ylamine (0.62 mmol) and K$_2$CO$_3$ (3.08 mmol) in EtOAc (10 mL) and H$_2$O (10 mL) at 0° C., and the reaction mixture is warmed to rt and stirred overnight. EtOAc is evaporated in vacuo, and the resulting solid is collected by filtration. The solid is triturated with DCM to afford 2-(3-fluoro-phenyl)-pyrimidine-5-carboxylic acid (5-methanesulfonyl-indol-1-yl)-amide (85 mg, 34%) as a solid. MS: 411 (M+H); $^1$H NMR (300 MHz, CD$_3$OD): δ 3.13 (s, 3H), 6.81 (m, H) 7.25-7.39 (m, H), 7.49-7.67 (m, 3H), 7.72-7.84 (m, H), 8.21-8.32 (m, 2H), 8.39 (d, H), 9.41 (s, 2H).

Example 113

2-(3-Fluoro-phenyl)-pyrimidine-5-carboxylic acid (6-methanesulfonyl-indol-1-yl)-amide

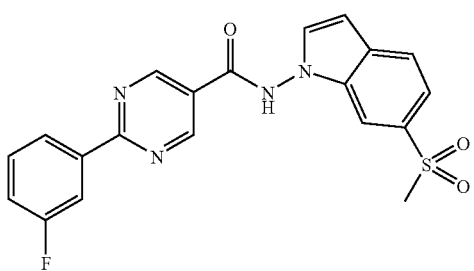

Step 1: A solution of 6-methanesulfonyl-1H-indole (2.66 mmol) and potassium tert-butoxide (5.32 mmol) in DMF (15 mL) is stirred at rt under N$_2$ for 2 h. 0.15 M NH$_2$Cl in ether (26.6 mL) is added drop-wise for 15 minutes at rt and the reaction mixture is stirred at rt for 2 h. The reaction mixture is quenched with 10% Na$_2$S$_2$O$_3$ aqueous solution, and extracted with ether (3×20 mL). The combined organic layer is washed with brine (20 mL), dried (Na$_2$SO$_4$), filtered and concentrated in vacuo. The residue is triturated with EtOAc to give 6-methanesulfonyl-indole-1-ylamine (270 mg, 51%) as a solid. MS: 211 (M+H); $^1$H NMR (300 MHz, CDCl$_3$): δ 3.09 (s, 3H), 6.49 (d, H), 7.41 (m, H), 7.61 (d, H), 7.71 (d, H), 8.12 (s, H).

Step 2: A solution of 2-(3-fluoro-phenyl)-pyrimidine-5-carboxylic acid chloride (0.65 mmol) in EtOAc (15 mL) is added to a stirred solution of 5-methanesulfonyl-indole-1-ylamine (0.65 mmol) and potassium carbonate (2.60 mmol) in EtOAc (10 mL) and H$_2$O (10 mL) at 0° C., and the reaction mixture is warmed to rt and stirred overnight. EtOAc is evaporated in vacuo, and the resulting solid is collected by filtration, and purified by silica gel chromatography eluting with 20-60% EtOAc in heptane to afford 2-(3-fluoro-phenyl)-pyrimidine-5-carboxylic acid (6-methanesulfonyl-indol-1-yl)-amide (85 mg, 33%) as a solid. MS: 411 (M+H); $^1$H NMR (300 MHz, CDCl$_3$): δ 3.08 (s, 3H), 6.62 (d, H) 7.33-7.44 (m, 2H), 7.46-7.59 (m, 2H), 7.75 (s, H), 8.29 (d, 2H), 8.39 (d, H), 9.42 (s, 2H), 10.80 (br, H). IC$_{50}$=8 nM.

Example 114

2-Pyridin-2-yl-pyrimidine-5-carboxylic acid (5-methanesulfonyl-indol-1-yl)-amide

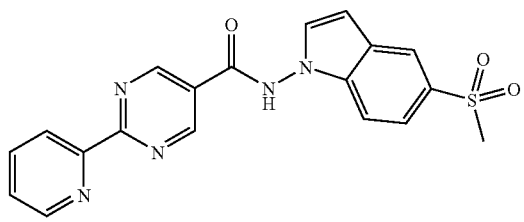

Diethyl-iso-propylamine (3.54 mmol) is added a solution of 2-pyridin-2-yl-pyrimidine-5-carboxylic acid HCl (1.18 mmol), 5-methanesulfonyl-indol-1-ylamine (1.18 mmol) and TBTU (1.77 mmol) in anhydrous DMF (16 mL) at rt. The reaction mixture is stirred at 90° C. overnight and then concentrated in vacuo. The residue is dissolved in EtOAc (50 mL) and water (50 mL). The organic layer is separated, washed with water (2×20 mL) and brine (20 mL), dried (Na$_2$SO$_4$), filtered and concentrated in vacuo. The residue is triturated with EtOAc and DCM to afford 2-pyridin-2-yl-pyrimidine-5-carboxylic acid (5-methanesulfonyl-indol-1-yl)-amide (125 mg, 27%) as a solid. MS: 394 (M+H); $^1$H NMR (300 MHz, CD$_3$OD): δ 3.14 (s, 3H), 6.82 (m, H) 7.50-7.72 (m, 3H), 7.80 (m, H), 8.07 (m, H), 8.30 (m, 2H), 8.70 (d, H), 8.80 (s, H), 9.51 (s, 2H).

Example 115

2-Pyridin-3-yl-pyrimidine-5-carboxylic acid (5-methanesulfonyl-indol-1-yl)-amide

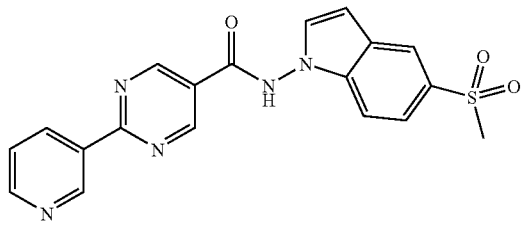

Diethyl-iso-propylamine (3.84 mmol) is added a solution of 2-pyridin-2-yl-pyrimidine-5-carboxylic acid hydrochloride (1.28 mmol), 5-methanesulfonyl-indol-1-ylamine (1.28 mmol) and TBTU (1.92 mmol) in anhydrous DMF (16 mL) at rt. The reaction mixture is stirred at 90° C. overnight and then concentrated in vacuo. The residue is dissolved in EtOAc (60 mL), and washed with water (2×30 mL) and brine (20 mL), The organic layer is separated, washed with water (2×20 mL) and brine (20 mL), dried (Na$_2$SO$_4$), filtered and concentrated in vacuo. The residue is purified by silica gel chromatography eluting with 0-5% MeOH in DCM to afford 2-pyridin-3-yl-pyrimidine-5-carboxylic acid (5-methanesulfonyl-indol-1-yl)-amide (125 mg, 25%) as a solid. MS: 394 (M+H); $^1$H NMR (300 MHz, CDCl$_3$): δ 3.10 (s, 3H), 6.61 (m, H) 6.98 (m, H), 7.34 (s, H), 7.51 (m, H), 7.91 (s, H), 8.83 (m, 2H), 9.49 (s, H), 9.77 (s, H), 10.10 (s, N—H).

Example 116

2-(3-Fluoro-phenyl)-4-methyl-pyrimidine-5-carboxylic acid (5-methanesulfonyl-indol-1-yl)-amide

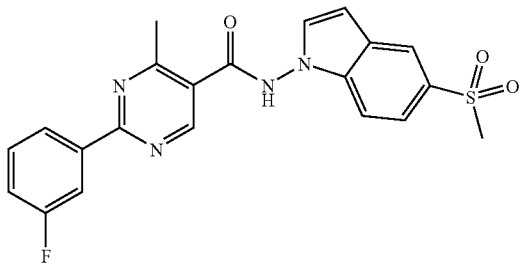

2.0 M of NaHMDS (sodium bis(trimethylsilyl)amide) in THF is added to a stirred solution of 2-(3-fluoro-phenyl)-4-methyl-pyrimidine-5-carboxylic acid chloride (0.72 mmol) and 5-methanesulfonyl-indol-1-ylamine (0.72 mmol) and in anhydrous pyridine (10 mL) at rt. The reaction mixture is stirred at 90° C. overnight and then concentrated in vacuo. The residue is purified ny silica gel chromatography eluting with 1.5% MeOH in DCM to afford 2-(3-fluoro-phenyl)-4-methyl-pyrimidine-5-carboxylic acid (5-methanesulfonyl-indol-1-yl)-amide (50 mg, 8%) as a solid. MS: 425 (M+H); $^1$H NMR (300 MHz, CDCl$_3$): δ 2.86 (s, 3H), 3.02 (s, 3H), 6.55 (s, H) 6.92 (d, H), 7.17-7.38 (m, 3H), 7.53 (m, H), 7.78 (s, H), 8.27 (d, H), 8.38 (d, H), 9.16 (s, H).

Example 117

2-(3-Fluoro-phenyl)-pyrimidine-5-carboxylic acid pyrrolo[2,3-b]pyridin-1-ylamide

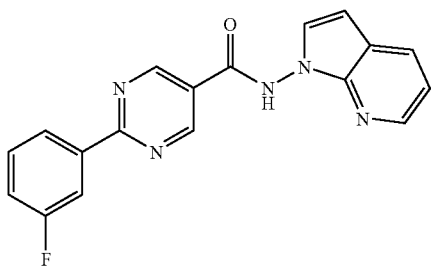

Step 1: A solution of pyrrolo[2,3-b]pyridine (16.9 mmol) and potassium tert-butoxide (33.8 mmol) in DMF (76 mL) is stirred at rt under N$_2$ for 2 h. 0.15 M NH$_2$Cl in ether (169.2 mL) is added drop-wise at rt and the reaction mixture is stirred at rt for 2 h. The reaction mixture is quenched with 5% Na$_2$S$_2$O$_3$ aqueous solution (100 mL), and extracted with ether for three times. The combined organic layer is washed with brine (20 mL), dried (Na$_2$SO$_4$), filtered and concentrated in vacuo. The residue is purified by silica gel chromatography eluting with 60-80% EtOAc in heptane to afford pyrrolo[2,3-b]pyridin-1-ylamine (703 mg, 31%) as a solid. MS: 134 (M+H); $^1$H NMR (300 MHz, CDCl$_3$): δ 5.04 (br, 2N—H), 6.35 (d, H), 7.09 (m, H), 7.35 (m, H), 7.91 (m, H), 8.34 (d, H).

Step 2: A solution of 2-(3-fluoro-phenyl)-pyrimidine-5-carboxylic acid chloride (1.13 mmol) in EtOAc (20 mL) is added to a stirred solution of pyrrolo[2,3-b]pyridin-1-ylamine (1.13 mmol) and K$_2$CO$_3$ (1.13 mmol) in EtOAc (10 mL) and H$_2$O (20 mL) at rt and the reaction mixture is stirred at rt overnight. EtOAc is evaporated in vacuo, and the resulting solid is collected by filtration to afford 2-(3-fluoro-phenyl)-pyrimidine-5-carboxylic acid pyrrolo[2,3-b]pyridin-1-ylamide (305 mg, 81%) as a solid. MS: 334 (M+H); $^1$H NMR (300 MHz, CDCl$_3$): δ 6.57 (d, H) 7.13-7.55 (m, 4H), 7.99 (m, H), 8.10-8.40 (m, 3H), 9.27 (s, 2H), 12.57 (br, N—H).

Example 118

2-(3-Fluoro-phenyl)-pyrimidine-5-carboxylic acid pyrrolo[3,2-b]pyridin-1-ylamide

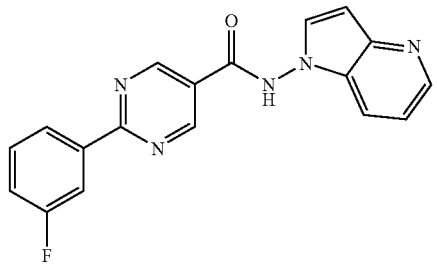

Step 1: A solution of pyrrolo[3,2-b]pyridine (1.64 mmol) and potassium tert-butoxide (3.29 mmol) in DMF (7.3 mL) is stirred at rt under N$_2$ for 2 h. 0.15 M NH$_2$Cl. in ether (16.3 mL) is added drop-wise at rt and the reaction mixture is stirred at rt for 3 h. The reaction mixture is quenched with 5% Na$_2$S$_2$O$_3$ aqueous solution (10 mL), and extracted with ether. The combined organic layer is washed with brine, dried (Na$_2$SO$_4$), filtered and concentrated in vacuo. The residue is purified by silica gel chromatography eluting with EtOAc to afford pyrrolo[3,2-b]pyridin-1-ylamine (136 mg, 62%) as a solid. MS: 134 (M+H); $^1$H NMR (300 MHz, CDCl$_3$): δ 4.89 (br, 2N—H), 6.61 (d, H), 7.16 (m, H), 7.38 (d, H), 7.76 (d, H), 8.47 (d, H).

Step 2: A solution of 2-(3-fluoro-phenyl)-pyrimidine-5-carboxylic acid chloride (0.45 mmol) in EtOAc (8 mL) is added to a stirred solution of pyrrolo[3,2-b]pyridin-1-ylamine (0.45 mmol) and K$_2$CO$_3$ (0.45 mmol) in EtOAc (4 mL) and H$_2$O (8 mL) at rt, and the reaction mixture is stirred at rt for 30 min. EtOAc is evaporated in vacuo, and the resulting solid is collected by filtration to afford 2-(3-fluoro-phenyl)-pyrimidine-5-carboxylic acid pyrrolo[3,2-b]pyridin-1-ylamide (116 mg, 77%) as a solid. MS: 334 (M+H); $^1$H NMR (300 MHz, CDCl$_3$): δ 6.60 (d, H) 7.15-7.60 (m, 4H), 8.01 (m, H), 8.10-8.41 (m, 3H), 9.27 (s, 2H), 12.45 (br, N—H). IC$_{50}$=18 nM.

Example 119

2-(3-Fluoro-phenyl)-pyrimidine-5-carboxylic acid (5-fluoro-indol-1-yl)-amide

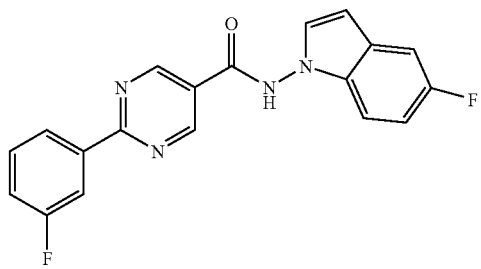

105

A solution of 2-(3-fluoro-phenyl)-pyrimidine-5-carboxylic acid chloride (1 mmol) in EtOAc (20 mL) is added to a stirred solution of 5-fluoro-indol-1-ylamine (1 mmol) and potassium carbonate (1 mmol) in EtOAc (10 mL) and H$_2$O (20 mL) at rt and the reaction mixture is stirred at rt overnight. EtOAc is evaporated in vacuo, and the resulting solid is collected by filtration to afford 2-(3-fluoro-phenyl)-pyrimidine-5-carboxylic acid (5-fluoro-indol-1-yl)-amide (148 mg, 42%) as a solid. MS: 351 (M+H); $^1$H NMR (300 MHz, CDCl$_3$): δ 6.56 (m, H) 7.02 (m, H), 7.12-7.34 (m, 3H), 7.51 (m, H), 8.24 (d, H), 8.34 (s, H), 8.92 (br, H), 9.24 (br, 2H).

Example 120

2-(2-Methoxy-phenyl)-pyrimidine-5-carboxylic acid (6-methyl-3-oxo-2,5-dihydro-3H-[1,2,4]triazin-4-yl)-amide

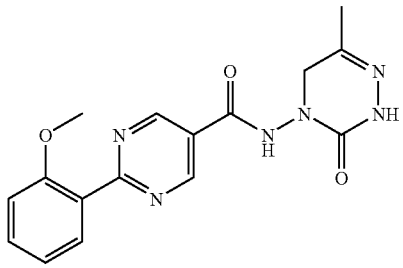

Step 1: Following the procedures similar to those of Example 59, step 1, but substituting 2-methoxyphenylboronic acid for 3-methoxyphenylboronic acid, there is prepared 2-(2-methoxy-phenyl)-pyrimidine-5-carboxylic acid methyl ester.

Step 2: Following the procedures similar to those of Example 59, step 2, but substituting 2-(2-methoxy-phenyl)-pyrimidine-5-carboxylic acid methyl ester for 2-(3-methoxy-phenyl)-pyrimidine-5-carboxylic acid methyl ester, there is prepared 2-(2-methoxy-phenyl)-pyrimidine-5-carboxylic acid.

Step 3: Following the procedures similar to those of Example 59, step 3, but substituting 2-(2-methoxy-phenyl)-pyrimidine-5-carboxylic acid for 2-(3-methoxy-phenyl)-pyrimidine-5-carboxylic acid, there is prepared 2-(2-methoxy-phenyl)-pyrimidine-5-carboxylic acid (6-methyl-3-oxo-2,5-dihydro-3H-[1,2,4]triazin-4-yl)-amide. MS: 341 (M+H); $^1$H NMR (DMSO-d$_6$): δ 1.91 (s, 3H), 3.79 (s, 2H), 4.22 (s, 2H), 7.09 (m, 1H), 7.19 (d, J=8.2 Hz, 1H), 7.52 (m, 1H), 7.65 (m, 1H), 9.24 (s, 2H), 9.96 (s, 1H), 11.06 (s, 1H). IC$_{50}$=199 nM.

Example 121

2-(3-Fluoro-phenyl)-4-methyl-pyrimidine-5-carboxylic acid pyrrolo[3,2-b]pyridin-1-ylamide

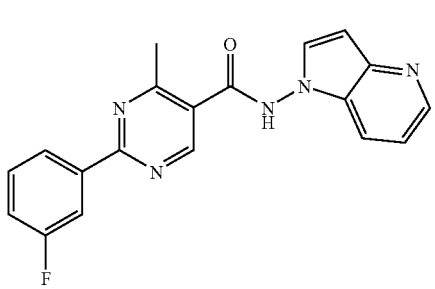

A solution of 2-(3-fluoro-phenyl)-4-methyl-pyrimidine-5-carboxylic acid chloride (0.45 mmol) in EtOAc (8 mL) is added to a stirred solution of pyrrolo[3,2-b]pyridin-1-ylamine (0.45 mmol) and potassium carbonate (0.45 mmol) in EtOAc (4 mL) and H$_2$O (8 mL) at rt and the reaction mixture is stirred at rt overnight. EtOAc is evaporated in vacuo, and the resulting solid is collected by filtration. The solid is purified by silica gel chromatography eluting with 20-80% EtOAc in heptane to afford 2-(3-fluoro-phenyl)-4-methyl-pyrimidine-5-carboxylic acid pyrrolo[3,2-b]pyridin-1-ylamide (38 mg, 24%) as a solid. MS: 348 (M+H); $^1$H NMR (300 MHz, CDCl$_3$): δ 2.76 (s, 3H), 6.59 (m, H) 7.07-7.64 (m, 4H), 7.96 (m, H), 8.23 (m, H), 8.32 (m, 2H), 9.12 (s, H), 10.01 (br, N—H).

Example 122

2-(3-Fluoro-phenyl)-4-methyl-pyrimidine-5-carboxylic acid pyrrolo[2,3-b]pyridin-1-ylamide

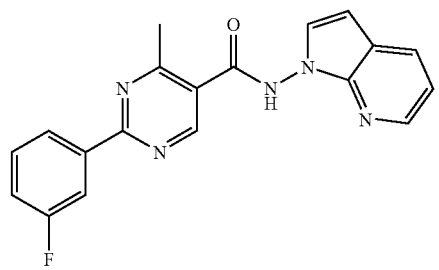

A solution of 2-(3-fluoro-phenyl)-4-methyl-pyrimidine-5-carboxylic acid chloride (1 mmol) in EtOAc (10 mL) is added to a stirred solution of pyrrolo[2,3-b]pyridin-1-ylamine (1 mmol) and K$_2$CO$_3$ (1 mmol) in EtOAc (20 mL) and H$_2$O (20 mL) at rt, then stirred at rt overnight. EtOAc is evaporated in vacuo, and the resulting solid is collected by filtration. The solid is purified by silica gel chromatography eluting with 20-80% EtOAc in heptane to afford 2-(3-fluoro-phenyl)-4-methyl-pyrimidine-5-carboxylic acid pyrrolo[2,3-b]pyridin-1-ylamide (162 mg, 47%) as a solid. MS: 348 (M+H); $^1$H NMR (300 MHz, CDCl$_3$): δ 2.78 (s, 3H), 6.59 (m, H) 7.09-7.58 (m, 4H), 7.96 (m, H), 8.22 (m, H), 8.31 (d, 2H), 9.14 (s, 2H). IC$_{50}$=12 nM.

Example 123

4-Methyl-2-pyridin-2-yl-pyrimidine-5-carboxylic acid (5-fluoro-indol-1-yl)-amide

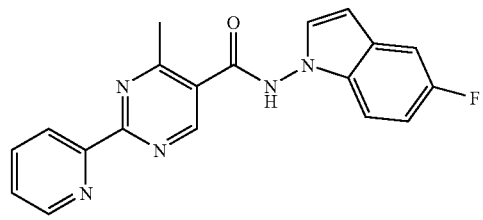

A solution of 4-methyl-2-pyridin-2-yl-pyrimidine-5-carboxylic acid chloride (1 mmol) in EtOAc (20 mL) is added to a stirred solution of 5-fluoro-indol-1-ylamine (1.20 mmol) and K$_2$CO$_3$ (2 mmol) in EtOAc (10 mL) and H$_2$O (20 mL) at rt, and the reaction mixture is stirred at rt overnight. The reaction mixture is extracted with EtOAc. The organic layer is washed with brine, dried (Na$_2$SO$_4$), filtered and concentrated in vacuo. The residue is purified by silica gel chromatography eluting with 0-10% MeOH in DCM to give a solid. The solid is triturated with EtOAc/heptane to afford 4-methyl-2-pyridin-2-yl-pyrimidine-5-carboxylic acid (5-fluoro-indol-1-yl)-amide (122 mg, 35%) as a solid. MS: 348 (M+H); $^1$H NMR (300 MHz, CD$_3$OD): δ 2.77 (s, 3H), 6.55 (m, H) 7.06 (m, H), 7.32-7.66 (m, 4H), 8.02 (m, H), 8.45 (d, H), 8.79 (s, H), 9.26 (s, H), 12.00 (s, N—H). IC$_{50}$=17 nM.

Example 124

2-Pyridin-2-yl-pyrimidine-5-carboxylic acid (5-fluoro-indol-1-yl)-amide

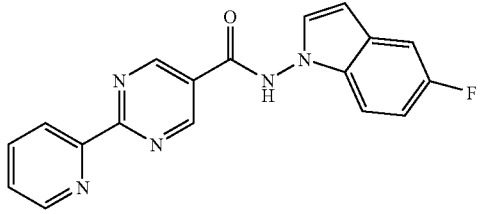

A solution of 2-pyridin-2-yl-pyrimidine-5-carboxylic acid chloride (1 mmol) in EtOAc (20 mL) is added to a stirred solution of 5-fluoro-indol-1-ylamine (1 mmol) and K$_2$CO$_3$ (2 mmol) in EtOAc (10 mL) and H$_2$O (20 mL) at rt, and the reaction mixture is stirred at rt overnight. EtOAc is evaporated in vacuo, and the resulting solid is collected by filtration. The solid is purified by silica gel chromatography eluting with 0-10% MeOH in DCM to afford 2-pyridin-2-yl-pyrimidine-5-carboxylic acid (5-fluoro-indol-1-yl)-amide (65 mg, 20%) as a solid. MS: 334 (M+H); $^1$H NMR (300 MHz, CD$_3$OD): δ 6.56 (m, H) 7.04 (m, H), 7.28-7.79 (m, 3H), 8.04 (m, H), 8.49 (m, H), 8.81 (m, H), 9.48 (s, 2H), 12.22 (s, N—H). IC$_{50}$=18 nM.

Example 125

2-Pyridin-2-yl-pyrimidine-5-carboxylic acid pyrrolo[2,3-b]pyridine-1-ylamide

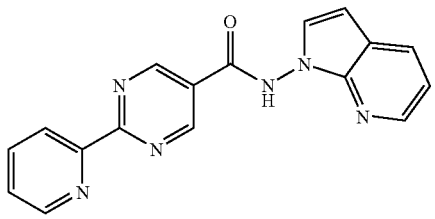

Diethyl-iso-propylamine (1.13 mmol) is added a solution of 2-pyridin-2-yl-pyrimidine-5-carboxylic acid (0.75 mmol), pyrrolo[2,3-b]pyridine-1-ylamine (0.75 mmol) and TBTU in anhydrous DMF (7 mL) at rt, and the reaction mixture is stirred at 80° C. overnight. The reaction mixture is concentrated in vacuo. The residue is dissolved in EtOAc, washed with water twice, dried (Na$_2$SO$_4$), filtered and concentrated in vacuo. The residue is purified by silica gel chromatography eluting with 10% MeOH in DCM to give a crude product. The product is crystallized from EtOAc to afford 2-pyridin-2-yl-pyrimidine-5-carboxylic acid pyrrolo[2,3-b]pyridine-1-ylamide (78 mg, 25%) as a solid. MS: 317 (M+H); $^1$H NMR (300 MHz, CD$_3$OD): δ 6.56 (m, H) 7.24 (m, H), 7.53 (m, H), 7.61 (m, H), 8.01-8.17 (m, 2H), 8.27 (d, H), 8.69 (m, H), 8.78 (m, H), 9.51 (s, 2H).

Example 126

4-Methyl-2-pyridin-2-yl-pyrimidine-5-carboxylic acid pyrrolo[2,3-b]pyridine-1-ylamide

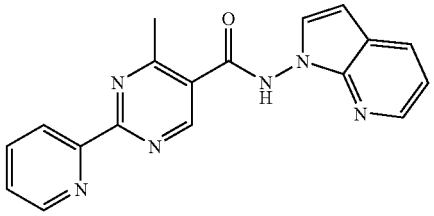

Diethyl-iso-propylamine (1.13 mmol) is added a solution of 4-methyl-2-pyridin-2-yl-pyrimidine-5-carboxylic acid (0.75 mmol), pyrrolo[2,3-b]pyridine-1-ylamine (0.75 mmol) and TBTU (0.9 mmol) in anhydrous DMF (7 mL) at rt, and the reaction mixture is stirred at 80° C. overnight. The reaction mixture is concentrated in vacuo. The residue is dissolved in EtOAc, washed with saturated aqueous Na$_2$CO$_3$ and water, dried (Na$_2$SO$_4$), filtered and concentrated in vacuo. The residue is purified by silica gel chromatography eluting with 10% CH$_3$CN in DCM to give a crude product. The crude product is crystallized from EtOAc to afford 4-methyl-2-pyridin-2-yl-pyrimidine-5-carboxylic acid pyrrol[2,3-b]pyridine-1-ylamide (95 mg, 38%) as a solid. MS: 331 (M+H); $^1$H NMR (300 MHz, CD$_3$OD): δ 2.89 (s, 3H), 6.65 (d, H), 7.23 (m, H), 7.48-7.66 (m, 2H), 8.01-8.15 (m, 2H), 8.29 (m, H), 8.64 (d, H), 8.77 (d, H), 9.33 (s, 2H).

Example 127

4-Methyl-2-pyridin-2-yl-pyrimidine-5-carboxylic acid pyrrolo[3,2-b]pyridine-1-ylamide

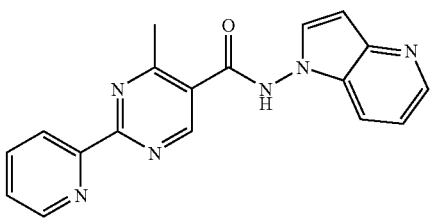

Diethyl-iso-propylamine (1.88 mmol) is added a solution of 4-methyl-2-pyridin-2-yl-pyrimidine-5-carboxylic acid (0.75 mmol), pyrrolo[3,2-b]pyridine-1-ylamine (0.75 mmol) and TBTU (0.9 mmol) in anhydrous DMF (7 mL) at rt, and the reaction mixture is stirred at 80° C. for 8 h. The reaction mixture is concentrated in vacuo. The residue is purified by silica gel chromatography eluting with 0-10% MeOH in DCM to afford 4-methyl-2-pyridin-2-yl-pyrimidine-5-carboxylic acid pyrrol[3,2-b]pyridine-1-ylamide (155 mg, 63%) as a solid. MS: 331 (M+H); $^1$H NMR (300 MHz, CD$_3$OD): δ

2.89 (s, 3H), 7.01 (d, H), 7.64-7.77 (m, 2H), 8.15 (m, H), 8.25 (m, H), 8.59-8.76 (m, 3H), 8.82 (d, H), 9.31 (s, 2H). IC$_{50}$=13 nM.

Example 128

2-(3-Fluoro-phenyl)-4-methyl-pyrimidine-5-carboxylic acid pyrrolo[2,3-c]pyridin-1-ylamide

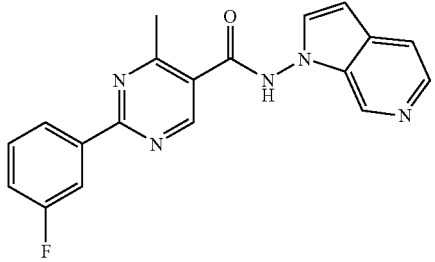

Step 1: A solution of pyrrolo[2,3-c]pyridine (8.47 mmol) and potassium tert-butoxide (16.9 mmol) in DMF (38 mL) is stirred at rt under N$_2$ for 2 h. 0.15 M NH$_2$Cl in ether (84.6 mL) is added drop-wise at rt, and the reaction mixture is stirring at rt for 2 h., quenched with 5% Na$_2$S$_2$O$_3$ aqueous solution (10 mL), and extracted with ether. The organic layer is separated, washed with brine, dried (Na$_2$SO$_4$), filtered and concentrated in vacuo. The residue is purified by silica gel chromatography eluting with 0-10% MeOH in DCM to afford pyrrolo [2,3-c]pyridin-1-ylamine (226 mg, 11%) as a solid. MS: 134 (M+H); $^1$H NMR (300 MHz, CDCl$_3$): δ 4.96 (br, 2N—H), 6.43 (d, H), 7.29 (m, H), 7.50 (d, H), 8.29 (d, H), 8.89 (s, H).
Step 2: Diethyl-iso-propylamine (1.13 mmol) is added a solution of 2-(3-fluoro-phenyl)-4-methyl-pyrimidine-5-carboxylic acid (0.75 mmol), pyrrolo[2,3-c]pyridine-1-ylamine (0.75 mmol) and TBTU (0.9 mmol) in anhydrous DMF (7 mL) at rt, and the reaction mixture is stirred at 80° C. overnight. Water is added and the mixture is extracted with EtOAc. The organic layer is separated, washed with water and brine, dried (Na$_2$SO$_4$), filtered and concentrated in vacuo. The residue is purified by silica gel chromatography eluting with 40-100% MeOH in DCM to afford 2-(3-fluoro-phenyl)-4-methyl-pyrimidine-5-carboxylic acid pyrrolo[2,3-c]pyridin-1-ylamide (117 mg, 45%) as a solid. MS: 348 (M+H); $^1$H NMR (300 MHz, CD$_3$OD): δ 2.84 (s, 3H), 6.72 (d, H), 7.29 (m, H), 7.55 (m, H), 7.71 (m, H), 8.14-8.29 (m, 2H), 8.36 (d, 3), 8.75 (s, H), 9.17 (s, H). IC$_{50}$=28.5 nM.

Example 129

4-Methyl-2-pyridin-2-yl-pyrimidine-5-carboxylic acid pyrrolo[2,3-c]pyridin-1-ylamide

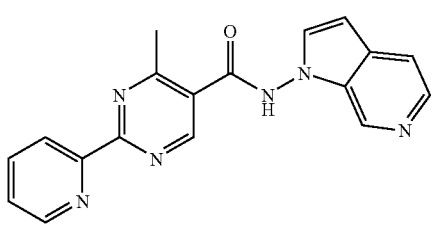

Following procedures similar to those of Example 127 but substituting pyrrolo[2,3-c]pyridine-1-ylamine for pyrrolo[3,2-b]pyridine-1-ylamine, there is prepared 4-methyl-2-pyridin-2-yl-pyrimidine-5-carboxylic acid pyrrol[2,3-c]pyridine-1-ylamide (46%) as a solid. MS: 331 (M+H); $^1$H NMR (300 MHz, CD$_3$OD): δ 2.79 (s, 3H), 6.64 (d, H), 7.53-7.65 (m, 2H), 7.78 (d, H), 8.02 (m, H), 8.22 (m, H), 8.46 (m, H), 8.80 (d, H), 8.87 (s, H), 9.30 (s, H).

Example 130

4-Methyl-2-pyridin-3-yl-pyrimidine-5-carboxylic acid pyrrolo[3,2-b]pyridin-1-ylamide

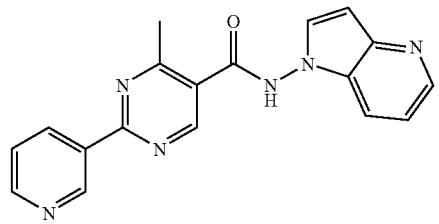

Following procedures similar to those of Example 127 but substituting 4-methyl-2-pyridin-3-yl-pyrimidine-5-carboxylic acid for 4-methyl-2-pyridin-2-yl-pyrimidine-5-carboxylic acid, there is prepared 4-methyl-2-pyridin-2-yl-pyrimidine-5-carboxylic acid pyrrolo [32-b]pyridine-1-ylamide (40%) as a solid. MS: 331 (M+H); $^1$H NMR (300 MHz, CD$_3$OD): δ 2.86 (s, 3H), 6.74 (m, H), 7.31 (m, H), 7.61 (m, H), 7.71 (d, H), 7.92 (d, H), 8.41 (d, H), 8.71 (d, H), 8.91 (d, H), 9.20 (s, H), 9.64 (s, H). IC$_{50}$=14 nM.

Example 131

4-Methyl-2-pyridin-3-yl-pyrimidine-5-carboxylic acid (5-fluoro-indol-1-yl)-amide

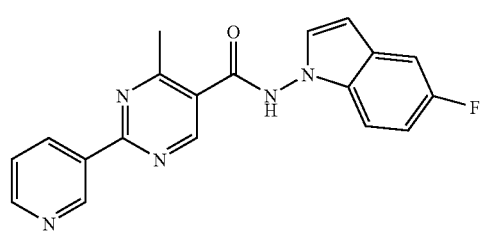

Following procedures similar to those of Example 127 but substituting 4-methyl-2-pyridin-3-yl-pyrimidine-5-carboxylic acid for 4-methyl-2-pyridin-2-yl-pyrimidine-5-carboxylic acid, and substituting 5-fluoro-indol-1-ylamine for pyrrolo[3,2-b]pyridine-1-ylamine, there is prepared 4-methyl-2-pyridin-2-yl-pyrimidine-5-carboxylic acid (5-fluoro-indol-1-yl)-amide (34%) as a solid. MS: 348 (M+H); $^1$H NMR (300 MHz, CD$_3$OD): δ 2.85 (s, 3H), 6.57 (m, H), 7.02 (m, H), 7.23-7.46 (m, 2H), 7.62 (m, H), 8.70 (d, H), 8.91 (d, H), 9.17 (s, H), 9.63 (s, H).

Example 132

2-(3-Fluoro-phenyl)-4-methyl-pyrimidine-5-carboxylic acid (5-fluoro-indol-1-yl)-amide

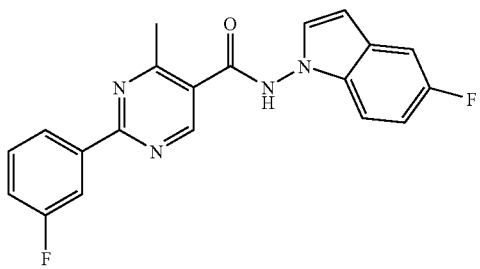

Method A: Following procedures similar to those of Example 127 but substituting 2-(3-fluoro-phenyl)-4-methyl-pyrimidine-5-carboxylic acid for 4-methyl-2-pyridin-2-yl-pyrimidine-5-carboxylic acid, and substituting 5-fluoro-indol-1-ylamine for pyrrolo[3,2-b]pyridine-1-ylamine, there is prepared 2-(3-fluoro-phenyl)-4-methyl-pyrimidine-5-carboxylic acid (5-fluoro-indol-1-yl)-amide (17%) as a solid. MS: 365 (M+H); $^1$H NMR (300 MHz, CD$_3$OD): δ 6.56 (d, H), 7.02 (m, H), 7.22-7.44 (m, 4H), 7.55 (m, H), 8.22 (d, H), 8.36 (d, H), 9.13 (s, H).

Method B: A solution of 2-(3-fluoro-phenyl)-4-methyl-pyrimidine-5-carboxylic acid chloride (1 mmol) in EtOAc (20 mL) is added to a stirred solution of 5-fluoro-indol-1-ylamine (1 mmol) and K$_2$CO$_3$ (1 mmol) in EtOAc (10 mL) and H$_2$O (20 mL) at rt, then stirred at rt overnight. EtOAc is evaporated in vacuo, and the resulting solid is collected by filtration. The solid is crystallized from EtOAc/heptane to afford 2-(3-fluoro-phenyl)-4-methyl-pyrimidine-5-carboxylic acid (5-fluoro-indol-1-yl)-amide (62 mg, 17%) as a solid. MS: 365 (M+H); $^1$H NMR (300 MHz, CDCl$_3$): δ 2.82 (s, H), 6.55 (s, H) 6.90-7.41 (m, 4H), 7.49 (m, H), 8.26 (d, 2H), 8.57 (br, H), 8.96 (br, H). IC$_{50}$=19 nM.

Example 133

2-(3-Fluoro-phenyl)-4-methyl-pyrimidine-5-carboxylic acid (5-methoxy-indol-1-yl)-amide

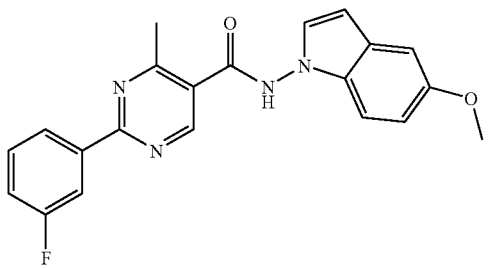

Step 1: A solution of 5-methoxy-1H-indole (16.9 mmol) and potassium tert-butoxide (33.8 mmol) in DMF (76 mL) is stirred at rt under N$_2$ for 2 h. 0.15 M NH$_2$Cl in ether (169.2 mL) is added drop-wise for 15 minutes at rt. The reaction mixture is stirred at rt for 2 h, quenched with 5% Na$_2$S$_2$O$_3$ aqueous solution (100 mL), and stirred at rt overnight. The mixture is extracted with ether. The organic layer is separated, washed with brine, dried (Na$_2$SO$_4$), filtered and concentrated in vacuo. The residue is purified by silica gel chromatography eluting with 0-20% EtOAc in heptane to afford 5-methoxy-indole-1-ylamine (388 mg, 14%) as a solid. $^1$H NMR (300 MHz, CDCl$_3$): δ 4.78 (br, 2N—H), 6.35 (d, H), 6.94 (d, H), 7.08 (d, H), 7.17 (d, H), 7.30-7.39 (d, H).

Step 2: Following procedures similar to those of Example 127 but substituting 2-(3-fluoro-phenyl)-4-methyl-pyrimidine-5-carboxylic acid for 4-methyl-2-pyridin-2-yl-pyrimidine-5-carboxylic acid, and substituting 5-methoxy-indol-1-ylamine for pyrrolo[3,2-b]pyridine-1-ylamine, there is prepared 2-(3-fluoro-phenyl)-4-methyl-pyrimidine-5-carboxylic acid (5-methoxy-indol-1-yl)-amide (43%) as a solid. MS: 377 (M+H); $^1$H NMR (300 MHz, CD$_3$OD): δ 2.83 (s, 3H), 3.84 (s, 3H), 6.50 (d, H), 6.90 (m, H), 7.12 (d, H), 7.22-7.36 (m, 3H), 7.55 (m, H), 8.22 (d, H), 8.36 (d, H), 9.11 (s, H). IC$_{50}$=6 nM.

Example 134

2-(3-Fluoro-phenyl)-4-methyl-pyrimidine-5-carboxylic acid (5-cyano-indol-1-yl)-amide

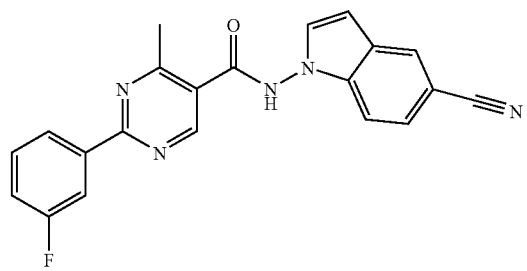

Step 1: NaH (60%, 60 mmol) is portion-wise added to a solution of 5-cyano-1H-indole (20 mmol) in NMP (35 mL), and the reaction mixture is 0° C. for 1 h. A solution of HOSA (60 mmol) in NMP (14 mL) is added drop-wise at 0° C. The reaction mixture is warmed to rt and stirred overnight, then quenched with water and extracted with EtOAc. The organic layer is separated, washed with water three times and with brine, dried (Na$_2$SO$_4$), filtered and concentrated in vacuo. The residue is purified by silica gel chromatography eluting with 20-40% EtOAc in heptane to afford 5-cyano-indole-1-ylamine (531 mg, 16%) as a solid. $^1$H NMR (300 MHz, CDCl$_3$): δ 4.88 (br, 2N—H), 6.53 (d, H), 7.32 (d, H), 7.54 (q, 2H), 7.98 (d, H).

Step 2: Following procedures similar to those of Example 127 but substituting 2-(3-fluoro-phenyl)-4-methyl-pyrimidine-5-carboxylic acid for 4-methyl-2-pyridin-2-yl-pyrimidine-5-carboxylic acid, and substituting 5-cyano-indol-1-ylamine for pyrrolo[3,2-b]pyridine-1-ylamine, there is prepared 2-(3-fluoro-phenyl)-4-methyl-pyrimidine-5-carboxylic acid (5-cyano-indol-1-yl)-amide (39%) as a solid. MS: 372 (M+H); $^1$H NMR (300 MHz, DMSO-d$^6$): δ 2.77 (s, 3H), 6.73 (d, H), 7.45 (m, H), 7.53-7.82 (m, 4H), 8.08-8.23 (m, 2H), 8.32 (d, H), 9.27 (s, H), 12.15 (br, N—H).

Example 135

2-(3-Fluoro-phenyl)-4-methyl-pyrimidine-5-carboxylic acid (4-cyano-indol-1-yl)-amide

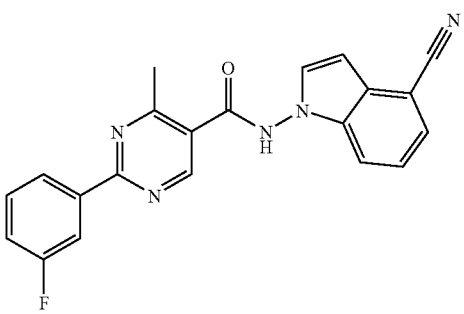

Step 1: Following procedures similar to those of Example 134, step 1, but substituting 4-cyano-1H-indole for 5-cyano-1H-indole, there is prepared 4-cyano-indole-1-ylamine (33%) as a solid. $^1$H NMR (300 MHz, CDCl$_3$): δ 4.1 (br, 2N—H), 6.88 (d, H), 7.22-7.40 (m, 2H), 7.51 (d, H), 7.72 (d, H).

Step 2: Following procedures similar to those of Example 127, but substituting 2-(3-fluoro-phenyl)-4-methyl-pyrimidine-5-carboxylic acid for 4-methyl-2-pyridin-2-yl-pyrimidine-5-carboxylic acid, and substituting 4-cyano-indol-1-ylamine for pyrrolo[3,2-b]pyridine-1-ylamine, there is prepared 2-(3-fluoro-phenyl)-4-methyl-pyrimidine-5-carboxylic acid (4-cyano-indol-1-yl)-amide (29%) as a solid. MS: 372 (M+H); $^1$H NMR (300 MHz, DMSO-d$^6$): δ 2.77 (s, 3H), 6.71 (s, H), 7.32-7.51 (m, 2H), 7.57-7.69 (m, 2H), 7.88 (m, 2H), 8.16 (d, H), 8.31 (d, H), 9.25 (s, H).

Example 136

2-(3-Fluoro-phenyl)-4-methyl-pyrimidine-5-carboxylic acid [4-(1H-tetrazol-5-yl)-indol-1-yl]-amide

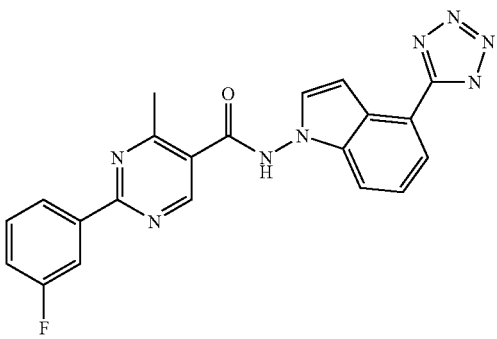

A solution of (0.5 mmol), ammonia chloride (6 mmol) and sodium azide (6 mmol) in anhydrous DMF (6 mL) is heated in the microwave at 200° C. for 1 h. The reaction mixture is quenched with saturated aqueous Na$_2$CO$_3$ solution, and washed with EtOAc. The aqueous layer is separated, acidified with concentrated aqueous HCl to adjust pH to ~1, and extracted with EtOAc. The organic layer is separated, dried (Na$_2$SO$_4$), filtered and concentrated in vacuo. The residue is purified by silica gel chromatography eluting with 3% MeOH in DCM to afford 2-(3-fluoro-phenyl)-4-methyl-pyrimidine-5-carboxylic acid [4-(1H-tetrazol-5-yl)-indol-1-y]-amide (18 mg, 9%) as a solid. MS: 415 (M+H); $^1$H NMR (300 MHz, CD$_3$OD): δ 2.85 (s, 3H), 7.20-7.35 (m, 2H), 7.44 (m, H), 7.52-7.59 (m, 2H), 7.65 (m, H), 7.77 (d, H), 8.23 (d, H), 8.37 (d, H), 9.18 (s, H).

Example 137

1-{[2-(3-Fluoro-phenyl)-4-methyl-pyrimidine-5-carbonyl]-amino}-1H-indol-4-carboxylic acid methyl ester

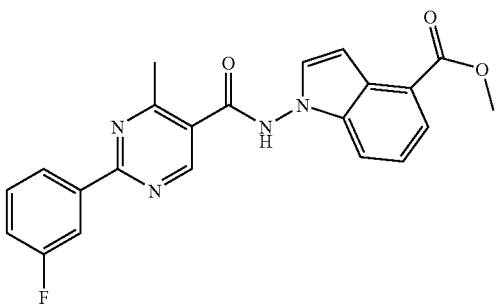

Step 1: Following procedures similar to those of Example 133, step 1, but substituting 1H-indole-4-carboxylic acid methyl ester for 5-methoxy-1H-indole, there is prepared 1-amino-1H-indole-4-carboxylic acid methyl ester (10%) as a solid. $^1$H NMR (300 MHz, CDCl$_3$): δ 4.88 (br, 2N—H), 7.03 (d, H), 7.33 (m, 2H), 7.49 (d, H), 7.94 (d, H).

Step 2: Following procedures similar to those of Example 127, but substituting 2-(3-fluoro-phenyl)-4-methyl-pyrimidine-5-carboxylic acid for 4-methyl-2-pyridin-2-yl-pyrimidine-5-carboxylic acid, substituting 1-amino-1H-indole-4-carboxylic acid methyl ester for pyrrolo[3,2-b]pyridine-1-ylamine, and the reaction is stirred at 15° C. for 45 minutes, there is prepared 1-{[2-(3-fluoro-phenyl)-4-methyl-pyrimidine-5-carbonyl]-amino}-1H-indol-4-carboxylic acid methyl ester (33%) as a solid. MS: 405 (M+H); $^1$H NMR (300 MHz, DMSO-d$^6$): δ 2.77 (s, 3H), 3.92 (s, 3H), 7.44 (m, H), 7.63 (m, H), 7.72 (m, H), 7.76-7.88 (m, 2H), 8.17 (d, H), 8.31 (d, H), 9.26(s, H), 12.06 (br, N—H).

Example 138

1-{[2-(3-Fluoro-phenyl)-4-methyl-pyrimidine-5-carbonyl]-amino}-1H-indol-4-carboxylic acid

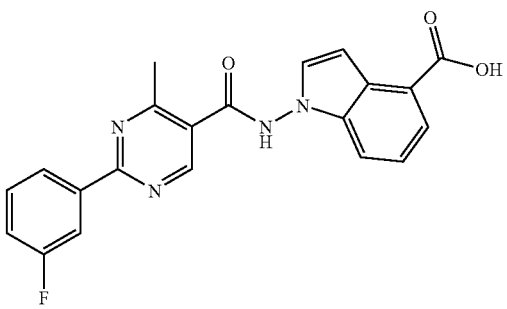

A solution of 1-{[2-(3-fluoro-phenyl)-4-methyl-pyrimidine-5-carbonyl]-amino}-1H-indol-4-carboxylic acid methyl ester (0.48 mmol) and LiOH (1.91 mmol) in Methanol/THF/H2O (1:1:1, 6 mL) is stirred at rt overnight. The reaction mixture is diluted with water and washed with DCM. The aqueous layer is separated and acidified with 10% aqueous HCl to adjust pH to 1. The mixture is extracted with ether twice. The organic layer is dried (Na$_2$SO$_4$), filtered and concentrated in vacuo to afford 1-{[2-(3-fluoro-phenyl)-4-methyl-pyrimidine-5-carbonyl]-amino}-1H-indol-4-carboxylic acid (186 mg, 99%) as a solid. MS: 391 (M+H); $^1$H NMR (300 MHz, CD$_3$OD): δ 2.85 (s, 3H), 7.20 (m, H), 7.24-7.40 (m, 2H), 7.46-7.61 (m, 2H), 7.66 (d, H), 7.92 (d, H), 8.23 (d, H), 8.37 (d, H), 9.16 (s, H).

Example 139

2-(3-Fluoro-phenyl)-4-methyl-pyrimidine-5-carboxylic acid (3-cyanomethyl-indol-1-yl)-amide

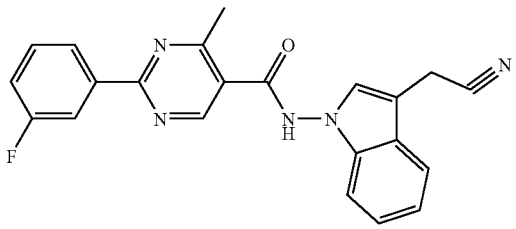

Step 1: Following procedures similar to those of Example 133, step 1, but substituting 1H-indol-3-yl-acetonitrile for 5-methoxy-1H-indole, there is prepared (1-amino-1H-indol-3-yl)-acetonitrile (17%) as a solid. $^1$H NMR (300 MHz, CDCl$_3$): δ 3.83 (s, 2H), 4.80 (br, 2N—H), 7.17-7.25 (m, 2H), 7.33 (t, H), 7.46 (d, H), 7.59 (d, H).

Step 2: Following procedures similar to those of Example 127, but substituting 2-(3-fluoro-phenyl)-4-methyl-pyrimidine-5-carboxylic acid for 4-methyl-2-pyridin-2-yl-pyrimidine-5-carboxylic acid, substituting 3-cyanomethyl-indol-1-ylamine for pyrrolo[3,2-b]pyridine-1-ylamine, and the reaction is stirred at 150° C. for 1 h, there is prepared 2-(3-fluoro-phenyl)-4-methyl-pyrimidine-5-carboxylic acid (3-cyanomethyl-indol-1-yl)-amide (42%) as a solid. MS: 386 (M+H); $^1$H NMR (300 MHz, CD$_3$OD): δ 2.84 (s, 3H), 4.03 (s, 2H), 7.15-7.48 (m, 5H), 7.55 (m, H), 7.70 (d, H), 8.23 (d, H), 8.37 (d, H), 9.14 (s, H).

Example 140

4-Methyl-2-pyridin-2-yl-pyrimidine-5-carboxylic acid (5-methoxy-indol-1-yl)-amide

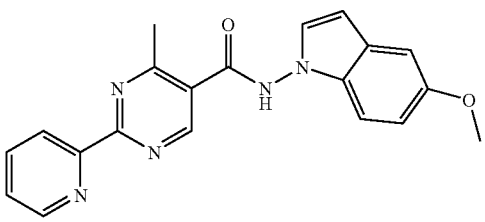

Following procedures similar to those of Example 127, but substituting 5-methoxy-indol-1-ylamine for pyrrolo[3,2-b]pyridine-1-ylamine, and the reaction is stirred at 150° C. for 1 h, there is prepared 2-pyridin-2-yl-pyrimidine-5-carboxylic acid (5-methoxy-indol-1-yl)-amide (22%) as a solid. MS: 360 (M+H); $^1$H NMR (300 MHz, CD$_3$OD): δ 2.88 (s, 3H), 3.84 (s, 3H), 6.50 (d, H) 6.90 (m, H), 7.13 (d, H), 7.25-7.34 (m, 2H), 7.60 (m, H), 8.05 (m, H), 8.65 (d, H), 8.79 (d, H), 9.20 (s, 2H).

Example 141

2-(3-Fluoro-phenyl)-4-methyl-pyrimidine-5-carboxylic acid [3-(1H-tetrazol-5-ylmethyl)-indol-1-yl]-amide

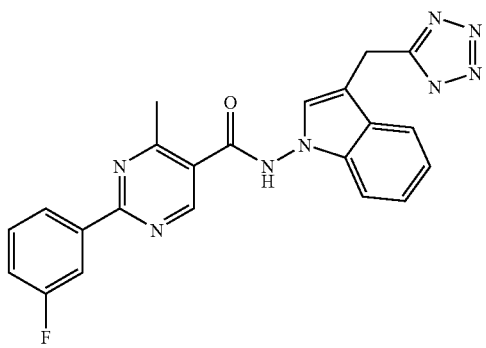

Following procedures similar to those of Example 136, but substituting 2-(3-fluoro-phenyl)-4-methyl-pyrimidine-5-carboxylic acid (3-cyanomethyl-indol-1-yl)-amide for 2-(3-fluoro-phenyl)-4-methyl-pyrimidine-5-carboxylic acid (4-cyano-indol-1-yl)-amide, there is prepared 2-(3-fluoro-phenyl)-4-methyl-pyrimidine-5-carboxylic acid [3-(1H-tetrazol-5-ylmethyl)-indol-1-y]-amide (12%) as a solid. MS: 429 (M+H); $^1$H NMR (300 MHz, CD$_3$OD): δ 2.85 (s, 3H), 4.52 (s, 2H), 7.15 (m, H), 7.24-7.35 (m, 2H), 7.36-7.50 (m, 2H), 7.55 (m, H), 8.23 (d, H), 8.37 (d, H), 9.15 (s, H).

Example 142

2-(2-Phenyl-pyrimidine-5-carbonyl)-1-hydrazinecarboxamide

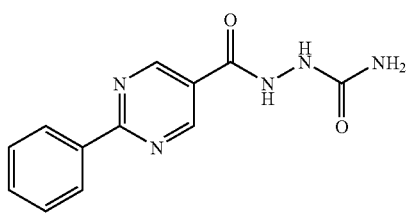

Following procedures similar to those of Example 64 but substituting semicarbazide hydrochloride for 3-{3-amino-2,4-dioxo-1,2,3,4-tetrahydro-pyrimidin-5-propionic acid methyl ester, there is prepared 2-(2-phenyl-pyrimidine-5-carbonyl)-1-hydrozinecarboximide (62%) as a solid. MS: 258 (M+H).

Example 143

2-(2-Phenyl-pyrimidine-5-carbonyl)-1-hydrazine-1-carbothioamide

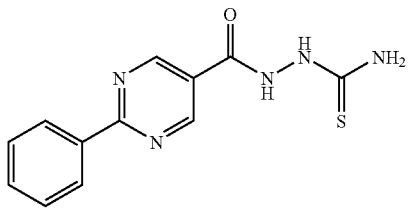

Following procedures similar to those of Example 64, but substituting thiosemicarbazide for 3-{3-amino-2,4-dioxo-1,2,3,4-tetrahydro-pyrimidin-5-propionic acid methyl ester, there is prepared 2-(2-phenyl-pyrimidine-5-carbonyl)-1-hydrozine-1-carbothioamide (27%) as a solid. MS: 274 (M+H).

Example 144

2-Phenyl-pyrimidine-5-carboxylic acid (2,4-dioxo-imidazolidin-1-yl)-amide

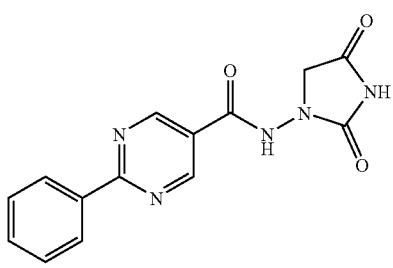

Following procedures similar to those of Example 64 but substituting 2,4-dioxo-imidazolidin-1-ylamine for 3-{3-amino-2,4-dioxo-1,2,3,4-tetrahydro-pyrimidin-5-propionic acid methyl ester, there is prepared 2-phenyl-pyrimidine-5-carboxylic acid (2,4-dioxo-imidazolidin-1-yl)-amide (8%) as a solid. MS: 298 (M+H).

Example 145

2-Phenyl-pyrimidine-5-carboxylic acid (6-methyl-3-oxo-2,5-dihydro-3H-[1,2,4]triazin-4-yl)-amide

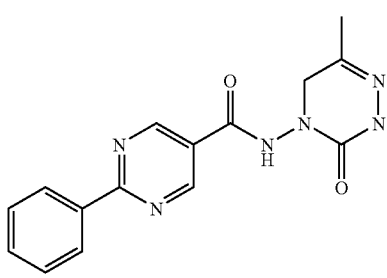

Following procedures similar to those of Example 64 but substituting 6-methyl-3-oxo-2,5-dihydro-3H-[1,2,4]triazin-4-ylamine for 3-{3-amino-2,4-dioxo-1,2,3,4-tetrahydro-pyrimidin-5-propionic acid methyl ester, there is prepared 2-phenyl-pyrimidine-5-carboxylic acid (6-methyl-3-oxo-2,5-dihydro-3H-[1,2,4]triazin-4-yl)-amide (39%) as a solid. MS: 311 (M+H); $^1$H NMR (300 MHz, CD$_3$OD): δ 1.98 (s, 3H), 4.32 (s, 2H), 7.45-7.63 (m, 3H), 8.50 (d, 2H), 9.24 (s, 2H).

Example 146

2-Phenyl-pyrimidine-5-carboxylic acid N'-phenyl-hydrazide

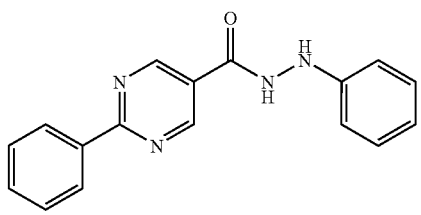

Following procedures similar to those of Example 64 but substituting N'-phenyl-hydrazine for 3-{3-amino-2,4-dioxo-1,2,3,4-tetrahydro-pyrimidin-5-propionic acid methyl ester, there is prepared 2-phenyl-pyrimidine-5-carboxylic acid N'-phenyl-hydrazide (18%) as a solid. MS: 291 (M+H); $^1$H NMR (300 MHz, CDCl$_3$): δ 6.34 (s, N—H), 6.82-7.04 (m, 2H), 7.15-7.39 (m, 3H), 7.40-7.63 (m, 3H), 7.94 (s, N—H), 8.51 (d, 2H), 9.20 (s, 2H).

Example 147

Pyridine-2-carboxylic acid N'-(2-phenyl-pyrimidine-5-carbonyl)-hydrazide

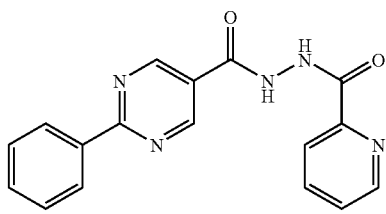

Following procedures similar to those of Example 64, but substituting 2-pyridine-2-carboxylic acid hydrazide for 3-{3-amino-2,4-dioxo-1,2,3,4-tetrahydro-pyrimidin-5-propionic acid methyl ester, there is prepared pyridine-2-carboxylic acid N'-(2-phenyl-pyrimidine-5-carbonyl)-hydrazide (52%) as a solid. MS: 320 (M+H); $^1$H NMR (300 MHz, DMSO-d$_6$): δ 7.75(m, 4H), 7.98-8.14 (m, 2H), 8.46 (d, 2H), 8.73 (d, H), 9.32 (s, 2H), 10.81 (s, N—H), 10.96 (br, N—H).

Example 148

4-[N'-(2-Phenyl-pyrimidine-5-carbonyl)-hydrazino]-benzenesulfonamide

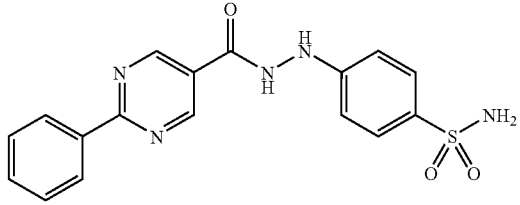

Following procedures similar to those of Example 64, but using substituting 4-hydrazino-benzebesulfonamide for 3-{3-amino-2,4-dioxo-1,2,3,4-tetrahydro-pyrimidin-5-propionic acid methyl ester, there is prepared 4-[N'-(2-phenyl-pyrimidine-5-carbonyl)-hydrazino]-benzenesulfonamide (36%) as a solid. MS: 370 (M+H).

Example 149

3-Hydroxy-benzoic acid N'-(2-phenyl-pyrimidine-5-carbonyl)-hydrazide

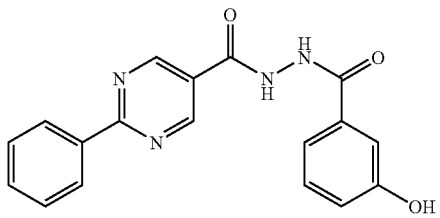

Following procedures similar to those of Example 64, but substituting 3-hydroxy-benzoic acid hydrazide for 3-{3-amino-2,4-dioxo-1,2,3,4-tetrahydro-pyrimidin-5-propionic acid methyl ester, there is prepared 3-hydroxy-benzoic acid N'-(2-phenyl-pyrimidine-5-carbonyl)-hydrazide (56%) as a solid. MS: 335 (M+H).

Example 150

Benzo[1,3]dioxo-5-carboxylic acid N'-(phenyl-pyrimidine-5-carbonyl)-hydrazide

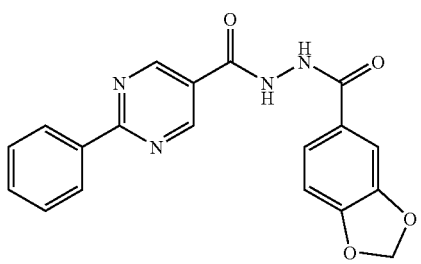

Following procedures similar to those of Example 64, but substituting benzo[1,3]dioxo-5-carboxylic acid hydrazide for 3-{3-amino-2,4-dioxo-1,2,3,4-tetrahydro-pyrimidin-5-propionic acid methyl ester, there is prepared benzo[1,3]-dioxo-5-carboxylic acid N'-(phenyl-pyrimidine-5-carbonyl)-hydrazide (83%) as a solid. MS: 363 (M+H).

Example 151

3,4-Dimethoxy-benzoic acid N'-(phenyl-pyrimidine-5-carbonyl)-hydrazide

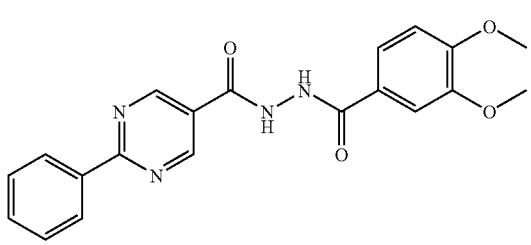

Following procedures similar to those of Example 64 but substituting 3,4-dimethoxy-benzoic acid hydrazide for 3-{3-amino-2,4-dioxo-1,2,3,4-tetrahydro-pyrimidin-5-propionic acid methyl ester, there is prepared 3,4-dimethoxy-benzoic acid N'-(phenyl-pyrimidine-5-carbonyl)-hydrazide (76%) as a solid. MS: 379 (M+H).

Example 152

2-Phenyl-pyrimidine-5-carboxylic acid N'-methyl-N'-phenyl-hydrazide

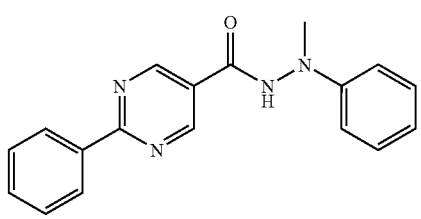

Following procedures similar to those of Example 64, but substituting N'-methyl-N'-phenyl-hydrazine for 3-{3-amino-2,4-dioxo-1,2,3,4-tetrahydro-pyrimidin-5-propionic acid methyl ester, there is prepared 2-phenyl-pyrimidine-5-carboxylic acid N'-methyl-N'-phenyl-hydrazide (80 mg, 88%) as a solid. MS: 305 (M+H).

Example 153

2-(3-Fluoro-phenyl)-4-methyl-pyrimidine-5-carboxylic acid (5-methoxy-3-methyl-indol-1-yl)-amide

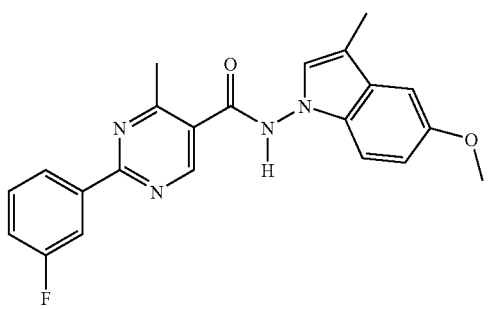

Step 1: A solution of potassium tert-butoxide (5.23 g, 46.62 mmol) and 5-methoxy-3-methylindole (3.41 g, 21.15 mmol) in DMF (20 mL) is stirred at rt for 45 min. A solution of monochloroamine in ether (400 mL, 60 mmol) is added via an addition funnel over 15 min.

The resulting mixture is stirred for 2 h. The solvent is removed and the residue is partitioned between EtOAc and water. The organic phase is separated, washed with saturated aqueous $NaHCO_3$, water and brine, dried ($MgSO_4$), filtered and concentrated in vacuo. The residue is purified by column chromatography eluting with 10% EtOAc in heptane to afford 5-methoxy-3-methyl-indol-1-ylamine (1.42 g, 38%) as a solid. MS: 176 (M+H); $^1$H NMR (300 MHz, $CDCl_3$): δ 7.26-7.23 (m, 1H), 6.98-6.97 (m, 1H), 6.91-6.87 (m, 2H), 4.64 (br s, 2H), 3.86 (s, 3H), 2.26-2.25 (m, 3H).

Step 2: A microwave vial (20 mL) is charged with 2-(3-fluoro-phenyl)-4-methyl-pyrimidine-5-carboxylic acid (657 mg, 2.83 mmol), HOTT (1.16 g, 3.11 mmol), DIPEA (1.35 mL, 7.73 mmol) and DMF (6 mL). The mixture is stirred at 23° C. under $N_2$ for 15 min. 5-Methoxy-3-methyl-indol-1-ylamine (456 mg, 2.59 mmol) is added and the vial is capped. The resulting mixture is heated in a microwave (Biotage-Initiator) at 150° C. for 6 min. The mixture is portioned between EtOAc and water. The organic phase is separated, washed with saturated aqueous $NaHCO_3$, water and brine, dried ($MgSO_4$), filtered and concentrated in vacuo. The residue is purified by column chromatography eluting with 45% EtOAc in heptane to afford 2-(3-fluoro-phenyl)-4-methyl-pyrimidine-5-carboxylic acid (5-methoxy-3-methyl-indol-1-yl)-amide (327 mg, 32%) as a solid. MS: 391 (M+H); $^1$H NMR (300 MHz, $d_6$-DMSO): δ 11.75 (s, 1H), 9.19 (s, 1H), 8.32 (d, 1H), 8.18-8.16 (m, 1H), 7.66-7.62 (m, 1H), 7.45 (td, 1H), 7.30 (d, 1H), 7.22 (s, 1H), 7.05 (d, 1H), 6.85 (dd, 1H), 3.81 (s, 3H), 2.76 (s, 3H), 2.27 (s, 3H).

Example 154

2-(3-Hydroxy-phenyl)-pyrimidine-5-carboxylic acid (6-methyl-3-oxo-2,5-dihydro-3H-[1,2,4]triazin-4-yl)-amide

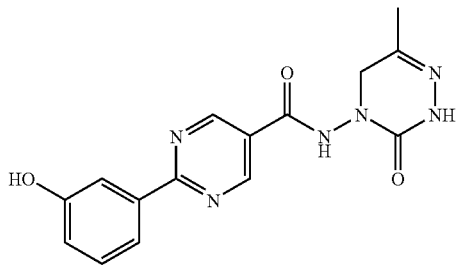

Step 1: Following the procedures similar to those of Example 59, step 1, but substituting 3-hydroxyphenylboronic acid for 3-methoxyphenylboronic acid, there is prepared 2-(3-hydroxy-phenyl)-pyrimidine-5-carboxylic acid methyl ester.

Step 2: Following the procedures similar to those of Example 59, step 2, but substituting 2-(3-hydroxy-phenyl)-pyrimidine-5-carboxylic acid methyl ester for 2-(3-methoxy-phenyl)-pyrimidine-5-carboxylic acid methyl ester, there is prepared 2-(3-hydroxy-phenyl)-pyrimidine-5-carboxylic acid.

Step 3: Following the procedures similar to those of Example 59, step 3, but substituting 2-(3-hydroxy-phenyl)-pyrimidine-5-carboxylic acid for 2-(3-methoxy-phenyl)-pyrimidine-5-carboxylic acid, there is prepared 2-(3-hydroxy-phenyl)-pyrimidine-5-carboxylic acid (6-methyl-3-oxo-2,5-dihydro-3H-[1,2,4]triazin-4-yl)-amide. MS: 327 (M+H); $^1$H NMR (DMSO-$d_6$): δ 1.91 (s, 3H), 4.22(s, 2H), 5.75 (s, 1H), 6.98 (m, 1H), 7.36 (m, 1H), 7.90 (m, 1H), 9.25 (s, 2H), 9.71 (s, 1H), 9.95 (s, 1H), 11.05 (s, 1H). $IC_{50}$=21 nM.

Example 155

2-(2-Hydroxy-phenyl)-pyrimidine-5-carboxylic acid (6-methyl-3-oxo-2,5-dihydro-3H-[1,2,4]triazin-4-yl)-amide

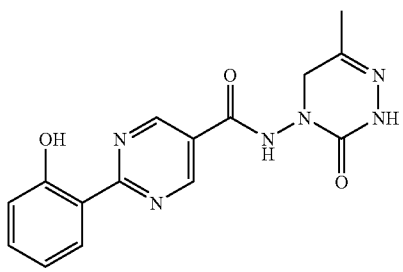

Step 1: Following the procedures similar to those of Example 59, step 1, but substituting 2-hydroxyphenylboronic acid for 3-methoxyphenylboronic acid, there is prepared 2-(2-hydroxy-phenyl)-pyrimidine-5-carboxylic acid methyl ester.

Step 2: Following the procedures similar to those of Example 59, step 2, but substituting 2-(2-hydroxy-phenyl)-pyrimidine-5-carboxylic acid methyl ester for 2-(3-methoxy-phenyl)-pyrimidine-5-carboxylic acid methyl ester, there is prepared 2-(2-hydroxy-phenyl)-pyrimidine-5-carboxylic acid.

Step 3: Following the procedures similar to those of Example 59, step 3, but substituting 2-(2-hydroxy-phenyl)-pyrimidine-5-carboxylic acid for 2-(3-methoxy-phenyl)-pyrimidine-5-carboxylic acid, there is prepared 2-(2-hydroxy-phenyl)-pyrimidine-5-carboxylic acid (6-methyl-3-oxo-2,5-dihydro-3H-[1,2,4]triazin-4-yl)-amide. MS: 327 (M+H); H1 NMR (DMSO-$d_6$): δ=1.91 (s, 3H), 4.22(s, 2H), 7.02 (m, 2H), 7.50 (m, 1H), 8.46 (m, 1H), 9.32 (s, 2H), 9.97 (s, 1H), 11.12 (s, 1H), 12.95 (s, 1H).

Example 156

2-(4-Hydroxy-phenyl)-pyrimidine-5-carboxylic acid (6-methyl-3-oxo-2,5-dihydro-3H-[1,2,4]triazin-4-yl)-amide

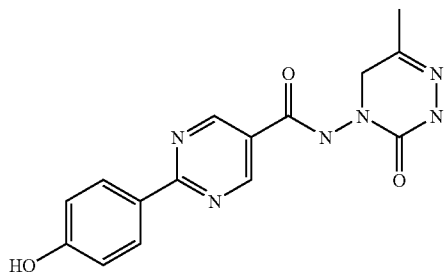

A mixture of 2-(4-methoxy-phenyl)-pyrimidine-5-carboxylic acid (6-methyl-3-oxo-2,5-dihydro-3H-[1,2,4]triazin-4-yl)-amide (100 mg, 0.29 mmol), sodium methanethiolate (206 mg, 2.9 mmol) and DMF (2 mL) is stirred at 110° C. for 6 h., and then cooled to rt. The reaction mixture is concentrated in vacuo, and the residue is purified on a reverse phase HPLC chromatography to afford 2-(4-hydroxy-phenyl)-pyrimidine-5-carboxylic acid (6-methyl-3-oxo-2,5-dihydro-3H-[1,2,4]triazin-4-yl)-amide (32 mg). MS: 327 (M+H); $^1$H NMR (DMSO-$d_6$): δ 1.87 (s, 3H), 4.17 (s, 2H), 6.74 (m, 2H), 8.21 (d, J=6.9 Hz, 2H), 9.08 (s, 2H), 9.53 (s, 1H).

Example 157

4-Methyl-[2,2']bipyrimidinyl-5-carboxylic acid (5-fluoro-3-methyl-indol-1-yl)-amide

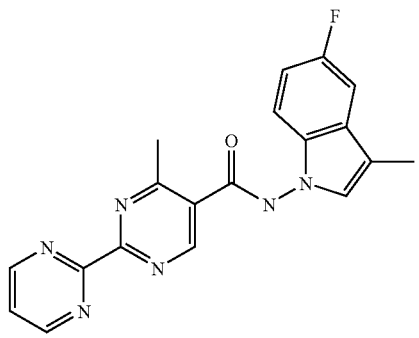

Step 1: A flask containing 2-cyanopyrimidine (16.6 g, 158 mmol), ammonium acetate (14.6 g, 189.6 mmol) and N-acetylcysteine (2.58 g, 15.8 mmol) and ethanol (160 mL) is heated to reflux. After 1.25 h, the reaction is allowed to cool slightly (to approximately 50° C.), and sodium tert-butoxide (15.18 g, 158 mmol) and ethanol (160 mL) are added. After stirring for 10 minutes, 2-dimethylaminomethylene-3-oxobutyric acid ethyl ester (33.6 g, 181.7 mmol) is added. The reaction is then heated to reflux for an additional 2 h. The reaction is then allowed to cool to rt, and sodium hydroxide (12.6 g, 316 mmol) in water (50 mL) is added. After 2 h, the reaction is chilled in an ice water bath and the reaction pH is adjusted to 3 using a solution of 12M aqueous HCl. The reaction mixture is then reduced in vacuo to 100 mL. Additional water (100 mL) is added and the suspension is chilled in an ice water bath, filtered and the solids are washed with minimal chilled water. The solids are then dried in vacuo to afford 4-methyl-[2,2']bipyrimidinyl-5-carboxylic acid (85%). MS: 217 (M+H); $^1$H NMR (300 MHz, CDCl$_3$): δ=2.80 (s, 3H), 7.66 (t, 1H), 9.01 (d, 2H), 9.14 (s, 1H).

Step 2. 4-Methyl-[2,2]bipyrimidinyl-5-carboxylic acid (0.5 g, 2.31 mmol) is combined with 5-fluoro-3-methyl-indol-1-yl-ammonium chloride (464 mg, 2.31 mmol), N-methylmorpholine (233 mg, 2.31 mmol) and DMF (10 mL). The suspension is stirred for 5 minutes at rt, then 4-(4,6-dimethoxy-[1,3,5]triazin-2-yl)-4-methyl-morpholin-4-ium chloride is added (640 mg, 2.31 mmol). The reaction is heated to 50° C. for 4 h. The reaction is then poured into water (50 mL), the suspension is chilled for 2 h in the refrigerator, and then filtered. The solids are then suspended in acetonitrile at 50° C. for 4 h, cooled, then filtered to afford 4-methyl-[2,2']bipyrimidinyl-5-carboxylic acid (5-fluoro-3-methyl-indol-1-yl)-amide (60%). MS: 363 (M+H); $^1$H NMR (300 MHz, CDCl$_3$): δ=2.27 (s, 3H), 2.77 (s, 3H), 7.07 (dt, 1H), 7.36 (dd, 1H), 7.38 (s, 1H), 7.44-7.48 (m, 1H), 7.70 (t, 1H), 9.05 (d, 2H), 9.29 (s, 1H), 11.9 (s, 1H). IC$_{50}$=4.5 nM.

Example 158

2-Thiazol-2-yl-pyrimidine-5-carboxylic acid (5-fluoro-3-methyl-indol-1-yl)-amide

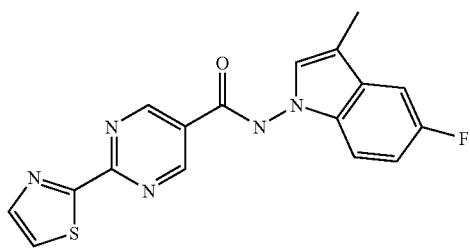

Step 1: A flask is charged with 2-cyanothiazole (6.7 g, 60.9 mmol), ammonium acetate (5.63 g, 73 mmol), N-acetylcysteine (993 mg, 6.09 mmol), and methanol (60 mL). The reaction is then heated to reflux overnight. The reaction is reduced in vacuo to yield a residue that is used in the next step without further modifications.

Step 2: The crude residue from Step 1 is suspended in DMF (100 mL). To this is added sodium 2-ethoxycarbonyl-3-oxobut-1-en-1-olate (13.86 g, 70 mmol). The reaction is then heated to 10° C. for 1.5 h then allowed to cool to rt. The reaction is then poured into ice water (1 L). The suspension is filtered and the filtrate is successively extracted with DCM (100 mL) and EtOAc (200 mL). The organic layers are dried (Na$_2$SO$_4$), filtered and concentrated to yield a residue (10.31 g).

Step 3: The residue from Step 2 (6.26 g, 28.32 mmol) is combined with a solution of sodium hydroxide (2.26 g, 56.65 mmol) in water (90 mL) and methanol (90 mL) and stirred at rt overnight. The volume of solution is reduced by half under vacuo and the pH is adjusted to 3 with aqueous HCl (approximately 12 M). The solid is collected by filtration and dried in vacuo to afford 2-thiazol-2-yl-pyrimidine-5-carboxylic acid (56% over 3 steps). MS: 208 (M+H); $^1$H NMR (300 MHz, CDCl$_3$): δ=8.11 (d, 1H), 8.16 (d, 1H), 9.32 (s, 2H).

Step 4: A mixture of 2-thiazol-2-yl-pyrimidine-5-carboxylic acid (50 mg, 0.244 mmol), 5-fluoro-3-methyl-indol-1-yl-ammonium chloride (49 mg, 0.244 mmol), diisopropylethylamine (31.5 mg, 0.244 mmol) in DMF (1 mL) is stirred at rt for 5 min. 4-(4,6-Dimethoxy-[1,3,5]triazin-2-yl)-4-methyl-morpholin-4-ium chloride (37 mg, 0.244 mmol) is added. The reaction is heated to 50° C. for 1.5 h and then concentrated in vacuo. The residue is taken up in DMSO-d$^6$ then purified via reverse phase C18 HPLC chromatography eluting with water and acetonitrile containing 0.1% TFA buffer to afford 2-thiazol-2-yl-pyrimidine-5-carboxylic acid (5-fluoro-3-methyl-indol-1-yl)-amide (58%). MS: 354 (M+H); $^1$H NMR (300 MHz, CDCl$_3$): δ=2.27 (s, 3H), 7.05 (dt, 1H), 7.32 (s, 1H), 7.32-7.44 (m, 2H), 8.11 (d, 1H), 8.19 (d, 1H), 9.42 (s, 2H), 12.12 (s, 1H).

Example 159

4-Methyl-2-thiazol-2-yl-pyrimidine-5-carboxylic acid (5-fluoro-3-methyl-indol-1-yl)-amide

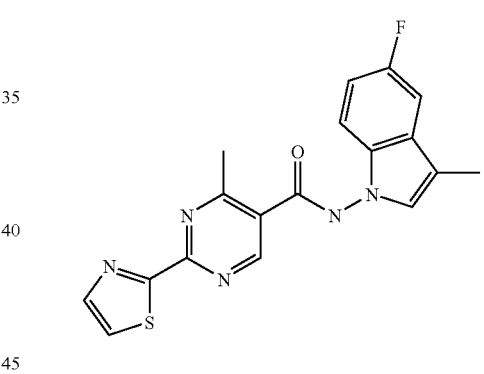

Step 1: A solution of 2-cyanothiazole (1.55 g, 14.2 mmol) in MeOH (12 mL) is treated with N-acetylcysteine (234 mg, 1.42 mmol), ammonium acetate (1.5 g, 18.5 mmol) and heated in a microwave at 120° C. for 15 min. The mixture is then treated with 2-dimethylaminomethylene-3-oxo-butyric acid ethyl ester (3.2 g, 17.0 mmol) and KOt-Bu (2.2 g, 20 mmol), and heated in a microwave at 120° C. for an additional 15 min. The mixture is then treated with a solution of KOH (1.2 g, 20 mmol) in H$_2$O (5 mL) and heated at reflux for 1 h. The mixture is neutralized with concentrated aqueous HCl. The precipitate is collected by filtration and dried to afford 4-methyl-2-thiazol-2-yl-pyrimidine-5-carboxylic acid (1.95 g, 62%). MS: 222 (M+H); $^1$H NMR (300 MHz, DMSO-d$_6$): δ 13.77 (s. OH, 1H), 9.18 (s, 1H), 8.13 (d, 1H), 8.07 (d, 1H), 2.81 (s, 3H).

Step 2: A mixture of 4-methyl-2-thiazol-2-yl-pyrimidine-5-carboxylic acid (221 mg, 1 mmol), 5-fluoro-3-methyl-indol-1-yl-ammonium chloride (200 mg, 1 mmol) and N-methylmorpholine (101 mg, 1 mmol) in DMF (5 mL) is stirred at rt for 5 min. 4-(4,6-Dimethoxy-[1,3,5]triazin-2-yl)-4-methyl-morpholin-4-ium chloride (277 mg, 1 mmol) is added and the reaction is heated to 50° C. for 4 h. The reaction mixture is then poured into water (50 mL). The precipitate is collected via filtration and dried in vacuo to provide 4-methyl-2-thiazol-2-yl-pyrimidine-5-carboxylic acid (5-fluoro-3-methyl-indol-1-yl)-amide (68%). MS: 368 (M+H); $^1$H NMR (300 MHz, CDCl$_3$): δ=2.27 (s, 3H), 2.76 (s, 3H), 7.06 (dt, 1H), 7.35-7.38 (m, 2H), 7.42-7.47 (m, 1H), 8.07 (d, 1H), 8.14 (d, 1H), 9.22 (s, 1H), 11.9 (s, 1H).

Example 160

[2,2']Bipyrimidinyl-5-carboxylic acid (5-fluoro-3-methyl-indol-1-yl)-amide

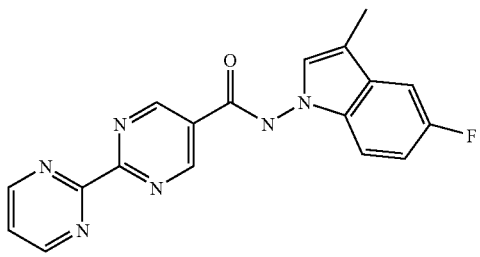

Step 1: A pressure vessel is charged with 2-cyanopyrimidine (7.88 g, 75 mmol), N-acetyl cysteine (1.22 g, 7.5 mmol), ammonium acetate (6.93 g, 90 mmol), and MeOH (75 mL). The vessel is sealed and heated at 110° C. for 1.5 h, and then cooled to rt. To the reaction mixture is added sodium 2-ethoxycarbonyl-3-oxo-but-1-en-1-olate (17 g, 86.25 mmol) and MeOH (75 mL). The mixture is heated to reflux for 1.5 h and then cooled to rt. NaOH (6 g, 150 mmol) and water (80 mL) are added. The mixture is stirred for 30 min or until LC-MS indicates complete hydrolysis of the intermediate ester. The pH of the reaction mixture is adjusted to 3 with concentrated (12 M) aqueous HCl. MeOH is evaporated in vacuo, and the resulting precipitate is collected via filtration and washed with minimal chilled water to yield [2,2']bipyrimidinyl-5-carboxylic acid (59%). MS: 203 (M+H); $^1$H NMR (300 MHz, CDCl$_3$): δ=7.71 (t, 1H), 9.06 (d, 2H), 9.40 (s, 2H).

Step 2: A mixture of [2,2']bipyrimidinyl-5-carboxylic acid (166 mg, 0.82 mmol), 5-fluoro-3-methyl-indol-1-yl-ammonium chloride (164 mg, 0.82 mmol) and DIPEA (106 mg, 0.82 mmol) in DMF (5 mL) is stirred at rt for 5 min. 4-(4,6-Dimethoxy-[1,3,5]triazin-2-yl)-4-methyl-morpholin-4-ium chloride (226 mg, 0.82 mmol) is added. The reaction mixture is heated to 50° C. for 1.5 h and then concentrated in vacuo. The residue is taken up in DMSO-d$^6$ and then purified via reverse phase C18 HPLC chromatography eluting with water and acetonitrile containing 0.1% TFA buffer to afford [2,2']bipyrimidinyl-5-carboxylic acid (5-fluoro-3-methyl-indol-1-yl)-amide (56%). MS: 349 (M+H); $^1$H NMR (300 MHz, CDCl$_3$): δ=2.27 (s, 3H), 7.05 (dt, 1H), 7.33 (s, 1H), 7.36 (dd, 1H), 7.42-7.46 (m, 1H), 7.72 (t, 1H), 9.07 (d, 2H), 9.51 (s, 2H), 12.17 (s, 1H).

Example 161

2-(3-Fluoro-phenyl)-4-methyl-pyrimidine-5-carboxylicacid(3 chloro-5-fluoro-indol-1-yl)-amide

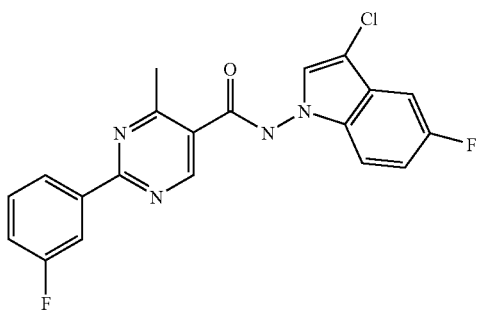

A solution of 2-(3-fluoro-phenyl)-4-methyl-pyrimidine-5-carboxylic acid (5-fluoro-indol-1-yl)-amide (300 mg, 0.824 mmol) in MeCN (20 mL) is treated with NCS (185 mg, 1.42 mmol) and the mixture is stirred at 60° C. in a sealed flask for 2 h. The mixture is then concentrated, diluted with 10% aqueous Na$_2$S$_2$O$_8$ (20 mL), and extracted with EtOAc (3×20 mL). The combined organic layer is separated, dried (Na$_2$SO$_4$), filtered and concentrated in vacuo. The residue is purified by silica gel chromatography eluting with 10%-20% EtOAc in heptane to afford 2-(3-fluoro-phenyl)-4-methyl-pyrimidine-5-carboxylicacid(3 chloro-5-fluoro-indol-1-yl)-amide (160 mg, 49%). MS: 399 (M+H); $^1$H NMR (300 MHz, CDCl$_3$): δ 8.79 (s, 1H), 8.04 (d, 1H), 7.92 (d, 1H), 7.18 (m, 1H), 7.04 (s, 1H), 7.00 (m, 3), 6.76 (m, 1), 2.52 (s, 3H).

Example 162

5-Fluoro-1-{[2-(3-fluoro-phenyl)-4-methyl-pyrimidine-5-carbonyl]-amino}-1H-indole-3-carboxylic acid amide

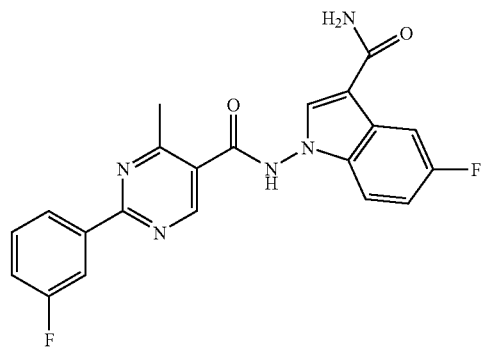

A solution of 2-(3-fluoro-phenyl)-4-methyl-pyrimidine-5-carboxylic acid (5-fluoro-indol-1-yl)-amide (300 mg, 0.82 mmol) in 2-Me-THF (7 mL) is treated with chlorosulfonyl isocyanate (CSI) (85 uL, 2.0 mmol) at 0° C., and the mixture is warmed to rt for 2 h. The mixture is then cooled to 0° C., treated with 1 M NaOH (1 mL), diluted with brine (20 mL), and extracted with EtOAc (3×20 mL). The combined organic layer is separated, dried (Na$_2$SO$_4$), filtered and concentrated in vacuo to afford 5-fluoro-1-{[2-(3-fluoro-phenyl)-4-methyl-pyrimidine-5-carbonyl]-amino}-1H-indole-3-carboxylic acid amide (275 mg, 83%). MS: 408 (M+H); $^1$H NMR (300 MHz, DMSO-d$_6$): δ 9.27 (s, 1H), 8.35 (d, 1H), 8.26 (s, 1H), 8.20 (d, 1H), 7.95 (d, 1H), 7.59 (m, 3H), 7.15 (m, 1H), 2.78 (s, 3H). IC$_{50}$=8 nM.

Example 163

2-{1,5-Fluoro-1-[(4-methyl-2-pyridin-2-yl-pyrimidine-5-carbonyl)-amino]-1H-indol-3-yl}-2-methyl-propionic acid

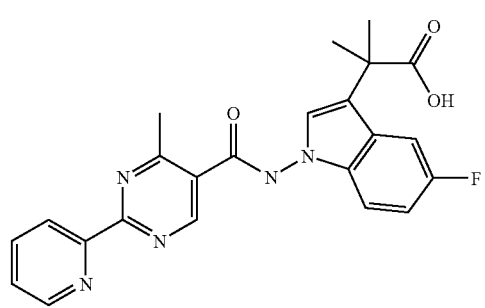

Step 1: A solution of (5-fluoro-1H-indol-3-yl)-acetic acid methyl ester (3 g, 14.8 mmol) in MeCN (25 mL) is treated with Boc$_2$O (4.3 g, 16.3 mmol) and DMAP (200 mg, 1.63 mmol), and the mixture is stirred at rt for 1 h. The mixture is diluted with saturated aqueous NH$_4$Cl (50 mL), and extracted with DCM (3×50 mL). The combined organic layer is dried (Na$_2$SO$_4$), filtered and concentrated in vacuo. The residue is purified by silica gel chromatography eluting with 8% EtOAc in heptane to afford 5-fluoro-3-methoxycarbonylmethyl-indole-1-carboxylic acid tert-butyl ester (1.6 g, 35%). MS: 371 (M+Na$^+$ACN); $^1$H NMR (300 MHz, CDCl$_3$): δ 8.09 (m, 1H), 7.59 (s, 1H), 7.17 (m, 1H), 7.04 (m, 1H), 3.72 (s, 3H), 3.67 (s, 2H), 1.55 (s, 9H).

Step 2: A solution of 5-fluoro-3-methoxycarbonylmethyl-indole-1-carboxylic acid tert-butyl ester (1.6 g, 5.2 mmol) in 2-Me-THF (50 mL) at −78° C. is treated with LDA (5.7 mL 1.8 M in THF, 10.4 mmol) and stirred for 0.5 h. MeI (1.02 mL, 15.6 mmol) is added and the mixture is warmed to 0° C. over 2 h. The mixture is diluted with saturated aqueous NH$_4$Cl (50 mL), and extracted with EtOAc (3×50 mL). The combined organic layer is separated, dried (Na$_2$SO$_4$), filtered and concentrated in vacuo to afford 5-fluoro-3-(1-methoxycarbonyl-1-methyl-ethyl)-indole-1-carboxylic acid tert-butyl ester, which is used in the next step without further purification.

Step 3: A solution of 5-fluoro-3-(1-methoxycarbonyl-1-methyl-ethyl)-indole-1-carboxylic acid tert-butyl ester (5.2 mmol) in MeOH (25 mL) is treated with K$_2$CO$_3$ (720 mg, 5.2 mmol) and heated at reflux for 2 h. The mixture is diluted with brine (50 mL) and extracted with EtOAc (3×50 mL). The combined organic layer is dried (Na$_2$SO$_4$), filtered and concentrated in vacuo to afford 2-(5-fluoro-1H-indol-3-yl)-2-methyl-propionic acid methyl ester (650 mg, 53%, 2 steps), which is used in the next step without further purification. MS: 236 (M+H); $^1$H NMR (300 MHz, DMSO-d$_6$): δ 7.35 (m, 1H), 7.30 (m, 1H), 7.14 (m, 1H), 6.91 (m, 1H), 3.54 (s, 3H), 1.57 (s, 6H).

Step 4: A suspension of NaH (1.02 g, 25.5 mmol, 60% in mineral oil) in DMF (25 mL) at 0° C. is treated with 2-(5-fluoro-1H-indol-3-yl)-2-methyl-propionic acid methyl ester (400 mg, 1.7 mmol) and stirred at 0° C. for 0.5 h. The mixture is treated with HOSA (960 mg, 8.5 mmol) portion wise and warmed to rt over 2 h. The mixture is then poured over ice, filtered through a pad of Celite, and extracted with EtOAc (3×100 mL). The combined organic layer is dried (Na$_2$SO$_4$), filtered and concentrated in vacuo to afford 2-(1-amino-5-fluoro-1H-indol-3-yl)-2-methyl-propionic acid methyl ester, which is used in the next step without further purification.

Step 5: A solution of 2-(1-amino-5-fluoro-1H-indol-3-yl)-2-methyl-propionic acid methyl ester (0.85 mmol) and 4-methyl-2-pyridin-2-yl-pyrimidine-5-carboxylic acid (201 mg, 0.935 mmol) in DMF (8.5 mL) is stirred at 40° C. for 0.5 h. The mixture is treated with DMTMM (246 mg, 0.89 mmol) and stirred at 60° C. for 1 h. The mixture is concentrated in vacuo, diluted with saturated aqueous Na$_2$CO$_3$ (20 mL), and extracted with EtOAc (3×20 mL). The combined organic layer is dried (Na$_2$SO$_4$), filtered and concentrated in vacuo to afford 2-{5-fluoro-1-[(4-methyl-2-pyridin-2-yl-pyrimidine-5-carbonyl)-amino]-1H-indol-3-yl}-2-methyl-propionic acid methyl ester, which is used in the next step without further purification.

Step 6: A solution of 2-{5-fluoro-1-[(4-methyl-2-pyridin-2-yl-pyrimidine-5-carbonyl)-amino]-1H-indol-3-yl}-2-methyl-propionic acid methyl ester (0.85 mmol) in MeOH (5 mL) is treated with 10% aqueous NaOH (2 mL) and stirred at rt overnight. The mixture is then concentrated, diluted with EtOAc (50 mL), and extracted with 10% aqueous NaOH (3×50 mL). The aqueous layer is acidified with 12 M aqueous HCl, extracted with DCM (3×50 mL). The combined organic layer is dried (Na$_2$SO$_4$), filtered and concentrated. The residue is triturated with Et$_2$O to afford 2-[5-fluoro-1-[(4-methyl-2-pyridin-2-yl-pyrimidine-5-carbonyl)-amino]-1H-indol-3-yl]-2-methyl-propionic acid (100 mg, 27%, 3 steps). MS: 434 (M+H); $^1$H NMR (300 MHz, DMSO-d$_6$): δ 9.26 (s, 1H), 8.79 (m, 1H), 8.44 (d, 1H), 8.03 (t, 1H), 7.59 (m, 1H), 7.53 (s, 1H), 7.49 (m, 1H), 7.35 (d, 1H), 7.08 (t, 1H), 2.79 (s, 3H), 1.59 (s, 6H).

Example 164

2-(5-Fluoro-1-{[2-(3-fluoro-phenyl)-4-methyl-pyrimidine-5-carbonyl]-amino}-1H-indol-3-yl)-2-methyl-propionic acid

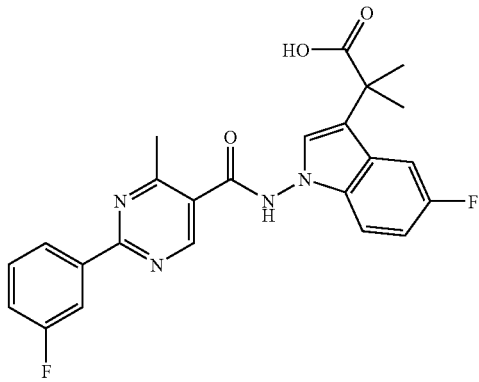

Step 1: A solution of 2-(1-amino-5-fluoro-1H-indol-3-yl)-2-methyl-propionic acid methyl ester (0.85 mmol) and 2-(3-fluoro-phenyl)-4-methyl-pyrimidine-5-carboxylic acid (217 mg, 0.935 mmol) in DMF (8.5 mL) is stirred at 40° C. for 0.5 h. The mixture is treated with DMTMM (246 mg, 0.89 mmol) and stirred at 60° C. for 1 h. The mixture is concentrated in vacuo, diluted with saturated aqueous Na$_2$CO$_3$ (20 mL), and extracted with EtOAc (3×20 mL). The combined organic layer is separated, dried (Na$_2$SO$_4$), filtered and concentrated in vacuo to afford 2-(5-fluoro-1-{[2-(3-fluoro-phenyl)-4-methyl-pyrimidine-5-carbonyl]-amino}-1H-indol-3-yl)-2-methyl-propionic acid methyl ester, which is used in the next step without further purification.

Step 2: A solution of 2-(5-fluoro-1-{[2-(3-fluoro-phenyl)-4-methyl-pyrimidine-5-carbonyl]-amino}-1H-indol-3-yl)-2-methyl-propionic acid methyl ester (0.85 mmol) in MeOH (5 mL) is treated with 10% aqueous NaOH (2 mL) and stirred at rt overnight. The mixture is then concentrated, diluted with EtOAc (50 mL), and extracted with 10% aqueous NaOH (3×50 mL). The aqueous layer is acidified with 12 M HCl, and extracted with DCM (3×50 mL). The combined organic layer is dried (Na$_2$SO$_4$), filtered and concentrated. The residue is triturated with Et$_2$O to afford 2-(5-fluoro-1-{[2-(3-fluoro-phenyl)-4-methyl-pyrimidine-5-carbonyl-amino}-1H-indol-3-yl)-2-methyl-propionic acid (139 mg). MS: 451 (M+H); $^1$H NMR (300 MHz, DMSO-d$_6$): δ 9.22 (s, 1H), 8.33 (d, 1H), 8.18 (d, 1H), 7.63 (m, 1H), 7.50 (m, 3H), 7.33 (m, 1H), 7.07 (m, 1H), 2.78 (s, 3H), 1.59 (s, 6H). IC$_{50}$=7 nM.

Example 165

2-(3-Fluoro-phenyl)-4-methyl-pyrimidine-5-carboxylic acid [5-fluoro-3-(3-hydroxy-3-methyl-butyl)-indol-1-yl]-amide

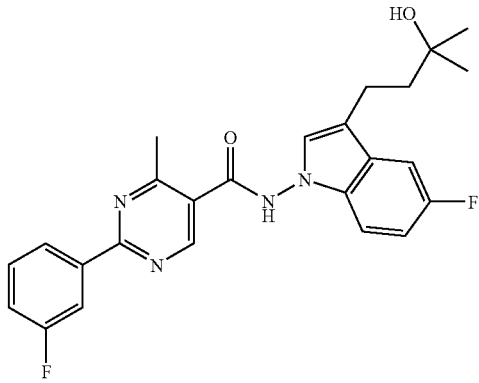

Step 1: A solution of 5-fluoroindole (10.5 g, 78 mmol) in MeCN (150 mL) at 0° C. is treated with methyl vinyl ketone (9.5 mL, 117 mmol) and Sc(OTf)$_3$ (383 mg, 0.78 mmol) and stirred for 1 h. The mixture is then stirred an additional 6 h at rt. The mixture is concentrated in vacuo. The residue is purified by silica gel chromatography eluting with 10%-50% EtOAc in heptane to afford 4-(5-fluoro-1H-indol-3-yl)-butan-2-one (11.1 g, 70%).

Step 2: A solution of 4-(5-fluoro-1H-indol-3-yl)-butan-2-one (11.1 g, 54.1 mmol) in THF (200 mL) at 0° C. is treated with MeMgBr (54.1 mL, 3 M in THF, 162.3 mmol) and stirred at 0° C. for 2 h, and warmed to rt overnight. The mixture is then poured over ice, treated with solid NH$_4$Cl (3 g), and extracted with EtOAc (3×120 mL). The combined organic layer is dried (Na$_2$SO$_4$), filtered and concentrated in vacuo. The residue is purified by silica gel chromatography eluting with 10%-60% EtOAc in heptane to afford 4-(5-fluoro-1H-indol-3-yl)-2-methyl-butan-2-ol (3.07 g, 26%). MS: 222 (M+H); $^1$H NMR (300 MHz, CDCl$_3$): δ 7.94 (s, NH, 1H), 7.22 (m, 2H), 7.03 (s, 1H), 6.93 (m, 1H), 2.81 (m, 2H), 1.90 (m, 2H), 1.33 (s, 6H).

Step 3: A suspension of NaH (8.1 g, 204 mmol, 60% in mineral oil) in DMF (100 mL) at 0° C. is treated with 4-(5-fluoro-1H-indol-3-yl)-2-methyl-butan-2-ol (3 g, 13.6 mmol) and stirred at 0° C. for 0.5 h. The mixture is treated with HOSA (7.7 g, 68 mmol) portion wise and warmed to rt over 2 h. The mixture is then poured over ice, filtered through a pad of Celite, and extracted with EtOAc (3×100 mL). The combined organic layer is dried (Na$_2$SO$_4$), filtered and concentrated in vacuo. The residue is purified by filtration through a short plug of silica gel to afford 4-(1-amino-5-fluoro-1H-indol-3-yl)-2-methyl-butan-2-ol, which is used in the next step without further purification. MS: 237 (M+H); $^1$H NMR (300 MHz, CDCl$_3$): δ 7.30 (m, 1H), 7.22 (m, 1H), 6.98 (m, 2H), 4.71 (s, NH$_2$, 2H), 2.75 (m, 2H), 1.86 (m, 2H), 1.31 (s, 6H).

Step 4: A solution of 2-(3-fluoro-phenyl)-4-methyl-pyrimidine-5-carboxylic acid (278 mg, 1.2 mmol) and 4-(1-amino-5-fluoro-1H-indol-3-yl)-2-methyl-butan-2-ol (1.2 mmol) in DMF (10 mL) is stirred at 50° C. for 1 h. The mixture is treated with DMTMM (331 mg, 1.2 mmol) and stirred at 50° C. for 1 h. The mixture is concentrated in vacuo, diluted with saturated aqueous Na$_2$CO$_3$ (50 mL), and extracted with EtOAc (3×50 mL). The combined organic layer is dried (Na$_2$SO$_4$), filtered and concentrated in vacuo. The residue is purified by silica gel chromatography eluting with 50% EtOAc in heptane to afford 2-(3-fluoro-phenyl)-4-methyl-pyrimidine-5-carboxylic acid [5-fluoro-3-(3-hydroxy-3-methyl-butyl)-indol-1-yl]-amide (330 mg, 61%). MS: 451 (M+H); $^1$H NMR (300 MHz, CD$_3$OD): δ 9.10 (s, 1H), 8.36 (d, 1H), 8.23 (d, 1H), 7.55 (m, 1H), 7.32 (m, 3H), 7.18 (s, 1H), 7.03 (m, 1H), 3.91 (s, OH, 1H), 2.84 (s, 3H), 2.82 (m, 2H), 1.91 (m, 2H), 1.31 (s, 6H).

Example 166

4-Methyl-2-pyridin-2-yl-pyrimidine-5-carboxylic acid [5-fluoro-3-(3-hydroxy-3-methyl-butyl)-indol-1-yl]-amide

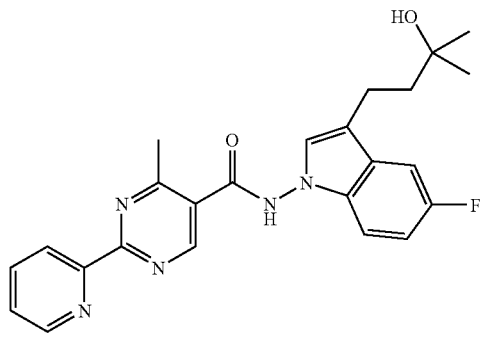

A solution of 2-(2-pyridyl)-4-methyl-pyrimidine-5-carboxylic acid (516 mg, 4 mmol) and 4-(1-amino-5-fluoro-1H-indol-3-yl)-2-methyl-butan-2-ol (566 mg, 4 mmol) in DMF (5 mL) is stirred at 50° C. for 1 h. The mixture is treated with DMTMM (662 mg, 4 mmol) and stirred at 50° C. for 1 h. The mixture is diluted with saturated aqueous Na$_2$CO$_3$ (50 mL), and extracted with EtOAc (3×50 mL). The combined organic layer is dried (Na$_2$SO$_4$), filtered and concentrated in vacuo. The residue is purified by silica gel chromatography eluting with 4%-10% MeOH in DCM to afford 4-methyl-2-pyridin-2-yl-pyrimidine-5-carboxylic acid [5-fluoro-3-(3-hydroxy-3-methyl-butyl)-indol-1-yl]-amide (450 mg, 44%). MS: 434 (M+H); $^1$H NMR (300 MHz, DMSO-d$_6$): δ 9.25 (s, 1H), 8.81 (d, 1H), 8.47 (d, 1H), 8.02 (m, 1H), 7.58 (m, 1H), 7.43 (m, 3H), 7.06 (m, 1H), 4.29 (s, OH, 1H), 2.78 (s, 3H), 2.72 (m, 2H), 1.77 (m, 2H), 120 (s, 6H).

Example 167

2-(3-Fluoro-phenyl)-4-methyl-pyrimidine-5-carboxylic acid [5-fluoro-3-(2-pyridin-3-yl-ethyl)-indol-1-yl]-amide

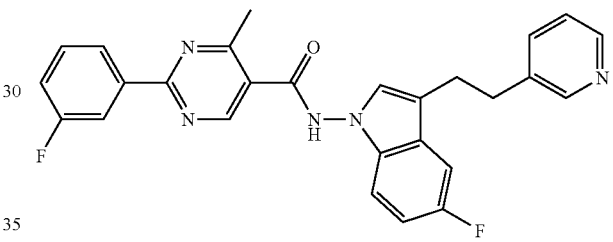

Step 1: A solution of 5-fluorogramine (576 mg, 3 mmol) and pyridine-3-carboxaldehyde (531 mg, 3 mmol) in MeCN (6 mL) is treated with Bu$_3$P (1.12 mL, 4.5 mmol) and stirred at 90° C. for 24 h. The mixture is concentrated, filtered through a pad of silica gel eluting with 30% EtOAc in heptane to afford 5-fluoro-3-(2-pyridin-3-yl-vinyl)-1H-indole as a mixture of olefin isomers, which is used in the next step without further purification.

Step 2: A solution of 5-fluoro-3-(2-pyridin-3-yl-vinyl)-1H-indole (3 mmol) in MeOH (10 mL) is treated with Pd/C (200 mg) and shaken in a Parr apparatus under 40 atm of H$_2$ for 18 h. The mixture is filtered through Celite and the filtrate is concentrated in vacuo. The residue is purified by silica gel chromatography eluting with 0%-10% MeOH in DCM to afford 5-fluoro-3-(2-pyridin-3-yl-ethyl)-1H-indole (360 mg, 50%, 2 steps).

Step 3: A suspension of NaH (600 mg, 15 mmol, 60% in mineral oil) in DMF (10 mL) at 0° C. is treated with 5-fluoro-3-(2-pyridin-3-yl-ethyl)-1H-indole (240 mg, 1 mmol) and stirred at 0° C. for 0.5 h. The mixture is treated with HOSA (565 mg, 5 mmol) portion wise and warmed to rt over 2 h. The mixture is then poured over ice, filtered through a pad of Celite, and extracted with EtOAc (3×1050 mL). The combined organic layer is dried (Na$_2$SO$_4$), filtered and concentrated in vacuo to afford 5-fluoro-3-(2-pyridin-3-yl-ethyl)-indol-1-ylamine, which is used in the next step without further purification.

Step 4: A solution of 2-(3-fluoro-phenyl)-4-methyl-pyrimidine-5-carboxylic acid (232 mg, 1 mmol) and 5-fluoro-3-(2-pyridin-3-yl-ethyl)-indol-1-ylamine (255 mmol) in DMF (10 mL) is stirred at 50° C. for 10 min. The mixture is treated with DMTMM (276 mg, 1 mmol) and stirred at 50° C. for 0.5 h. The mixture is diluted with saturated aqueous Na$_2$CO$_3$ (50 mL), and extracted with EtOAc (3×50 mL). The combined organic layer is dried (Na$_2$SO$_4$), filtered and concentrated in vacuo. The residue is purified by triturating in MeOH:H$_2$O (2:1) to afford 2-(3-fluoro-phenyl)-4-methyl-pyrimidine-5-carboxylic acid [5-fluoro-3-(2-pyridin-3-yl-ethyl)-indol-1-yl]-amide (6 mg, 1%). MS: 470 (M+H); $^1$H NMR (300 MHz, DMSO-d$_6$): δ 9.21 (s, 1H), 8.51 (m, 1H), 8.40 (m, 1H), 8.33 (d, 1H), 8.19 (d, 1H), 7.74 (d, 1H), 7.63 (m, 1H), 7.45 (m, 4H), 7.33 (m, 1H), 7.06 (m, 1H), 3.29 (s, 2H), 3.01 (s, 2H), 2.77 (s, 3H).

Example 168

4-Methyl-2-pyridin-2-yl-pyrimidine-5-carboxylic acid (5-fluoro-3-formyl-indol-1-yl)-amide

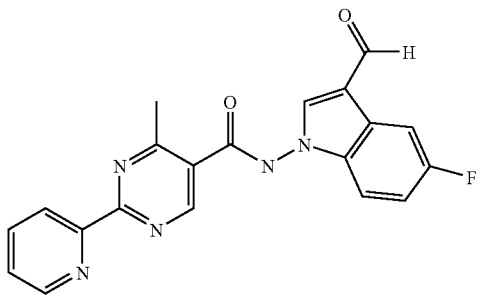

A solution of 4-methyl-2-pyridin-2-yl-pyrimidine-5-carboxylic acid (5-fluoro-indol-1-yl)-amide (250 mg, 0.55 mmol) in H$_2$O (5.5 mL) is treated with DDQ (369 mg, 1.6 mmol) in EtOAc (0.5 mL), and stirred at rt for 2 h. The mixture is diluted with EtOAc (50 mL), washed with brine (50 mL), and extracted with saturated aqueous NaHCO$_3$ (3×50 mL). The aqueous layer is acidified to pH 2 with HCl (conc.) and washed with Et$_2$O (50 mL). The aqueous layer is neutralized with 10% aqueous NaOH and extracted with EtOAc (3×50 mL). The combined organic layer is dried (Na$_2$SO$_4$), filtered and concentrated in vacuo. The residue is purified by triturating in Et$_2$O to afford 4-methyl-2-pyridin-2-yl-pyrimidine-5-carboxylic acid (5-fluoro-3-formyl-indol-1-yl)-amide (87 mg, 43%). MS: 376 (M+H); $^1$H NMR (300 MHz, DMSO-d$_6$): δ 12.53 (s, NH, 1H), 10.00 (s, 1H), 9.34 (m, 1H), 8.81 (m, 1H), 8.66 (s, 1H), 8.48 (m, 1H), 8.04 (m, 1H), 7.86 (m, 1H), 7.72 (m, 1H), 7.61 (m, 1H), 7.27 (m, 1H), 2.80 (s, 3H).

Example 169

5-Fluoro-1-[(4-methyl-2-pyridin-2-yl-pyrimidine-5-carbonyl)-amino]-1H-indole-3-carboxylic acid

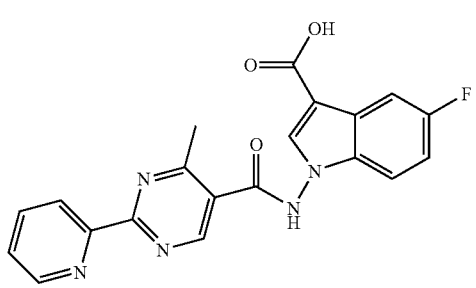

Step 1: A solution of 5-fluoro-1H-indole-3-carboxylic acid methyl ester (510 mg, 2.6 mmol) in NMP (6.5 mL) at rt is treated with KOt-Bu (342 mg, 2.9 mmol) and stirred at rt for 0.5 h.

A solution of O-amino-4-nitrobenzoic acid (558 mg, 3.0 mmol) in NMP (2.5 mL) is added and the mixture is stirred for 3 h. The mixture is diluted with EtOAc (50 mL) and washed with 10% aqueous NaHCO$_3$ (50 mL). The organic layer is separated, dried (Na$_2$SO$_4$), filtered and concentrated in vacuo to afford 1-amino-5-fluoro-1H-indole-3-carboxylic acid methyl ester, which is used in the next step without further purification.

Step 2: A solution of 2-(2-pyridyl)-4-methyl-pyrimidine-5-carboxylic acid (559 mg, 2.6 mmol) and 1-amino-5-fluoro-1H-indole-3-carboxylic acid methyl ester (540 mg, 2.6 mmol) in DMF (25 mL) is stirred at 50° C. for 0.5 h. The mixture is treated with DMTMM (718 mg, 2.6 mmol) and stirred at 50° C. for 1 h. The mixture is diluted with saturated aqueous Na$_2$CO$_3$ (50 mL), and extracted with EtOAc (3×50 mL). The combined organic layer is dried (Na$_2$SO$_4$), filtered and concentrated in vacuo. The residue is purified by silica gel chromatography eluting with 1%-10% MeOH in DCM to afford 5-fluoro-1-[(4-methyl-2-pyridin-2-yl-pyrimidine-5-carbonyl)-amino]-1H-indole-3-carboxylic acid methyl ester.

Step 3: A solution of 5-fluoro-1-[(4-methyl-2-pyridin-2-yl-pyrimidine-5-carbonyl)-amino]-1H-indole-3-carboxylic acid methyl ester (2.6 mmol) in MeOH (10 mL) is treated with an aqueous solution of KOH (500 mg, 8.9 mmol) in H$_2$O (200 mL) and heated at reflux for 2 h. The mixture is diluted with EtOAc (50 mL) and extracted with 1% aqueous KOH (3×50 mL). The combined aqueous layer is neutralized with HCl (conc.), and the precipitate is collected by filtration and dried in vacuo to afford 5-fluoro-1-[(4-methyl-2-pyridin-2-yl-pyrimidine-5-carbonyl)-amino]-1H-indole-3-carboxylic acid (195 mg, 19%, 3 steps). MS: 392 (M+H); $^1$H NMR (300 MHz, DMSO-d$_6$): δ 12.44 (s, OH, 1H), 12.31 (s, NH, 1H), 9.31 (s, 1H), 8.81 (d, 1H), 8.48 (d, 1H), 8.35 (s, 1H), 8.03 (m, 1H), 7.77 (m, 1H), 7.62 (m, 2H), 7.19 (m, 1H), 2.79 (s, 3H).

Example 170

4-Methyl-2-pyridin-2-yl-pyrimidine-5-carboxylic acid (5-fluoro-3-hydroxymethyl-indol-1-yl)-amide

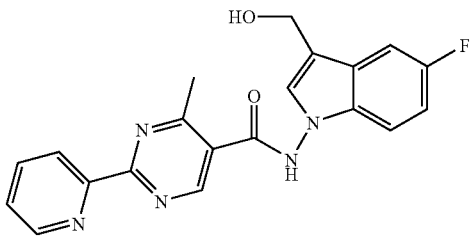

A solution of 4-methyl-2-pyridin-2-yl-pyrimidine-5-carboxylic acid (5-fluoro-3-formyl-indol-1-yl)-amide (230 mg, 0.614 mmol) in MeOH (10 mL) is treated with NaBH$_4$ (233 mg, 6.14 mmol) and stirred at rt for 1 h. The mixture is diluted with EtOAc (50 mL) and H$_2$O, neutralized with HCl (conc.), and extracted with EtOAc (3×50 mL). The combined organic layer is dried (Na$_2$SO$_4$), filtered and concentrated in vacuo. The residue is purified by preparative reverse-phase HPLC eluting with 20%-100% MeCN in H$_2$O to afford 4-methyl-2-pyridin-2-yl-pyrimidine-5-carboxylic acid (5-fluoro-3-hydroxymethyl-indol-1-yl)-amide (90 mg, 8%). MS: 378 (M+H); $^1$H NMR (300 MHz, DMSO-d$_6$): δ 11.92 (s, NH, 1H), 9.27 (s, 1H), 8.81 (d, 1H), 8.47 (d, 1H), 8.05 (m, 1H), 7.61 (m, 1H), 7.44 (m, 3H), 7.10 (m, 1H), 5.00 (t, OH, 1H), 4.66 (d, 2H), 2.78 (s, 3H).

Example 171

4-Methyl-[2,2']bipyrimidinyl-5-carboxylic acid [5-fluoro-3-(3-hydroxy-3-methyl-butyl)-indol-1-yl]-amide

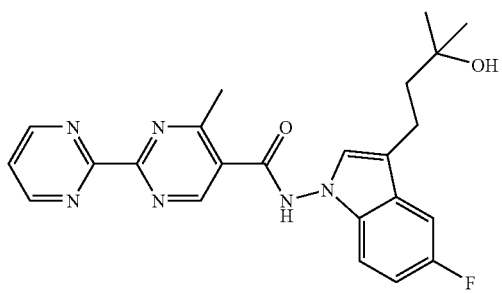

A solution of 4-methyl-[2,2']bipyrimidinyl-5-carboxylic acid (300 mg, 1.38 mmol) and 4-(1-amino-5-fluoro-1H-indol-3-yl)-2-methyl-butan-2-ol (325 mg, 1.38 mmol) in DMF (5 mL) is stirred at 50° C. for 1 h. The mixture is treated with DMTMM (380 mg, 1.38 mmol) and stirred at 50° C. for 2 h. The mixture is diluted with saturated aqueous $Na_2CO_3$ (50 mL), and extracted with EtOAc (3×50 mL). The combined organic layer is dried ($Na_2SO_4$), filtered and concentrated in vacuo. The residue is purified by silica gel chromatography eluting with 0%-7% MeOH in DCM to afford 4-methyl-[2,2']bipyrimidinyl-5-carboxylic acid [5-fluoro-3-(3-hydroxy-3-methyl-butyl)-indol-1-yl]-amide (200 mg, 33%). MS: 435 (M+H); $^1$H NMR (300 MHz, $CD_3OD$): δ 9.26 (s, 1H), 9.09 (d, 2H), 7.70 (t, 1H), 7.29 (m, 2H), 7.22 (s, 1H), 7.01 (m, 1H), 2.90 (s, 3H), 2.82 (m, 2H), 1.91 (m, 2H), 1.31 (s, 6H).

Example 172

4-Methyl-2-thiazol-2-yl-pyrimidine-5-carboxylic acid [5-fluoro-3-(3-hydroxy-3-methyl-butyl)-indol-1-yl]-amide

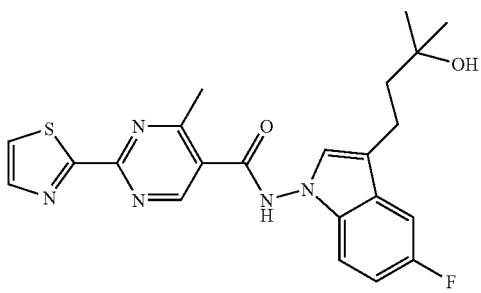

A solution of 4-methyl-2-thiazol-2-yl-pyrimidine-5-carboxylic acid (300 mg, 1.36 mmol) and 4-(1-amino-5-fluoro-1H-indol-3-yl)-2-methyl-butan-2-ol (325 mg, 1.38 mmol) in DMF (5 mL) is stirred at 50° C. for 1 h. The mixture is treated with DMTMM (380 mg, 1.38 mmol) and stirred at 50° C. for 2 h. The mixture is diluted with saturated aqueous $Na_2CO_3$ (50 mL), and extracted with EtOAc (3×50 mL). The combined organic layer is dried ($Na_2SO_4$), filtered and concentrated in vacuo. The residue is purified by silica gel chromatography eluting with 0%-7% MeOH in DCM to afford 4-methyl-2-thiazol-2-yl-pyrimidine-5-carboxylic acid [5-fluoro-3-(3-hydroxy-3-methyl-butyl)-indol-1-yl]-amide (155 mg, 26%). MS: 440 (M+H); $^1$H NMR (300 MHz, DMSO-$d_6$): δ 9.22 (s, 1H), 8.14 (d, 1H), 8.08 (d, 1H), 7.40 (m, 3H), 7.06 (m, 1H), 4.31 (s, OH, 1H), 2.76 (s, 3H), 2.71 (m, 2H), 1.77 (m, 2H), 1.20 (s, 6H). $IC_{50}$=5 nM.

Example 173

2-(3-Fluoro-phenyl)-4-methyl-pyrimidine-5-carboxylic acid (3-ethyl-5-trifluoromethyl-indol-1-yl)-amide

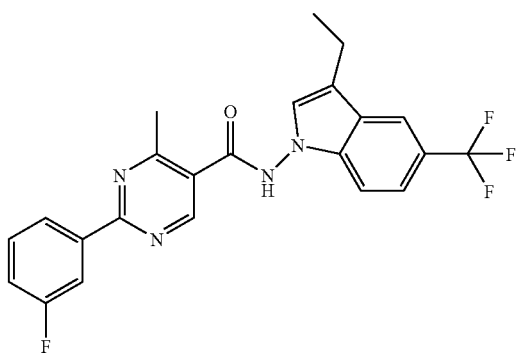

Step 1: A solution of 2-iodo-4-trifluoromethyl-phenylamine (10 g, 34.8 mmol) in DCM (100 mL) is treated with TFAA (5.55 mL, 41.8 mmol) and pyridine (3.4 mL, 41.8 mmol), and stirred at rt for 1 h. The mixture is diluted with $H_2O$ (150 mL), and extracted with DCM (3×150 mL). The combined organic layer is dried ($Na_2SO_4$), filtered and concentrated in vacuo. The residue is diluted with MeCN (100 mL), treated with trans-crotyl bromide (5.4 mL, 52.2 mmol) and $K_2CO_3$ (9.6 g, 69.6 mmol), and heated at reflux for 2 h. The mixture is cooled, filtered through a pad of Celite and concentrated. The residue is purified by silica gel chromatography eluting with 0%-10% EtOAc in heptane to afford N-but-2-enyl-2,2,2-trifluoro-N-(2-iodo-4-trifluoromethyl-phenyl)-acetamide (12.7 g, 84%). MS: 438 (M+H); $^1$H NMR (300 MHz, $CDCl_3$): δ 8.18 (s, 1H), 7.67 (s, 1H), 7.26 (m, 1H), 5.52 (m, 2H), 4.88 (m, 1H), 3.51 (m, 1H), 1.68 (d, 3H).

Step 2: A solution of N-but-2-enyl-2,2,2-trifluoro-N-(2-iodo-4-trifluoromethyl-phenyl)-acetamide (12.7 g, 29 mmol) in DMF (60 mL) is treated with n-$Bu_4NCl$ (8.8 g, 32 mmol), $Pd(OAc)_2$ (131 mg, 0.58 mmol), and stirred at 100° C. for 2 h. The mixture is cooled to rt, diluted with EtOAc (150 mL), filtered through a pad of silica gel, and washed with 1 M HCl (150 mL). The organic layer is separated, dried ($Na_2SO_4$), filtered and concentrated in vacuo. The residue is purified by silica gel chromatography eluting with 10%-30% EtOAc in heptane to afford 3-ethyl-5-trifluoromethyl-1H-indole (2.6 g, 42%). MS: 214 (M+H); $^1$H NMR (300 MHz, $CDCl_3$): δ 8.08 (s, NH, 1H), 7.89 (s, 1H), 7.41 (m, 2H), 7.07 (m, 1H), 2.81 (q, 2H), 1.34 (t, 3H).

Step 3: A suspension of NaH (7 g, 176 mmol, 60% in mineral oil) in DMF (50 mL) at 0° C. is treated with 3-ethyl-5-trifluoromethyl-1H-indole (2.4 g, 11.3 mmol) and stirred at 0° C. for 1 h. The mixture is treated with HOSA (6.6 g, 59 mmol) portion wise and warmed to rt over 2 h. The mixture is then poured over ice, filtered through a pad of Celite, and extracted with EtOAc (3×150 mL). The combined organic layer is dried ($Na_2SO_4$), filtered and concentrated in vacuo. The residue is purified by silica gel chromatography eluting with 10%-50% EtOAc in heptane to afford 3-ethyl-5-trifluoromethyl-indol-1-ylamine (1.3 g, 50%). MS: 229 (M+H); $^1$H NMR (300 MHz, CDCl₃): δ 7.84 (s, 1H), 7.45 (s, 2H), 7.02 (s, 1H), 4.74 (s, NH₂, 2H), 2.77 (q, 2H), 1.31 (t, 3H).

Step 4: A solution of 2-(3-fluoro-phenyl)-4-methyl-pyrimidine-5-carboxylic acid (232 mg, 1.0 mmol) and 3-ethyl-5-trifluoromethyl-indol-1-ylamine (228 mg, 1 mmol) in DMF (5 mL) is stirred at 50° C. for 1 h. The mixture is treated with DMTMM (276 mg, 1 mmol) and stirred at 50° C. for 2 h. The mixture is diluted with saturated aqueous Na₂CO₃ (5 mL) and stirred for 5 min. The precipitate is collected by filtration and dried in vacuo to afford 2-(3-fluoro-phenyl)-4-methyl-pyrimidine-5-carboxylic acid (3-ethyl-5-trifluoromethyl-indol-1-yl)-amide (240 mg, 54%). MS: 443 (M+H); ¹H NMR (300 MHz, DMSO-d₆): δ 9.24 (s, 1H), 8.34 (d, 1H), 8.26 (d, 1H), 8.19 (s, 1H), 7.58 (m, 2H), 7.42 (m, 3H), 2.84 (q, 2H), 2.78 (s, 3H), 1.31 (t, 3H).

Example 174

4-Methyl-2-pyridin-2-yl-pyrimidine-5-carboxylic acid (3-ethyl-5-trifluoromethyl-indol-1-yl)-amide

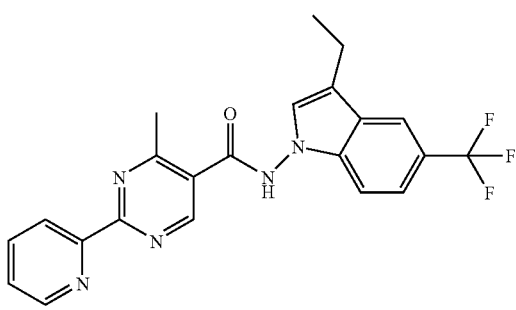

A solution of 2-(2-pyridyl)-4-methyl-pyrimidine-5-carboxylic acid (215 mg, 1 mmol) and 3-ethyl-5-trifluoromethyl-indol-1-ylamine (228 mg, 1 mmol) in DMF (5 mL) is stirred at 50° C. for 1 h. The mixture is treated with DMTMM (276 mg, 1 mmol) and stirred at 50° C. for 2 h. The mixture is diluted with saturated aqueous Na₂CO₃ (5 mL) and stirred for 5 min. The precipitate is collected by filtration and dried in vacuo to afford 4-methyl-2-pyridin-2-yl-pyrimidine-5-carboxylic acid (3-ethyl-5-trifluoromethyl-indol-1-yl)-amide (235 mg, 55%). MS: 426 (M+H); ¹H NMR (300 MHz, DMSO-d₆): δ 9.28 (s, 1H), 8.81 (d, 1H), 8.48 (d, 1H), 8.03 (m, 1H), 7.99 (s, 1H), 7.60 (m, 4H), 2.82 (q, 2H), 2.79 (s, 3H), 1.31 (t, 3H).

Example 175

4-Methyl-2-thiazol-2-yl-pyrimidine-5-carboxylic acid (3-ethyl-5-trifluoromethyl-indol-1-yl)-amide

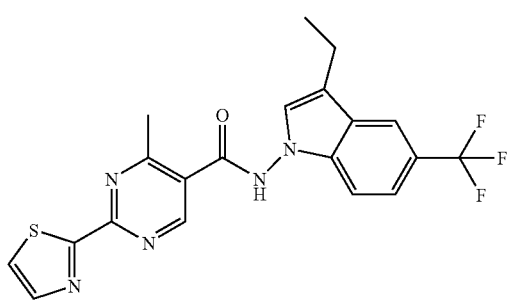

A solution of 4-methyl-2-thiazol-2-yl-pyrimidine-5-carboxylic acid (221 mg, 1 mmol) and 3-ethyl-5-trifluoromethyl-indol-1-ylamine (228 mg, 1 mmol) in DMF (5 mL) is stirred at 50° C. for 1 h. The mixture is treated with DMTMM (276 mg, 1 mmol) and stirred at 50° C. for 2 h. The mixture is diluted with saturated aqueous Na₂CO₃ (5 mL) and stirred for 5 min. The precipitate is collected by filtration and dried in vacuo to afford 4-methyl-2-thiazol-2-yl-pyrimidine-5-carboxylic acid (3-ethyl-5-trifluoromethyl-indol-1-yl)-amide (250 mg, 58%). MS: 432 (M+H); ¹H NMR (300 MHz, DMSO-d₆): δ 12.07 (s, NH, 1H), 9.25 (s, 1H), 8.15 (d, 1H), 8.09 (d, 1H), 7.99 (s, 1H), 7.68 (d, 1H), 7.51 (m, 2H), 2.77 (s, 3H), 2.74 (q, 2H), 1.29 (t, 3H).

Example 176

4-Methyl-[2,2']bipyrimidinyl-5-carboxylic acid (3-ethyl-5-trifluoromethyl-indol-1-yl)-amide

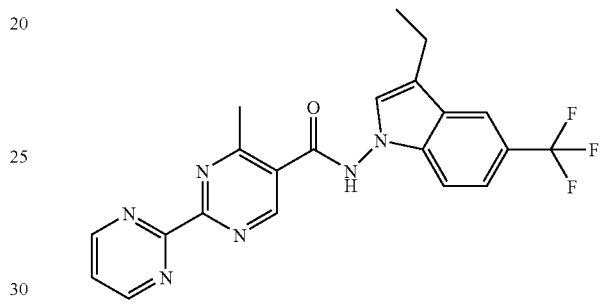

A solution of 4-methyl-[2,2']bipyrimidinyl-5-carboxylic acid (216 mg, 1 mmol) and 3-ethyl-5-trifluoromethyl-indol-1-ylamine (228 mg, 1 mmol) in DMF (5 mL) is stirred at 50° C. for 1 h. The mixture is treated with DMTMM (276 mg, 1 mmol) and stirred at 50° C. for 2 h. The mixture is diluted with saturated aqueous Na₂CO₃ (5 mL) and stirred for 5 min. The precipitate is collected by filtration and dried in vacuo. The solid is triturated in Et₂O to afford 4-methyl-[22']bipyrimidinyl-5-carboxylic acid (3-ethyl-5-trifluoromethyl-indol-1-yl)-amide (100 mg, 23%). MS: 427 (M+H); ¹H NMR (300 MHz, DMSO-d₆): δ 12.11 (s, NH, 1H), 9.32 (s, 1H), 9.07 (d, 2H), 8.00 (s, 1H), 7.69 (m, 2H), 7.53 (m, 2H), 2.80 (q, 2H), 2.79 (s, 3H), 1.31 (t, 3H). IC₅₀=8 nM.

Example 177

2-(3-Fluoro-phenyl)-4-methyl-pyrimidine-5-carboxylic acid (3-ethyl-5-trifluoromethoxy-indol-1-yl)-amide

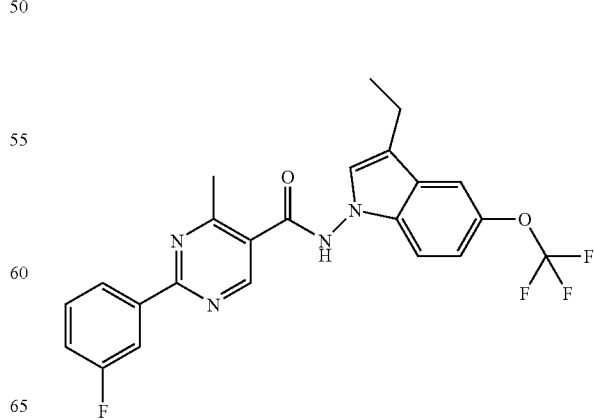

Step 1: A solution of 2-bromo-4-trifluoromethoxy-phenylamine (7.6 g, 29.7 mmol) in DCM (60 mL) is treated with TFAA (5 mL, 35.6 mmol) and pyridine (2.87 mL, 35.6 mmol), and stirred at rt overnight. The mixture is diluted with H$_2$O (150 mL), and extracted with DCM (3×150 mL). The combined organic layer is dried (Na$_2$SO$_4$), filtered and concentrated in vacuo. The residue is diluted with MeCN (60 mL), treated with trans-crotyl bromide (4.6 mL, 44.5 mmol) and K$_2$CO$_3$ (8.1 g, 59 mmol), heated at reflux for 1 h, and then stirred at rt for 2 h. The mixture is filtered through a pad of Celite and the filtrate is concentrated. The residue is purified by silica gel chromatography eluting with 0%-15% EtOAc in heptane to afford N-(2-bromo-4-trifluoromethoxy-phenyl)-N-but-2-enyl-2,2,2-trifluoro-acetamide (10.5 g, 87%). MS: 406 (M+); $^1$H NMR (300 MHz, CDCl$_3$): δ 7.56 (s, 1H), 7.22 (m, 2H), 5.52 (m, 2H), 4.86 (m, 1H), 3.57 (m, 1H), 1.65 (d, 3H).

Step 2: A solution of N-(2-bromo-4-trifluoromethoxy-phenyl)-N-but-2-enyl-2,2,2-trifluoro-acetamide (10 g, 24.7 mmol) in DMF (50 mL) is treated with n-Bu$_4$NCl (7.5 g, 27.2 mmol), Pd(OAc)$_2$ (221 mg, 0.98 mmol), and stirred at 100° C. for 1 h. H$_2$O (10 mL) is added, and the mixture is cooled to rt, filtered through a pad of silica gel. The filtrate is extracted with heptane (3×50 mL). The combined organic layer is dried (Na$_2$SO$_4$), filtered and concentrated in vacuo. The residue is purified by silica gel chromatography eluting with 0%-25% EtOAc in heptane to afford 3-ethyl-5-trifluoromethoxy-1H-indole (3.1 g, 55%). MS: 230 (M+H); $^1$H NMR (300 MHz, CDCl$_3$): δ 7.97 (s, NH, 1H), 7.44 (s, 1H), 7.29 (m, 1H), 7.07 (m, 2H), 2.77 (q, 2H), 1.32 (t, 3H).

Step 3: A suspension of NaH (7.9 g, 197 mmol, 60% in mineral oil) in DMF (60 mL) at 0° C. is treated with 3-ethyl-5-trifluoromethoxy-1H-indole (3 g, 13.1 mmol) and stirred at 0° C. for 1 h. The mixture is treated with HOSA (7.4 g, 65.5 mmol) portion wise and warmed to rt over 2 h. The mixture is then poured over ice and filtered through a pad of Celite. The filtrate is extracted with heptane (3×50 mL). The combined organic layer is dried (Na$_2$SO$_4$), filtered and concentrated in vacuo. The residue is purified by silica gel chromatography eluting with 10%-30% EtOAc in heptane to afford 3-ethyl-5-trifluoromethoxy-indol-1-ylamine (2.05 g, 64%). MS: 245 (M+H); $^1$H NMR (300 MHz, CDCl$_3$): δ 7.37 (m, 2H), 7.11 (m, 1H), 7.00 (s, 1H), 4.72 (s, NH$_2$, 2H), 2.73 (q, 2H), 1.29 (t, 3H).

Step 4: A solution of 2-(3-fluoro-phenyl)-4-methyl-pyrimidine-5-carboxylic acid (250 mg, 1.1 mmol) and 3-ethyl-5-trifluoromethoxy-indol-1-ylamine (244 mg, 1 mmol) in DMF (5 mL) is stirred at 50° C. for 1 h. The mixture is treated with DMTMM (276 mg, 1 mmol) and stirred at 50° C. for 1 h. The mixture is diluted with saturated aqueous Na$_2$CO$_3$ (5 mL) and stirred for 10 min. The precipitate is collected by filtration, washed with H$_2$O (50 mL) and heptane (50 mL), and dried in vacuo to afford 2-(3-fluoro-phenyl)-4-methyl-pyrimidine-5-carboxylic acid (3-ethyl-5-trifluoromethoxy-indol-1-yl)-amide (270 mg, 59%). MS: 459 (M+H); $^1$H NMR (300 MHz, CDCl$_3$): δ 11.51 (s, NH, 1H), 9.08 (s, 1H), 8.35 (d, 1H), 8.24 (d, 1H), 7.48 (m, 2H), 7.22 (m, 2H), 7.11 (m, 2H), 2.85 (s, 3H), 2.80 (q, 2H), 1.35 (t, 3H).

Example 178

4-Methyl-2-pyridin-2-yl-pyrimidine-5-carboxylic acid (3-ethyl-5-trifluoromethoxy-indol-1-yl)-amide

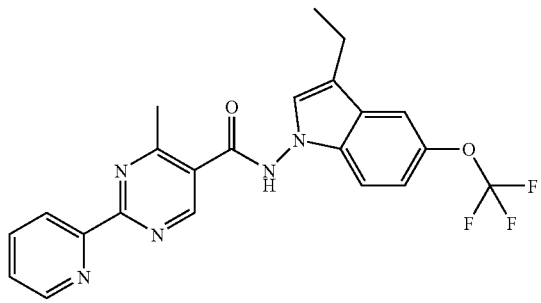

A solution of 2-(2-pyridyl)-4-methyl-pyrimidine-5-carboxylic acid (250 mg, 1.1 mmol) and 3-ethyl-5-trifluoromethoxy-indol-1-ylamine (244 mg, 1.0 mmol) in DMF (5 mL) is stirred at 50° C. for 1 h. The mixture is treated with DMTMM (276 mg, 1.0 mmol) and stirred at 50° C. for 1 h. The mixture is diluted with saturated aqueous Na$_2$CO$_3$ (5 mL) and stirred for 10 min. The precipitate is collected by filtration, washed with H$_2$O (50 mL) and heptane (50 mL), and dried in vacuo to afford 4-methyl-2-pyridin-2-yl-pyrimidine-5-carboxylic acid (3-ethyl-5-trifluoromethoxy-indol-1-yl)-amide (300 mg, 68%). MS: 442 (M+H); $^1$H NMR (300 MHz, DMSO-d$_6$): δ 9.27 (s, 1H), 8.81 (d, 1H), 8.47 (d, 1H), 8.03 (m, 1H), 7.57 (m, 3H), 7.47 (s, 1H), 7.21 (d, 1H), 2.78 (s, 3H), 2.74 (q, 2H), 1.29 (t, 3H).

Example 179

4-Methyl-[2,2']bipyrimidinyl-5-carboxylic acid (3-ethyl-5-trifluoromethoxy-indol-1-yl)-amide

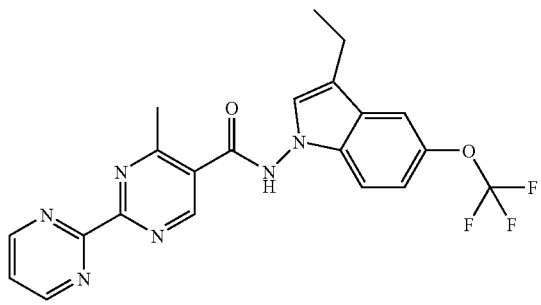

A solution of 4-methyl-[2,2']bipyrimidinyl-5-carboxylic acid (250 mg, 1.1 mmol) and 3-ethyl-5-trifluoromethoxy-indol-1-ylamine (244 mg, 1 mmol) in DMF (5 mL) is stirred at 50° C. for 1 h. The mixture is treated with DMTMM (276 mg, 1.0 mmol) and stirred at 50° C. for 1 h. The mixture is diluted with saturated aqueous Na$_2$CO$_3$ (5 mL) and stirred for 10 min. The precipitate is collected by filtration, washed with H$_2$O (50 mL) and heptane (50 mL), and dried in vacuo to afford 4-methyl-[2,2']bipyrimidinyl-5-carboxylic acid (3-ethyl-5-trifluoromethoxy-indol-1-yl)-amide (130 mg, 29%). MS: 443 (M+H); $^1$H NMR (300 MHz, DMSO-d$_6$): δ

9.25 (s, 1H), 9.05 (d, 2H), 7.69 (t, 1H), 7.64 (s, 1H), 7.54 (m, 2H), 7.14 (d, 1H), 2.80 (s, 3H), 2.76 (q, 2H), 1.29 (t, 3H).

Example 180

4-Methyl-2-thiazol-2-yl-pyrimidine-5-carboxylic acid (3-ethyl-5-trifluoromethoxy-indol-1-yl)-amide

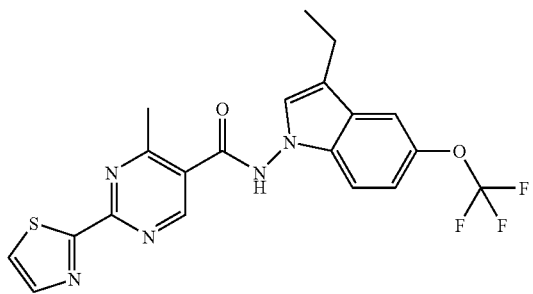

A solution of 4-methyl-2-thiazol-2-yl-pyrimidine-5-carboxylic acid (250 mg, 1.1 mmol) and 3-ethyl-5-trifluoromethoxy-indol-1-ylamine (244 mg, 1.0 mmol) in DMF (5 mL) is stirred at 50° C. for 1 h. The mixture is treated with DMTMM (276 mg, 1.0 mmol) and stirred at 50° C. for 1 h. The mixture is diluted with saturated aqueous Na$_2$CO$_3$ (5 mL) and stirred for 10 min.

The precipitate is collected by filtration, washed with H$_2$O (50 mL) and heptane (50 mL), and dried in vacuo to afford 4-methyl-2-thiazol-2-yl-pyrimidine-5-carboxylic acid (3-ethyl-5-trifluoromethoxy-indol-1-yl)-amide (250 mg, 56%). MS: 448 (M+H); $^1$H NMR (300 MHz, DMSO-d$_6$): δ 9.23 (s, 1H), 8.15 (m, 1H), 8.09 (m, 1H), 7.55 (m, 2H), 7.48 (s, 1H), 7.19 (d, 1H), 2.78 (s, 3H), 2.71 (m, 2H), 1.29 (t, 3H).

Example 181

2-(3-Fluoro-phenyl)-4-methyl-pyrimidine-5-carboxylic acid (6-trifluoromethyl-indol-1-yl)-amide

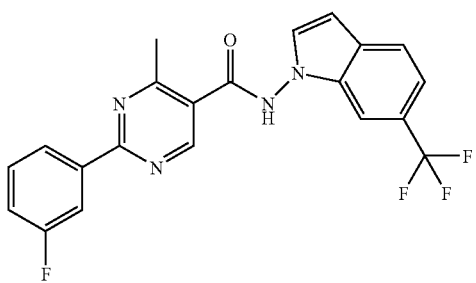

Step 1: A suspension of NaH (6.5 g, 162 mmol, 60% in mineral oil) in DMF (54 mL) at 0° C. is treated with 6-trifluoromethylindole (2.0 g, 10.8 mmol) and stirred at 0° C. for 0.5 h. The mixture is treated with HOSA (6.1 g, 54 mmol) portion wise and warmed to rt over 2 h. The mixture is then poured over ice and filtered through a pad of Celite. The filtrate is extracted with Et$_2$O (3×50 mL). The combined organic layer is dried (Na$_2$SO$_4$), filtered and concentrated in vacuo. The residue is purified by silica gel chromatography eluting with 10%-30% EtOAc in heptane to afford 6-trifluoromethyl-indol-1-ylamine (1.79 g, 83%). MS: 201 (M+H); $^1$H NMR (300 MHz, CDCl$_3$): δ 7.74 (s, 1H), 7.67 (d, 1H), 7.35 (d, 1H), 7.30 (m, 1H), 6.45 (d, 1H), 4.83 (s, NH$_2$, 2H).

Step 2: A solution of 2-(3-fluoro-phenyl)-4-methyl-pyrimidine-5-carboxylic acid (278 mg, 1.2 mmol) and 6-trifluoromethyl-indol-1-ylamine (200 mg, 1 mmol) in DMF (5 mL) is stirred at 50° C. for 0.5 h. The mixture is treated with DMTMM (290 mg, 1.05 mmol) and stirred at 50° C. for 1 h. The mixture is diluted with saturated aqueous Na$_2$CO$_3$ (5 mL) and extracted with EtOAc (3×50 mL). The combined organic layer is dried (Na$_2$SO$_4$), filtered and concentrated in vacuo. The residue is triturated with Et$_2$O/heptane overnight. The precipitate is collected by filtration, washed with H$_2$O (50 mL) and heptane (50 mL), and dried in vacuo to afford 2-(3-fluoro-phenyl)-4-methyl-pyrimidine-5-carboxylic acid (6-trifluoromethyl-indol-1-yl)-amide (180 mg, 44%). MS: 415 (M+H); $^1$H NMR (300 MHz, DMSO-d$_6$): δ 12.09 (s, NH, 1H), 9.33 (s, 1H), 8.35 (d, 1H), 8.20 (d, 1H), 7.90 (s, 1H), 7.79 (m, 2H), 7.65 (m, 1H), 7.46 (m, 2H), 6.74 (d, 1H), 2.79 (s, 3H).

Example 182

4-Methyl-2-pyridin-2-yl-pyrimidine-5-carboxylic acid (6-trifluoromethyl-indol-1-yl)-amide

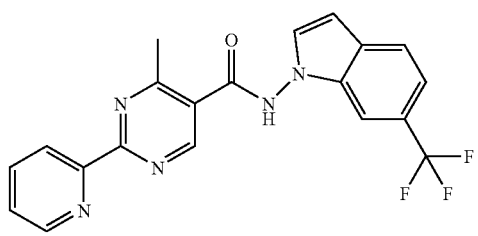

A solution of 2-(2-pyridyl)-4-methyl-pyrimidine-5-carboxylic acid (258 mg, 1.2 mmol) and 6-trifluoromethyl-indol-1-ylamine (200 mg, 1 mmol) in DMF (5 mL) is stirred at 50° C. for 0.5 h. The mixture is treated with DMTMM (290 mg, 1.05 mmol) and stirred at 50° C. for 1 h. The mixture is diluted with saturated aqueous Na$_2$CO$_3$ (5 mL) and extracted with EtOAc (3×50 mL). The combined organic layer is dried (Na$_2$SO$_4$), filtered and concentrated in vacuo. The residue is triturated with Et$_2$O/heptane overnight. The precipitate is collected by filtration, washed with H$_2$O (50 mL) and heptane (50 mL), and dried in vacuo to afford 4-methyl-2-pyridin-2-yl-pyrimidine-5-carboxylic acid (6-trifluoromethyl-indol-1-yl)-amide (160 mg, 40%). MS: 398 (M+H); $^1$H NMR (300 MHz, DMSO-d$_6$): δ 12.13 (s, NH, 1H), 9.36 (s, 1H), 8.82 (d, 1H), 8.48 (d, 1H), 8.04 (m, 1H), 7.83 (m, 3H), 7.60 (m, 1H), 7.44 (d, 1H), 6.74 (d, 1H), 2.80 (s, 3H).

Example 183

4-Methyl-2-thiazol-2-yl-pyrimidine-5-carboxylic acid (6-trifluoromethyl-indol-1-yl)-amide

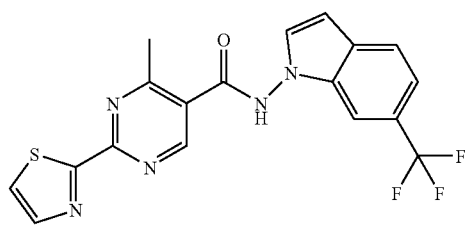

A solution of 4-methyl-2-thiazol-2-yl-pyrimidine-5-carboxylic acid (265 mg, 1.2 mmol) and 6-trifluoromethyl-indol-1-ylamine (200 mg, 1 mmol) in DMF (5 mL) is stirred at 50° C. for 0.5 h. The mixture is treated with DMTMM (290 mg, 1.05 mmol) and stirred at 50° C. for 1 h.

The mixture is diluted with saturated aqueous $Na_2CO_3$ (5 mL) and extracted with EtOAc (3×50 mL). The combined organic layer is dried ($Na_2SO_4$), filtered and concentrated in vacuo.

The residue is triturated with $Et_2O$/heptane overnight. The precipitate is collected by filtration, washed with $H_2O$ (50 mL) and heptane (50 mL), and dried in vacuo to afford 4-methyl-2-thiazol-2-yl-pyrimidine-5-carboxylic acid (6-trifluoromethyl-indol-1-yl)-amide (160 mg, 40%). MS: 404 (M+H); $^1$H NMR (300 MHz, DMSO-$d_6$): δ 12.12 (s, NH, 1H), 9.33 (s, 1H), 8.15 (d, 1H), 8.05 (d, 1H), 7.91 (s, 1H), 7.79 (m, 2H), 7.44 (m, 1H), 6.73 (d, 1H), 2.77 (s, 3H).

Example 184

4-Methyl-[2,2']bipyrimidinyl-5-carboxylic acid (6-trifluoromethyl-indol-1-yl)-amide

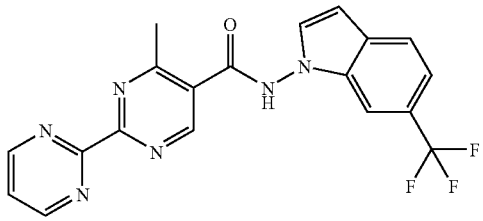

A solution of 4-methyl-[2,2']bipyrimidinyl-5-carboxylic acid (259 mg, 1.2 mmol) and 6-trifluoromethyl-indol-1-ylamine (200 mg, 1 mmol) in DMF (5 mL) is stirred at 50° C. for 0.5 h. The mixture is treated with DMTMM (290 mg, 1.05 mmol) and stirred at 50° C. for 1 h. The mixture is diluted with saturated aqueous $Na_2CO_3$ (5 mL) and extracted with EtOAc (3×50 mL). The combined organic layer is dried ($Na_2SO_4$), filtered and concentrated in vacuo. The residue is triturated with $Et_2O$/heptane overnight. The precipitate is collected by filtration, washed with $H_2O$ (50 mL) and heptane (50 mL), and dried in vacuo to afford 4-methyl-[2,2']bipyrimidinyl-5-carboxylic acid (6-trifluoromethyl-indol-1-yl)-amide (100 mg, 25%). MS: 399 (M+H); $^1$H NMR (300 MHz, DMSO-$d_6$): δ 12.16 (s, NH, 1H), 9.39 (s, 1H), 9.06 (d, 2H), 7.92 (s, 1H), 7.81 (m, 2H), 7.70 (t, 1H), 7.44 (d, 1H), 6.74 (d, 1H), 2.79 (s, 3H).

Example 185

2-(3-Fluoro-phenyl)-4-methyl-pyrimidine-5-carboxylic acid (3-ethyl-5-trifluoromethyl-pyrrolo[3,2-b]pyridin-1-yl)-amide

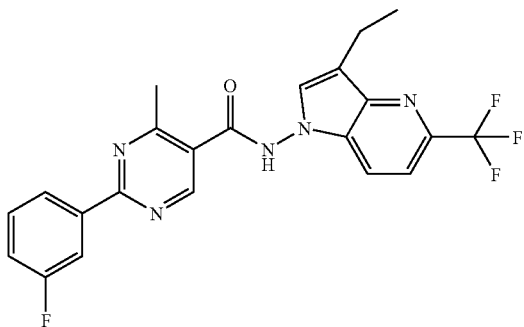

Step 1: A solution of 2-iodo-6-trifluoromethyl-pyridin-3-ylamine (5.09 g, 17.7 mmol) in DCM (50 mL) is treated with TFAA (3 mL, 21.2 mmol) and pyridine (1.7 mL, 21.2 mmol), and stirred at rt for 1 h. The mixture is diluted with $H_2O$ (150 mL), and extracted with DCM (3×150 mL). The combined organic layer is dried ($Na_2SO_4$), filtered and concentrated in vacuo. The residue is diluted with MeCN (50 mL), treated with trans-crotyl bromide (2.8 mL, 26.6 mmol) and $K_2CO_3$ (4.7 g, 34.4 mmol), and heated at reflux for 2 h. The mixture is filtered through a pad of Celite. The filtrate is concentrated in vacuo. The residue is purified by silica gel chromatography eluting with 0%-25% EtOAc in heptane to afford N-but-2-enyl-2,2,2-trifluoro-N-(2-iodo-6-trifluoromethyl-pyridin-3-yl)-acetamide (5.5 g, 71%). MS: 439 (M+H); $^1$H NMR (300 MHz, $CDCl_3$): δ 7.71 (d, 1H), 7.53 (d, 1H), 5.52 (m, 2H), 4.98 (m, 1H), 3.58 (m, 1H), 1.68 (d, 3H).

Step 2: A solution of N-but-2-enyl-2,2,2-trifluoro-N-(2-iodo-6-trifluoromethyl-pyridin-3-yl)-acetamide (5.2 g, 11.9 mmol) in DMF (24 mL) is treated with n-$Bu_4$NCl (3.6 g, 13.1 mmol), Pd(OAc)$_2$ (107 mg, 0.48 mmol), and stirred at 100° C. for 1 h. $H_2O$ (10 mL) is added, and the mixture is cooled to rt and filtered through a pad of silica gel. The filtrate is extracted with EtOAc/heptane (3×50 mL) (1:1). The combined organic layer is dried ($Na_2SO_4$), filtered and concentrated in vacuo. The residue is purified by silica gel chromatography eluting with 5%-50% EtOAc in heptane to afford 3-ethyl-5-trifluoromethyl-1H-pyrrolo[3,2-b]pyridine (2.2 g, 86%). MS: 215 (M+H); $^1$H NMR (300 MHz, $CDCl_3$): δ 8.24 (s, NH, 1H), 7.73 (d, 1H), 7.50 (d, 1H), 7.34 (d, 1H), 2.93 (q, 2H), 1.36 (t, 3H).

Step 3: A suspension of NaH (4.65 g, 116 mmol, 60% in mineral oil) in DMF (40 mL) at 0° C. is treated with 3-ethyl-5-trifluoromethyl-1H-pyrrolo[3,2-b]pyridine (2 g, 7.75 mmol) and stirred at 0° C. for 1 h. The mixture is treated with HOSA (4.4 g, 38.8 mmol) portion wise and warmed to rt over 2 h. The mixture is then poured over ice, treated with solid $NH_4Cl$ (3 g), and filtered through a pad of Celite. The filtrate is extracted with $Et_2O$ (3×150 mL). The combined organic layer is dried ($Na_2SO_4$), filtered and concentrated in vacuo. The residue is purified by silica gel chromatography eluting with 30%-50% EtOAc in heptane to afford 3-ethyl-5-trifluoromethyl-pyrrolo[3,2-b]pyridin-1-ylamine (1.5 g, 84%). MS: 230 (M+H); $^1$H NMR (300 MHz, DMSO-$d_6$): δ 7.97 (d, 1H), 7.59 (d, 1H), 7.54 (s, 1H), 6.12 (s, $NH_2$, 2H), 2.78 (q, 2H), 1.28 (t, 3H).

Step 4: A solution of 2-(3-fluoro-phenyl)-4-methyl-pyrimidine-5-carboxylic acid (278 mg, 1.1 mmol) and 3-ethyl-5-trifluoromethyl-pyrrolo[3,2-b]pyridin-1-ylamine (230 mg, 1 mmol) in DMF (5 mL) is stirred at 50° C. for 1 h. The mixture is treated with DMTMM (290 mg, 1.05 mmol) and stirred at 50° C. overnight. The mixture is diluted with saturated aqueous $Na_2CO_3$ (5 mL) and stirred for 10 min. The precipitate is collected by filtration, washed with $H_2O$ (50 mL) and heptane (50 mL), and dried in vacuo to afford 2-(3-fluoro-phenyl)-4-methyl-pyrimidine-5-carboxylic acid (3-ethyl-5-trifluoromethyl-pyrrolo [32-b]pyridin-1-yl)-amide (195 mg, 44%). MS: 444 (M+H); $^1$H NMR (300 MHz, DMSO-$d_6$): δ 12.16 (s, NH, 1H), 9.28 (s, 1H), 8.34 (d, 1H), 8.18 (m, 2H), 7.86 (s, 1H), 7.65 (m, 2H), 7.45 (m, 1H), 2.83 (q, 2H), 2.78 (s, 3H), 1.35 (t, 3H).

Example 186

4-Methyl-2-pyridin-2-yl-pyrimidine-5-carboxylic acid (3-ethyl-5-trifluoromethyl-pyrrolo [32-b]pyridin-1-yl)-amide

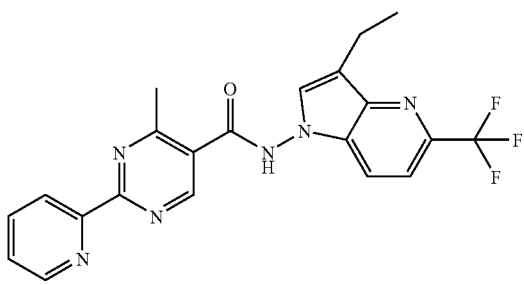

A solution of 2-(2-pyridyl)-4-methyl-pyrimidine-5-carboxylic acid (258 mg, 1.1 mmol) and 3-ethyl-5-trifluoromethyl-pyrrolo[3,2-b]pyridin-1-ylamine (230 mg, 1.0 mmol) in DMF (5 mL) is stirred at 50° C. for 1 h. The mixture is treated with DMTMM (290 mg, 1.05 mmol) and stirred at 50° C. overnight. The mixture is diluted with saturated aqueous $Na_2CO_3$ (5 mL) and stirred for 10 min. The precipitate is collected by filtration, washed with $H_2O$ (50 mL) and heptane (50 mL), and dried in vacuo to afford 4-methyl-2-pyridin-2-yl-pyrimidine-5-carboxylic acid (3-ethyl-5-trifluoromethyl-pyrrolo [32-b]pyridin-1-yl)-amide (175 mg, 41%). MS: 427 (M+H); $^1$H NMR (300 MHz, DMSO-$d_6$): δ 12.18 (s, NH, 1H), 9.31 (s, 1H), 8.80 (d, 1H), 8.45 (d, 1H), 8.16 (d, 1H), 8.01 (m, 1H), 7.88 (s, 1H), 7.72 (d, 1H), 7.59 (m, 1H), 2.81 (q, 2H), 2.79 (s, 3H), 1.35 (t, 3H).

Example 187

4-Methyl-2-thiazol-2-yl-pyrimidine-5-carboxylic acid (3-ethyl-5-trifluoromethyl-pyrrolo[3,2-b]pyridin-1-yl)-amide

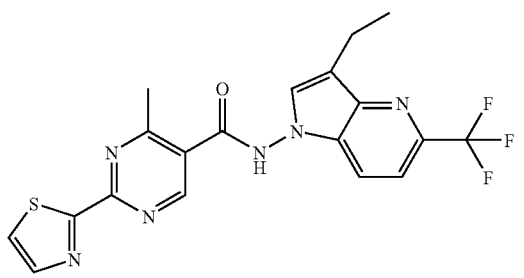

A solution of 4-methyl-2-thiazol-2-yl-pyrimidine-5-carboxylic acid (88 mg, 0.40 mmol) and 3-ethyl-5-trifluoromethyl-pyrrolo[3,2-b]pyridin-1-ylamine (89 mg, 0.40 mmol) in DMF (5 mL) is stirred at 50° C. for 1 h. The mixture is treated with DMTMM (113 mg, 0.41 mmol) and stirred at 50° C. overnight. The mixture is diluted with saturated aqueous $Na_2CO_3$ (5 mL) and stirred for 10 min. The precipitate is collected by filtration, washed with $H_2O$ (50 mL) and heptane (50 mL), and dried in vacuo to afford 4-methyl-2-thiazol-2-yl-pyrimidine-5-carboxylic acid (3-ethyl-5-trifluoromethyl-pyrrolo[3,2-b]pyridin-1-yl)-amide (75 mg, 40%). MS: 433 (M+H); $^1$H NMR (300 MHz, DMSO-$d_6$): δ 12.19 (s, NH, 1H), 9.28 (s, 1H), 8.15 (m, 2H), 8.08 (d, 1H), 7.87 (s, 1H), 7.72 (d, 1H), 2.83 (q, 2H), 2.77 (s, 3H), 1.35 (t, 3H).

Example 188

4-Methyl-[2,2']bipyrimidinyl-5-carboxylic acid (3-ethyl-5-trifluoromethyl-pyrrolo[3,2-b]pyridin-1-yl)-amide

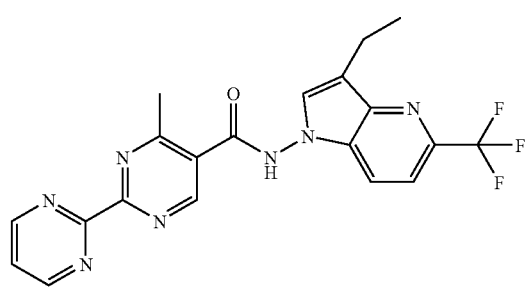

A solution of 4-methyl-[2,2']bipyrimidinyl-5-carboxylic acid (259 mg, 1.2 mmol) and 3-ethyl-5-trifluoromethyl-pyrrolo[3,2-b]pyridin-1-ylamine (230 mg, 1.0 mmol) in DMF (5 mL) is stirred at 50° C. for 0.5 h. The mixture is treated with DMTMM (290 mg, 1.05 mmol) and stirred at 50° C. overnight. The mixture is diluted with saturated aqueous $Na_2CO_3$ (5 mL) and extracted with EtOAc (3×50 mL). The combined organic layer is dried ($Na_2SO_4$), filtered and concentrated in vacuo. The residue is purified by preparative reverse-phase HPLC eluting with 20%-100% MeCN in $H_2O$ to afford 4-methyl-[2,2']bipyrimidinyl-5-carboxylic acid (3-ethyl-5-trifluoromethyl-pyrrolo [32-b]pyridin-1-yl)-amide (230 mg, 54%). MS: 428 (M+H); $^1$H NMR (300 MHz, DMSO-$d_6$): δ 9.28 (s, 1H), 9.05 (d, 2H), 8.11 (d, 1H), 7.98 (s, 1H), 7.69 (t, 1H), 7.64 (d, 1H), 2.83 (q, 2H), 2.80 (s, 3H), 1.34 (t, 3H).

Example 189

2-(3-Fluoro-phenyl)-4-methyl-pyrimidine-5-carboxylic acid (5-methoxy-2-methyl-indol-1-yl)-amide

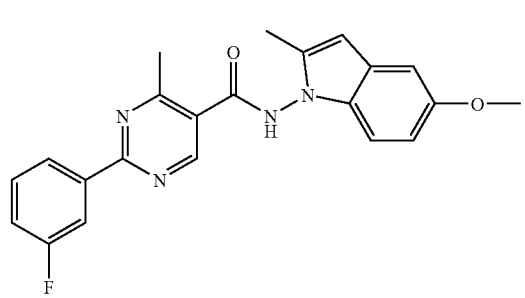

Step 1: A suspension of NaH (1.25 g, 51 mmol, 60% in mineral oil) in DMF (47 mL) at 0° C. is treated with 5-methoxy-2-methylindole (500 mg, 3.1 mmol) and stirred at 0° C. for 0.5 h. The mixture is treated with HOSA (1.92 g, 17.0 mmol) portion wise and warmed to rt over 2 h. The mixture is then poured over ice, and extracted with EtOAc (3×50 mL). The combined organic layer is dried ($Na_2SO_4$), filtered and concentrated in vacuo to afford 5-methoxy-2-methyl-indol-1-ylamine, which is used in the next step without further purification.

Step 2: A solution of 2-(3-fluoro-phenyl)-4-methyl-pyrimidine-5-carboxylic acid (719 mg, 3.1 mmol) and 5-methoxy-2-methyl-indol-1-ylamine (550 mg, 3.1 mmol) in DMF (4 mL) is stirred at 50° C. for 15 min. The mixture is treated with DMTMM (856 mg, 3.1 mmol) and stirred at 50° C. for 1 h. The mixture is concentrated in vacuo, diluted with EtOAc (50 mL), and washed with saturated aqueous $Na_2CO_3$ (50 mL). The organic layer is separated, dried ($Na_2SO_4$), filtered and concentrated in vacuo. The residue is purified by silica gel chromatography eluting with 30% EtOAc in heptane to afford 2-(3-fluoro-phenyl)-4-methyl-pyrimidine-5-carboxylic acid (5-methoxy-2-methyl-indol-1-yl)-amide (180 mg, 15%, 2 steps). MS: 391 (M+H); $^1$H NMR (300 MHz, DMSO-$d_6$): δ 9.23 (s, 1H), 8.34 (d, 1H), 8.18 (d, 1H), 7.63 (m, 1H), 7.46 (m, 1H), 7.31 (d, 1H), 7.02 (d, 1H), 6.77 (m, 1H), 6.25 (s, 1H), 3.76 (s, 3H), 2.77 (s, 3H), 2.34 (s, 3H).

Example 190

2-(3-Fluoro-phenyl)-4-methyl-pyrimidine-5-carboxylic acid N',N'-diphenyl-hydrazide

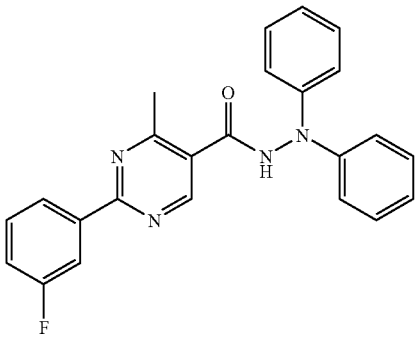

A solution of 2-(3-fluoro-phenyl)-4-methyl-pyrimidine-5-carboxylic acid (500 mg, 2.2 mmol) and N,N-diphenyl-hydrazine (422 mg, 2.2 mmol) in DMF (3 mL) is stirred at 50° C. for 15 min. The mixture is treated with DMTMM (633 mg, 2.2 mmol) and stirred at 50° C. for 3 h. The mixture is diluted with EtOAc (50 mL), and washed with saturated aqueous $Na_2CO_3$ (50 mL). The organic layer is separated, dried ($Na_2SO_4$), filtered and concentrated in vacuo. The residue is purified by silica gel chromatography eluting with 75% EtOAc in heptane to afford 2-(3-fluoro-phenyl)-4-methyl-pyrimidine-5-carboxylic acid N',N'-diphenyl-hydrazide (60 mg, 7%). MS: 399 (M+H); $^1$H NMR (300 MHz, DMSO-$d_6$): δ 9.04 (s, 1H), 8.30 (d, 1H), 8.15 (m, 1H), 7.61 (m, 1H), 7.44 (m, 1H), 7.35 (m, 4H), 7.22 (m, 4H), 7.04 (m, 2H), 2.64 (s, 3H). $IC_{50}$=16 nM.

Example 191

2-(3-Fluoro-phenyl)-4-methyl-pyrimidine-5-carboxylic acid (7-fluoro-3-methyl-indol-1-yl)-amide

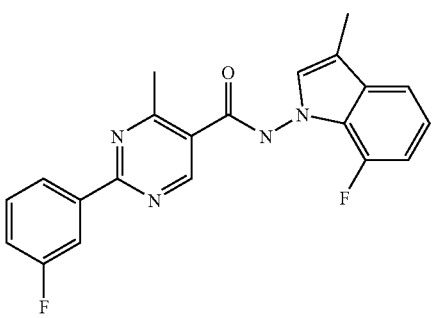

Step 1: A suspension of NaH (805 mg, 20.1 mmol, 60% in mineral oil) in DMF (5 mL) at 0° C. is treated with 7-fluoro-3-methylindole (200 mg, 1.34 mmol) and stirred at 0° C. for 1 h. The mixture is treated with HOSA (757 mg, 6.7 mmol) portion wise and warmed to rt over 2 h. The mixture is then poured over ice, and extracted with EtOAc (3×100 mL). The combined organic layer is dried ($Na_2SO_4$), filtered and concentrated in vacuo to afford 7-fluoro-3-methyl-indol-1-ylamine, which is used in the next step without further purification.

Step 2: A solution of 2-(3-fluoro-phenyl)-4-methyl-pyrimidine-5-carboxylic acid (1.34 mmol) and 7-fluoro-3-methyl-indol-1-ylamine (342 mg, 1.47 mmol) in DMF (15 mL) is stirred at 50° C. for 1 h. The mixture is treated with DMTMM (407 mg, 1.47 mmol) and stirred at 50° C. for 4 h. The mixture is concentrated in vacuo, diluted with $Et_2O$ (50 mL), and washed with saturated aqueous $Na_2CO_3$ (50 mL). The organic layer is separated, dried ($Na_2SO_4$), filtered and concentrated in vacuo. The residue is purified by silica gel chromatography eluting with 0%-100% DCM in EtOAc to afford 2-(3-fluoro-phenyl)-4-methyl-pyrimidine-5-carboxylic acid (7-fluoro-3-methyl-indol-1-yl)-amide (241 mg, 48%). MS: 379 (M+H); $^1$H NMR (300 MHz, DMSO-$d_6$): δ 9.05 (s, 1H), 8.32 (d, 1H), 8.18 (d, 1H), 7.64 (m, 1H), 7.45 (m, 1H), 7.40 (m, 1H), 7.31 (s, 1H), 7.05 (m, 2H), 2.74 (s, 3H), 2.29 (s, 3H).

Example 192

2-(3-Fluoro-phenyl)-4-methyl-pyrimidine-5-carboxylic acid (5-methanesulfonyl-3-methyl-indol-1-yl)-amide

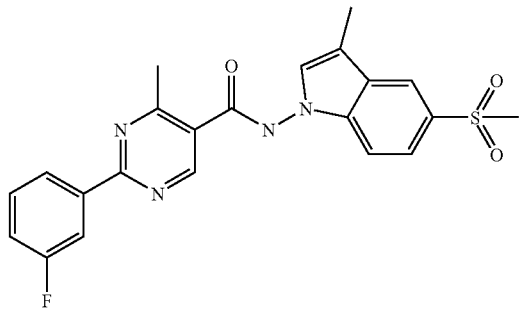

Step 1: A solution of allyl-(2-iodo-4-methanesulfonyl-phenyl)-amine (1.43 g, 4.1 mmol) in DMF (20 mL) is treated with n-$Bu_4$NCl (1.47 g, 5.32 mmol), Pd(OAc)$_2$ (56.6 mg, 0.2 mmol), and stirred at 100° C. for 1 h. HCl (5.3 mL, 3 M) is added, and the mixture is cooled to rt, filtered through a pad of Celite, and extracted with EtOAc (3×50 mL). The combined organic layer is dried ($Na_2SO_4$), filtered and concentrated in vacuo. The residue is purified by silica gel chromatography eluting with 60% EtOAc in heptane to afford 5-methanesulfonyl-3-methyl-1H-indole (370 mg, 43%).

Step 2: A suspension of NaH (1.06 g, 26.6 mmol, 60% in mineral oil) in DMF (15 mL) at 0° C. is treated with 5-methanesulfonyl-3-methyl-1H-indole (370 mg, 1.77 mmol) and stirred at 0° C. for 1 h. The mixture is treated with HOSA (1 g, 8.85 mmol) portion wise and warmed to rt overnight. The mixture is then poured over ice, and extracted with EtOAc (3×100 mL). The combined organic layer is dried ($Na_2SO_4$), filtered and concentrated in vacuo to afford 5-methanesulfonyl-3-methyl-indol-1-ylamine, which is used in the next step without further purification.

Step 3: A solution of 2-(3-fluoro-phenyl)-4-methyl-pyrimidine-5-carboxylic acid (1.77 mmol) and 5-methanesulfonyl-3-methyl-indol-1-ylamine (452 mg, 1.95 mmol) in DMF (15 mL) is stirred at rt for 1 h. The mixture is treated with DMTMM (538 mg, 1.95 mmol) and stirred at 60° C. for 1.5 h. The mixture is diluted with EtOAc (50 mL), and washed with saturated aqueous $Na_2CO_3$ (50 mL). The organic layer is separated, dried ($Na_2SO_4$), filtered and concentrated in vacuo. The residue is purified by silica gel chromatography eluting with 0%-100% EtOAc in heptane, and then by triturating in $Et_2O$ to afford 2-(3-fluoro-phenyl)-4-methyl-pyrimidine-5-carboxylic acid (5-methanesulfonyl-3-methyl-indol-1-yl)-amide (106 mg, 14%). MS: 439 (M+H); $^1$H NMR (300 MHz, DMSO-$d_6$): δ 9.15 (s, 1H), 8.37 (d, 1H), 8.24 (m, 2H), 7.82 (m, 1H), 7.59 (d, 1H), 7.54 (m, 1H), 7.34 (s, 1H), 7.29 (m, 1H), 3.13 (s, 3H), 2.83 (s, 3H), 2.42 (s, 3H).

Example 193

4-Methyl-2-pyridin-2-yl-pyrimidine-5-carboxylic acid (3-ethyl-pyrrolo[2,3-b]pyridin-1-yl)-amide trifluoroacetic acid salt

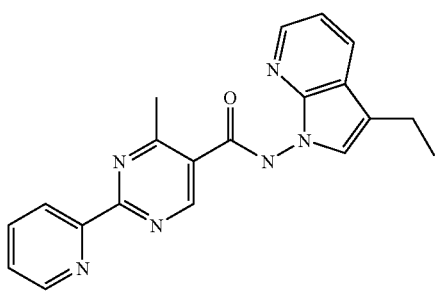

Step 1: (Ref.: J. Org. Chem. 2002, 67, 6226-6227) 7-Azaindole (5 g, 42.3 mmol) is added to a stirred suspension of $AlCl_3$ (22.6 g, 169 mmol) in DCM (300 mL). After stirring at rt for 1 h, acetyl chloride (13.3 g, 169 mmol) is added dropwise and the resulting mixture is stirred for 18 h. The mixture is cooled to 0° C., quenched with MeOH (150 mL) and stirred for 1 h. Silica gel is added to the mixture, the solvents are removed under vacuum, and the residue is purified by silica gel chromatography eluting with 10% MeOH in DCM to afford 1-(1H-pyrrolo[2,3-b]pyridin-3-yl)-ethanone (1.6 g). $^1$H NMR (300 MHz, $CH_3OD$): δ 8.93(d, 1H), 8.45(s, 2H), 7.50(t, 1H), 3.30(s, 3H).

Step 2: To a solution of 1-(1H-Pyrrolo[2,3-b]pyridin-3-yl)-ethanone (1.34 g, 8.38 mmol) in TFA (25 mL) is added triethylsilane (6.09 g, 52.4 mmol) and stirred at rt for 18 h. The mixture is concentrated, diluted with 2 N aqueous KOH solution and extracted three times with DCM. The combined organic layer is dried ($Na_2SO_4$), filtered and evaporated. The resulting residue is chromatographed through silica gel eluting with 10% MeOH in DCM to afford 3-ethyl-1H-pyrrolo[2,3-b]pyridine (0.91 g). MS: 147 (M+H); $^1$H NMR (300 MHz, $CDCl_3$): δ 9.23 (broad s, 1H), 8.32 (d, 1H), 7.94 (s, 1H), 7.05-7.14 (m, 2H), 2.80 (q, 2H), 1.35 (t, 3H).

Step 3: 3-Ethyl-1H-pyrrolo[2,3-b]pyridine (0.91 g, 6.2 mmol) and KOtBu (1.39 g, 12.4 mmol) are dissolved in DMF (28 mL) and stirred for 2 h at rt. While vigorously sparging with nitrogen, $NH_2Cl$ (92 ml 0.15 M in ether) is added in portions. The reaction mixture is stirred at rt for 2 h. The mixture is cooled 0° C. and then quenched with $Na_2S_2O_3$ (2.7 g) in water (50 mL). After standing at rt for 18 h, the mixture is concentrated, triturated in DCM and filtered. The filtrate is concentrated and chromatographed through silica gel eluting with 10% MeOH in DCM to afford 3-ethyl-pyrrolo[2,3-b]pyridin-1-yl-amine (380 mg). MS: 162 (M+H); $^1$H NMR (300 MHz, $CDCl_3$): δ 8.32 (d, 1H), 7.90 (d, 1H), 7.04-7.13(m, 2H), 4.96 (broad s, 2H), 2.76 (q, 2H), 1.33 (t, 3H).

Step 4. A mixture of 3-ethyl-pyrrolo[2,3-b]pyridin-1-ylamine (126 mg, 0.78 mmol), 4-methyl-2-pyridin-2-yl-pyrimidine-5-carboxylic acid (168 mg, 0.78 mmol), HATU (356 mg, 0.936 mmol) and DIPEA (302 mg, 2.34 mmol) in DMF (4 mL) is heated at 150° C. for 1 h. The reaction is quenched with water and extracted with EtOAC. The organic layer is dried ($Na_2SO_4$), filtered and concentrated. The residue is first chromatographed through silica gel eluting with 10% MeOH in DCM. The resulting product is chromatographed again using reverse phase HPLC eluting with 0.1% TFA in water and acetonitrile to afford 4-methyl-2-pyridin-2-yl-pyrimidine-5-carboxylic acid (3-ethyl-pyrrolo[2,3-b]pyridin-1-yl)-amide trifluoroacetic acid salt (29 mg). MS: 359 (M+H); $^1$H NMR (300 MHz, $CD_3OD$): δ 9.45 (s, 1H), 9.04 (d, 1H), 8.93 (d, 1H), 8.67 (t, 1H), 8.31 (d, 1H), 8.19-8.08 (m, 2H), 7.34 (s, 1H), 7.27 (dd, 1H), 2.96 (s, 3H), 2.85 (q, 2H), 1.39 (t, 3H).

Example 194

2-(3-Fluoro-phenyl)-4-methyl-pyrimidine-5-carboxylic acid (3-ethyl-pyrrolo[2,3-b]pyridin-1-yl)-amide

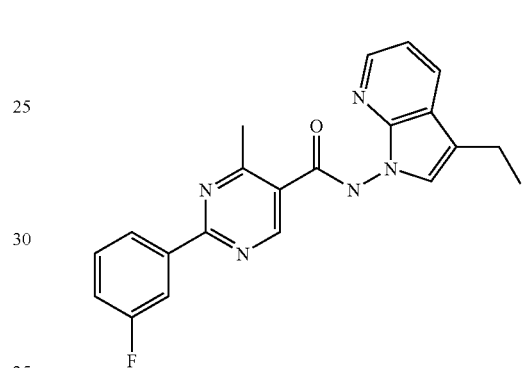

A mixture of 3-ethyl-pyrrolo[2,3-b]pyridin-1-ylamine (126 mg, 0.78 mmol), 2-(3-Fluoro-phenyl)-4-methyl-pyrimidine-5-carboxylic acid (180 mg, 0.78 mmol), HATU (356 mg, 0.036 mmol) and DIPEA (302 mg, 2.34 mmol) in DMF (4 mL) is heated at 150° C. for 1 h. The reaction is quenched with water and extracted with EtOAc. The organic layer is dried ($Na_2SO_4$), filtered and concentrated. The residue is chromatographed through silica gel eluting with 0-100% ethyl acetate in heptane to afford 2-(3-fluoro-phenyl)-4-methyl-pyrimidine-5-carboxylic acid (3-ethyl-pyrrolo[2,3-b]pyridin-1-yl)-amide (128 mg). MS: 376 (M+H); $^1$H NMR (300 MHz, DMSO-$d_6$): δ 9.10 (s, 1H), 8.25-8.33 (m, 2H), 8.16 (d, 1H), 8.05 (d, 1H), 7.62 (q, 1H), 7.39-7.48 (m, 2H), 7.16 (dd, 1H), 2.78 (s, 3H), 2.75 (q, 2H), 1.29(t, 3H).

Example 195

2-(3-Fluoro-phenyl)-4-methyl-pyrimidine-5-carboxylic acid (3-ethyl-pyrrolo[2,3c]pyridin-1-yl)-amide

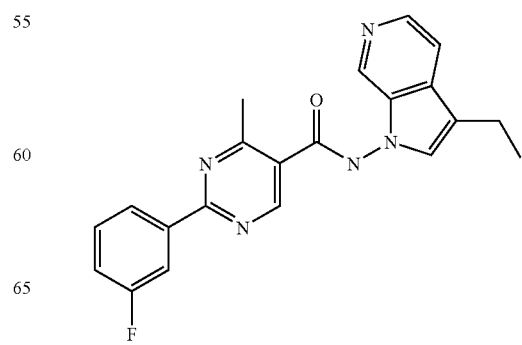

A mixture of 3-ethyl-pyrrolo[2,3-c]pyridin-1-ylamine (93 mg, 0.577 mmol), 2-(3-Fluoro-phenyl)-4-methyl-pyrimidine-5-carboxylic acid (134 mg, 0.757 mmol), HATU (263 mg, 0.692 mmol) and DIPEA (223 mg, 1.73 mmol) in DMF (3 mL) is heated at 150° C. for 1 h. The reaction is quenched with water and extracted with EtOAc. The organic layer is dried (Na$_2$SO$_4$), filtered and concentrated. The residue is purified by silica gel column chromatography eluting with 0-100% ethyl acetate in heptane to afford 2-(3-Fluoro-phenyl)-4-methyl-pyrimidine-5-carboxylic acid (3-ethyl-pyrrolo[2,3-c]pyridin-1-yl)-amide (86 mg). MS: 376 (M+H); $^1$H NMR (300 MHz, CD$_3$OD): δ 9.15 (s, 1H), 8.69 (s, 1H), 8.37 (d, 1H), 8.15-8.26 (m, 2H), 7.70 (d, 1H), 7.55 (q, 1H), 7.49 (s, 1H), 7.29 (t, 1H), 2.80-2.90 (m, 5H), 1.38 (t, 3H). IC$_{50}$=7 nM.

Example 196

4-Methyl-2-pyridin-2-yl-pyrimidine-5-carboxylic acid (3-ethyl-pyrrolo[2,3-c]pyridin-1-yl)-amide trifluoroacetic acid salt

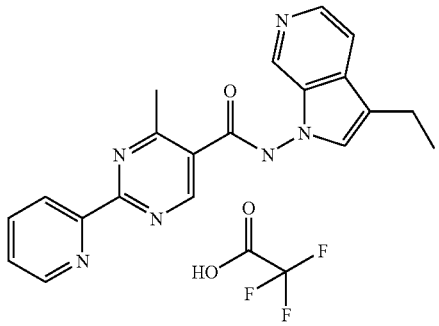

Step 1: (Ref.: J. Org. Chem. 2002, 67, 6226-6227) 6-Azaindole (2.5 g, 21.25 mmol) is added to a stirred suspension of AlCl$_3$ (11.3 g, 84.5 mmol) in CH$_2$Cl$_2$ (150 mL). After stirring at rt for 1 h, acetyl chloride (6.65 g, 84.5 mmol) is added dropwise and the resulting mixture is stirred for 18 h. The mixture is cooled to 0° C., quenched with MeOH (75 mL) and stirred for 1 h. Silica gel (40 mL), MeOH and DCM are added to the mixture, the solvents are removed under vacuum and the residue is purified by silica gel chromatography eluting with 10% MeOHl in DCM to afford 1-(1H-pyrrolo[2,3-c]pyridin-3-yl)-ethanone (1.52 g, 45%). MS: 161 (M+H); $^1$H NMR (300 MHz, CD$_3$OD): δ 9.20 (s, 1H), 8.95 (s, H), 7.82(d, 1H), 8.72 (d, 1H), 8.43 (d, 1-H), 2.64(s, 3H).

Step 2: To a solution of 1-(1H-pyrrolo[2,3-c]pyridin-3-yl)-ethanone (1.53 g, 9.55 mmol) in TFA (29 mL) triethylsilane (6.88 g, 59.21 mmol) is added and stirred at rt for 18 h. The mixture is concentrated and extracted with EtOAc. The organic layer is washed with 2 N aqueous KOH, dried (Na$_2$SO$_4$), filtered and evaporated. The residue is chromatographed through silica gel eluting with 10% MeOH in DCM to afford 3-ethyl-1H-pyrrolo[2,3-c]pyridine (1.35 g, 97%). MS: 147 (M+H); $^1$H NMR (300 MHz, CDCl$_3$): δ 13.3 (broad, N—H) 9.46 (s, 1H), 8.04 (s, 1H), 7.71-7.88 (m, 2H), 2.88 (q, 2H), 1.39 (t, 3H).

Step 3: 3-Ethyl-1H-pyrrolo[2,3-c]pyridine (1.21 g, 8.29 mmol) and KOtBu (1.86 g, 16.57 mmol) are dissolved in DMF (47 mL) and stirred for 2 h at rt. While vigorously purging with nitrogen, NH$_2$Cl (101 mL 0.15 M in ether) is added in portions. The reaction mixture is stirred at rt for 1 h. The mixture is then cooled to 0° C. and quenched with Na$_2$S$_2$O$_3$ (4.3 g) in water (80 mL). After standing at rt for 2 days, the layers are separated. Brine is added to the aqueous layer and then extracted with EtOAc. The organic layers are combined and dried (Na$_2$SO$_4$) to give a mixture of 3-ethyl-pyrrolo[2,3-c]pyridin-1-ylamine and starting material. This mixture is purified by chromatography through silica gel eluting with 10% MeOH in DCM to afford 3-ethyl-pyrrolo[2,3-c]pyridin-1-ylamine (93 mg). The remaining mixture of starting material and product is collected and dissolved in DCM. This solution is cooled to 0° C. and charged with BOC$_2$O (164 mg, 0.75 mmol). The resulting mixture is purified by silica gel chromatography eluting with 10% MeOH in DCM to afford additional 3-ethyl-pyrrolo[2,3-c]pyridin-1-ylamine (145 mg). $^1$H NMR (300 MHz, CDCl$_3$): δ 8.85 (s, 1H), 8.25 (d, 1H), 7.48 (d, 1H), 7.10 (s, 1H), 4.88 (s, 2H), 2.75 (q, 2H), 1.35(t, 3H).

Step 4. A mixture of 3-ethyl-pyrrolo[2,3-c]pyridin-1-ylamine (122 mg, 0.757 mmol), 4-methyl-2-pyridin-2-yl-pyrimidine-5-carboxylic acid (163 mg, 0.757 mmol), HATU (356 mg, 0.936 mmol) and DIPEA (294 mg, 2.27 mmol) in DMF (4 mL) is heated at 150° C. for 1 h. The reaction is quenched with water and the extracted with EtOAc. The organic layer is dried (Na$_2$SO$_4$), filtered and concentrated. The residue is chromatographed through silica gel eluting with 10% MeOH in DCM. The resulting product is chromatographed again using reverse phase HPLC eluting with 0.1% TFA in water and acetonitrile to afford 4-methyl-2-pyridin-2-yl-pyrimidine-5-carboxylic acid (3-ethyl-pyrrolo[2,3-c]pyridin-1-yl)-amide trifluoroacetic acid salt (42 mg, 9.5%). MS: 359 (M+H); $^1$H NMR (300 MHz, DMSO-d$^6$): δ 9.43 (s, 1H), 9.37 (s, 1H), 8.80 (d, 1H), 8.45 (t, 2H), 8.26 (s, 1H), 8.22 (d, 1H), 8.03 (t, 1H), 7.59 (t, 1H), 2.86 (q, 2H), 2.80 (s, 3H), 1.32 (t, 3H).

Example 197

2-(3-Fluoro-phenyl)-4-methyl-pyrimidine-5-carboxylic acid (3-methyl-pyrrolo [32-b]pyridin-1-yl)-amide

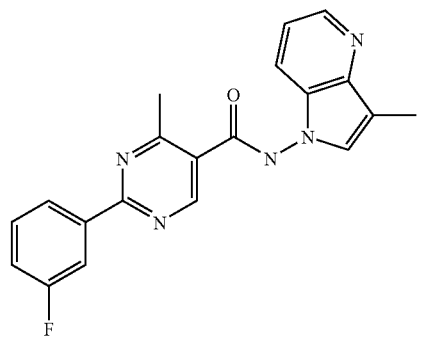

A mixture of 3-methyl-pyrrolo[3,2-b]pyridin-1-yl amine (75% pure) (240 mg, <1.63 mmol), 2-(3-fluoro-phenyl)-4-methyl-pyrimidine-5-carboxylic acid (379 mg, 1.63 mmol), HATU (744 mg, 1.96 mmol) and DIPEA (388 mg, 4.89 mmol) in DMF (5 mL) is heated at 150° C. for 1 h. The reaction is quenched with water, extracted with EtOAc. The organic layer is dried (Na$_2$SO$_4$), filtered and concentrated. The residue is chromatographed through silica gel eluting with 10% MeOH in DCM. The resulting product is recrystallized with ether to afford 2-(3-fluoro-phenyl)-4-methyl-pyrimidine-5-carboxylic acid (3-methyl-pyrrolo[3,2-b]pyridin-1-yl)-amide (197 mg, 44%). MS: 362 (M+H); $^1$H NMR (300 MHz, CD$_3$OD): δ 9.14 (s, 1H), 8.40 (d, 1H), 8.36 (d, 1H), 8.22

(d, 1H), 7.85(d, 1H), 7.55 (q 1H), 7.47 (s, 1H), 7.25-7.34 (m, 2H), 2.83 (s, 3H), 2.42(s, 3H). IC$_{50}$=2 nM.

Example 198

4-Methyl-2-pyridin-2-yl-pyrimidine-5-carboxylic acid (3-methyl-5-trifluoromethyl-indol-1-yl)-amide

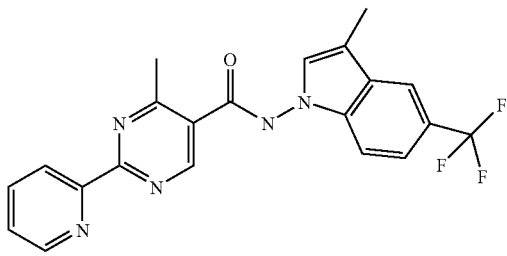

Step 1: To a mixture of 2-iodo-4-trifluoromethyl-aniline (5 g, 17.4 mmol), KOt-Bu (2.05 g, 18.3 mmol) and THF (200 mL) at −78° C., is added allyl bromide (2.21 g, 18.3 mmol). The resulting mixture is warmed to rt and stirred for 18 h. Water is added, and the mixture is extracted with EtOAc. The organic layer is separated, dried (Na$_2$SO$_4$), filtered and concentrated. The residue is chromatographed through silica gel eluting with 0-50% EtOAc in heptane to afford allyl-(2-iodo-4-trifluoromethyl-phenyl)-amine (1.9 g, 33%). MS 328 (M+H); $^1$H NMR (300 MHz, CDCl$_3$): δ 7.90 (s, 1H), 7.45 (d, 1 H), 5.88-6.02 (m, 1H), 5.33 (d, 1 H), 5.25 (d, 1H), 4.72 (broad s, 1H), 3.90 (s, 2H).

Step 2: A mixture of allyl-(2-iodo-4-trifluoromethyl-phenyl)-amine (1.75 g, 5.35 mmol), tetrabutylammonium chloride (1.68 g, 5.35 mmol), palladium acetate (120 mg, 0.54 mmol) and potassium carbonate (2.22 g, 16.0 mmol) in DMF (50 mL) is heated at 80° C. for 1.5 h. The reaction is quenched with water and extracted three times with DCM. The combined organic layer is dried (Na$_2$SO$_4$), filtered and concentrated. The residue is chromatographed through silica gel eluting with 0-40% EtOAc in heptane to afford 3-methyl-5-trifluoromethyl-1H-indole (401 mg). $^1$H NMR (300 MHz, CDCl$_3$): δ=8.09 (broad s, 1H), 7.90 (s, 1 H), 7.44 (s, 1H), 7.10 (s, 1H), 2.38 (s, 3H).

Step 3: 60% NaH (1.21 g, 30.2 mmol) is added to a stirred solution of 3-methyl-5-trifluoromethyl-1H-indole (400 mg, 2.01 mmol) in DMF (6 mL) at 0° C. in portions. The mixture is stirred at 0° C. for 1 h. HOSA (1.14 g, 10.0 mmol) is added in portions at 0° C. and the mixture is allowed to warm to rt over 2 h. The reaction is quenched with aqueous saturated ammonium chloride, extracted with extracted three times with DCM. The combined organic layer is dried (Na$_2$SO$_4$), filtered and concentrated. The residue is chromatographed through silica gel eluting with 0-40% EtOAc in heptane to afford 3-methyl-5-trifluoromethyl-indol-1-ylamine (223 mg, 52%). MS: 215 (M+H); $^1$H NMR (300 MHz, CDCl$_3$): δ=7.84 (s, 1H), 7.48 (s, 2H), 7.04 (s, 1H), 4.77 (s, 2H), 2.34 (s, 3H).

Step 4: A mixture of 3-methyl-5-trifluoromethyl-indol-1-ylamine (223 mg, 1.04 mmol), 4-methyl-2-pyridin-2-yl-pyrimidine-5-carboxylic acid (224 g, 1.04 mmol), HATU (475 mg, 1.25 mmol), DIPEA (404 mg 3.13 mmol) is stirred in DMF at 150° C. for 1 h. The reaction is quenched with water, extracted with extracted with EtOAc. The organic layer is dried (Na$_2$SO$_4$), filtered and concentrated. The residue is chromatographed through silica gel eluting with 10% MeOH in DCM to afford 4-methyl-2-pyridin-2-yl-pyrimidine-5-carboxylic acid (3-methyl-5-trifluoromethyl-indol-1-yl)-amide (122 mg, 28%). MS: 412 (M+H); $^1$H NMR (300 MHz, CD$_3$OD): δ 9.22 (s, 1H), 8.79 (d, 1H), 8.66 (d, 1H), 8.06 (t, 1H), 7.91 (s, 1H), 7.60 (dd, 1H), 7.51 (s, 2H), 7.29 (s, 3H), 2.88 (s, 3H), 2.40 (s, 3H).

Example 199

4-Methyl-2-pyridin-2-yl-pyrimidine-5-carboxylic acid (3-methyl-pyrrolo[3,2-b]pyridin-1-yl)-amide

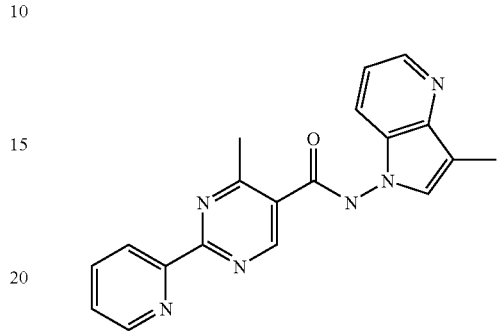

Step 1: To a solution of 3-amino-2-chloropyridine (5 g 38.9 mmol) in THF (35 mL) is added 2 M NaHMDS in THF (38.9 mL, 77.8 mmol). After stirring at rt for 15 min, BOC$_2$O (7.7 g, 35.6 mmol) in THF (20 mL) is added in one portion and then stirred for 5 h at rt. 0.1% aqueous HCl is added. The mixture is extracted with EtOAc. The organic layer is dried (Na$_2$SO$_4$), filtered and concentrated. The residue is chromatographed through silica gel eluting with 0-50% EtOAc in heptane to afford (2-chloro-pyridin-3-yl)-carbamic acid tert-butyl ester (7.18 g, 89%). MS: 229 (M+H); $^1$H NMR (300 MHz, CDCl$_3$): δ 8.52 (d, 1H), 8.05 (dd, 1H), 7.23 (dd, 1H), 7.02 (broad s, 1H), 1.55 (s, 9H)).

Step 2: A mixture of (2-chloro-pyridin-3-yl)-carbamic acid tert-butyl ester (7 g, 30.7 mmol), allyl bromide (5.26 g, 40.8 mmol) and cesium carbonate (20.8 g, 63.8 mmol) in DMF (280 mL) is heated at 60° C. for 1 h. The reaction is quenched with water, extracted with EtOAC. The organic layer is dried (Na$_2$SO$_4$), filtered and concentrated to afford allyl-(2-chloro-pyridin-3-yl)-carbamic acid tert-butyl ester (8.03 g, 98%), which is sued in the next step with no further purification.

Step 3: A mixture of allyl-(2-chloro-pyridin-3-yl)-carbamic acid tert-butyl ester (8.03 g, 30 mmol), tetrabutylammonium chloride (9.4 g, 30 mmol), palladium acetate (673 mg, 3 mmol) and potassium carbonate (12.4 g, 3 mmol) in DMF (300 mL) is heated at 80° C. for 1.5 h. The reaction is quenched with DCM and washed with water. The organic layer is dried (Na$_2$SO$_4$), filtered and concentrated. The residue is chromatographed through silica gel eluting with 0-40% EtOAc in heptane to afford 3-methyl-pyrrolo[3,2-b]pyridine-1-carboxylic acid tert-butyl ester and 3-methylene-2,3-dihydro-pyrrolo[3,2-b]pyridine-1-carboxylic acid tert-butyl ester (1.58 g).

Step 4: The above mixture is then stirred in DCM (10 mL) and TFA (10 mL) at rt for 3 h. The reaction is concentrated, and 2 M KOH aqueous solution and DCM are added. The precipitate is collected by filtration to afford 3-methyl-1H-pyrrolo[3,2-b]pyridine potassium salt (1 g, 20%). MS: 133 (M+H); $^1$H NMR (300 MHz, CD$_3$OD): δ 8.26(d, 1H), 7.75(d, 1H), 7.33(s, 1H), 7.12(dd, 1H), 2.36 (s, 3H).

Step 5: A mixture of 3-methyl-1H-pyrrolo[3,2-b]pyridine potassium salt (1 g, 5.88 mmol), KOtBu (660 mg, 5.88 mmol) in DMF (26 mL) is purged with N$_2$ and stirred at rt for 2 h. Chloramine in ether (0.15 M, 29 mL) is added and the mixture is stirred for 45 min. The reaction is cooled to 0° C., Na$_2$S$_2$O$_3$ (3.4 g) in water (70 mL) is added and the mixture is stirred for 15 min. The mixture is concentrated in vacuo. The residue is triturated with DCM and then filtered. The filtrate is washed with 2 M aqueous KOH, dried (Na₂SO₄), filtered and concentrated. The residue is chromatographed through silica gel eluting with 10% MeOH in DCM to afford a mixture of starting material and 3-methyl-pyrrolo[3,2-b]pyridin-1-yl amine (839 mg, ~64%, ~66 mol % pure), which is used in the next step without further purification.

Step 6: A mixture of 3-methyl-pyrrolo[3,2-b]pyridin-1-yl amine (839 mg, <5.71 mmol), 4-methyl-2-pyridin-2-yl-pyrimidine-5-carboxylic acid (1.32 g, 6.13 mmol), HATU (2.6 g, 6.85 mmol), DIPEA (2.21 g 17.1 mmol) in DMF (17 mL) is stirred at 150° C. for 1 h. The reaction is quenched with water and ether. The water layer is concentrated in vacuo. The residue is chromatographed through silica gel eluting with a mixture of DCM, MeOH and triethylamine (9.5:0.5:0.05) to afford 4-methyl-2-pyridin-2-yl-pyrimidine-5-carboxylic acid (3-methyl-pyrrolo[3,2-b]pyridin-1-yl)-amide (134 mg). MS: 345 345 (M+H); $^1$H NMR (300 MHz, CD₃OD): δ 9.22 (s, 1H), 8.79 (d, 1H), 8.64 (d, 1H), 8.40(d, 1H), 8.05 (t, 1H), 7.87 (d, 1H), 7.60 (t, 1H), 7.49 (s, 1H) 7.30 (dd, 1H), 2.87 (s, 3H), 2.42 (s, 3H).

Example 200

2-(3-Fluoro-phenyl)-4-methyl-pyrimidine-5-carboxylic acid (3-methyl-pyrrolo[2,3c]pyridin-1-yl)-amide

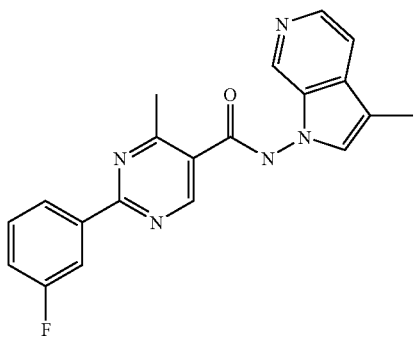

Step 1: 60% Sodium hydride (6.69 g, 167 mmol) is added to a stirred solution of 3-methyl-1H-pyrrolo[2,3-c]pyridine (1.47 g, 11.2 mmol) in DMF (33 mL) portion wise at 0° C. for 1 h. Hydroxylamine-O-sulfonic acid (6.3 g, 55.8 mmol) is added in portions at 0° C. and stirred for 2 h at 0° C. The reaction mixture is quenched at 0° C. with water, concentrated in vacuo to remove DMF. The residue is triturated in DCM. The solid is filtered off and the filtrate is concentrated in vacuo. The residue is purified by silica gel chromatography eluting with 10% MeOH in DCM to afford 3-methyl-pyrrolo[2,3-c]pyridin-1-ylamine (1 g, 61%). MS: 148 (M+H); $^1$H NMR (300 MHz, CDCl₃): δ 8.85 (s, 1H), 8.27 (d, 1H), 7.46 (d, 1H), 7.09 (s, 1H), 2.30 (s, 3H).

Step 2: A mixture of 3-methyl-pyrrolo[2,3-c]pyridin-1-ylamine (224 mg, 1.53 mmol), 2-(3-fluoro-phenyl)-4-methyl-pyrimidine-5-carboxylic acid (354 mg, 1.53 mmol), HATU (693 mg, 1.82 mmol) and DIPEA (593 mg, 4.59 mmol) in DMF (8 mL) is stirred at 150° C. for 1 h. The reaction is quenched with water, extracted with EtOAc. The organic layer is dried (Na₂SO₄), filtered and concentrated in vacuo. The residue is purified by silica gel chromatography eluting with 0-100% EtOAc in heptane to afford 2-(3-fluoro-phenyl)-4-methyl-pyrimidine-5-carboxylic acid (3-methyl-pyrrolo[2,3-c]pyridin-1-yl)-amide (55 mg). MS: 362 (M+H); $^1$H NMR (300 MHz, CD₃OD): δ 9.15 (s, 1H), 8.69 (s, 1H), 8.37 (d, 1H), 8.24 (s, 1H), 8.20 (d, 1H), 7.68 (d, 1H), 7.55 (q, 1H), 7.47 (s, 1H), 7.29 (t, 1H), 2.84(s, 3H), 2.39 (s, 3H).

Example 201

4-Methyl-2-pyridin-2-yl-pyrimidine-5-carboxylic acid (3-methyl-pyrrolo[2,3-c]pyridin-1-yl)-amide

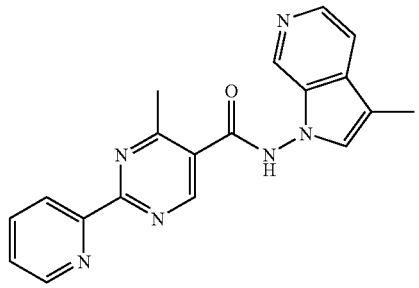

Step 1: To a solution of 3-amino-4-chloropyridine (6.56 g, 51 mmol) in THF (46 mL) is added 2 M NaHMDS in THF (50 mL, 100 mmol). After stirring at rt for 15 min BOC₂O (10.1 g, 46.4 mmol) in THF (26 mL) is added in one portion and the mixture is stirred for 3 h at rt. 0.1% aqueous HCl (590 mL) is added. The mixture is extracted with EtOAc. The organic layer is dried (Na₂SO₄), filtered and concentrated. The residue is purified by silica gel chromatography eluting with 0-50% EtOAc in heptane to afford (4-chloro-pyridin-3-yl)-carbamic acid tert-butyl ester (6.78 g, 76%). MS: 229 (M+H); $^1$H NMR (300 MHz, CDCl₃): δ 9.38 (ms 1H), 8.23 (d, 1H), 7.30 (dd, 1H), 6.85 (broad s, 1H), 1.57 (s, 9H).

Step 2: A mixture of (4-chloro-pyridin-3-yl)-carbamic acid tert-butyl ester (6.78 g, 29.7 mmol), allyl bromide (5.1 g, 40.8 mmol) and cesium carbonate (20.1 g, 61.8 mmol) in DMF (200 mL) is heated at 60° C. for 1 h. The reaction is quenched with water, extracted with EtOAc. The organic layer is dried (Na₂SO₄), filtered and concentrated. The residue is purified by silica gel column chromatography eluting with 0-40% EtOAc in heptane to afford allyl-(4-chloro-pyridin-3-yl)-carbamic acid tert-butyl ester (5.66 g, 71%). MS: 269 (M+H); $^1$H NMR (300 MHz, CDCl₃): δ 8.42(d, 1H), 7.40 (d, 1H), 5.80-5.98 (m, 1H), 4.35-4.51 (m, 1H), 3.90-4.07 (m, 1H).

Step 3: A mixture of allyl-(4-chloro-pyridin-3-yl)-carbamic acid tert-butyl ester (7.68 g, 28.7 mmol), tetrabutylammonium chloride (9.0 g, 28.7 mmol), palladium acetate (643 mg, 2.87 mmol) and potassium carbonate (11.9 g, 86.0 mmol) in DMF (200 mL) is heated at 80° C. for 1.5 h. The reaction mixture is diluted with DCM and washed three times with water. The organic layer is dried (Na₂SO₄), filtered and concentrated. The residue is purified by silica gel column chromatography eluting with 0-40% EtOAc in heptane to afford a mixture of 3-methyl-pyrrolo[2,3-c]pyridine-1-carboxylic acid tert-butyl ester and 3-methylene-2,3-dihydro-pyrrolo[2,3-c]pyridine-1-carboxylic acid tert-butyl ester (3.1 g total).

Step 4: The above mixture is stirred in DCM (10 mL) and TFA (10 mL) at rt for 18 h and then concentrated in vacuo. 2 M aqueous KOH is added. The mixture is extracted with EtOAC. The organic layer is dried (Na₂SO₄), filtered and concentrated. The residue is purified by silica gel column chromatography eluting with 10% MeOH in DCM to afford 3-methyl-1H-pyrrolo[2,3-c]pyridine (1.98 g, 69%). MS: 133 (M+H); $^1$H NMR (300 MHz, CDCl₃): δ 9.10 (broad s, 1H), 8.79 (s, 1H), 8.28 (d, 1H), 7.52 (d, 1H), 7.20 (s, 1H) 2.36 (s, 2H).

Step 5: A mixture of 3-methyl-1H-pyrrolo[2,3-c]pyridine (1.21 g, 9.16 mmol), KOtBu (2.05 g, 18.3 mmol) in DMF (41 mL) is purged with $N_2$ and stirred at rt for 2 h. Chloramine in ether (0.15 M, 92 mL) is added and the mixture is stirred for 20 min. The reaction is cooled to 0° C. and a solution of $Na_2S_2O_3$ (5 g) in water (80 mL) is added. The mixture is stirred for 10 min, and then concentrated in vacuo. The residue is triturated in DCM and filtered. DCM is added, cooled to 0° C. and charged with $BOC_2O$ (541 mg, 2.48 mmol). The resulting mixture is separated by silica gel chromatography eluting with 10% MeOH in DCM to afford 3-methyl-pyrrolo[2,3-c]pyridin-1-yl amine (468 mg, 35%). MS: 148 (M+H); $^1$H NMR (300 MHz, $CDCl_3$): δ 8.85 (s, 1H), 8.27 (d, 1H), 7.46 (d, 1H), 7.09 (s, 1H), 2.30 (s, 3H).

Step 6: A mixture of 3-methyl-pyrrolo[2,3-c]pyridin-1-yl amine (467 mg, 3.18 mmol), 4-methyl-2-pyridin-2-yl-pyrimidine-5-carboxylic acid (683 g, 3.18 mmol), HATU (1.45 g, 3.81 mmol), DIPEA (1.23 g 9.54 mmol) in DMF (10 mL) is stirred at 150° C. for 1 h. The reaction is quenched with water, and $NaHCO_3$ (320 mg, 3.81 mmol) and EtOAC are added. The resulting solid is collected by filtration and then triturated with hot water. The mixture is filtered again and the solid is dried under vacuum to afford 4-methyl-2-pyridin-2-yl-pyrimidine-5-carboxylic acid (3-methyl-pyrrolo[2,3-c]pyridin-1-yl)-amide (484 mg). MS: 345 (M+H); $^1$H NMR (300 MHz, $CD_3OD$): δ 9.24 (s, 1H), 8.79 (d, 2H), 8.65 (d, 1H), 8.21 (d, 1H), 8.05 (t, 1H), 7.72 (d, 1H), 7.60 (s, 1H), 7.57 (s, 1H), 2.88 (s, 3H), 2.40 (s, 3H).

Example 202

4-Methyl-2-pyridin-2-yl-pyrimidine-5-carboxylic acid (3-methyl-pyrrolo [3,2-c]pyridin-1-yl)-amide

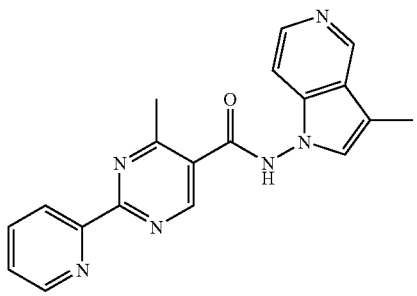

Step 1: To a solution of 4-amino-3-chloropyridine (15 g, 116.7 mmol) in THF (60 mL) is added NaHMDS in THF (1 M, 233. mL, 233 mmol). After stirring at rt for 30 min, $BOC_{20}$ (23.2 g, 106 mmol) in THF (45 mL) is added in one portion and the mixture is stirred for 3 h at rt. Additional $BOC_2O$ (2 g, 9.0 mmol) in THF (40 mL) is added and the reaction is stirred for 18 h at rt. 0.1% aqueous HCl (1.35 L) is added. The mixture is extracted with EtOAc. The organic layer is dried ($Na_2SO_4$), filtered and concentrated. The residue is recrystallized from ether to afford (3-chloro-pyridin-4-yl)-carbamic acid tert-butyl ester (4 g). The mother liquor is purified by silica gel column chromatography eluting with 0-50% EtOAc in heptane. The collected product is crystallized from ether to afford additional 4.5 g of (3-chloro-pyridin-4-yl)-carbamic acid tert-butyl ester (total yield 8.5 g). MS: 229 (M+H); $^1$H NMR (300 MHz, $CDCl_3$): δ 8.48 (s, 1H), 8.38 (d, 1H), 8.17 (d, 1H), 7.18 (broad s, 1H) 1.57 (s, 9H).

Step 2: A mixture of (3-chloro-pyridin-3-yl)-carbamic acid tert-butyl ester (8.4 g, 36.8 mmol), allyl bromide (7.46 g, 39.1 mmol) and cesium carbonate (24.9 g, 76.4 mmol) in DMF (100 mL) is heated at 60° C. for 1 h. The reaction is quenched with water, extracted with EtOAc. The organic layer is dried ($Na_2SO_4$), filtered, and concentrated in vacuo. The residue is purified by silica gel chromatography eluting with 0-40% EtOAc in heptane to afford allyl-(3-chloro-pyridin-3-yl)-carbamic acid tert-butyl ester (8.4 g, 85%). MS: 269 (M+H); $^1$H NMR (300 MHz, $CDCl_3$): δ=8.66 (s, 1H), 8.49 (d, 1H), 7.18 (d, 1H), 5.80-5.96 (m, 1H) 5.15 (s, 1H), 5.10(d, 1H), 4.2 (broad s, 1H), 1.43 (s, 9H).

Step 3: A mixture of allyl-(3-chloro-pyridin-4-yl)-carbamic acid tert-butyl ester (8.25 g, 30.8 mmol), tetrabutylammonium chloride (9.67 g, 30.8 mmol), palladium acetate (691 mg, 3.08 mmol) and potassium carbonate (12.8 g, 92.3 mmol) in DMF (100 mL) is heated at 80° C. for 1.5 h. The reaction is diluted with DCM and washed three times with water. The organic layer is dried ($Na_2SO_4$), filtered and concentrated. The residue is chromatographed through silica gel eluting with 0-40% EtOAc in heptane to afford a mixture 3-methyl-pyrrolo [3,2-c]pyridine-1-carboxylic acid tert-butyl ester and 3-methylene-2,3-dihydro-pyrrolo[3,2-c]pyridine-1-carboxylic acid tert-butyl ester (4.21 g, total).

Step 4: The mixture from step 3 is stirred in DCM (10 mL) and TFA (10 mL) at rt for 18 h.

The reaction is concentrated. 2 M aqueous KOH solution is added, and the mixture is extracted with EtOAc. The organic layer is dried ($Na_2SO_4$), filtered and concentrated. The residue is chromatographed through silica gel eluting with 10% MeOH in DCM to afford of 3-methyl-1H-pyrrolo[3,2-c]pyridine (1.91 g, 47%). MS: 133 (M+H); $^1$H NMR (300 MHz, $CDCl_3$): δ 8.89 (s, 1H), 8.24 (d, 1H), 7.37 (d, 1H), 7.11 (s, 1H) 2.40 (s, 3H).

Step 5: A mixture of 3-methyl-1H-pyrrolo[3,2-c]pyridine (1.91 g, 14.47 mmol) and KOtBu (3.25 g, 28.9 mmol) in DMF (65 mL) is purged with $N_2$ and stirred at rt for 2 h. Chloramine in ether (0.15 M, 145 mL) is added and the mixture is stirred for 20 min. The reaction is cooled to 0° C. and a solution of $Na_2S_2O_3$ (800 mg) in water (130 mL) is added. The mixture is stirred for 10 min at 0° C., and then concentrated in vacuo. The residue is triturated in DCM and filtered. DCM is added to the filtrate, cooled to 0° C. and treated with $BOC_2O$ (793 mg, 3.6 mmol). The mixture is concentrated in vacuo, and the residue is purified by silica gel chromatography eluting with 10% MeOH in DCM to afford 3-methyl-pyrrolo [3,2-c]pyridin-1-yl amine (842 mg, 35%). MS: 148 (M+H); $^1$H NMR (300 MHz, $CDCl_3$): δ 8.85 (s, 1H), 8.36 (d, 1H), 7.32 (d, 1H), 6.95 (s, 1H) 4.77 (s, 2H), 2.37 (s, 3H).

Step 6: A mixture of 3-methyl-pyrrolo[3,2-c]pyridin-1-yl amine (223 mg, 1.52 mmol), 4-methyl-2-pyridin-2-yl-pyrimidine-5-carboxylic acid (329 mg, 1.52 mmol), HATU (693 mg, 1.82 mmol) and DIPEA (593 mg, 4.59 mmol) in DMF (8 mL) is stirred at 150° C. for 1 h. The reaction is quenched with water and $NaHCO_3$ (168 mg, 2 mmol). The mixture is concentrated in vacuo. The residue is purified by silica gel chromatography eluting with 10% meOH in DCM to afford 4-methyl-2-pyridin-2-yl-pyrimidine-5-carboxylic acid (3-methyl-pyrrolo[3,2-c]pyridin-1-yl)-amide (91 mg, 17%). MS: 345 (M+H); $^1$H NMR (300 MHz, DMSO-$d_6$): δ=9.34 (s, 2H), 8.79 (d, 1H), 8.53 (d, 1H), 8.45 (d, 1H), 8.13 (d, 1H), 8.02 (t, 1H), 7.86 (s, 1H), 7.59 (t, 1H), 2.77 (s, 3H), 2.43 (s, 3H).

Example 203

2-(3-Fluoro-phenyl)-4-methyl-pyrimidine-5-carboxylic acid (3-methyl-pyrrolo [3,2-c]pyridin-1-yl)-amide

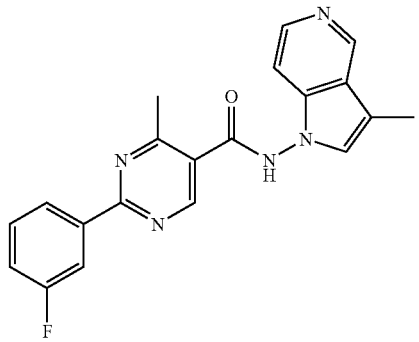

A mixture of 3-methyl-pyrrolo[3,2-c]pyridin-1-ylamine (224 mg, 1.52 mmol), 2-(3-fluoro-phenyl)-4-methyl-pyrimidine-5-carboxylic acid (354 mg, 1.52 mmol), HATU (693 mg, 1.82 mmol) and DIPEA (593 mg, 4.59 mmol) in DMF (8 mL) is heated at 150° C. for 1 h. The reaction is quenched with water, NaHCO$_3$ (168 mg, 2 mmol) is added and the mixture is extracted with EtOAc. The organic layer is separated, dried (Na$_2$SO$_4$), filtered and concentrated. The residue is first purified by silica gel column chromatography eluting with 10% MeOH in DCM and then recrystallized from EtOAc to afford 2-(3-fluoro-phenyl)-4-methyl-pyrimidine-5-carboxylic acid (3-methyl-pyrrolo[3,2-c]pyridin-1-yl)-amide (198 mg). MS: 362 (M+H); $^1$H NMR (300 MHz, CD$_3$OD): δ 9.12 (s, 1H), 8.86 (s, 1H), 8.35 (d, 1H), 8.15-8.31 (m, 2H), 7.47-7.60 (m, 2H), 7.35 (s, 1H), 7.29 (t, 1H), 2.84 (s, 3H), 2.44 (s, 3H).

Example 204

2-(3-Fluoro-phenyl)-4-methyl-pyrimidine-5-carboxylic acid (5-nitro-indol-1-yl)-amide

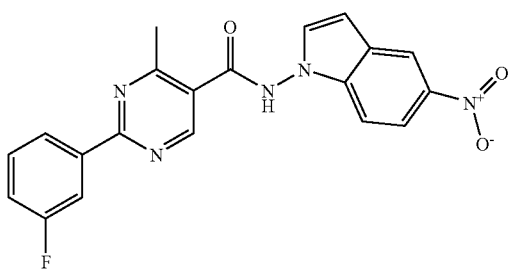

Step 1: NaH (60%, 421.5 mmol) is added portion-wise to a solution of 5-nitro-1H-indole (28.1 mmol) in anhydrous DMF (80 mL) at 0° C. and the mixture is stirred at 0° C. under N$_2$ for 10 min. HOSA (140.5 mmol) is added portion-wise for 30 minutes and the mixture is stirred at 0° C. for 2 h. The reaction is quenched with water. Additional water (250 mL) is added and the mixture is extracted with EtOAc (3×100 mL). The combined organic layer is washed with water (2×30 mL), brine (30 mL), dried (Na$_2$SO$_4$), filtered and concentrated. The residue is washed with heptane (2×20 mL) and recrystallized from EtOAc to afford 5-nitro-indole-1-ylamine (4.84 g, 97%) as a solid. MS: 178 (M+H); $^1$H NMR (300 MHz, CDCl$_3$): δ 4.93(br, 2N—H), 6.62(d, H), 7.30(d, H), 7.52(d, H), 8.17(d, H), 8.58 (s, H).

Step 2: DIPEA (12.65 mmol) is added a solution of 2-(3-fluoro-phenyl)-4-methyl-pyrimidine-5-carboxylic acid (4.22 mmol), 5-nitro-indole-1-ylamine (4.22 mmol) and HOTT (S-(1-oxido-2-pyridyl)-thio-N,N,N',N'-tetramethyluronium hexafluorophosphate) (7.6 mmol) in anhydrous DMF (15 mL) and the mixture is heated at 80-90° C. overnight. After evaporation of solvent, the residue is dissolved in EtOAc (150 mL), washed with water (20 mL), 5% sodium sulfate (20 mL), water (mL) and brine (20 mL). The organic layer is dried (Na$_2$SO$_4$), filtered and concentrated. The residue is kept at rt overnight to yield 4-methyl-2-(3-fluoro-phenyl)-pyrimidine-5-carboxylic acid (5-nitro-indol-1-yl)-amide (730 mg, 44%) as a solid. MS: 392 (M+H); $^1$H NMR (300 MHz, DMSO-d$^6$): δ 2.78(s, 3H), 6.88(d, H), 7.38-7.53(m, H), 7.57-7.76(m, 2H), 7.81(d, H), 8.06-8.32(m, 2H), 8.34(d, H), 8.65(d, H), 9.27(s, 2H).

Example 205

2-(3-fluoro-phenyl)-4-methyl-pyrimidine-5-carboxylic acid (5-amino-indol-1-yl)-amide

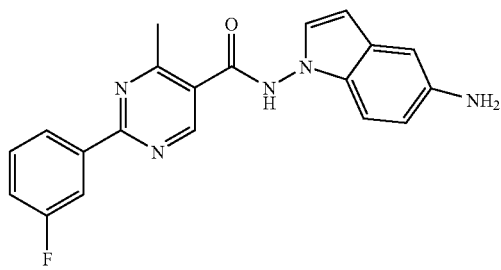

A solution of 4-methyl-2-(3-fluoro-phenyl)-pyrimidine-5-carboxylic acid (5-nitro-indol-1-yl)-amide (1.64 mmol) in MeOH (45 mL) and 10% Pd/C (0.16 mmol) is hydrogenated in a 500 mL Parr bottle under 50 psi at rt overnight. Pd/C is filtered off. The filtrate is concentrated to afford 2-(3-fluoro-phenyl)-4-methyl-pyrimidine-5-carboxylic acid (5-amino-indol-1-yl)-amide (545 mg, 92%) as a solid. MS: 362 (M+H); $^1$H NMR (300 MHz, CD$_3$OD): δ 3.84(s, H), 6.37(d, H), 6.81(dd, H), 7.01(d, H), 7.16-7.36(m, 3H), 7.55(m, H), 8.23 (d, H), 8.36(d, H), 9.50(s, H).

Example 206

2-(3-fluoro-phenyl)-4-methyl-pyrimidine-5-carboxylic acid [5-(dimethanesulfonyl)-amino-indol-1-yl]-amide A mixture of 2-(3-fluoro-phenyl)-4-methyl-pyrimidine-5-carboxylic acid (5-amino-indol-1-yl)-amide (0.43 mmol) and methanesulfonyl chloride (0.52 mmol) in anhydrous DCM (10 mL) is stirred at 0° C. and triethylamine (1.29 mmol) is added. The reaction mixture is stirred at 0° C. for 1 h, and then warmed to rt and stirred for 30 minutes. DCM is added (20 mL), and the mixture is washed with 4% HCl (15 mL), water (10 mL) and brine (15 mL). The organic layer is dried (Na$_2$SO$_4$), filtered and concentrated. The residue is purified by chromatography using silica gel eluting with 0-60% EtOAC in DCM to afford 2-(3-fluoro-phenyl)-4-methyl-pyrimidine-5-carboxylic acid [5-(dimethanesulfonyl)-amino-indol-1-yl]-amide (85 mg, 38%) as a solid. MS: 518 (M+H);

¹H NMR (300 MHz, CDCl₃): δ 2.75(s, 3H), 2.90(s, 3H), 3.66(s, 3H), 6.51(s, H), 7.04-7.53(m, 6H), 8.03(d, H), 8.12(d, H), 8.60(s, H).

Example 207

2-(3-Fluoro-phenyl)-4-methyl-pyrimidine-5-carboxylic acid (5-benzoylamino-indol-1-yl)-amide

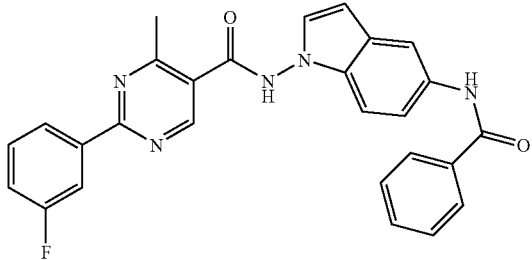

A solution of benzoyl chloride (0.85 mmol) in anhydrous DCM (2 mL) is added drop-wise to a solution of 4-methyl-2-(3-fluoro-phenyl)-pyrimidine-5-carboxylic acid (5-amino-indol-1-yl)-amide (0.47 mmol) and triethylamine (1.41 mmol) in anhydrous DCM (16 mL) and the mixture is stirred at rt overnight. The reaction mixture is concentrated in vacuo. The residue is dissolved in EtOAc (25 mL), and washed with water (2×20 mL) and brine (10 mL). The organic layer is dried (Na₂SO₄), filtered and concentrated. The residue is triturated with EtOAc to afford 2-(3-fluoro-phenyl)-4-methyl-pyrimidine-5-carboxylic acid (5-benzoylamino-indol-1-yl)-amide (95 mg, 43%) as a solid. MS: 466 (M+H); ¹H NMR (300 MHz, DMSO-d⁶): δ 2.99(s, 3H), 6.72(d, H), 7.38-7.48(m, H), 7.48-7.80(m, 6H), 7.83-8.016(m, 3H), 8.07-8.20(m, H), 8.23-8.35(m, 2H), 9.24(s, H), 10.25(br, H).

Example 208

4-Methyl-2-pyridin-2-yl-pyrimidine-5-carboxylic acid [5-fluoro-3-(1,2,3,6-tetrahydro-pyridin-4-yl)-indol-1-yl]-amide dichlorochloride

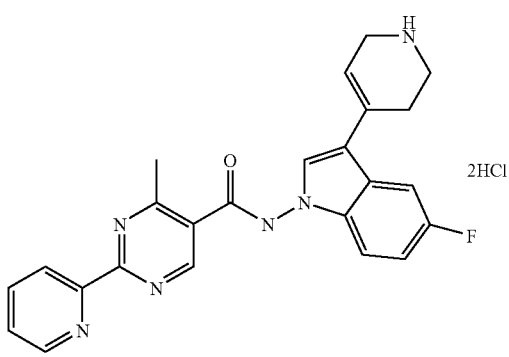

Step 1: A mixture of 5-fluoroindole (6.65 g, 49.2 mmol) and 4-piperidone hydrate hydrochloride (18.9 g, 123 mmol) in methanol solution of 2 N KOH (90 mL) is refluxed for 6 h. After cooling to rt, water (150 mL) is added and stirred at rt for 30 minutes. The resulting precipitate is filtered, washed with water (10 mL) and ether (15 mL), and dried in vacuo to afford 5-fluoro-3-(1,2,3,6-tetrahydropyridin-4-yl)-indole (6.34 g, 60%). MS: 217 (M+H); ¹H NMR (300 MHz, CDCl₃): δ 8.40 (br, H), 7.57 (dd, H), 7.24-7.37 (m, H), 7.23 (s, H), 6.98 (t, H), 6.20 (s, H), 3.62 (m, 2H), 3.16 (m, 2H), 2.50 (s, 2H).

Step 2: A solution of di-tert-butyl dicarbonate (504 mg, 2.31 mmol) in DCM (10 mL) is added to a stirred solution of 5-fluoro-3-(1,2,3,6-tetrahydropyridin-4-yl)-indole (500 mg, 2.31 mmol) in DCM (20 mL) at rt and stirred at rt overnight. The reaction mixture is concentrated in vacuo to afford 4-(5-Fluoro-1H-indol-3-yl)-3,6-dihydro-2H-pyridine-1-carboxylic acid tert-butyl ester (730 mg). MS: 317 (M+H); ¹H NMR (300 MHz, CDCl₃): δ 8.17 (br, H), 7.56 (d, H), 7.31 (m, H), 7.26 (s, H), 6.99 (t, H), 6.13 (s, H), 4.17(m, 2H), 3.70 (m, 2H), 2.57 (s, 2H), 1.54 (s, 9H).

Step 3: A solution of 4-(5-fluoro-1H-indol-3-yl)-3,6-dihydro-2H-pyridine-1-carboxylic acid tert-butyl ester (730 mg, 2.31 mmol) in anhydrous DMF is added slowly to a stirred solution of 60% NaH (1108 mg, 27.72 mmol) in anhydrous DMF (20 mL) at 0° C. under N₂ and stirred at rt for an hour. HOSA (1305 mg, 11.55 mmol) is added portion-wise at 0° C., stirred at 0° C. for 5 hours, poured into ice/water (350 mL) and extracted with ether (3×35 mL). The combined organic extract is washed with water (2×20 mL) and brine (20 mL), dried (Na₂SO₄), filtered and concentrated in vacuo. The residue is washed with heptane (3×5 mL) to afford 4-(1-Amino-5-fluoro-1H-indol-3-yl)-3,6-dihydro-2H-pyridine-1-carboxylic acid tert-butyl ester (715 mg, 94%) as a solid. MS: 332 (M+H); ¹H NMR (300 MHz, CDCl₃): δ 7.52 (d, H), 7.36 (m, H), 7.20 (s, H), 7.04 (t, H), 6.06 (s, H), 4.78 (s, 2H), 4.15(m, 2H), 3.69 (t, 2H), 2.54 (s, 2H), 1.55 (s, 9H).

Step 4: Triethylamine (2.6 mmol) is added to a stirred solution of 4-methyl-2-pyridin-2-yl-pyrimidine-5-carboxylic acid (1.30 mmol) and iso-butyl chloroformate (1.95 mmol) in anhydrous DCM (20 mL) at rt under N₂ and stirred at rt for 2 h. The reaction mixture is concentrated in vacuo. The residue is dried in vacuo and THF (30 mL) is added. The mixture is filtered and the filtrate is concentrated to afford iso-butyl-[1-(4-methyl-2-pyridin-2-yl-pyrimidin-5-yl)]-carbonate (350 mg, 85%).

Step 5: Sodium bis(trimethylsilyl)amide (2 N) in THF (0.83 mL) is added to a stirred solution of 4-(1-amino-5-fluoro-1H-indol-3-yl)-3,6-dihydro-2H-pyridine-1-carboxylic acid tert-butyl ester (367 mg, 1.11 mmol) in anhydrous DMF (20 mL) at rt under N₂, then stirred at rt for 15 min. A solution of iso-butyl-[1-(4-methyl-2-pyridin-2-yl-pyrimidin-5-yl]]-carbonate (350 mg, 1.11 mmol) in anhydrous DMF (5 mL) is added slowly at rt and stirred at 60° C. for 18 hours under N₂. DMF is evaporated off. The residue is dissolved in EtOAc (60 mL), washed with water (3×20 mL) and brine (20 mL), dried (Na₂SO₄), filtered and concentrated in vacuo. The residue is purified by silica gel chromatography eluting with 0-20% MeOH in DCM to afford 4-[5-fluoro-1-[(4-methyl-2-pyridin-2-yl-pyrimidine-5-carbonyl)-amino]-1H-indol-3-yl]-3,6-dihydro-2H-pyridine-1-carboxylic acid tert-butyl ester (158 mg, 28%).

Step 6: A solution of 4-{5-fluoro-1-[(4-methyl-2-pyridin-2-yl-pyrimidine-5-carbonyl)-amino]-1H-indol-3-yl}-3,6-dihydro-2H-pyridine-1-carboxylic acid tert-butyl ester (158 mg) in DCM (15 ml) is bubbled with HCl gas for 10 min at rt, then stirred at rt for 18 h. DCM is evaporated off and the residue is triturated with MeOH (2 mL). The solid is collected by filtration and dried to afford 4-methyl-2-pyridin-2-yl-pyrimidine-5-carboxylic acid [5-fluoro-3-(1,2,3,6-tetrahydro-pyridin-4-yl)-indol-1-yl]-amide dichlorochloride (81 mg, 54%). MS: 429 (M+H); ¹H NMR (300 MHz, CD₃OD): δ=2.89(m, 2H), 2.96(s, 3H), 3.53(t, 2H), 3.94(m, H), 6.27(s, H), 7.12(t, H), 7.46(q, H), 7.59-7.71(m, H), 8.28 (t, H), 8.85 (t, H), 8.99(d, H), 9.15(d, H), 9.41 (s, H).

Example 209

2-Pyridin-2-yl-4-trifluoromethyl-pyrimidine-5-carboxylic acid (5-fluoro-3-methyl-indol-1-yl)-amide

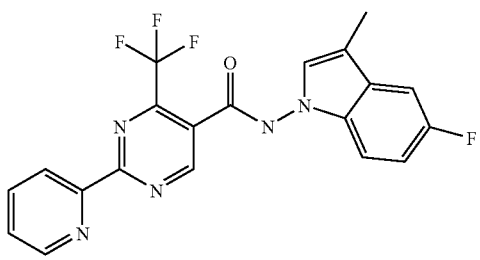

A solution of 2-pyridin-2-yl-4-trifluoromethyl-pyrimidine-5-carboxylic acid (219 mg, 0.81 mmol), 5-fluoro-3-methyl-indol-1-ylamine (0.98 mmol), DIPEA (158 mg, 1.23 mmol) and HATU (1.06 mmol) in anhydrous DMF (8 mL) is stirred at 80° C. overnight. The reaction mixture is diluted with EtOAc (40 mL) and washed with water (4×20 mL) and brine (20 mL).

The organic layer is dried ($Na_2SO_4$), filtered and concentrated in vacuo. The residue is purified by silica gel chromatography eluting with 1%-50% EtOAc in DCM. The collected product is recrystallized from DCM to afford 2-pyridin-2-yl-4-trifluoromethyl-pyrimidine-5-carboxylic acid (5-fluoro-3-methyl-indol-1-yl)-amide (105 mg, 31%) as a solid. MS: 416 (M+H); $^1$H NMR (300 MHz, $CD_3OD$): δ=2.32(s, 3H), 7.04 (t, H), 7.16(s, H), 7.25(dd, H), 7.34(q, H), 7.67(dd, H), 8.11 (t, H), 8.70 (d, H), 8.82(d, H), 9.57(s, H). $IC_{50}$=8 nM.

Example 210

2-(3-Fluoro-phenyl)-4-methyl-pyrimidine-5-carboxylic acid (2-methyl-indol-1-yl)-amide

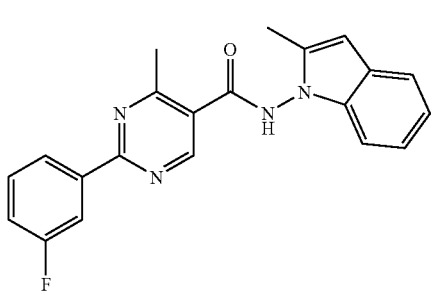

A mixture of 2-(3-fluoro-phenyl)-4-methyl-pyrimidine-5-carboxylic acid (2-methyl-2,3-dihydro-indol-1-yl)-amide (246 mg, 0.68 mmol) and $MnO_2$ (296 mg, 3.4 mmol) in DCM (10 mL) is stirred at rt for 1.5 h. The reaction mixture is filtered and the filtrate is concentrated in vacuo. The residue is triturated with ether to afford 2-(3-fluoro-phenyl)-4-methyl-pyrimidine-5-carboxylic acid (2-methyl-indol-1-yl)-amide (158, 65%). MS: 361 (M+H); $^1$H NMR (300 MHz, $CDCl_3$): δ 2.39 (s, 3H), 2.83 (s, 3H), 6.36 (s, H), 7.10-7.29 (m, 3H), 7.44-7.62 (m, H), 8.17 (s, H), 8.25 (d, H), 8.35 (d, H), 8.97 (s, H).

Example 211

2-(3-Fluoro-phenyl)-pyrimidine-5-carboxylic acid (6-fluoro-2,3-dihydro-1,4-benzoxazin-4-yl)-amide

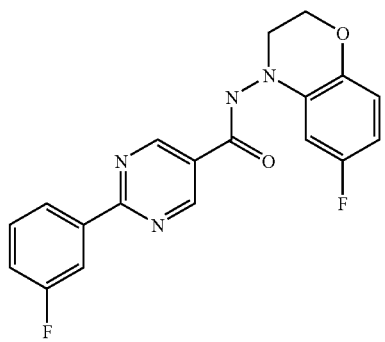

Step 1: $LiAlH_4$ (14.7 mmol, 1 M solution in THF) is added to a solution of 6-fluoro-4H-benzo[1,4]oxazin-3-one (1.23 g, 7.35 mmol) in THF at rt and heated to reflux for 2 hrs. The reaction mixture is quenched with a few drops of water followed by slow addition of ethyl acetate (10 mL). The solid is filtered off, and washed with EtOAc. The filtrate is concentrated in vacuo to afford 6-fluoro-3,4-dihydro-2H-benzo[1,4]oxazine (1 g). MS: 154 (M+H).

Step 2: Isoamyl nitrite is added to a solution of 6-fluoro-3,4-dihydro-2H-benzo[1,4]oxazine (1 g) in DCM (15 mL) and heated to reflux overnight. The reaction mixture is concentrated in vacuo and the residue is purified by silica gel chromatography eluting with 10% EtOAc in heptane to give 6-Fluoro-4-nitroso-3,4-dihydro-2H-benzo[1,4]oxazine (0.83 g).

Step 3: $LiAlH_4$ in THF (1 M, 6.58 mL) is added to a solution of 6-fluoro-4-nitroso-3,4-dihydro-2H-benzo[1,4]oxazine (0.8 g) in THF (10 mL) at 0° C. and then stirred at rt overnight. The reaction mixture is quenched with a few drops of water followed by addition of EtOAc (10 mL). The solid is filtered off and washed with EtOAc (15 mL). The filtrate is concentrated in vacuo and the residue is purified by silica gel column chromatography eluting with 15% EtOAc in heptane to afford 6-fluoro-2,3-dihydro-benzo[1,4]oxazin-4-ylamine (0.44 mg).

Step 4: DIPEA (174 µL) is added to a mixture of 2-(3-fluoro-phenyl)-pyrimidine-5-carboxylic acid (218 mg), HATU (380 mg) and 6-fluoro-2,3-dihydro-benzo[1,4]oxazin-4-ylamine (220 mg) in DMF (15 mL) and then heated at 80° C. overnight. The reaction mixture is concentrated in vacuo and the residue is purified by silica gel column chromatography eluting with 30% EtOAc in heptane to afford 2-(3-fluoro-phenyl)-pyrimidine-5-carboxylic acid (6-fluoro-2,3-dihydro-1,4-benzoxazin-4-yl)-amide (81 mg). MS: 369 (M+H); $^1$H NMR (300 MHz, DMSO-$D_6$): δ 11.05 (s, 1H), 9.35 (s, 2H), 8.32 (dd, 1H), 8.18 (dd, 1H), 7.65 (m, 1H), 7.5

(m, 1H), 6.8-6.7 (m, 2H), 6.52-6.45 (m, 1H), 4.36-4.33 (m, 2H), 3.65 (m, 2H). IC$_{50}$=12 nM.

Example 212

2-Phenyl-pyrimidine-5-carboxylic acid (6-fluoro-2,3-dihydro-1,4-benzoxazin-4-yl)-amide

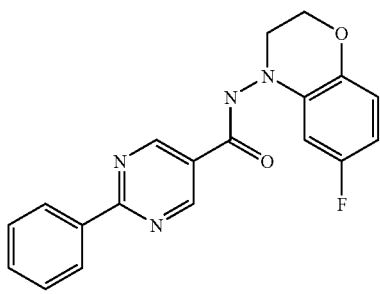

Following procedures similar to those of step 4 in Example 211, but substituting 2-phenyl-pyrimidine-5-carboxylic acid for 2-(3-fluoro-phenyl)-pyrimidine-5-carboxylic acid, there is prepared 2-phenyl-pyrimidine-5-carboxylic acid (6-fluoro-2,3-dihydro-1,4-benzoxazin-4-yl)-amide as solid. MS: 351 (M+H); $^1$H NMR (300 MHz, DMSO-D$_6$): δ 11.03 (s, 1H), 9.33 (s, 2H), 8.49-8.46 (m, 2H), 7.61-7.55 (m, 3H), 6.8-6.7 (m, 2H), 6.52-6.45 (m, 1H), 4.36-4.33 (m, 2H), 3.65-3.25 (m, 2H). IC$_{50}$=21 nM.

Example 213

4-Methyl-2-pyridin-2-yl-pyrimidine-5-carboxylic acid (3-ethyl-5-fluoro-pyrrolo[2,3-b]pyridin-1-yl)-amide

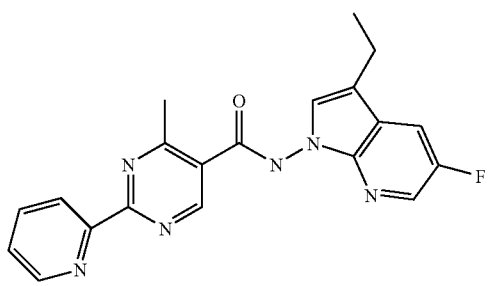

Step 1: A solution of 5-fluoro-3-iodo-pyridin-2-ylamine (3 g, 12.6 mmol) in DCM (40 mL) is treated with TFAA (2.1 mL, 15.1 mmol) and pyridine (1.2 mL, 15.1 mmol), and stirred at rt for 2 h. The mixture is diluted with H$_2$O (150 mL), and extracted with DCM (3×150 mL). The combined organic layer is dried (Na$_2$SO$_4$), filtered and concentrated in vacuo. The residue is diluted with MeCN (40 mL), treated with trans-crotyl bromide (2 mL, 18.9 mmol) and K$_2$CO$_3$ (3.5 g, 25.2 mmol), and heated at reflux for 2 h. The mixture is cooled, filtered through a pad of Celite and concentrated. The residue is purified by silica gel chromatography eluting with 5%-30% EtOAc in heptane to afford N-but-2-enyl-2,2,2-trifluoro-N-(5-fluoro-3-iodo-pyridin-2-yl)-acetamide (2.5 g, 51%). MS: 389 (M+H); $^1$H NMR (300 MHz, CDCl$_3$): δ 8.36 (m, 1H), 7.98 (s, 1H), 5.55 (m, 2H), 4.62 (m, 1H), 3.96 (m, 1H), 1.61 (m, 3H).

Step 2: A solution of N-but-2-enyl-2,2,2-trifluoro-N-(5-fluoro-3-iodo-pyridin-2-yl)-acetamide (2.57 g, 6.5 mmol) in DMF (10 mL) is treated with n-Bu$_4$NCl (2 g, 7.15 mmol), Pd(OAc)$_2$ (59 mg, 0.26 mmol), and stirred at 100° C. for 2 h. The mixture is cooled to rt, diluted with EtOAc (50 mL), filtered through a pad of silica gel, and washed with 1 M HCl (50 mL). The organic layer is separated, dried (Na$_2$SO$_4$), filtered and concentrated in vacuo. The residue is purified by silica gel chromatography eluting with 25%-70% EtOAc in heptane to afford 3-ethyl-5-fluoro-1H-pyrrolo[2,3-b]pyridine (0.75 g, 70%). MS: 165 (M+H); $^1$H NMR (300 MHz, CDCl$_3$): δ 9.62 (s, NH, 1H), 8.17 (m, 1H), 7.60 (m, 1H), 7.16 (s, 1H), 2.74 (q, 2H), 1.31 (t, 3H).

Step 3: A suspension of NaH (2.7 g, 68 mmol, 60% in mineral oil) in DMF (20 mL) at 0° C. is treated with 3-ethyl-5-fluoro-1H-pyrrolo[2,3-b]pyridine (745 mg, 4.5 mmol) and stirred at 0° C. for 1 h. The mixture is treated with HOSA (2.5 g, 22.5 mmol) portion wise and warmed to rt over 2 h. The mixture is then poured over ice, filtered through a pad of Celite, and extracted with EtOAc (3×50 mL). The combined organic layer is dried (Na$_2$SO$_4$), filtered and concentrated in vacuo. The residue is purified by silica gel chromatography eluting with 30% -50% EtOAc in heptane to afford 3-ethyl-5-fluoropyrrolo[2,3-b]pyridin-1-ylamine (685 mg, 84%). MS: 180 (M+H); $^1$H NMR (300 MHz, CDCl$_3$): δ 8.16 (s, 1H), 7.56 (m, 1H), 7.14 (s, 1H), 4.93 (s, NH$_2$, 2H), 2.697 (q, 2H), 1.28 (t, 3H).

Step 4: A solution of 4-methyl-2-pyridin-2-yl-pyrimidine-5-carboxylic acid (490 mg, 2.28 mmol) and 3-ethyl-5-fluoropyrrolo[2,3-b]pyridin-1-ylamine (340 mg, 1.9 mmol) in DMF (6 mL) is stirred at 40° C. for 1 h. The mixture is treated with DMTMM (524 mg, 1.9 mmol) and stirred at 40° C. for 1 h. The mixture is diluted with saturated aqueous Na$_2$CO$_3$ (5 mL) and stirred for 5 min. The precipitate is collected by filtration and dried in vacuo to afford 4-methyl-2-pyridin-2-yl-pyrimidine-5-carboxylic acid (3-ethyl-5-fluoro-pyrrolo[2,3-b]pyridin-1-yl)-amide (427 mg, 60%). MS: 377 (M+H); $^1$H NMR (300 MHz, DMSO-d$_6$): δ 11.94 (s, NH, 1H), 9.14 (s, 1H), 8.81 (d, 1H), 8.47 (d, 1H), 8.30 (s, 1H), 8.03 (m, 2H), 7.61 (m, 2H), 2.81 (s, 3H), 2.75 (q, 2H), 1.29 (t, 3H).

Example 214

4-Methyl-2-thiazol-2-yl-pyrimidine-5-carboxylic acid (3-ethyl-5-fluoro-pyrrolo[2,3-b]pyridin-1-yl)-amide

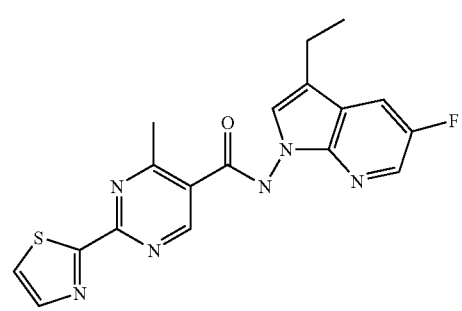

A solution of 4-methyl-2-thiazol-2-yl-pyrimidine-5-carboxylic acid (509 mg, 2.28 mmol) and 3-ethyl-5-fluoropyrrolo[2,3-b]pyridin-1-ylamine (340 mg, 1.9 mmol) in DMF (6 mL) is stirred at 40° C. for 1 h. The mixture is treated with DMTMM (524 mg, 1.9 mmol) and stirred at 40° C. for 1 h. The mixture is diluted with saturated aqueous Na$_2$CO$_3$ (5 mL) and stirred for 5 min. The precipitate is collected by filtration and dried in vacuo to afford 4-methyl-2-thiazol-2-yl-pyrimidine-5-carboxylic acid (3-ethyl-5-fluoro-pyrrolo[2,3-b]pyridin-1-yl)-amide (481 mg, 66%). MS: 383 (M+H); $^1$H NMR (300 MHz, DMSO-d$_6$): δ 11.95 (s, NH, 1H), 9.10 (s, 1H), 8.29 (s, 1H), 8.14 (d, 1H), 8.08 (d, 1H), 8.00 (m, 1H), 7.57 (s, 1H), 2.79 (s, 3H), 2.75 (q, 2H), 1.29 (t, 3H).

Example 215

2-(3-Fluoro-phenyl)-4-methyl-pyrimidine-5-carboxylic acid (5-fluoro-pyrrolo[2,3-b]pyridin-1-yl)-amide

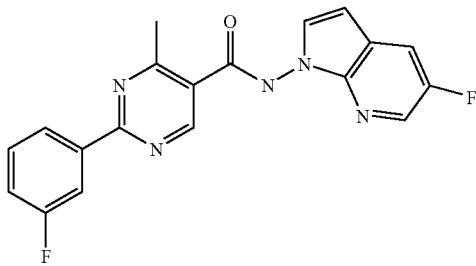

Step 1: A solution of 5-fluoro-3-iodo-pyridin-2-ylamine (4 g, 16.8 mmol) in THF (50 mL) and trimethylsilylacetylene (4.7 mL, 33.6 mmol) is treated with PdCl$_2$(PPh$_3$)$_4$ (353 mg, 0.5 mmol), CuI (96 mg, 0.5 mmol) and triethylamine (7 mL, 50.4 mmol) and stirred at rt for 2 h. The mixture is filtered through Celite and concentrated. The residue is purified by silica gel chromatography eluting with 10%-35% EtOAc in heptane to afford 5-fluoro-3-trimethylsilanylethynyl-pyridin-2-ylamine (3.3 g, 94%). MS: 209 (M+H); $^1$H NMR (300 MHz, CDCl$_3$): δ 7.90 (d, 1H), 7.30 (m, 1H), 4.89 (s, NH$_2$, 2H), 0.25 (s, 9H).

Step 2: A solution of 5-fluoro-3-trimethylsilanylethynyl-pyridin-2-ylamine (3.2 g, 15.4 mmol) in MeOH (77 mL) and K$_2$CO$_3$ (11 g, 7.7 mmol) is stirred at rt for 0.5 h. The mixture is filtered through Celite and concentrated. The residue is purified by silica gel chromatography eluting with 15%-55% EtOAc in heptane to afford 3-ethynyl-5-fluoro-pyridin-2-ylamine (1.55 g, 74%). MS: 137 (M+H); $^1$H NMR (300 MHz, CDCl$_3$): δ 7.94 (d, 1H), 7.35 (m, 1H), 4.91 (s, NH$_2$, 2H), 3.44 (s, 1H).

Step 3: A solution of 3-ethynyl-5-fluoro-pyridin-2-ylamine (1.25 g, 9.2 mmol) in DMF (20 mL) is treated with (Rh(cod)$_2$Cl)$_2$ (23 mg, 0.023 mmol) and tris-(4-fluoro-phenyl)-phosphane (115 mg, 0.368 mmol) and stirred at 85° C. for 0.5 h. The mixture is then poured over brine (50 mL), and extracted with EtOAc (3×50 mL). The combined organic layer is dried (Na$_2$SO$_4$), filtered and concentrated in vacuo. The residue is purified by silica gel chromatography eluting with 35%-75% EtOAc in heptane to afford 5-fluoro-1H-pyrrolo[2,3-b]pyridine (1.05 g, 84%). MS: 137 (M+H); $^1$H NMR (300 MHz, CDCl$_3$): δ 9.15 (s, NH, 1H), 7.99 (s, 1H), 7.44 (d, 1H), 7.18 (s, 1H), 6.28 (s, 1H).

Step 4: A suspension of NaH (4.4 g, 110 mmol, 60% in mineral oil) in DMF (37 mL) at 0° C. is treated with 5-fluoro-1H-pyrrolo[2,3-b]pyridine (1.0 g, 7.4 mmol) and stirred at 0° C. for 1 h. The mixture is treated with HOSA (4.2 g, 37 mmol) portion wise and warmed to rt over 2 h. The mixture is then poured over ice, filtered through a pad of Celite, and extracted with EtOAc (3×50 mL). The combined organic layer is dried (Na$_2$SO$_4$), filtered and concentrated in vacuo. The residue is purified by silica gel chromatography eluting with 30%-70% EtOAc in heptane to afford 5-fluoro-pyrrolo[2,3-b]pyridin-1-ylamine (980 mg, 88%). MS: 152 (M+H); $^1$H NMR (300 MHz, CDCl$_3$): δ 8.20 (s, 1H), 7.60 (m, 1H), 7.42 (m, 1H), 6.36 (s, 1H), 5.01 (s, NH$_2$, 2H).

Step 5: A solution of 2-(3-fluoro-phenyl)-4-methyl-pyrimidine-5-carboxylic acid (529 mg, 2.28 mmol) and 5-fluoro-pyrrolo[2,3-b]pyridin-1-ylamine (288 mg, 1.9 mmol) in DMF (6 mL) is stirred at 40° C. for 1 h. The mixture is treated with DMTMM (524 mg, 1.9 mmol) and stirred at 40° C. for 1 h. The mixture is diluted with saturated aqueous Na$_2$CO$_3$ (5 mL) and stirred for 5 min. The precipitate is collected by filtration and dried in vacuo to afford 2-(3-fluoro-phenyl)-4-methyl-pyrimidine-5-carboxylic acid (5-fluoro-pyrrolo[2,3-b]pyridin-1-yl)-amide (475 mg, 68%). MS: 366 (M+H); $^1$H NMR (300 MHz, DMSO-d$_6$): δ 9.12 (s, 1H), 8.30 (m, 2H), 8.18 (d, 1H), 7.97 (d, 1H), 7.82 (d, 1H), 7.59 (m, 1H), 7.44 (m, 1H), 6.59 (d, 1H), 2.80 (s, 3H).

Example 216

4-Methyl-2-pyridin-2-yl-pyrimidine-5-carboxylic acid (5-fluoro-pyrrolo[2,3-b]pyridin-1-yl)-amide

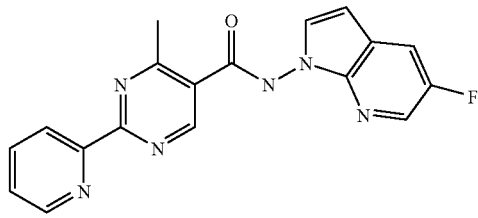

A solution of 4-methyl-2-pyridin-2-yl-pyrimidine-5-carboxylic acid (440 mg, 2.28 mmol) and 5-fluoro-pyrrolo[2,3-b]pyridin-1-ylamine (288 mg, 1.9 mmol) in DMF (6 mL) is stirred at 40° C. for 1 h. The mixture is treated with DMTMM (524 mg, 1.9 mmol) and stirred at 40° C. for 1 h. The mixture is diluted with saturated aqueous Na$_2$CO$_3$ (5 mL) and stirred for 5 min. The precipitate is collected by filtration and dried in vacuo to afford 4-methyl-2-pyridin-2-yl-pyrimidine-5-carboxylic acid (5-fluoro-pyrrolo[2,3-b]pyridin-1-yl)-amide (343 mg, 52%). MS: 349 (M+H); $^1$H NMR (300 MHz, DMSO-d$_6$): δ 9.17 (s, 1H), 8.81 (d, 1H), 8.53 (d, 1H), 8.27 (s, 1H), 8.01 (m, 1H), 7.90 (m, 1H), 7.77 (d, 1H), 7.57 (m, 1H), 6.60 (d. 1H), 2.84 (s, 3H).

Example 217

4-Methyl-[2,2']bipyrimidinyl-5-carboxylic acid (2-cyclopropyl-5-fluoro-indol-1-yl)-amide

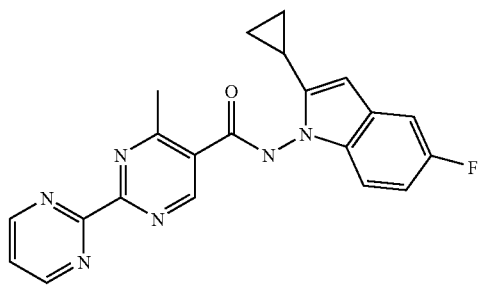

Step 1: A solution of 4-fluoro-2-iodoaniline (2 g, 8.4 mmol) in THF (15 mL) and cyclopropylacetylene (1.4 mL, 16.9 mmol) is treated with PdCl$_2$(PPh$_3$)$_4$ (177 mg, 0.25 mmol), CuI (48 mg, 0.25 mmol) and triethylamine (3.5 mL, 25.2 mmol) and stirred at rt for 2 h. The mixture is filtered through Celite and concentrated. The residue is purified by silica gel chromatography eluting with 0%-35% EtOAc in heptane to afford 2-cyclopropylethynyl-4-fluoro-phenylamine (1.1 g, 74%). MS: 176 (M+H); $^1$H NMR (300 MHz, CDCl$_3$): δ 6.93 (m, 1H), 6.81 (m, 1H), 6.59 (m, 1H), 4.00 (s, NH$_2$, 2H), 1.49 (m, 1H), 0.82 (m, 4H).

Step 2: A solution of 2-cyclopropylethynyl-4-fluoro-phenylamine (0.80 g, 4.5 mmol) in PhMe (16 mL) is treated with InBr$_3$ (80 mg, 0.23 mmol) and stirred at 110° C. for 0.5 h. The mixture is then poured over brine (20 mL), and extracted with EtOAc (3×20 mL). The combined organic layer is dried (Na$_2$SO$_4$), filtered and concentrated in vacuo. The residue is purified by silica gel chromatography eluting with 0%-25% EtOAc in heptane to afford 2-cyclopropyl-5-fluoro-1H-indole (610 mg, 78%). MS: 176 (M+H); $^1$H NMR (300 MHz, CDCl$_3$): δ 7.88 (s, NH, 1H), 7.12 (m, 2H), 6.83 (m, 1H), 6.09 (s, 1H), 1.90 (m, 1H), 0.95 (m, 2H), 0.77 (m, 2H).

Step 3: A suspension of NaH (1.9 g, 47 mmol, 60% in mineral oil) in DMF (20 mL) at 0° C. is treated with 2-cyclopropyl-5-fluoro-1H-indole (550 mg, 3.14 mmol) and stirred at 0° C. for 1 h. The mixture is treated with HOSA (1.8 g, 15.7 mmol) portion wise and warmed to rt over 2 h. The mixture is then poured over ice, filtered through a pad of Celite, and extracted with EtOAc (3×50 mL). The combined organic layer is dried (Na$_2$SO$_4$), filtered and concentrated in vacuo. The residue is purified by silica gel chromatography eluting with 5%-35% EtOAc in heptane to afford 2-cyclopropyl-5-fluoro-indol-1-ylamine (420 mg, 70%). MS: 191 (M+H); $^1$H NMR (300 MHz, CDCl$_3$): δ 7.30 (m, 1H), 7.11 (m, 1H), 6.92 (m, 1H), 5.90 (s, 1H), 4.57 (s, NH$_2$, 2H), 2.07 (m, 1H), 1.02 (m, 2H), 0.75 (m, 2H).

Step 4: A solution of 4-methyl-[2,2']bipyrimidinyl-5-carboxylic acid (184 mg, 0.85 mmol) and 2-cyclopropyl-5-fluoro-indol-1-ylamine (135 mg, 0.71 mmol) in DMF (3 mL) is stirred at 40° C. for 1 h. The mixture is treated with DMTMM (235 mg, 0.71 mmol) and stirred at 40° C. for 1 h. The mixture is diluted with saturated aqueous Na$_2$CO$_3$ (5 mL) and stirred for 5 min. The precipitate is collected by filtration and dried in vacuo to afford 4-methyl-[2,2']bipyrimidinyl-5-carboxylic acid (2-cyclopropyl-5-fluoro-indol-1-yl)-amide (35 mg, 13%). MS: 389 (M+H); $^1$H NMR (300 MHz, DMSO-d$_6$): δ 11.93 (s, NH, 1H), 9.31 (s, 1H), 9.06 (d, 2H), 7.70 (m, 1H), 7.42 (m, 1H), 7.26 (m, 1H), 6.97 (m, 1H), 6.16 (s, 1H), 2.79 (s, 3H), 1.97 (m, 1H), 1.01 (m, 2H), 0.74 (m, 2H).

Example 218

4-Methyl-2-thiazol-2-yl-pyrimidine-5-carboxylic acid (2-cyclopropyl-5-fluoro-indol-1-yl)-amide

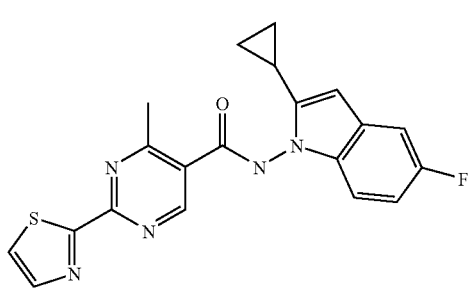

A solution of 4-methyl-2-thiazol-2-yl-pyrimidine-5-carboxylic acid (188 mg, 0.85 mmol) and 2-cyclopropyl-5-fluoro-indol-1-ylamine (135 mg, 0.71 mmol) in DMF (3 mL) is stirred at 40° C. for 1 h. The mixture is treated with DMTMM (235 mg, 0.71 mmol) and stirred at 40° C. for 1 h. The mixture is diluted with saturated aqueous Na$_2$CO$_3$ (5 mL) and stirred for 5 min. The precipitate is collected by filtration and dried in vacuo to afford 4-methyl-2-thiazol-2-yl-pyrimidine-5-carboxylic acid (2-cyclopropyl-5-fluoro-indol-1-yl)-amide (60 mg). MS: 394 (M+H); $^1$H NMR (300 MHz, DMSO-d$_6$): δ 9.26 (s, 1H), 8.15 (d, 1H), 8.08 (d, 1H), 7.43 (m, 1H), 7.24 (m, 1H), 6.97 (m, 1H), 6.18 (s, 1H), 2.77 (s, 3H), 1.95 (m, 1H), 1.01 (m, 2H), 0.73 (m, 2H).

Example 219

2-Pyrimidin-2-yl-4-methyl-pyrimidine-5-carboxylic acid (5-methoxyl-indol-1-yl)-amide

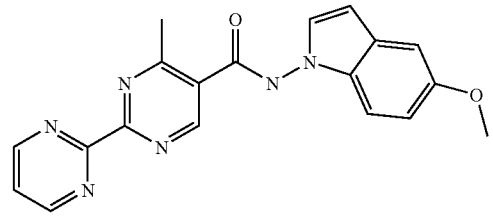

A solution of 2-pyrimidin-2-yl-4-methyl-pyrimidine-5-carboxylic acid (496 mg, 2.30 mmol) and 5-methoxy-indol-1-ylamine (0.98 mmol) in anhydrous DMF (10 mL) is stirred at 50° C. for 30 min. DMTMM (555 mg, 2.01 mmol) is added and stirred at 50° C. for an hour. DMF is evaporated off. The residue is mixed with water (40 mL) and stirred at rt for 20 minutes. The solid is collected by filtration, washed with water (3×5 mL) and dried in vacuum to afford 2-pyrimidin-2-yl-4-methyl-pyrimidine-5-carboxylic acid (5-methoxyl-indol-1-yl)-amide (410 mg) as a solid. MS: 361 (M+H); $^1$H NMR (300 MHz, CD$_3$OD): δ 2.93(s, 3H), 4.84(s, 3H), 7.04(t, H), 6.50(d, H), 6.92(d, H), 7.14(s, H), 7.26-7.37(m, 2H), 7.72 (t, H), 9.09 (d, 2H), 9.27(s, H).

Example 220

4-Methyl-[2,2']bipyrimidinyl-5-carboxylic acid (5-fluoro-3-methyl-pyrrolo [32-b]pyridin-1-yl)-amide

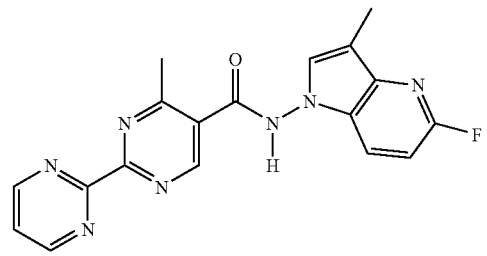

Step 1: Bromine (1.96 g, 12.2 mmol) is added to a mixture of 2-fluoro-5-aminopyridine (1.37 g, 12.2 mmol) and sodium acetate (2 mg, 24.4 mmol) in acetic acid (30 mL) and stirred at rt for 4 hours. Acetic acid is evaporated off in vacuo. The residue is dissolved in EtOAc (50 mL), washed with saturated aqueous Na$_2$CO$_3$ (10 mL), water (20 mL) and brine (10 mL), dried (Na$_2$SO$_4$), filtered, and concentrated in vacuo to afford 2-bromo-3-amino-6-fluoropyridine (2.1 g) as a solid. MS: 190 (M+H); $^1$H NMR (300 MHz, CDCl$_3$): δ 4.04 (br, 2H), 6.77 (dd, H), 7.17(dd, H).

Step 2: TFAA (8.31 g, 39.57 mmol) is added drop-wise to a stirred solution of 2-bromo-3-amino-6-fluoropyridine (6.30 g, 33.0 mmol) and pyridine (3.91 g, 49.46 mmol) in DCM (80 mL) at rt, and stirred at rt for an hour. Water (40 mL) is added. The organic layer is separated, dried (Na$_2$SO$_4$), filtered, and concentrated in vacuo to afford N-(2-bromo-6-fluoropyridin-3-yl)-2,2,2-trifluoro-acetamide (9.37 g, >99%) as a solid. $^1$H NMR (300 MHz, CDCl$_3$): δ 7.06 (m, H), 8.40 (br, N—H), 9.75 (dd, H).

Step 3: A solution of N-(2-bromo-6-fluoropyridin-3-yl)-2,2,2-trifluoro-acetamide (9.16 g, 31.9 mmol), allyl bromide (6.18 g, 47.9 mmol) and sodium carbonate (8.82 g, 63.8 mmol) in CH$_3$CN (80 mL) is stirred at 80° C. for 2 h. The reaction mixture is concentrated in vacuo and the residue is purified by silica gel chromatography eluting with 0-60% DCM in heptane to afford N-allyl-N-(2-bromo-6-fluoro-pyridin-3-yl)-2,2,2-trifluoro-acetamide (9.05 g) as an oil. $^1$H NMR (300 MHz, CDCl$_3$) δ 3.68 (q, H), 5.01 (q, H), 5.17 (d, H), 5.29 (d, H), 6.85(m, H), 7.00 (dd, H), 7.64(t, H).

Step 4: A solution of N-allyl-N-(2-bromo-6-fluoro-pyridin-3-yl)-2,2,2-trifluoro-acetamide (3.41 g, 10.43 mmol), palladium acetate (94 mg, 0.42 mmol), tetra(n-butylammonium) chloride (3.19 g, 11.47 mmol) and triethylamine (2.37 g, 23.4 mmol) in anhydrous DMF (20 mL) is stirred at 10° C. under N$_2$ for an hour. DMF is evaporated off and the residue is mixed with water (12 mL) and stirred at rt for an hour. EtOAc (15 mL) is added and stirred at rt overnight. The organic layer is separated and the aqueous layer is extracted with EtOAc (35 mL). The combined organic layer is dried (Na$_2$SO$_4$), filtered, and concentrated in vacuo. The residue is purified by silica gel chromatography eluting with 10-60% EtOAc in heptane to afford 5-fluoro-3-methyl-1H-pyrrolo[3,2-b]pyridine (1.5 g) as a solid. MS: 151 (M+H); $^1$H NMR (300 MHz, CDCl$_3$) δ 2.38(s, 3H), 6.77(d, H), 7.28(s, H), 7.74(dd, H).

Step 5: A solution of 5-fluoro-3-methyl-1H-pyrrolo[3,2-b]pyridine (10.7 mmol) in anhydrous DMF (15 mL) is added drop-wise to a stirred solution of NaH (60%, 160 mmol) in anhydrous DMF (25 mL) under N$_2$ at 0° C. for 20 min and stirred at 0° C. under N$_2$ for 30 minutes. HOSA (53.5 mmol) is added portion-wise for 30 minutes at 0° C., and stirred at 0° C. for 1.5 hours. After quenching with ice-water (400 mL), the mixture is extracted with ether (3×60 mL). The combined organic layer is washed with water (2×30 mL) and brine (20 mL), dried (Na$_2$SO$_4$), filtered, and concentrated in vacuo. The residue is purified by silica gel column chromatography eluting with 0-60% EtOAc in heptane to afford 5-fluoro-3-methyl-pyrrolo[3,2-b]pyridin-1-ylamine (570 mg). MS: 166 (M+H); $^1$H NMR (300 MHz, CDCl$_3$) δ 2.32 (s, 3H), 4.82 (br, 2N—H), 6.76 (d, H), 7.17 (s, H), 7.77 (dd, H).

Step 6: A solution of 2-pyrimidin-2-yl-4-methyl-pyrimidine-5-carboxylic acid (1.41 mmol), 5-fluoro-3-methyl-pyrrolo[3,2-b]pyridin-1-ylamine (1.41 mmol), DIPEA (158 mg, 4.22 mmol) and HATU (1.69 mmol) in anhydrous DMF (8 mL) is stirred at 90° C. for 16 hours. DMF is evaporated off in vacuo. The residue is dissolved in EtOAc (40 mL), washed with water (3×10 mL) and brine (10 mL), dried (Na$_2$SO$_4$), filtered, and concentrated in vacuo. The residue is purified by silica gel chromatography eluting with 1-20% MeOH in DCM to afford 4-methyl-[2,2']bipyrimidinyl-5-carboxylic acid (5-fluoro-3-methyl-pyrrolo[3,2-b]pyridin-1-yl)-amide (125 mg) as a solid. MS: 364 (M+H); $^1$H NMR (300 MHz, CD$_3$OD): δ 2.31 (s, 3H), 2.87 (s, 3H), 6.87 (d, H), 7.50 (s, H), 7.66 (t, H), 7.96 (t, H), 9.04 (d, 2H), 9.27 (s, H).

Example 221

4-Methyl-2-pyridin-2-yl-pyrimidine-5-carboxylic acid (5-fluoro-3-methyl-pyrrolo[3,2-b]pyridin-1-yl)-amide

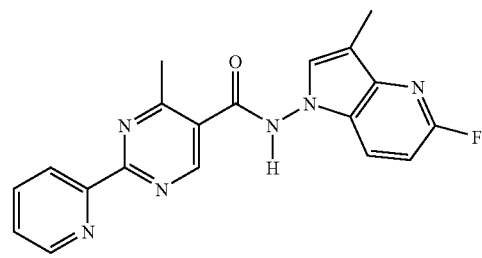

A solution of 2-pyridin-2-yl-4-methyl-pyrimidine-5-carboxylic acid (1.36 mmol), 5-fluoro-3-methyl-pyrrolo[3,2-b]pyridin-1-ylamine (1.36 mmol), DIPEA (158 mg, 4.07 mmol) and HATU (1.63 mmol) in anhydrous DMF (8 mL) is stirred at 90° C. for 15 hours. DMF is evaporated in vacuo. The residue is dissolved in EtOAc (40 mL), washed with water (3×15 mL) and brine (10 mL), dried (Na$_2$SO$_4$), filtered, and concentrated in vacuo. The residue is recrystallized from EtOAc to afford 4-methyl-2-pyridin-2-yl-pyrimidine-5-carboxylic acid (5-fluoro-3-methyl-pyrrolo[3,2-b]pyridin-1-yl)-amide (285 mg) as a solid. MS: 363 (M+H); $^1$H NMR (300 MHz, CD$_3$OD): δ 2.35 (s, 3H), 2.87 (s, 3H), 6.92 (d, H), 7.51 (s, H), 7.60 (t, H), 7.97 (t, H), 8.05 (t, H), 8.65 (d, H), 8.78 (d, H), 9.23 (s, H).

Example 222

2-(3-Fluoro-phenyl)-4-methyl-pyrimidine-5-carboxylic acid (5-fluoro-3-methyl-pyrrolo[3,2-b]pyridin-1-yl)-amide

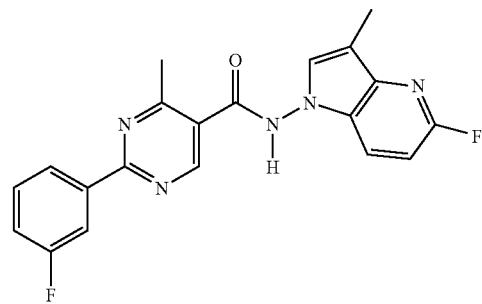

A solution of 2-(3-fluoro-phenyl)-4-methyl-pyrimidine-5-carboxylic acid (1.34 mmol), 5-fluoro-3-methyl-pyrrolo[3,2-b]pyridin-1-ylamine (1.34 mmol), DIPEA (158 mg, 4.02 mmol) and HATU (1.60 mmol) in anhydrous DMF (8 mL) is stirred at 90° C. for 16 h. DMF is evaporated off in vacuo. The residue is dissolved in EtOAc (40 mL), and washed with water (3×20 mL) and brine (10 mL). The organic layer is dried (Na$_2$SO$_4$), filtered, and concentrated in vacuo. The residue is purified by silica gel chromatography eluting with 0-60% EtOAc in heptane to afford 2-(3-fluoro-phenyl)-4-methylpyrimidine-5-carboxylic acid (5-fluoro-3-methyl-pyrrolo[3,2-b]pyridin-1-yl)-amide (340 mg) as a solid. MS: 380 (M+H); $^1$H NMR (300 MHz, CDCl$_3$): δ 2.36 (s, 3H), 2.86 (s, 3H), 6.84 (d, H), 7.12-7.35 (m, 2H), 7.52 (q, H), 7.63 (t, H), 8.10-8.43 (m, 2H), 8.98 (br, N—H).

Example 223

4-Methyl-2-pyridin-2-yl-pyrimidine-5-carboxylic acid (5-methoxy-3-methyl-pyrrolo[3,2-b]pyridin-1-yl)-amide

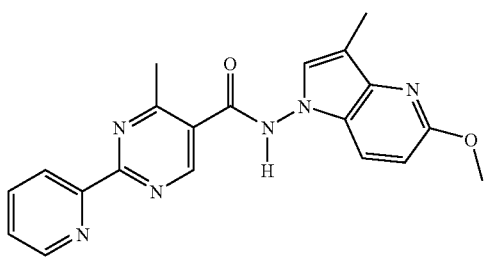

Step 1: Bromine (4.72 g, 29.5 mmol) is added to a mixture of 2-methoxy-5-aminopyridine (3.66 g, 29.5 mmol) and sodium acetate (4.84 g, 7.32 mmol) in acetic acid (50 mL) and stirred at rt for 20 minutes. Acetic acid is evaporated off in vacuo. The residue is dissolved in EtOAc (40 mL), and washed with water (40 mL), saturated sodium carbonate aqueous solution (20 mL), water (20 mL) and brine (20 mL). The organic layer is dried (Na$_2$SO$_4$), filtered, and concentrated in vacuo. The residue is purified by silica gel chromatography eluting with 0-40% EtOAc in heptane to afford 2-bromo-3-amino-6-methoxypyridine (4.35 g) as an oil. MS: 202 (M+H); $^1$H NMR (300 MHz, CDCl$_3$): δ 3.89 (s, 3H), 6.60(d, H), 7.07(d, H).

Step 2: TFAA (5.15 g, 24.5 mmol) is added drop-wise to a stirred solution of 2-bromo-3-amino-6-methoxypyridine (4.15 g, 20.5 mmol) and pyridine (1.94 g, 24.5 mmol) in DCM (60 mL) at rt and stirred at rt for 2.5 h. Water (40 mL) is added. The organic layer is separated, dried (Na$_2$SO$_4$), filtered, and concentrated in vacuo to afford N-(2-bromo-6-methoxy-pyridin-3-yl)-2,2,2-trifluoro-acetamide (5.68 g) as a solid. $^1$H NMR (300 MHz, CDCl$_3$): δ 3.96 (s, H), 6.80(s, H), 8.23 (br, N—H), 8.42(d, H).

Step 3: A mixture of N-(2-bromo-6-methoxy-pyridin-3-yl)-2,2,2-trifluoro-acetamide (5.52 g, 18.5 mmol), allyl bromide (3.57 g, 27.7 mmol) and sodium carbonate (5.1 g, 11 mmol) in CH$_3$CN (60 mL) is stirred at 80° C. for 3 h. The mixture is filtered and the filtrate is concentrated in vacuo. The residue is purified by silica gel column chromatography eluting with 0-60% DCM in heptane to afford N-allyl-N-(2-bromo-6-methoxy-pyridin-3-yl)-2,2,2-trifluoro-acetamide (5.55 g) as an oil. $^1$H NMR (300 MHz, CDCl$_3$): δ 3.66 (q, H), 4.00 (s, H), 5.95 (q, H), 5.08-5.30 (q, 2H), 5.75-5.94 (m, H), 6.74 (d, H), 7.38 (d, H).

Step 4: A solution of N-allyl-N-(2-bromo-6-methoxy-pyridin-3-yl)-2,2,2-trifluoro-acetamide (5.54 g, 16.3 mmol), palladium acetate (147 mg, 0.65 mmol), tetra(n-butylammonium) chloride (4.99 g, 17.9 mmol) and triethylamine (3.72 g, 26.8 mmol) in anhydrous DMF (35 mL) is stirred at 10° C. under N$_2$ for an hour. DMF is evaporated off, and the residue is mixed with water (20 mL) and stirred at rt overnight. EtOAc (50 mL) is added. The organic layer is separated, dried (Na$_2$SO$_4$), filtered, and concentrated in vacuo. The residue is purified by silica gel column chromatography eluting with 30-70% EtOAc in heptane to afford 5-methoxy-3-methyl-1H-pyrrolo[3,2-b]pyridine (2.62 g) as a solid. $^1$H NMR (300 MHz, CDCl$_3$): δ 2.38 (s, 3H), 4.05 (s, 3H), 6.62 (s, H), 7.12 (s, H), 7.54 (d, H), 7.94 (br, N—H).

Step 5: A solution of 5-methoxy-3-methyl-1H-pyrrolo[3,2-b]pyridine (17.3 mmol) in anhydrous DMF (20 mL) is added drop-wise to a stirred solution of NaH (60%, 260 mmol) in anhydrous DMF (35 mL) under N$_2$ at 0° C. for 40 min and then stirred at 0° C. under nitrogen for 30 minutes. HOSA is added portion-wise for 45 minutes at 0° C. and then stirred at 0° C. for 2 hours. After quenching with ice-water (500 mL), the reaction mixture is extracted with ether (3×40 mL). The combined organic layer is washed with water (20 mL) and brine (20 mL), dried (Na$_2$SO$_4$), filtered, and concentrated in vacuo. The residue is purified by silica gel column chromatography eluting with 5-60% EtOAc in heptane to afford 5-methoxy-3-methyl-pyrrolo[3,2-b]pyridin-1-ylamine (1.73 g) as a solid. MS: 178 (M+H); $^1$H NMR (300 MHz, CDCl$_3$): δ 2.34 (s, 3H), 4.04(s, 3H), 4.75(br, 2N—H), 6.63(d, H), 7.04(s, H), 7.60(d, H).

Step 6: A solution of 2-pyridin-2-yl-4-methyl-pyrimidine-5-carboxylic acid (1.69 mmol), 5-methoxy-3-methyl-pyrrolo[3,2-b]pyridin-1-ylamine (1.69 mmol), DIPEA (5.01 mmol) and HATU (2.03 mmol) in anhydrous DMF (8 mL) is stirred at 90° C. for 16 h. DMF is evaporated in vacuo. The residue is dissolved in EtOAc (40 mL), and washed with water (3×10 mL) and brine (10 mL). The organic layer is dried (Na$_2$SO$_4$), filtered, and concentrated in vacuo. The residue is purified by silica gel column chromatography eluting with 0-15% MeOH in DCM to afford 4-methyl-2-pyridin-2-yl-pyrimidine-5-carboxylic acid (5-methoxy-3-methyl-pyrrolo[3,2-b]pyridin-1-yl)-amide (295 mg) as a solid. MS: 375 (M+H); $^1$H NMR (300 MHz, CD$_3$OD): δ 2.40 (s, 3H), 2.84 (s, 3H), 4.02 (s, 3H), 6.70 (d, H), 7.13 (s, H), 7.41 (m, H), 7.50 (d, H), 7.85 (t, H), 8.51 (m, 2H), 8.78 (s, 2H), 10.57 (br, N—H).

Example 224

2-(3-Fluoro-phenyl)-4-methyl-pyrimidine-5-carboxylic acid (5-methoxy-3-methyl-pyrrolo[3,2-b]pyridin-1-yl)-amide

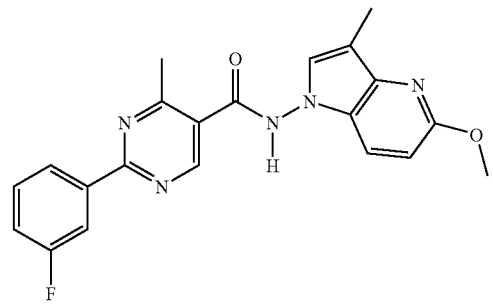

A solution of 2-(3-phenyl)-4-methyl-pyrimidine-5-carboxylic acid (1.13 mmol), 5-methoxy-3-methyl-pyrrolo[3,2-b]pyridin-1-ylamine (1.13 mmol), DIPEA (3.39 mmol) and HATU (1.36 mmol) in anhydrous DMF (8 mL) is stirred at 90° C. for 16 h. DMF is evaporated off in vacuo. The residue is dissolved in EtOAc (45 mL), and washed with water (3×20 mL) and brine (10 mL). The organic layer is dried (Na$_2$SO$_4$), filtered, and concentrated in vacuo. The residue is is triturated with DCM to afford 2-(3-fluoro-phenyl)-4-methyl-pyrimidine-5-carboxylic acid (5-methoxy-3-methyl-pyrrolo[3,2-b]pyridin-1-yl)-amide (265 mg) as a solid. MS: 392 (M+H); $^1$H NMR (300 MHz, CD$_3$OD): δ 2.33 (s, 3H), 2.79 (s, 3H), 3.97

(s, 3H), 6.67 (d, H), 7.20-7.60 (m, 2H), 7.53 (m, H), 7.64 (d, H), 8.17 (t, H), 8.34 (t, 2H), 9.05-9.20 (d, H).

Example 225

4-Methyl-2-(1-oxy-pyridin-2-yl)-pyrimidin-5-carboxylic acid (5-fluoro-3-methyl-indol-1-yl)-amide

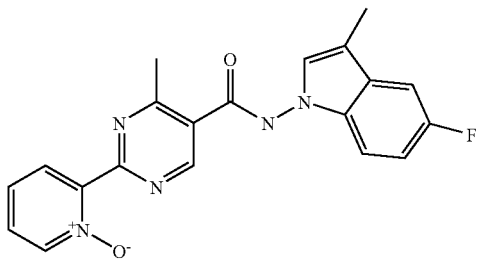

Step 1: A solution of 2-cyanopyridine (1.67 g, 16 mmol), 30% $H_2O_2$ (3.2 mL) and methyltrioxorhenium (0.2 g, 0.8 mmol) in DCM (6.4 mL) is stirred at rt overnight. The reaction mixture is concentrated in vacuo and the residue is purified by silica gel chromatography eluting with 3-10% MeOH in DCM to afford 1-oxy-pyridine-2-carbonitrile (0.69 g) as a solid. $^1$H NMR (300 MHz, $CDCl_3$): δ 7.34 (t, H), 7.49(t, H), 7.67(d, H), 8.30 (d, H).

Step 2: A solution of 1-oxy-pyridine-2-carbonitrile (532 mg, 4.43 mmol) and sodium methoxide (0.5 M in MeOH, 0.88 mL) in MeOH (1.8 mL) is stirred at rt overnight. Ammonium chloride (261 mg. 4.87 mmol) is added and stirred at 56° C. for an hour, and then 7 N ammonia in MeOH (1.5 mL) is added. The reaction mixture is sealed in a tube and stirred at 40° C. for an hour, and then cooled to 0° C. Sodium methoxide is added (0.5 M in MeOH, 8.86 mL). The mixture is filtered and the filtrate is concentrated in vacuo. The residue is recrystallized from ethanol to afford 1-oxy-pyridine-2-carboxamidine (370 mg) as a solid. $^1$H NMR (300 MHz, $CD_3OD$): δ 7.52-7.68(m, 2H), 7.96(dd, H), 8.35 (d, H).

Step 3: A solution of 1-oxy-pyridine-2-carboxamidine (366 mg, 2.67 mmol) and N,N-dimethylaminomethylene acetoacetate (495 mg, 2.76 mmol) in ethanol (3 mL) and DMF (3 ml) is stirred at 90° C. for 16 hours. The reaction mixture is concentrated in vacuo and the residue is purified by silica gel column chromatography eluting with 2.5% MeOH in DCM to afford 4-methyl-2-(1-oxy-pyridin-2-yl)-pyrimidine-5-carboxylic acid ethyl ester (127 mg) as a solid. $^1$H NMR (300 MHz, $CDCl_3$): δ 1.47 (t, 3H), 2.95 (s, 3H), 4.50 (q, 2H), 7.39 (m, H), 7.70(q, H), 8.36(q, H), 9.37 (s, H).

Step 4: A solution of 4-methyl-2-(-1oxy-pyridin-2-yl)-pyrimidine-5-carboxylic acid ethyl ester (123 mg, 0.48 mmol) and sodium hydroxide (123 mg, 3.07 mmol) in a mixture of MeOH/THF/$H_2O$ (3 mL, 1:1:1) is stirred at 65° C. for 5 minutes, and then stirred at rt overnight (16 hours). 1 N HCl aqueous solution (3.07 mL) is added. The resulting solution is concentrated to afford 4-methyl-2-(1-oxy-pyridin-2-yl)-pyrimidine-5-carboxylic acid and sodium chloride (313 mg), which is used in the next step without further purification.

Step 5: A solution of 4-methyl-2-(1-oxy-pyridin-2-yl)-pyrimidine-5-carboxylic acid and sodium chloride (313 mg), 3-methyl-5-fluoro-indol-1-ylamine (78 mg, 0.48 mmol), DIEA (92 mg, 0.71 mmol) and HATU (217 mg, 0.57 mmol) in anhydrous DMF (2.4 mL) is stirred at 150° C. for 1 hour. DMF is vaporated off. The residue is purified by silica gel column chromatography eluting with 2.5-10% MeOH in DCM to afford 4-methyl-2-(1-oxy-pyridin-2-yl)-pyrimidine-5-carboxylic acid (5-fluoro-3-methyl-indol-1-yl)-amide (169 mg) as a solid. MS: 378 (M+H); $^1$H NMR (300 MHz, $CD_3OD$): δ=1.52(s, 3H), 2.84(s, 3H), 7.02(t, H), 7.18(s, H), 7.25 (d, H), 7.35(q, H), 7.62-7.80 (m, 2H), 7.85 (dd, H), 8.48 (d, H), 9.21(s, H). $IC_{50}$=851.5 nM.

Example 226

2-(3-Difluoromethyl-phenyl)-pyrimidine-5-carboxylic acid (5-fluoro-3-methyl-indol-1-yl)-amide

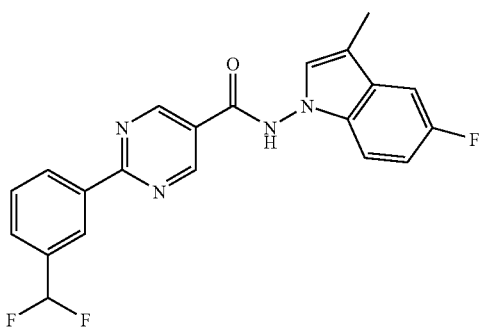

Following procedures similar to those of Example 158, step 4, but substituting 2-(3-difluoromethyl-phenyl)-2-yl-pyrimidine-5-carboxylic acid for 2-thiazol-2-yl-pyrimidine-5-carboxylic acid, there is prepared 2-(3-difluoromethyl-phenyl)-pyrimidine-5-carboxylic acid (5-fluoro-3-methyl-indol-1-yl)-amide. MS: 397 (M+H); $^1$H NMR (300 MHz, DMSO-$d_6$): δ 2.27 (s, 3H), 7.04 (dt, 1H), 7.13 (d, 1H), 7.32 (s, 1H), 7.34-7.44 (m, 2H), 7.73-7.85 (m, 2H), 8.66 (d, 1H), 8.69 (s, 1H), 9.45 (s, 2H). $IC_{50}$=17 nM.

Example 227

2-(3-Trifluoromethyl-phenyl)-pyrimidine-5-carboxylic acid (5-fluoro-3-methyl-indol-1-yl)-amide

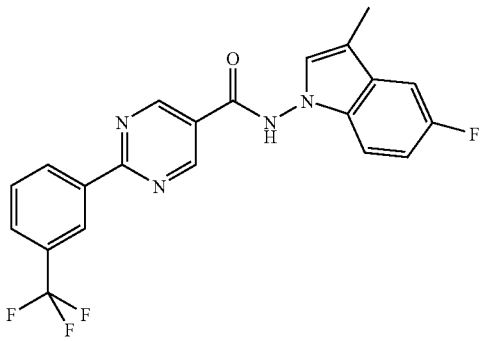

Following procedures similar to those of Example 158, step 4, but substituting 2-(3-trifluoromethyl-phenyl)-2-yl-pyrimidine-5-carboxylic acid for 2-thiazol-2-yl-pyrimidine-5-carboxylic acid, there is prepared 2-(3-trifluoromethyl-phenyl)-pyrimidine-5-carboxylic acid (5-fluoro-3-methyl-indol-1-yl)-amide. MS: 415 (M+H). $^1$H NMR (300 MHz, DMSO-$d_6$): δ 2.27 (s, 3H), 7.04 (dt, 1H), 7.33 (s, 1H), 7.34-7.44 (m, 2H), 7.86 (t, 1H), 8.00-8.02 (m, 1H), 8.75-8.79 (m, 2H), 9.47 (s, 2H). $IC_{50}$=262 nM.

Following procedures similar to those described in the above examples, the following compounds are made:

2-Phenyl-pyrimidine-5-carboxylic acid (4-benzyl-piperazin-1-yl)-amide,
2-Phenyl-pyrimidine-5-carboxylic acid piperazin-1-ylamide,
2-Phenyl-pyrimidine-5-carboxylic acid (4-methanesulfonyl-piperazin-1-yl)-amide,
2-(2-Methyl-thiazol-4-yl)-pyrimidine-5-carboxylic acid morpholin-4-ylamide,
2-Phenyl-pyrimidine-5-carboxylic acid [4-(1-methyl-1H-imidazole-2-carbonyl)-piperazin-1-yl]-amide,
2-Phenyl-pyrimidine-5-carboxylic acid [4-(1-methyl-1H-imidazole-4-carbonyl)-piperazin-1-yl]-amide,
4-[(2-Phenyl-pyrimidine-5-carbonyl)-amino]-piperazine-1-carboxylic acid tert-butyl ester,
2-Phenyl-pyrimidine-5-carboxylic acid [4-(4-trifluoromethyl-phenoxy)-piperidin-1-yl]-amide,
2-(3-Fluoro-phenyl)-pyrimidine-5-carboxylic acid [4-(4-trifluoromethyl-phenoxy)-piperidin-1-yl]-amide,
2-(3-Fluoro-phenyl)-pyrimidine-5-carboxylic acid morpholin-4-ylamide,
2-Phenyl-pyrimidine-5-carboxylic acid indol-1-ylamide,
2-Phenyl-pyrimidine-5-carboxylic acid (4-methoxy-piperidin-1-yl)-amide,
2-(3-Fluoro-phenyl)-4-methyl-pyrimidine-5-carboxylic acid (2-methyl-indol-1-yl)-amide,
2-(3-Fluoro-phenyl)-pyrimidine-5-carboxylic acid (6-fluoro-2,3-dihydro-benzo[1,4]oxazin-4-yl)-amide,
2-Phenyl-pyrimidine-5-carboxylic acid (6-fluoro-2,3-dihydro-benzo[1,4]oxazin-4-yl)-amide,
1-{[2-(3-Fluoro-phenyl)-4-methyl-pyrimidine-5-carbonyl]-amino}-3-(2-morpholin-4-yl-ethyl)-1H-indole-6-carboxylic acid methyl ester,
2-(3-Fluoro-phenyl)-4-methyl-pyrimidine-5-carboxylic acid [5-fluoro-3-(tetrahydro-pyran-4-yl)-indol-1-yl]-amide,
N-methyl-N-(5-fluoro)-indol-3-ylsulfonyl N'-[2-(3-fluoro)-phenyl-pyrimidine-5-carbonyl]-hydrazide,
4-Methyl-2-pyridin-2-yl-pyrimidine-5-carboxylic acid [5-fluoro-3-(tetrahydro-pyran-4-yl)-indol-1-yl]-amide,
4-Methyl-2-pyridin-2-yl-pyrimidine-5-carboxylic acid (5-fluoro-3-methyl-indol-1-yl)-amide,
4-Methyl-2-pyridin-2-yl-pyrimidine-5-carboxylic acid (3-methyl-pyrrolo[3,2-b]pyridin-1-yl)-amide,
4-Methyl-2-(4-methyl-thiazol-2-yl)-pyrimidine-5-carboxylic acid pyrrolo[2,3-b]pyridin-1-ylamide,
4-Methyl-2-(4-methyl-thiazol-2-yl)-pyrimidine-5-carboxylic acid (3-methyl-pyrrolo[2,3-b]pyridin-1-yl)-amide,
4-Methyl-2-(4-methyl-thiazol-2-yl)-pyrimidine-5-carboxylic acid (3-isopropyl-pyrrolo[2,3-b]pyridin-1-yl)-amide,
4-Methyl-2-(4-methyl-thiazol-2-yl)-pyrimidine-5-carboxylic acid (3-difluoromethyl-pyrrolo[2,3-b]pyridin-1-yl)-amide,
4-Methyl-2-(4-methyl-thiazol-2-yl)-pyrimidine-5-carboxylic acid (3-trifluoromethyl-pyrrolo[2,3-b]pyridin-1-yl)-amide,
4-Methyl-2-(4-methyl-thiazol-2-yl)-pyrimidine-5-carboxylic acid (3-methyl-pyrrolo[2,3-c]pyridin-1-yl)-amide,
4-Methyl-2-(4-methyl-thiazol-2-yl)-pyrimidine-5-carboxylic acid pyrrolo[2,3-c]pyridin-1-ylamide,
4-Methyl-2-(4-methyl-thiazol-2-yl)-pyrimidine-5-carboxylic acid (3-isopropyl-pyrrolo[2,3-c]pyridin-1-yl)-amide,
4-Methyl-2-(4-methyl-thiazol-2-yl)-pyrimidine-5-carboxylic acid (3-difluoromethyl-pyrrolo[2,3-c]pyridin-1-yl)-amide,
4-Methyl-2-(4-methyl-thiazol-2-yl)-pyrimidine-5-carboxylic acid (3-trifluoromethyl-pyrrolo[2,3-c]pyridin-1-yl)-amide,
4-Methyl-2-(4-methyl-thiazol-2-yl)-pyrimidine-5-carboxylic acid (3-methyl-pyrrolo[3,2-c]pyridin-1-yl)-amide,
4-Methyl-2-(4-methyl-thiazol-2-yl)-pyrimidine-5-carboxylic acid pyrrolo[3,2-c]pyridin-1-ylamide,
4-Methyl-2-(4-methyl-thiazol-2-yl)-pyrimidine-5-carboxylic acid (3-isopropyl-pyrrolo[3,2-c]pyridin-1-yl)-amide,
4-Methyl-2-(4-methyl-thiazol-2-yl)-pyrimidine-5-carboxylic acid (3-difluoromethyl-pyrrolo[3,2-c]pyridin-1-yl)-amide,
4-Methyl-2-(4-methyl-thiazol-2-yl)-pyrimidine-5-carboxylic acid (3-trifluoromethyl-pyrrolo[3,2-c]pyridin-1-yl)-amide,
4-Methyl-2-thiazol-2-yl-pyrimidine-5-carboxylic acid pyrrolo[2,3-b]pyridin-1-ylamide,
4-Methyl-2-thiazol-2-yl-pyrimidine-5-carboxylic acid (3-methyl-pyrrolo[2,3-b]pyridin-1-yl)-amide,
4-Methyl-2-thiazol-2-yl-pyrimidine-5-carboxylic acid (3-isopropyl-pyrrolo[2,3-b]pyridin-1-yl)-amide,
4-Methyl-2-thiazol-2-yl-pyrimidine-5-carboxylic acid (3-difluoromethyl-pyrrolo[2,3-b]pyridin-1-yl)-amide,
4-Methyl-2-thiazol-2-yl-pyrimidine-5-carboxylic acid (3-trifluoromethyl-pyrrolo[2,3-b]pyridin-1-yl)-amide,
4-Methyl-2-thiazol-2-yl-pyrimidine-5-carboxylic acid pyrrolo[2,3-c]pyridin-1-ylamide,
4-Methyl-2-thiazol-2-yl-pyrimidine-5-carboxylic acid (3-methyl-pyrrolo[2,3-c]pyridin-1-yl)-amide,
4-Methyl-2-thiazol-2-yl-pyrimidine-5-carboxylic acid pyrrolo[2,3-c]pyridin-1-ylamide,
4-Methyl-2-thiazol-2-yl-pyrimidine-5-carboxylic acid (3-isopropyl-pyrrolo[2,3-c]pyridin-1-yl)-amide,
4-Methyl-2-thiazol-2-yl-pyrimidine-5-carboxylic acid (3-difluoromethyl-pyrrolo[2,3-c]pyridin-1-yl)-amide,
4-Methyl-2-thiazol-2-yl-pyrimidine-5-carboxylic acid (3-trifluoromethyl -pyrrolo[2,3-c]pyridin-1-yl)-amide,
4-Methyl-2-thiazol-2-yl-pyrimidine-5-carboxylic acid (3-methyl-pyrrolo[3,2-c]pyridin-1-yl)-amide,
4-Methyl-2-thiazol-2-yl-pyrimidine-5-carboxylic acid pyrrolo[3,2-c]pyridin-1-ylamide,
4-Methyl-2-thiazol-2-yl-pyrimidine-5-carboxylic acid (3-isopropyl-pyrrolo[3,2-c]pyridin-1-yl)-amide,
4-Methyl-2-thiazol-2-yl-pyrimidine-5-carboxylic acid (3-difluoromethyl-pyrrolo[3,2-c]pyridin-1-yl)-amide,
4-Methyl-2-thiazol-2-yl-pyrimidine-5-carboxylic acid (3-trifluoromethyl-pyrrolo[3,2-c]pyridin-1-yl)-amide,
4-Methyl-2-(4-chloro-thiazol-2-yl)-pyrimidine-5-carboxylic acid pyrrolo[2,3-b]pyridin-1-ylamide,
4-Methyl-2-(4-chloro-thiazol-2-yl)-pyrimidine-5-carboxylic acid (3-methyl-pyrrolo[2,3-b]pyridin-1-yl)-amide,
4-Methyl-2-(4-chloro-thiazol-2-yl)-pyrimidine-5-carboxylic acid (3-isopropyl-pyrrolo[2,3-b]pyridin-1-yl)-amide,
4-Methyl-2-(4-chloro-thiazol-2-yl)-pyrimidine-5-carboxylic acid (3-difluoromethyl-pyrrolo[2,3-b]pyridin-1-yl)-amide,
4-Methyl-2-(4-chloro-thiazol-2-yl)-pyrimidine-5-carboxylic acid (3-trifluoromethyl-pyrrolo[2,3-b]pyridin-1-yl)-amide,
4-Methyl-2-(4-chloro-thiazol-2-yl)-pyrimidine-5-carboxylic acid (3-methyl-pyrrolo[2,3-c]pyridin-1-yl)-amide,
4-Methyl-2-(4-chloro-thiazol-2-yl)-pyrimidine-5-carboxylic acid pyrrolo[2,3-c]pyridin-1-ylamide,
4-Methyl-2-(4-chloro-thiazol-2-yl)-pyrimidine-5-carboxylic acid (3-isopropyl-pyrrolo[2,3-c]pyridin-1-yl)-amide,
4-Methyl-2-(4-chloro-thiazol-2-yl)-pyrimidine-5-carboxylic acid (3-difluoromethyl-pyrrolo[2,3-c]pyridin-1-yl)-amide,
4-Methyl-2-(4-chloro-thiazol-2-yl)-pyrimidine-5-carboxylic acid (3-trifluoromethyl-pyrrolo[2,3-c]pyridin-1-yl)-amide,
4-Methyl-2-(4-chloro-thiazol-2-yl)-pyrimidine-5-carboxylic acid (3-methyl-pyrrolo[3,2-c]pyridin-1-yl)-amide,
4-Methyl-2-(4-chloro-thiazol-2-yl)-pyrimidine-5-carboxylic acid pyrrolo[3,2-c]pyridin-1-ylamide, 4-Methyl-2-(4-chloro-thiazol-2-yl)-pyrimidine-5-carboxylic acid (3-isopropyl-pyrrolo[3,2-c]pyridin-1-yl)-amide,
4-Methyl-2-(4-chloro-thiazol-2-yl)-pyrimidine-5-carboxylic acid (3-difluoromethyl-pyrrolo[3,2-c]pyridin-1-yl)-amide,
4-Methyl-2-(4-methyl-thiazol-2-yl)-pyrimidine-5-carboxylic acid (3-trifluoromethyl-pyrrolo[3,2-c]pyridin-1-yl)-amide,
2-(4-Chloro-thiazol-2-yl)-4-methyl-pyrimidine-5-carboxylic acid (5-fluoro-3-methyl-indol-1-yl)-amide,
2-(4-Methyl-thiazol-2-yl)-4-methyl-pyrimidine-5-carboxylic acid (5-fluoro-3-methyl-indol-1-yl)-amide,
2-(3-Fluoro-phenyl)-4-methyl-pyrimidine-5-carboxylic acid (2-methyl-3-oxo-2,3-dihydro-indazol-1-yl)amide,
2-(4-Chloro-thiazol-2-yl)-4-methyl-pyrimidine-5-carboxylic acid(5-fluoro-indol-1-yl)amide)amide,
6-(4-Chloro-thiazol-2-yl)-2-methyl-N-pyrrolo[2,3-c]pyridin-1-yl-nicotinamide,
2-(3-Fluoro-phenyl)-4-methyl-pyrimidine-5-carboxylic acid (5-methyl-4-oxo-4,5-dihydro-pyrrolo[3,2-c]pyridin-1-yl) amide,
4-Methyl-2-(4-methyl-thiazol-2-yl)-pyrimidine-5-carboxylic acid (5-trifluoromethyl-pyrrolo[3,2-b]pyridin-1-yl)-amide,
4-Methyl-2-(4-methyl-thiazol-2-yl)-pyrimidine-5-carboxylic acid (5-difluoromethyl-pyrrolo[3,2-b]pyridin-1-yl)-amide,
4-Methyl-2-(4-methyl-thiazol-2-yl)-pyrimidine-5-carboxylic acid (3-trifluoromethyl-pyrrolo[3,2-b]pyridin-1-yl)-amide,
4-Methyl-2-(4-methyl-thiazol-2-yl)-pyrimidine-5-carboxylic acid (3-difluoromethyl-pyrrolo[3,2-b]pyridin-1-yl)-amide,
4-Methyl-2-(4-methyl-thiazol-2-yl)-pyrimidine-5-carboxylic acid [3-(2,2,2-trifluoro-ethyl)-pyrrolo[3,2-b]pyridin-1-yl]-amide,
4-Methyl-2-(4-methyl-thiazol-2-yl)-pyrimidine-5-carboxylic acid [3-(2,2-difluoro-ethyl)-pyrrolo[3,2-b]pyridin-1-yl]-amide,
4-Methyl-2-(4-methyl-thiazol-2-yl)-pyrimidine-5-carboxylic acid [3-(2,2,2-trifluoro-ethyl)-pyrrolo[3,2-c]pyridin-1-yl]-amide,
4-Methyl-2-(4-methyl-thiazol-2-yl)-pyrimidine-5-carboxylic acid [3-(2,2-difluoro-ethyl)-pyrrolo[3,2-c]pyridin-1-yl]-amide,
4-Methyl-2-(4-methyl-thiazol-2-yl)-pyrimidine-5-carboxylic acid [3-(2,2,2-trifluoro-ethyl)-pyrrolo[2,3-c]pyridin-1-yl]-amide,
4-Methyl-2-(4-methyl-thiazol-2-yl)-pyrimidine-5-carboxylic acid [3-(2,2-difluoro-ethyl)-pyrrolo[2,3-c]pyridin-1-yl]-amide,
4-Methyl-2-(4-methyl-thiazol-2-yl)-pyrimidine-5-carboxylic acid [3-(2,2,2-trifluoro-ethyl)-pyrrolo[2,3-b]pyridin-1-yl]-amide,
4-Methyl-2-(4-methyl-thiazol-2-yl)-pyrimidine-5-carboxylic acid [3-(2,2-difluoro-ethyl)-pyrrolo[2,3-b]pyridin-1-yl]-amide,
4-Methyl-2-thiazol-2-yl-pyrimidine-5-carboxylic acid (5-trifluoromethyl-pyrrolo[3,2-b]pyridin-1-yl)-amide,
4-Methyl-2-thiazol-2-yl-pyrimidine-5-carboxylic acid (5-difluoromethyl-pyrrolo[3,2-b]pyridin-1-yl)-amide,
4-Methyl-2-thiazol-2-yl-pyrimidine-5-carboxylic acid (3-trifluoromethyl-pyrrolo[3,2-b]pyridin-1-yl)-amide,
4-Methyl-2-thiazol-2-yl-pyrimidine-5-carboxylic acid (3-difluoromethyl-pyrrolo[3,2-b]pyridin-1-yl)-amide,
4-Methyl-2-thiazol-2-yl-pyrimidine-5-carboxylic acid [3-(2,2,2-trifluoro-ethyl)-pyrrolo[3,2-b]pyridin-1-yl]-amide,
4-Methyl-2-thiazol-2-yl-pyrimidine-5-carboxylic acid [3-(2,2-difluoro-ethyl)-pyrrolo[3,2-b]pyridin-1-yl]-amide,
4-Methyl-2-thiazol-2-yl-pyrimidine-5-carboxylic acid [3-(2,2,2-trifluoro-ethyl)-pyrrolo[3,2-c]pyridin-1-yl]-amide,
4-Methyl-2-thiazol-2-yl-pyrimidine-5-carboxylic acid [3-(2,2-difluoro-ethyl)-pyrrolo[3,2-c]pyridin-1-yl]-amide,
4-Methyl-2-thiazol-2-yl-pyrimidine-5-carboxylic acid [3-(2,2,2-trifluoro-ethyl)-pyrrolo[2,3-c]pyridin-1-yl]-amide,
4-Methyl-2-thiazol-2-yl-pyrimidine-5-carboxylic acid [3-(2,2-difluoro-ethyl)-pyrrolo[2,3-c]pyridin-1-yl]-amide,
4-Methyl-2-thiazol-2-yl-pyrimidine-5-carboxylic acid [3-(2,2,2-trifluoro-ethyl)-pyrrolo[2,3-b]pyridin-1-yl]-amide,
4-Methyl-2-thiazol-2-yl-pyrimidine-5-carboxylic acid [3-(2,2-difluoro-ethyl)-pyrrolo[2,3-b]pyridin-1-yl]-amide,
2-(4-Chloro-thiazol-2-yl)-4-methyl-pyrimidine-5-carboxylic acid (5-trifluoromethyl-pyrrolo[3,2-b]pyridin-1-yl)-amide,
2-(4-Chloro-thiazol-2-yl)-4-methyl-pyrimidine-5-carboxylic acid (5-trifluoromethyl-pyrrolo[3,2-b]pyridin-1-yl)-amide,
2-(4-Chloro-thiazol-2-yl)-4-methyl-pyrimidine-5-carboxylic acid (3-trifluoromethyl-pyrrolo[3,2-b]pyridin-1-yl)-amide,
4-Methyl-2-(4-methyl-thiazol-2-yl)-pyrimidine-5-carboxylic acid (3-difluoromethyl-pyrrolo[3,2-b]pyridin-1-yl)-amide,
2-(4-Chloro-thiazol-2-yl)-4-methyl-pyrimidine-5-carboxylic acid [3-(2,2,2-trifluoro-ethyl)-pyrrolo[3,2-b]pyridin-1-yl]-amide,
2-(4-Chloro-thiazol-2-yl)-4-methyl-pyrimidine-5-carboxylic acid [3-(2,2-difluoro-ethyl)-pyrrolo[3,2-b]pyridin-1-yl]-amide,
2-(4-Chloro-thiazol-2-yl)-4-methyl-pyrimidine-5-carboxylic acid [3-(2,2,2-trifluoro-ethyl)-pyrrolo[3,2-c]pyridin-1-yl]-amide,
2-(4-Chloro-thiazol-2-yl)-4-methyl-pyrimidine-5-carboxylic acid [3-(2,2-difluoro-ethyl)-pyrrolo[3,2-c]pyridin-1-yl]-amide,
2-(4-Chloro-thiazol-2-yl)-4-methyl-pyrimidine-5-carboxylic acid [3-(2,2,2-trifluoro-ethyl)-pyrrolo[2,3-c]pyridin-1-yl]-amide,
2-(4-Chloro-thiazol-2-yl)-4-methyl-pyrimidine-5-carboxylic acid [3-(2,2-difluoro-ethyl)-pyrrolo[2,3-c]pyridin-1-yl]-amide,
2-(4-Chloro-thiazol-2-yl)-4-methyl-pyrimidine-5-carboxylic acid [3-(2,2,2-trifluoro-ethyl)-pyrrolo[2,3-b]pyridin-1-yl]-amide,
2-(4-Chloro-thiazol-2-yl)-4-methyl-pyrimidine-5-carboxylic acid [3-(2,2-difluoro-ethyl)-pyrrolo[2,3-b]pyridin-1-yl]-amide,
4-Methyl-[2,2']bipyrimidinyl-5-carboxylic acid (5-trifluoromethyl-pyrrolo[3,2-b]pyridin-1-yl)-amide,
4-Methyl-[2,2']bipyrimidinyl-5-carboxylic acid (5-difluoromethyl-pyrrolo[3,2-b]pyridin-1-yl)-amide,
4-Methyl-[2,2']bipyrimidinyl-5-carboxylic acid (3-trifluoromethyl-pyrrolo[3,2-b]pyridin-1-yl)-amide,
4-Methyl-[2,2']bipyrimidinyl-5-carboxylic acid (3-difluoromethyl-pyrrolo[3,2-b]pyridin-1-yl)-amide,
4-Methyl-[2,2']bipyrimidinyl-5-carboxylic acid [3-(2,2,2-trifluoro-ethyl)-pyrrolo[3,2-b]pyridin-1-yl]-amide,
4-Methyl-[2,2']bipyrimidinyl-5-carboxylic acid [3-(2,2-difluoro-ethyl)-pyrrolo[3,2-b]pyridin-1-yl]-amide,
4-Methyl-[2,2']bipyrimidinyl-5-carboxylic acid (3-trifluoromethyl-pyrrolo[3,2-c]pyridin-1-yl)-amide,
4-Methyl-[2,2']bipyrimidinyl-5-carboxylic acid (3-difluoromethyl-pyrrolo[3,2-c]pyridin-1-yl)-amide,
4-Methyl-[2,2']bipyrimidinyl-5-carboxylic acid [3-(2,2,2-trifluoro-ethyl)-pyrrolo[3,2-c]pyridin-1-yl]-amide,
4-Methyl-[2,2']bipyrimidinyl-5-carboxylic acid [3-2,2-difluoro-ethyl)-pyrrolo[3,2-c]pyridin-1-yl]-amide,
4-Methyl-[2,2']bipyrimidinyl-5-carboxylic acid (3-trifluoromethyl-pyrrolo[2,3-c]pyridin-1-yl)-amide, 4-Methyl-[2,2']bipyrimidinyl-5-carboxylic acid (3-difluoromethyl-pyrrolo[2,3-c]pyridin-1-yl)-amide,
4-Methyl-[2,2']bipyrimidinyl-5-carboxylic acid [3-(2,2,2-trifluoro-ethyl)-pyrrolo[2,3-c]pyridin-1-yl]-amide,
4-Methyl-[2,2']bipyrimidinyl-5-carboxylic acid [3-(2,2-difluoro-ethyl)-pyrrolo[2,3-c]pyridin-1-yl]-amide,
4-Methyl-[2,2']bipyrimidinyl-5-carboxylic acid (3-trifluoromethyl-pyrrolo[2,3-b]pyridin-1-yl)-amide,
4-Methyl-[2,2']bipyrimidinyl-5-carboxylic acid (3-difluoromethyl-pyrrolo[2,3-b]pyridin-1-yl)-amide,
4-Methyl-[2,2']bipyrimidinyl-5-carboxylic acid [3-(2,2,2-trifluoro-ethyl)-pyrrolo[2,3-b]pyridin-1-yl]-amide,
4-Methyl-[2,2']bipyrimidinyl-5-carboxylic acid [3-(2,2-difluoro-ethyl)-pyrrolo[2,3-b]pyridin-1-yl]-amide,
2-(3-Fluoro-phenyl)-4-methyl-pyrimidine-5-carboxylic acid (5-trifluoro methyl-pyrrolo[3,2-b]pyridin-1-yl)-amide,
2-(3-Fluoro-phenyl)-4-methyl-pyrimidine-5-carboxylic acid (5-difluoromethyl -pyrrolo[3,2-b]pyridin-1-yl)-amide,
2-(3-Fluoro-phenyl)-4-methyl-pyrimidine-5-carboxylic acid (3-trifluoro methyl-pyrrolo[3,2-b]pyridin-1-yl)-amide,
2-(3-Fluoro-phenyl)-4-methyl-pyrimidine-5-carboxylic acid (3-trifluoro methyl-pyrrolo[3,2-c]pyridin-1-yl)-amide,
2-(3-Fluoro-phenyl)-4-methyl-pyrimidine-5-carboxylic acid (3-trifluoro methyl-pyrrolo[2,3-c]pyridin-1-yl)-amide,
2-(3-Fluoro-phenyl)-4-methyl-pyrimidine-5-carboxylic acid (3-trifluoromethyl-pyrrolo[2,3-b]pyridin-1-yl)-amide,
2-(3-Fluoro-phenyl)-4-methyl-pyrimidine-5-carboxylic acid [3-(2,2-difluoro-ethyl)-pyrrolo[3,2-b]pyridin-1-yl]-amide,
2-(3-Fluoro-phenyl)-4-methyl-pyrimidine-5-carboxylic acid [3-(2,2,2-trifluoro-ethyl) -pyrrolo[3,2-b]pyridin-1-yl]-amide,
2-(3-Fluoro-phenyl)-4-methyl-pyrimidine-5-carboxylic acid [3-(2,2,2-trifluoro-ethyl)-pyrrolo[3,2-c]pyridin-1-yl]-amide,
2-(3-Fluoro-phenyl)-4-methyl-pyrimidine-5-carboxylic acid [3-(2,2,2-trifluoro-ethyl)-pyrrolo[2,3-c]pyridin-1-yl]-amide,
4-Methyl-2-pyridin-2-yl-pyrimidine-5-carboxylic acid (3-difluoromethyl-indol-1-yl)-amide,
2-(4-Chloro-thiazol-2-yl)-4-methyl-pyrimidine-5-carboxylic acid (3-difluoromethyl-indol-1-yl)-amide, and
4-Methyl-2-thiazol-2-yl-pyrimidine-5-carboxylic acid (3-difluoromethyl-indol-1-yl)-amide.

In Vitro Assay Protocols to Identify Inhibitors of Hematopoietic PGD2 Synthase The compounds of the present invention can be tested for enzymatic inhibiting activity against PGD2 Synthase according to either one of the following assays.

Assay 1: Fluorescence Polarization Assay
As described in PCT publication WO 2004/016223, Example II.

Assay 2: Enzyme Immunoassay (EIA) Method
I. Assay Solutions
  a. Preparation of 0.1M $K_2HPO_4/KH_2PO_4$ buffer (pH 7.4)
    Prepare 0.1 M $KH_2PO_4$ from 1M $KH_2PO_4$ (Sigma, Cat# P-8709)
    Prepare 0.1 M $K_2HPO_4$ from powder of $K_2HPO_4$ (Fisher, BP363-500)
    Mix 0.1 M $K_2HPO_4$ with 0.1 M $KH_2PO_4$ to adjust pH to 7.4.
  b. Preparation of 0.5% γ-globulin
    Add 0.1 g of γ-globulin (Sigma, Cat# G-5009) to 20 mL 0.1 M $K_2HPO_4/KH_2PO_4$ buffer (pH 7.4) and make 1-mL/vial aliquots and store in −80° C.
  c. Preparation of 100 mM GSH
    Add 307 mg of GSH (Sigma, Cat# G-6529) to 10 mL 0.1 M $K_2HPO_4/KH_2PO_4$ buffer (pH 7.4) and store at −80° C.
  d. Preparation of Reaction buffer:
    198 mL of 0.1M $K_2HPO_4/KH_2PO_4$ buffer (pH 7.4)
    2 mM GSH—Prepared from 100 mM GSH
    0.4 g Glycerol
    2 mL of 0.5% γ-globulin
    Add 0.4 g of glycerol and 2 mL of 0.5% γ-globulin to 198 mL of 0.1 M $K_2HPO_4/KH_2PO_4$ buffer (pH7.4).
    Add 0.4 mL of 100 mM GSH to 19.6 mL reaction buffer before the assay (enough for two 96-well plates).
  e. Preparation of $FeCl_2$/citric acid stopping solution: (8 mg/mL $FeCl_2$, 0.1 M citric acid)
    Add 40 mg fresh $FeCl_2$ (IGN, Cat# 158046) to 5 mL 0.1 M citric acid (Sigma, Cat# C0759).
  f. Preparation of MOX reagent:
    10% EtOH—Add 1 mL of EtOH to 9 mL of ultra pure $H_2O$
    Dissolve 0.1 g of methoxyl amine (Cayman, Cat# 400036/) in 10% EtOH (10 mL).
    Add 0.82 g of sodium acetate (Cayman, Cat#400037) to MOX solution and dissolve.
II. Materials and Method
  Dimethylsulfoxide (DMSO; Sigma; Cat# D2650)
  Prostaglandin D2-MOX express EIA kit (Caymen Chemical, Catalog No. 500151)
  Before the assay, cool down 10 mL of acetone in polypropylene tubes and empty 96 well plates in ice. All the procedures except compound dilution are performed on ice.
III. Compound Dilution
  1. Dilute compound in DMSO

| Vol of DMSO stock solution (μL) | DMSO (μL) | Compound concentration (mM) |
|---|---|---|
| 4 μL of 10 mM | 6 μL | 4 |
| 3 μL of 4 mM | 6 μL | 1.3333 |
| 3 μL of 1.33 mM | 6 μL | 0.4444 |
| 3 μL of 0.44 mM | 6 μL | 0.1481 |
| 3 μL of 0.148 mM | 6 μL | 0.0494 |
| 3 μL of 0.049 mM | 6 μL | 0.0165 |
| 3 μL of 0.016 mM | 6 μL | 0.0055 |

2. Dilute 2 μL of each above concentration of compound to 38 μL of reaction buffer in 96-well plates and mix.
IV. Enzyme and Substrate Solution Preparation
  1 Preparation of 0.39 ng/μL enzyme solution (0.35 ng/μL at final after compound addition).
    Mix 4 μL of 4 mg/mL human h-PGDS with 396 μL of reaction buffer (to give enzyme concentration 40 μg/mL). Add 46.8 μL of 40 μg/mL h-PGDS to 4.753 mL of reaction buffer to give a total volume of 4.8 mL
  2. Preparation of Substrate Solution (PGH2): Add 0.375 mL of 0.1 mg/mL of PGH2 to 1.625 mL acetone.
V. Enzyme Reaction:
  1. Add 60 μL of enzyme solution to compound well and positive control (without compound) in U-bottom polypropylene plate on ice.
  2. Add 60 μL of reaction buffer and 6.6 μL of 5% DMSO in reaction buffer into negative control wells in the plate.
  3. Add 6.6 μL of diluted compound in reaction buffer to the compound wells and mix.
  4. Add 6.6 μL of 5% DMSO in reaction buffer to the positive control well.
  5. Incubate the plate in ice for at least 30 min.

6. Add 20 µL of substrate (PGH2) solution to compound, negative and positive control wells in the U-bottom 96 well plate on ice.
7. Dry the plate in cold room for about 25-28 min.
8. Pipette 45 µL of enzyme solution (above) into 96-wells with dried PGH2 and mix 3 times. Incubate on the ice for 1 min.
9. Add 45 µL of FeCl$_2$ solution into each wells and mix.
10. Add 90 µL of MOX solution and mix.
11. Incubate for 30 min at 60° C.
12. Dilute the samples 2500× with EIA buffer.

VI. EIA Assay

Perform the assay according to the procedure in EIA kit provided by Cayman. Total PGD2 levels (pg/mL) were determined in the samples by EIA kits (Caymen Chemical, Catalog No. 500151)

Calculate Amount of PGD2 as Below

Calculated % Positive control according to the equation below;

% Positive control=(Compound value−Negative control)/(Positive value−Negative control value)× 100.

$$\% \text{ Positive control} = \frac{(\text{Compound value} - \text{Negative control})}{(\text{Positive value} - \text{Negative control value})} \times 100$$

Compound value=PGD2 levels (pg/mL) obtained from the standard curve in EIA assay for the samples with compound Negative control value=PGD2 levels (pg/mL) obtained from the standard curve in EIA assay for the samples without enzyme Positive control value=PGD2 levels (pg/mL) obtained from the standard curve in EIA assay for the samples with enzyme but without compound IC$_{50}$s are determined by excel fit to get the x value when y=1/2Ymax using 4 parameter logistic model for the IC$_{50}$ curves.

Results

Compounds within the scope of the invention produce 50% inhibition in the Fluorescence Polarization Assay or the EIA assay at concentrations within the range of about 1 nanomolar to about 30 micromolar, particularly about 1 nanomolar to about 1 micromolar, and more particularly about 1 nanomolar to about 100 nanomolar. IC$_{50}$s obtained by EIA assay for some of the examples are shown at the end of each of those examples.

The present invention may be embodied in other specific forms without departing from the spirit or essential attributes thereof.

We claim:

1. A compound of formula (I):

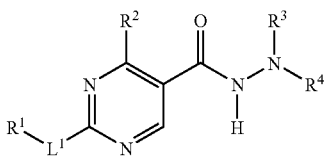

(I)

wherein:

R$^1$ is (C$_1$-C$_6$)-alkyl optionally substituted one or more times independently by halo, hydroxy, (C$_1$-C$_6$)-alkoxy, or (C$_1$-C$_4$)-haloalkoxy, or (C$_3$-C$_6$)-cycloalkyl, aryl or heteroaryl, each of which is optionally substituted one or more times independently by halo, (C$_1$-C$_6$)-alkyl, hydroxy, (C$_1$-C$_6$)-alkoxy, (C$_1$-C$_4$)-haloalkyl or (C$_1$-C$_4$)-haloalkoxy;

R$^2$ is hydrogen or (C$_1$-C$_4$)-alkyl optionally substituted one or more times by halogen;

R$^3$ is hydrogen, alkyl, aryl or heteroaryl,

R$^4$ is cycloalkyl, aryl, heterocyclyl, heteroaryl, heteroarylsulfonyl, —C(=O)—NY$^1$Y$^2$, —C(=S)—NY$^1$Y$^2$, R$^5$, —C(=O)—R$^5$ or —C(=S)—R$^5$, wherein the aryl, heteroaryl or heterocyclyl moiety is optionally substituted one or more times independently by R$^6$, or R$^3$ and R$^4$ together with the nitrogen atom to which they are attached form heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, each of which is optionally substituted one or more times independently by R$^6$;

R$^5$ is cycloalkyl, cycloalkenyl, aryl, heteroaryl, heterocyclyl, heterocyclenyl, or multicyclic alkaryl, each of which is optionally substituted one or more times independently by R$^6$;

L$^1$ is a bond, —O—, —C(=O)—, —NH—C(=O)—, or (C$_1$-C$_2$)-alkylene optionally substituted one or more times by halo;

R$^6$ is oxo, cyano, nitro, halo, hydroxy, carboxy, Y$^1$Y$^2$N—, Y$^1$Y$^2$N—C(=O)—, Y$^1$Y$^2$N—SO$_2$—, acyl, acyloxy, alkyl, alkenyl, alkynyl, alkoxy, alkoxycarbonyl, alkylthio, alkylsulfinyl, or alkylsulfonyl, each of which is optionally substituted one or more times independently by:

acyloxy, halo, alkoxy, haloalkoxy, hydroxy, carboxy, alkoxycarbonyl,

Y$^1$Y$^2$N—, Y$^1$Y$^2$N—C(=O)—, Y$^1$Y$^2$N—SO$_2$—, aryl, aryloxy, aroyl, heteroaryl, heteroaryloxy, heteroaroyl, heterocyclyl, heterocyclenyl, cycloalkyl, cycloalkenyl, or multicyclic alkaryl, each of which is optionally substituted one or more times independently by alkyl, halo, haloalkyl, alkoxy, haloalkoxy, hydroxy, amino, alkylamino, dialkylamino, carboxy, or alkoxycarbonyl, or aryl, heteroaryl, aroyl, heteroaroyl, aryloxy, heteroaryloxy, heterocyclyl, heterocyclenyl, cycloalkyl, cycloalkenyl, or multicyclic alkaryl, each of which is optionally substituted one or more times independently by alkyl, haloalkyl, halo, alkoxy, haloalkoxy, hydroxy, carboxy, alkoxycarbonyl, Y$^1$Y$^2$N—, or Y$^1$Y$^2$N—SO$_2$—, wherein the heterocyclyl, heterocyclenyl, cycloalkyl, cycloalkenyl, or multicyclic alkaryl moiety of R$^6$ is also optionally substituted one or more times independently by oxo;

Y$^1$ and Y$^2$ are each independently:

hydrogen, alkylsulfonyl, aroyl, heteroaroyl, or alkyl optionally substituted one or more times independently by hydroxy, carboxy, halo, amino, alkylamino, dialkylamino, alkoxy, heterocyclyl, aryl or heteroaryl, or Y$^1$ and Y$^2$ together with the nitrogen atom to which they are attached form heterocyclyl;

or an N-oxide thereof, or a pharmaceutically acceptable salt thereof.

2. The compound according to claim 1, wherein R$^1$ is aryl or heteroaryl, each of which is optionally substituted one or more times independently by halo, (C$_1$-C$_6$)-alkyl, hydroxy, (C$_1$-C$_6$)-alkoxy, (C$_1$-C$_4$)-haloalkyl or (C$_1$-C$_4$)-haloalkoxy, or an N-oxide thereof, or a pharmaceutically acceptable salt thereof.

3. The compound according to claim 1, wherein $R^1$ is phenyl or five or six membered heteroaryl, each of which is optionally substituted one or more times independently by halo, $(C_1-C_6)$-alkyl, hydroxy, or $(C_1-C_6)$-alkoxy, or an N-oxide thereof, or a pharmaceutically acceptable salt thereof.

4. The compound according to claim 1, wherein $R^1$ is phenyl, pyridyl, pyrimidinyl, thiazolyl, or oxadiazolyl, each of which is optionally substituted one or more times independently by halo, $(C_1-C_6)$-alkyl, hydroxy, or $(C_1-C_6)$-alkoxy, or an N-oxide thereof, or a pharmaceutically acceptable salt thereof.

5. The compound according to claim 1, wherein $R^1$ is phenyl, pyridyl or pyrimidinyl, each of which is optionally substituted independently at the ortho or meta position by halo, $(C_1-C_6)$-alkyl, hydroxy, or $(C_1-C_6)$-alkoxy, or an N-oxide thereof, or a pharmaceutically acceptable salt thereof.

6. The compound according to claim 1, wherein $R^1$ is phenyl optionally substituted independently at the ortho or meta position by halo, or an N-oxide thereof, or a pharmaceutically acceptable salt thereof.

7. The compound according to claim 1, wherein $R^1$ is pyridyl, or an N-oxide thereof, or a pharmaceutically acceptable salt thereof.

8. The compound according to claim 1, wherein $R^2$ is hydrogen, methyl or trifluoromethyl, or an N-oxide thereof, or a pharmaceutically acceptable salt thereof.

9. The compound according to claim 1, wherein $R^2$ is hydrogen, or an N-oxide thereof, or a pharmaceutically acceptable salt thereof.

10. The compound according to claim 1, wherein $R^2$ is methyl, or an N-oxide thereof, or a pharmaceutically acceptable salt thereof.

11. The compound according to claim 1, wherein $L^1$ is a bond, —O—, —C(=O)—, or —NH—C(=O)—, or an N-oxide thereof, or a pharmaceutically acceptable salt thereof.

12. The compound according to claim 1, wherein $L^1$ is a bond, or an N-oxide thereof, or a pharmaceutically acceptable salt thereof.

13. The compound according to claim 1, wherein:
$R^3$ and $R^4$ together with the nitrogen atom to which they are attached form heterocyclyl, heterocyclenyl, arylheterocyclyl, or heteroaryl, each of which is optionally substituted one or more times independently by $R^6$;
$R^6$ is alkoxy, hydroxyl, cycloalkyl, carboxy, cycloalkyl, halo, cyano, alkylsulfonyl, $Y^1Y^2N$—, $Y^1Y^2N$—$SO_2$—,
  alkyl optionally substituted one or more times independently by acyloxy, hydroxy, alkoxycarbonyl, alkoxy, carboxy, aryl, halo, alkylsulfonyl, cyano, $Y^1Y^2N$—, or $Y^1Y^2N$—C(=O)—,
  acyl or aryl, each of which is optionally substituted one or more times independently by halo,
  alkoxycarbonyl optionally substituted one or more times independently by aryl,
  heteroaroyl optionally substituted one or more times independently by alkyl,
  heterocyclyl optionally substituted one or more times by oxo, or
  aryloxy optionally substituted one or more times independently by haloalkyl; and
$Y^1$ and $Y^2$ are each independently hydrogen, alkylsulfonyl, aroyl, or alkyl optionally substituted by morpholinyl, or
$Y^1$ and $Y^2$ together with the nitrogen atom to which they are attached form morpholinyl;
or an N-oxide thereof, or a pharmaceutically acceptable salt thereof.

14. The compound according to claim 1, wherein:
$R^3$ and $R^4$ together with the nitrogen atom to which they are attached form [1,2,4]triazolyl, pyrrolyl, indolyl, pyrrolo[2,3-b]pyridyl, pyrrolo[3,2-b]pyridyl, or pyrrolo[2,3-c]pyridyl, each of which is optionally substituted one or more times independently by $R^6$;
$R^6$ is alkoxy, carboxy, cycloalkyl, halo, cyano, alkylsulfonyl, $Y^1Y^2N$—$SO_2$—,
  alkyl optionally substituted one or more times independently by $Y^1Y^2N$—C(=O)—, hydroxy, alkoxycarbonyl, alkoxy, carboxy, aryl, halo, heterocyclyl, cycloalkyl, alkylsulfonyl, cyano, heterocyclylcarbonyl,
  acyl or aryl, each of which is optionally substituted one or more times independently by halo,
  alkoxycarbonyl optionally substituted one or more times independently by aryl,
  heteroaroyl optionally substituted one or more times independently by alkyl,
  heterocyclyl optionally substituted one or more times by oxo, or
  aryloxy optionally substituted one or more times independently by haloalkyl; and
$Y^1$ and $Y^2$ are each independently hydrogen, or alkyl optionally substituted by morpholinyl, or
$Y^1$ and $Y^2$ together with the nitrogen atom to which they are attached form morpholinyl;
or an N-oxide thereof, or a pharmaceutically acceptable salt thereof.

15. The compound according to claim 1, wherein:
$R^3$ and $R^4$ together with the nitrogen atom to which they are attached form imidazolidinyl, [1,2,4]triazinanyl, piperazinyl, morpholinyl, pyrrolidinyl, 1,2,3,4-tetrahydropyrimidinyl, piperidinyl, oxazolidinyl, 2,3-dihydro-indolyl, octahydro-cyclopenta[c]pyrrolyl, or 3,4-dihydrobenzo[1,4]oxazine, each of which is optionally substituted one or more times independently by $R^6$;
$R^6$ is oxo, alkoxy, carboxy, cycloalkyl, halo, cyano, alkylsulfonyl, $Y^1Y^2N$—$SO_2$—,
  alkyl optionally substituted one or more times independently by hydorxy, alkoxycarbonyl, alkoxy, carboxy, aryl, halo, heterocyclyl, cycloalkyl, alkylsulfonyl, cyano, heterocyclylcarbonyl,
  acyl or aryl, each of which is optionally substituted one or more times independently by halo,
  alkoxycarbonyl optionally substituted one or more times independently by aryl,
  heteroaroyl optionally substituted one or more times independently by alkyl,
  heterocyclyl optionally substituted one or more times by oxo, or
  aryloxy optionally substituted one or more times independently by haloalkyl; and
$Y^1$ and $Y^2$ are each independently hydrogen, or alkyl optionally substituted by morpholinyl, or
$Y^1$ and $Y^2$ together with the nitrogen atom to which they are attached form morpholinyl;
or an N-oxide thereof, or a pharmaceutically acceptable salt thereof.

16. The compound according to claim 1, wherein:
$R^3$ and $R^4$ together with the nitrogen atom to which they are attached form indolyl, optionally substituted one or more times independently by $R^6$;
$R^6$ is $Y^1Y^2N$—$SO_2$—, alkoxycarbonyl, carboxyalkyl, cyano, halo, alkylsulfonyl, alkoxy, or acyl optionally substituted one or more times independently by halo; and
$Y^1$ and $Y^2$ are each independently hydrogen, or alkyl optionally substituted by morpholinyl, or
$Y^1$ and $Y^2$ together with the nitrogen atom to which they are attached form morpholinyl;
or an N-oxide thereof, or a pharmaceutically acceptable salt thereof.

17. The compound according to claim 1, wherein:

$R^5$ is phenyl, pyridyl, or benzo[1,3]dioxolyl, each of which is optionally substituted one or more times independently by $R^6$;

$R^6$ is $Y^1Y^2N$—$SO_2$—, hydroxy, alkoxy, halo, alkyl, or haloalkyl; and $Y^1$ and $Y^2$ are each independently hydrogen or alkyl, or an N-oxide thereof, or a pharmaceutically acceptable salt thereof.

18. The compound according to claim 1, which is

2-Pyridin-3-yl-pyrimidine-5-carboxylic acid (5-fluoro-2-methyl-indol-1-yl)-amide, 2-(3-Fluoro-phenyl)-4-methyl-pyrimidine-5-carboxylic acid (5-fluoro-2-methyl-indol-1-yl)amide, 4-Methyl-2-pyridin-2-yl-pyrimidine-5-carboxylic acid (5-fluoro-3-methyl-indol-1-yl)amide, 2-Pyridin-2-yl-pyrimidine-5-carboxylic acid (5-fluoro-3-methyl-indol-1-yl)-amide, 4-Methyl-2-pyridin-3-yl-pyrimidine-5-carboxylic acid (5-fluoro-3-methyl-indol-1-yl)-amide, 2-Pyridin-3-yl-pyrimidine-5-carboxylic acid (5-fluoro-3-methyl-indol-1-yl)-amide, 2-Pyridin-2-yl-pyrimidine-5-carboxylic acid (5-fluoro-2-methyl-indol-1-yl)-amide, 2-(3-Fluoro-phenyl)-pyrimidine-5-carboxylic acid (5-fluoro-3-methyl-indol-1-yl)-amide, 4-Methyl-2-pyridin-3-yl-pyrimidine-5-carboxylic acid (5-fluoro-2-methyl-indol-1-yl)-amide, 2-(3-Fluoro-phenyl)-4-methyl-pyrimidine-5-carboxylic acid (5-fluoro-3-methyl-indol-1-yl)-amide, 2-(3-Fluoro-phenyl)-pyrimidine-5-carboxylic acid (5-fluoro-2-methyl-indol-1-yl)amide, 4-Methyl-2-pyridin-2-yl-pyrimidine-5-carboxylic acid (5-fluoro-2-methyl-indol-1-yl)-amide, 2-(3-Fluoro-phenyl)-4-methyl-pyrimidine-5-carboxylic acid (5-fluoro-3,3-dimethyl-2,3-dihydro-indol-1-yl)-amide, 2-(3-Fluoro-phenyl)-4-methyl-pyrimidine-5-carboxylic acid [3-(2,2,2-trifluoro-acetyl)-indol-1-1yl]-amide, 4-Methyl-2-pyridin-2-yl-pyrimidine-5-carboxylic acid (5-fluoro-3,3-dimethyl-2,3-dihydro-indol-1-yl)-amide, 4-Methyl-2-pyridin-3-yl-pyrimidine-5-carboxylic acid (5-fluoro-3,3-dimethyl-2,3-dihydro-indol-1-yl)-amide, 2-(3-Fluoro-phenyl)-4-methyl-pyrimidine-5-carboxylic acid (2,3-dimethyl-indol-1-yl)-amide, 2-(3-Fluoro-phenyl)-4-methyl-pyrimidine-5-carboxylic acid (5-chloro-2-methyl-indol-1-yl)-amide, 2-(3-Fluoro-phenyl)-4-methyl-pyrimidine-5-carboxylic acid (5-bromo-indol-1-yl)-amide, 3-Oxo-4-[(2-phenyl-pyrimidine-5-carbonyl)-amino]-piperazine-1-carboxylic acid benzyl ester, 2-(3-Fluorophenyl)pyrimidine-5-carboxylic acid-(3-dimethylsulfamoyl-5-fluoro-indol-1-yl)amide, 2-(3-Fluorophenyl)-4-methylpyrimidine-5-carboxylic acid-(3-dimethylsulfamoyl-5-fluoroindol-1-yl)amide, 2-(3-Fluorophenyl)pyrimidine-5-carboxylicacid-[5-fluoro-3-(morpholine-4-sulfonyl)indol-1-yl]amide, 2-(3-Fluorophenyl)-4-methylpyrimidine-5-carboxylic acid-[5-fluoro-3-(morpholine-4-sulfonyl) indol-1-yl]amide, 2-(3-Fluorophenyl)pyrimidine-5-carboxylic acid-[5-fluoro-3-sulfamoylindol-1-yl]amide, 2-(3-Fluorophenyl)pyrimidine-5-carboxylic acid-[5-fluoro-3-methylsulfamoyl]indol-1-yl]amide, 2-(3-Fluorophenyl)pyrimidine-5-carboxylic acid-[5-fluoro-3-(2-morpholin-4-ylethylsulfamoyl)indol-1-yl]amide, 2-(3-Fluorophenyl)-4-methylpyrimidine-5-carboxylic acid-[5-fluoro-3-methylsulfamoyl]indol-1-yl]amide, 2-(3-Fluorophenyl)-4-methylpyrimidine-5-carboxylic acid-{5-fluoro-[(3-tetrahydropyran-4-ylmethyl)sulfamoyl]indol-1-yl}amide, 2-(3-Fluorophenyl)-4-methylpyrimidine-5-carboxylic acid-[5-fluoro-3-(2-morpholin-4-ylethylsulfamoyl)indol-1-yl]amide, 2-(3-Fluorophenyl)pyrimidine-5-carboxylic acid-(4-fluoroindol-1-yl)amide, 2-(3-Fluorophenyl)-4-methylpyrimidine-5-carboxylic acid-(4-fluoroindol-1-yl)amide, 2-(Pyridin-2-yl)-pyrimidine-5-carboxylic acid-(4-fluoroindol-1-yl)amide, 2-(Pyridin-2-yl)-4-methylpyrimidine-5-carboxylic acid-(4-fluoroindol-1-yl)amide, 2-Phenyl-pyrimidine-5-carboxylic acid [6-(4-fluoro-phenyl)-3-oxo-2,5-dihydro-3H-1,2,4-triazin-4-yl]-amide, 2-(3-Fluoro-phenyl)-pyrimidine-5-carboxylic acid-[4-(2-hydroxy-ethyl)-piperazin-1-yl]-amide, 2-(3-Fluoro-phenyl)-pyrimidine-5-carboxylic acid (6-methyl-3-oxo-2,5-dihydro-3H-[1,2,4] riazine-4-yl)-amide, 2-(3-Fluoro-phenyl)-pyrimidine-5-carboxylic acid[5-fluoro-3-(2-hydroxy-2-methyl-propyl)-indol-1-yl]-amide, 2-(3-Fluoro-phenyl)-4-methyl-pyrimidine-5-carboxylic acid [5-fluoro-3-(2-hydroxy-2-methyl-propyl)-indol-1-yl]-amide, 4-Methyl-2-pyridin-2-yl-pyrimidine-5-carboxylic acid [5-fluoro-3-(2-hydroxy-2-methyl-propyl)-indol-1-yl]-amide, 2-(3-Fluoro-phenyl)-4-methyl-pyrimidine-5-carboxylic acid (3-cyano-5-fluoro-indol-1-yl)-amide, 2-(3-Fluoro-phenyl)-4-methyl-pyrimidine-5-carboxylic acid [5-fluoro-3-(1H-tetrazol-5-yl)-indol-1-yl]-amide, 2-Phenyl-pyrimidine-5-carboxylic acid [1,2,4]triazol-4-ylamide, 2-phenyl-pyrimidine-5-carboxylic acid piperidin-1-ylamide, 2-Phenyl-pyrimidine-5-carboxylic acid N'-(2-fluoro-phenyl)-hydrazide, 2-Phenyl-pyrimidine-5-carboxylic acid N'-ethyl-N'-tolyl-hydrazide, 2-Phenyl-pyrimidine-5-carboxylic acid (3-oxo-morpholin-4-yl)-amide, 2-(5-Methyl-[1,2,4]oxadiazol-3-yl)-pyrimidine-5-carboxylic acid morpholin-4-ylamide, 2-Benzoyl-pyrimidine-5-carboxylic acid morpholin-4-ylamide, 2-Benzoyl-pyrimidine-5-carboxylic acid [4-(2-hydroxyethyl)-piperazin-1-yl]-amide, 2-Phenyl-pyrimidine-5-carboxylic acid N'-methyl-N'-[5-trifluoromethyl-pyridin-2-yl]-hydrazide, 2-Phenyl-pyrimidine-5-carboxylic acid N'-methyl-N'-[4-trifluoromethyl-pyridin-2-yl]-hydrazide, 2-Phenyl-pyrimidine-5-carboxylic acid N'-pyridin-2-yl-hydrazide, 2-Phenyl-pyrimidine-5-carboxylic acid N'-(2-chloro-phenyl)-hydrazide, 2-Phenyl-pyrimidine-5-carboxylic acid N'-(2-oxo-piperidin-1-yl)-amide, 2-Phenyl-pyrimidine-5-carboxylic acid N'-cyclohexyl-N'-methyl-hydrazide, 2-Phenyoxy-pyrimidine-5-carboxylic acid N'-morpholin-4-yl-amide, 2-Phenyl-pyrimidine-5-carboxylic acid (2,6-dimethyl-3-oxo-2,5-dihydro-3H-1,2,4-triazine-4-yl)-amide, 2-Phenyl-pyrimidine-5-carboxylic acid (6-tert-butyl-3-oxo-2,5-dihydro-3H-1,2,4-triazine-4-yl)-amide, 2-Pyridin-2-yl-pyrimidine-5-carboxylic acid (6-methyl-3-oxo-2,5-dihydro-3H-1,2,4-triazine-4-yl)-amide, 2-(3-Fluoro-phenyl)-pyrimidine-5-carboxylic acid (6-tert-butyl-3-oxo-2,5-dihydro-3H-1,2,4-triazine-4-yl)-amide,
3-{2,4-Dioxo-3-[(2-pheyl-pyrimidine-5-carbonyl)-amino]-1,2,3,4-tetrahydro-pyrimidin-5-yl}-propionic acid methyl ester,
3-{2,4-Dioxo-3-[(2-pheyl-pyrimidine-5-carbonyl)-amino]-1,2,3,4-tetrahydro-pyrimidin-5-yl}-propionic acid,
2-Phenyl-pyrimidine-5-carboxylic acid (4-methyl-piperazin-1-yl)-amide,
2-Phenyl-pyrimidine-5-carboxylic acid morpholin-4-ylamide,
2-Phenyl-pyrimidine-5-carboxylic acid [4-(2-hydroxy-ethyl)-piperazin-1-yl]-amide,
2-Phenyl-pyrimidine-5-carboxylic acid ((s)-2-methoxymethyl)-pyrrolidin-1-yl]-amide,
2-Phenyl-pyrimidine-5-carboxylic acid ((R)-2-methoxymethyl)-pyrrolidin-1-yl]-amide,
2-Phenyl-pyrimidine-5-carboxylic acid (5-bromo-2,4-dioxo-3,4-dihydro-2H-pyrimidin-1-yl)-amide,
2-Phenyl-pyrimidine-5-carboxylic acid (3-isopropyl-5-oxo-1,5-dihydro-[1,2,4]triazol-4-yl)-amide,
2-Phenyl-pyrimidine-5-carboxylic acid pyrrol-1-ylamide,
2-Phenyl-pyrimidine-5-carboxylic acid (5-morpholin-4-ylmethyl-2-oxo-oxazolidin-3-yl)-amide,
2-Phenyl-pyrimidine-5-carboxylic acid (4-cyclopentyl-piperazin-1-yl)-amide,
2-Phenyl-pyrimidine-5-carboxylic acid (2-oxo-oxazolidin-3-yl)-amide,
4-Methyl-2-phenyl-pyrimidine-5-carboxylic acid (6-methyl-3-oxo-2,5-dihydro-3H-[1,2,4]triazine-4-yl)-amide,
[N'-(2-Phenyl-pyrimidine-5-carbonyl)-hydrazino]-acetic acid ethyl ester,
2-[N'-(2-Phenyl-pyrimidine-5-carbonyl)-hydrazino]-acetamide,
4-[3-(4-Morpholino)propyl]-1-(2-phenyl-pyrimidine-5-carbonyl)-3-thiosemicarbazide,
2-Phenyl-pyrimidine-5-carboxylic acid (2,3-dihydro-indol-1-yl)-amide,
{4-[2-Phenyl-pyrimidine-5-carbonyl]-amino]-piperazin-1-yl}-acetic acid methyl ester,
2-Phenyl-pyrimidine-5-carboxylic acid (4-cyanomethyl-piperazin-1-yl)-amide,
Acetic acid 2-{4-[(2-phenyl-pyrimidine-5-carbonyl)-amino]-piperazin-1-yl}-ethyl ester,
2-Phenyl-pyrimidine-5-carboxylic acid (4-acetyl-piperazin-1-yl)-amide,
2-Phenyl-pyrimidine-5-carboxylic acid [4-(2-oxo-tetrahydro-furan-3-yl)-piperazin-1-yl]-amide,
2-Phenyl-pyrimidine-5-carboxylic acid [4-(2,2,2-trifluoro-acetyl)-piperazin-1-yl]-amide,
2-Phenyl-pyrimidine-5-carboxylic acid [4-(2-methoxyethyl)-piperazin-1-yl]-amide,
2-Phenyl-pyrimidine-5-carboxylic acid [4-(2-morpholin-4-yl-2-oxo-ethyl)-piperazin-1-yl]-amide,
2-(3-Fluoro-phenyl)-pyrimidine-5-carboxylic acid (2,3-dihydro-indol-1-yl)-amide,
2-(3-Fluoro-phenyl)-pyrimidine-5-carboxylic acid piperadin-1-yl-amide,
2-Phenyl-pyrimidine-5-carboxylic acid piperadin-1-yl-amide,
2-Phenyl-pyrimidine-5-carboxylic acid (hexahydro-cyclopenta[c]pyrrol-2-yl)-amide,
4-Methyl-2-phenyl-pyrimidine-5-carboxylic acid (2,3-dihydro-indol-1-yl)-amide,
2-Phenyl-pyrimidine-5-carboxylic acid pyrrolidin-1-yl-amide,
2-Phenyl-pyrimidine-5-carboxylic acid (2,6-dimethyl-piperadin-1-yl)-amide,
2-(3-Fluoro-phenyl)-pyrimidine-5-carboxylic acid (4-cyclopentyl-piperazin-1-yl)-amide,
2-Phenyl-pyrimidine-5-carboxylic acid (2-methyl-2,3-dihydro-indol-1-yl)-amide,
2-(3-Fluoro-phenyl)-pyrimidine-5-carboxylic acid (2-methyl-2,3-dihydro-indol-1-yl)-amide,
2-Phenyl-pyrimidine-5-carboxylic acid N'-methyl-N'-pyridin-2-yl-hydrazide,
2-Phenyl-pyrimidine-5-carboxylic acid (5-fluoro-indol-1-yl)-amide,
2-Pyridin-2-yl-pyrimidine-5-carboxylic acid (2,3-dihydro-indol-1-yl)-amide,
2-Pyridin-2-yl-pyrimidine-5-carboxylic acid indol-1-yl-amide,
2-(3-Fluoro-phenyl)-pyrimidine-5-carboxylic acid indol-1-yl-amide,
2-(3-Fluoro-phenyl)-4-methyl-pyrimidine-5-carboxylic acid (2,3-dihydro-indol-1-yl)-amide,
2-(3-Fluoro-phenyl)-4-methyl-pyrimidine-5-carboxylic acid (2-methyl-2,3-dihydro-indol-1-yl)-amide,
2-(3-Fluoro-phenyl)-pyrimidine-5-carboxylic acid (2-methyl-indol-1-yl)-amide,
2-(3-Fluoro-phenyl)-4-methyl-pyrimidine-5-carboxylic acid indol-1-ylamide,
4-Methyl-2-pyridin-2-yl-pyrimidine-5-carboxylic acid (2,3-dihydro-indol-1-yl)-amide,
4-Methyl-2-pyridin-2-yl-pyrimidine-5-carboxylic acid indol-1-ylamide,
2-(3-Fluoro-phenyl)-pyrimidine-5-carboxylic acid (5-methanesulfonyl-indol-1-yl)-amide,
2-(3-Fluoro-phenyl)-pyrimidine-5-carboxylic acid (6-methanesulfonyl-indol-1-yl)-amide,
2-Pyridin-2-yl-pyrimidine-5-carboxylic acid (5-methanesulfonyl-indol-1-yl)-amide,
2-Pyridin-3-yl-pyrimidine-5-carboxylic acid (5-methanesulfonyl-indol-1-yl)-amide,
2-(3-Fluoro-phenyl)-4-methyl-pyrimidine-5-carboxylic acid (5-methanesulfonyl-indol-1-yl)-amide,
2-(3-Fluoro-phenyl)-pyrimidine-5-carboxylic acid pyrrolo[2,3-b]pyridin-1-ylamide,
2-(3-Fluoro-phenyl)-pyrimidine-5-carboxylic acid pyrrolo[3,2-b]pyridin-1-ylamide,
2-(3-Fluoro-phenyl)-pyrimidine-5-carboxylic acid (5-fluoro-indol-1-yl)-amide,
2-(3-Fluoro-phenyl)-4-methyl-pyrimidine-5-carboxylic acid pyrrolo[3,2-b]pyridin-1-ylamide,
2-(3-Fluoro-phenyl)-4-methyl-pyrimidine-5-carboxylic acid pyrrolo[2,3-b]pyridin-1-ylamide,
4-Methyl-2-pyridin-2-yl-pyrimidine-5-carboxylic acid (5-fluoro-indol-1-yl)-amide,
2-Pyridin-2-yl-pyrimidine-5-carboxylic acid (5-fluoro-indol-1-yl)-amide,
2-Pyridin-2-yl-pyrimidine-5-carboxylic acid pyrrolo[2,3-b]pyridine-1-ylamide,
4-Methyl-2-pyridin-2-yl-pyrimidine-5-carboxylic acid pyrrolo[2,3-b]pyridin-1-ylamide,
4-Methyl-2-pyridin-2-yl-pyrimidine-5-carboxylic acid pyrrolo[3,2-b]pyridin-1-ylamide,
2-(3-Fluoro-phenyl)-4-methyl-pyrimidine-5-carboxylic acid pyrrolo[2,3-c]pyridin-1-ylamide,
4-Methyl-2-pyridin-2-yl-pyrimidine-5-carboxylic acid pyrrolo[2,3-c]pyridin-1-ylamide,
4-Methyl-2-pyridin-3-yl-pyrimidine-5-carboxylic acid pyrrolo[3,2-b]pyridin-1-ylamide,
4-Methyl-2-pyridin-3-yl-pyrimidine-5-carboxylic acid (5-fluoro-indol-1-yl)-amide,
2-(3-Fluoro-phenyl)-4-methyl-pyrimidine-5-carboxylic acid (5-fluoro-indol-1-yl)-amide, 2-(3-Fluoro-phenyl)-4-methyl-pyrimidine-5-carboxylic acid (5-methoxy-indol-1-yl)-amide,
2-(3-Fluoro-phenyl)-4-methyl-pyrimidine-5-carboxylic acid (5-cyano-indol-1-yl)-amide,
2-(3-Fluoro-phenyl)-4-methyl-pyrimidine-5-carboxylic acid (4-cyano-indol-1-yl)-amide,
2-(3-Fluoro-phenyl)-4-methyl-pyrimidine-5-carboxylic acid [4-(1H-tetrazol-5-yl)-indol-1-yl]-amide,
1-{[2-(3-Fluoro-phenyl)-4-methyl-pyrimidine-5-carbonyl]-amino}-1H-indol-4-carboxylic acid methyl ester,
1-{[2-(3-Fluoro-phenyl)-4-methyl-pyrimidine-5-carbonyl]-amino}-1H-indol-4-carboxylic acid,
2-(3-Fluoro-phenyl)-4-methyl-pyrimidine-5-carboxylic acid (3-cyanomethyl-indol-1-yl)-amide,
4-Methyl-2-pyridin-2-yl-pyrimidine-5-carboxylic acid (5-methoxy-indol-1-yl)-amide,
2-(3-Fluoro-phenyl)-4-methyl-pyrimidine-5-carboxylic acid [3-(1H-tetrazol-5-ylmethyl)-indol-1-yl]-amide,
2-(2-Phenyl-pyrimidine-5-carbonyl)-1-hydrazinecarboxamide,
2-(2-Phenyl-pyrimidine-5-carbonyl)-1-hydrazine-1-carbothioamide,
2-Phenyl-pyrimidine-5-carboxylic acid (2,4-dioxo-imidazolidin-1-yl)-amide,
2-Phenyl-pyrimidine-5-carboxylic acid (6-methyl-3-oxo-2,5-dihydro-3H-[1,2,4]riazine-4-yl)-amide,
2-Phenyl-pyrimidine-5-carboxylic acid N'-phenyl-hydrazide,
Pyridine-2-carboxylic acid N'-(2-phenyl-pyrimidine-5-carbonyl)-hydrazide,
4-[N'-(2-Phenyl-pyrimidine-5-carbonyl)-hydrazino]-benzenesulfonamide,
3-Hydroxy-benzoic acid N'-(2-phenyl-pyrimidine-5-carbonyl)-hydrazide,
Benzo[1,3]dioxo-5-carboxylic acid N'-(phenyl-pyrimidine-5-carbonyl)-hydrazide,
3,4-Dimethoxy-benzoic acid N'-(phenyl-pyrimidine-5-carbonyl)-hydrazide,
2-Phenyl-pyrimidine-5-carboxylic acid N'-methyl-N'-phenyl-hydrazide,
2-(3-Fluoro-phenyl)-4-methyl-pyrimidine-5-carboxylic acid (5-methoxy-3-methyl-indol-1-yl)-amide,
2-(3-Methoxy-phenyl)-pyrimidine-5-carboxylic acid (6-methyl-3-oxo-2,5-dihydro-3H-[1,2,4]triazine-4-yl)-amide,
2-(2-Methoxy-phenyl)-pyrimidine-5-carboxylic acid (6-methyl-3-oxo-2,5-dihydro-3H-[1,2,4]triazine-4-yl)-amide,
2-(4-Methoxy-phenyl)-pyrimidine-5-carboxylic acid (6-methyl-3-oxo-2,5-dihydro-3H-[1,2,4]triazine-4-yl)-amide,
2-(3-Hydroxy-phenyl)-pyrimidine-5-carboxylic acid (6-methyl-3-oxo-2,5-dihydro-3H-[1,2,4]triazine-4-yl)-amide,
2-(2-Hydroxy-phenyl)-pyrimidine-5-carboxylic acid (6-methyl-3-oxo-2,5-dihydro-3H-[1,2,4]triazine-4-yl)-amide,
2-(4-Hydroxy-phenyl)-pyrimidine-5-carboxylic acid (6-methyl-3-oxo-2,5-dihydro-3H-[1,2,4]triazine-4-yl)-amide,
4-Methyl-[2,2']bipyrimidinyl-5-carboxylic acid (5-fluoro-3-methyl-indol-1-yl)-amide,
2-Thiazol-2-yl-pyrimidine-5-carboxylic acid (5-fluoro-3-methyl-indol-1-yl)-amide,
4-Methyl-2-thiazol-2-yl-pyrimidine-5-carboxylic acid (5-fluoro-3-methyl-indol-1-yl)-amide,
[2,2']Bipyrimidinyl-5-carboxylic acid (5-fluoro-3-methyl-indol-1-yl)-amide,
2-(3-Fluoro-phenyl)-4-methyl-pyrimidine-5-carboxylicacid(3chloro-5-fluoro-indol-1-yl)-amide,
5-Fluoro-1-{[2-(3-fluoro-phenyl)-4-methyl-pyrimidine-5-carbonyl]-amino}-1H-indole-3-carboxylic acid amide,
2-{5-Fluoro-1-[(4-methyl-2-pyridin-2-yl-pyrimidine-5-carbonyl)-amino]-1H-indol-3-yl}-2-methyl-propionic acid,
2-(5-Fluoro-1-{[2-(3-fluoro-phenyl)-4-methyl-pyrimidine-5-carbonyl]-amino}-1H-indol-3-yl)-2-methyl-propionic acid,
2-(3-Fluoro-phenyl)-4-methyl-pyrimidine-5-carboxylic acid [5-fluoro-3-(3-hydroxy-3-methyl-butyl)-indol-1-yl]-amide,
4-Methyl-2-pyridin-2-yl-pyrimidine-5-carboxylic acid [5-fluoro-3-(3-hydroxy-3-methyl-butyl)-indol-1-yl]-amide,
2-(3-Fluoro-phenyl)-4-methyl-pyrimidine-5-carboxylic acid [5-fluoro-3-(2-pyridin-3-yl-ethyl)-indol-1-yl]-amide,
4-Methyl-2-pyridin-2-yl-pyrimidine-5-carboxylic acid (5-fluoro-3-formyl-indol-1-yl)-amide,
5-Fluoro-1-[(4-methyl-2-pyridin-2-yl-pyrimidine-5-carbonyl)-amino]-1H-indole-3-carboxylic acid,
4-Methyl-2-pyridin-2-yl-pyrimidine-5-carboxylic acid (5-fluoro-3-hydroxymethyl-indol-1-yl)-amide,
4-Methyl-[2,2']bipyrimidinyl-5-carboxylic acid [5-fluoro-3-(3-hydroxy-3-methyl-butyl)-indol-1-yl]-amide,
4-Methyl-2-thiazol-2-yl-pyrimidine-5-carboxylic acid [5-fluoro-3-(3-hydroxy-3-methyl-butyl)-indol-1-yl]-amide,
2-(3-Fluoro-phenyl)-4-methyl-pyrimidine-5-carboxylic acid (3-ethyl-5-trifluoromethyl-indol-1-yl)-amide,
4-Methyl-2-pyridin-2-yl-pyrimidine-5-carboxylic acid (3-ethyl-5-trifluoromethyl-indol-1-yl)-amide,
4-Methyl-2-thiazol-2-yl-pyrimidine-5-carboxylic acid (3-ethyl-5-trifluoromethyl-indol-1-yl)-amide,
4-Methyl-[2,2']bipyrimidinyl-5-carboxylic acid (3-ethyl-5-trifluoromethyl-indol-1-yl)-amide,
2-(3-Fluoro-phenyl)-4-methyl-pyrimidine-5-carboxylic acid (3-ethyl-5-trifluoromethoxy-indol-1-yl)-amide,
4-Methyl-2-pyridin-2-yl-pyrimidine-5-carboxylic acid (3-ethyl-5-trifluoromethoxy-indol-1-yl)-amide,
4-Methyl-[2,2']bipyrimidinyl-5-carboxylic acid (3-ethyl-5-trifluoromethoxy-indol-1-yl)-amide,
4-Methyl-2-thiazol-2-yl-pyrimidine-5-carboxylic acid (3-ethyl-5-trifluoromethoxy-indol-1-yl)-amide,
2-(3-Fluoro-phenyl)-4-methyl-pyrimidine-5-carboxylic acid (6-trifluoromethyl-indol-1-yl)-amide,
4-Methyl-2-pyridin-2-yl-pyrimidine-5-carboxylic acid (6-trifluoromethyl-indol-1-yl)-amide,
4-Methyl-2-thiazol-2-yl-pyrimidine-5-carboxylic acid (6-trifluoromethyl-indol-1-yl)-amide,
4-Methyl-[2,2']bipyrimidinyl-5-carboxylic acid (6-trifluoromethyl-indol-1-yl)-amide,
2-(3-Fluoro-phenyl)-4-methyl-pyrimidine-5-carboxylic acid (3-ethyl-5-trifluoromethyl-pyrrolo[3,2-b]pyridin-1-yl)-amide,
4-Methyl-2-pyridin-2-yl-pyrimidine-5-carboxylic acid (3-ethyl-5-trifluoromethyl-pyrrolo[3,2-b]pyridin-1-yl)-amide,
4-Methyl-2-thiazol-2-yl-pyrimidine-5-carboxylic acid (3-ethyl-5-trifluoromethyl-pyrrolo[3,2-b]pyridin-1-yl)-amide,
4-Methyl-[2,2']bipyrimidinyl-5-carboxylic acid (3-ethyl-5-trifluoromethyl-pyrrolo[3,2-b]pyridin-1-yl)-amide,
2-(3-Fluoro-phenyl)-4-methyl-pyrimidine-5-carboxylic acid (5-methoxy-2-methyl-indol-1-yl)-amide,
2-(3-Fluoro-phenyl)-4-methyl-pyrimidine-5-carboxylic acid N',N'-diphenyl-hydrazide
2-(3-Fluoro-phenyl)-4-methyl-pyrimidine-5-carboxylic acid (7-fluoro-3-methyl-indol-1-yl)-amide, 2-(3-Fluoro-phenyl)-4-methyl-pyrimidine-5-carboxylic acid (5-methanesulfonyl-3-methyl-indol-1-yl)-amide,
4-Methyl-2-pyridin-2-yl-pyrimidine-5-carboxylic acid (3-ethyl-pyrrolo[2,3-b]pyridin-1-yl)-amide,
2-(3-Fluoro-phenyl)-4-methyl-pyrimidine-5-carboxylic acid (3-ethyl-pyrrolo[2,3-b]pyridin-1-yl)-amide,
2-(3-Fluoro-phenyl)-4-methyl-pyrimidine-5-carboxylic acid (3-ethyl-pyrrolo[2,3-c]pyridin-1-yl)-amide,
4-Methyl-2-pyridin-2-yl-pyrimidine-5-carboxylic acid (3-ethyl-pyrrolo[2,3-c]pyridin-1-yl)-amide,
2-(3-Fluoro-phenyl)-4-methyl-pyrimidine-5-carboxylic acid (3-methyl-pyrrolo[3,2-b]pyridin-1-yl)-amide,
4-Methyl-2-pyridin-2-yl-pyrimidine-5-carboxylic acid (3-methyl-5-trifluoromethyl-indol-1-yl)-amide,
4-Methyl-2-pyridin-2-yl-pyrimidine-5-carboxylic acid (3-methyl-pyrrolo[3,2-b]pyridin-1-yl)-amide,
2-(3-Fluoro-phenyl)-4-methyl-pyrimidine-5-carboxylic acid (3-methyl-pyrrolo [2,3-c]pyridin-1-yl)-amide,
4-Methyl-2-pyridin-2-yl-pyrimidine-5-carboxylic acid (3-methyl-pyrrolo[2,3-c]pyridin-1-yl)-amide,
4-Methyl-2-pyridin-2-yl-pyrimidine-5-carboxylic acid (3-methyl-pyrrolo[3,2-c]pyridin-1-yl)-amide,
2-(3-Fluoro-phenyl)-4-methyl-pyrimidine-5-carboxylic acid (3-methyl-pyrrolo[3,2-c]pyridin-1-yl)-amide,
2-(3-Fluoro-phenyl)-4-methyl-pyrimidine-5-carboxylic acid (5-nitro-indol-1-yl)-amide,
2-(3-fluoro-phenyl)-4-methyl-pyrimidine-5-carboxylic acid (5-amino-indol-1-yl)-amide,
2-(3-fluoro-phenyl)-4-methyl-pyrimidine-5-carboxylic acid [5-(dimethanesulfonyl)-amino-indol-1-yl]-amide,
2-(3-Fluoro-phenyl)-4-methyl-pyrimidine-5-carboxylic acid (5-benzoylamino-indol-1-yl)-amide,
4-Methyl-2-pyridin-2-yl-pyrimidine-5-carboxylic acid [5-fluoro-3-(1,2,3,6-tetrahydro-pyridin-4-yl)-indol-1-yl]-amide,
2-Pyridin-2-yl-4-trifluoromethyl-pyrimidine-5-carboxylic acid (5-fluoro-3-methyl-indol-1-yl)-amide,
2-(3-Fluoro-phenyl)-4-methyl-pyrimidine-5-carboxylic acid (2-methyl-indol-1-yl)-amide,
2-(3-Fluoro-phenyl)-pyrimidine-5-carboxylic acid (6-fluoro-2,3-dihydro-1,4-benzoxazin-4-yl)-amide,
2-Phenyl-pyrimidine-5-carboxylic acid (6-fluoro-2,3-dihydro-1,4-benzoxazin-4-yl)-amide,
4-Methyl-2-pyridin-2-yl-pyrimidine-5-carboxylic acid (3-ethyl-5-fluoro-pyrrolo[2,3-b]pyridin-1-yl)-amide,
4-Methyl-2-thiazol-2-yl-pyrimidine-5-carboxylic acid (3-ethyl-5-fluoro-pyrrolo[2,3-b]pyridin-1-yl)-amide,
2-(3-Fluoro-phenyl)-4-methyl-pyrimidine-5-carboxylic acid (5-fluoro-pyrrolo[2,3-b]pyridin-1-yl)-amide,
4-Methyl-2-pyridin-2-yl-pyrimidine-5-carboxylic acid (5-fluoro-pyrrolo[2,3-b]pyridin-1-yl)-amide,
4-Methyl-[2,2']bipyrimidinyl-5-carboxylic acid (2-cyclopropyl-5-fluoro-indol-1-yl)-amide,
4-Methyl-2-thiazol-2-yl-pyrimidine-5-carboxylic acid (2-cyclopropyl-5-fluoro-indol-1-yl)-amide,
2-Pyrimidin-2-yl-4-methyl-pyrimidine-5-carboxylic acid (5-methoxyl-indol-1-yl)-amide,
4-Methyl-[2,2']bipyrimidinyl-5-carboxylic acid (5-fluoro-3-methyl-pyrrolo[3,2-b]pyridin-1-yl)-amide,
4-Methyl-2-pyridin-2-yl-pyrimidine-5-carboxylic acid (5-fluoro-3-methyl-pyrrolo[3,2-b]pyridin-1-yl)-amide,
2-(3-Fluoro-phenyl)-4-methyl-pyrimidine-5-carboxylic acid (5-fluoro-3-methyl-pyrrolo[3,2-b]pyridin-1-yl)-amide,
4-Methyl-2-pyridin-2-yl-pyrimidine-5-carboxylic acid (5-methoxy-3-methyl-pyrrolo[3,2-b]pyridin-1-yl)-amide,
2-(3-Fluoro-phenyl)-4-methyl-pyrimidine-5-carboxylic acid (5-methoxy-3-methyl-pyrrolo[3,2-b]pyridin-1-yl)-amide,
4-Methyl-2-(1-oxy-pyridin-2-yl)-pyrimidin-5-carboxylic acid (5-fluoro-3-methyl-indol-1-yl)-amide,
2-(3-Difluoromethyl-phenyl)-pyrimidine-5-carboxylic acid (5-fluoro-3-methyl-indol-1-yl)-amide, or
2-(3-Trifluoromethyl-phenyl)-pyrimidine-5-carboxylic acid (5-fluoro-3-methyl-indol-1-yl)-amide,
or an N-oxide thereof, or a pharmaceutically acceptable salt thereof.

19. The compound according to claim 1, which is:
2-Phenyl-pyrimidine-5-carboxylic acid (4-benzyl-piperazin-1-yl)-amide,
2-Phenyl-pyrimidine-5-carboxylic acid piperazin-1-ylamide,
2-Phenyl-pyrimidine-5-carboxylic acid (4-methanesulfonyl-piperazin-1-yl)-amide,
2-(2-Methyl-thiazol-4-yl)-pyrimidine-5-carboxylic acid morpholin-4-ylamide,
2-Phenyl-pyrimidine-5-carboxylic acid [4-(1-methyl-1H-imidazole-2-carbonyl)-piperazin-1-yl]-amide,
2-Phenyl-pyrimidine-5-carboxylic acid [4-(1-methyl-1H-imidazole-4-carbonyl)-piperazin-1-yl]-amide,
4-[(2-Phenyl-pyrimidine-5-carbonyl)-amino]-piperazine-1-carboxylic acid tert-butyl ester,
2-Phenyl-pyrimidine-5-carboxylic acid [4-(4-trifluoromethyl-phenoxy)-piperidin-1-yl]-amide,
2-(3-Fluoro-phenyl)-pyrimidine-5-carboxylic acid [4-(4-trifluoromethyl-phenoxy)-piperidin-1-yl]-amide,
2-(3-Fluoro-phenyl)-pyrimidine-5-carboxylic acid morpholin-4-ylamide,
2-Phenyl-pyrimidine-5-carboxylic acid indol-1-ylamide,
2-Phenyl-pyrimidine-5-carboxylic acid (4-methoxy-piperidin-1-yl)-amide,
2-(3-Fluoro-phenyl)-4-methyl-pyrimidine-5-carboxylic acid (2-methyl-indol-1-yl)-amide,
2-(3-Fluoro-phenyl)-pyrimidine-5-carboxylic acid (6-fluoro-2,3-dihydro-benzo[1,4]oxazin-4-yl)-amide,
2-Phenyl-pyrimidine-5-carboxylic acid (6-fluoro-2,3-dihydro-benzo[1,4]oxazin-4-yl)-amide,
1-{[2-(3-Fluoro-phenyl)-4-methyl-pyrimidine-5-carbonyl]-amino}-3-(2-morpholin-4-yl-ethyl)-1H-indole-6-carboxylic acid methyl ester,
2-(3-Fluoro-phenyl)-4-methyl-pyrimidine-5-carboxylic acid [5-fluoro-3-(tetrahydro-pyran-4-yl)-indol-1-yl]-amide,
N-methyl-N-(5-fluoro)-indol-3-ylsulfonyl N'-[2-(3-fluoro)-phenyl-pyrimidine-5-carbonyl]-hydrazide,
4-Methyl-2-pyridin-2-yl-pyrimidine-5-carboxylic acid [5-fluoro-3-(tetrahydro-pyran-4-yl)-indol-1-yl]-amide,
4-Methyl-2-pyridin-2-yl-pyrimidine-5-carboxylic acid (5-fluoro-3-methyl-indol-1-yl)-amide,
4-Methyl-2-pyridin-2-yl-pyrimidine-5-carboxylic acid (3-methyl-pyrrolo[3,2-b]pyridin-1-yl)-amide,
4-Methyl-2-(4-methyl-thiazol-2-yl)-pyrimidine-5-carboxylic acid pyrrolo[2,3-b]pyridin-1-ylamide,
4-Methyl-2-(4-methyl-thiazol-2-yl)-pyrimidine-5-carboxylic acid (3-methyl-pyrrolo[2,3-b]pyridin-1-yl)-amide,
4-Methyl-2-(4-methyl-thiazol-2-yl)-pyrimidine-5-carboxylic acid (3-isopropyl-pyrrolo[2,3-b]pyridin-1-yl)-amide,
4-Methyl-2-(4-methyl-thiazol-2-yl)-pyrimidine-5-carboxylic acid (3-difluoromethyl-pyrrolo[2,3-b]pyridin-1-yl)-amide,
4-Methyl-2-(4-methyl-thiazol-2-yl)-pyrimidine-5-carboxylic acid (3-trifluoromethyl-pyrrolo[2,3-b]pyridin-1-yl)-amide,
4-Methyl-2-(4-methyl-thiazol-2-yl)-pyrimidine-5-carboxylic acid (3-methyl-pyrrolo[2,3-c]pyridin-1-yl)-amide, 4-Methyl-2-(4-methyl-thiazol-2-yl)-pyrimidine-5-carboxylic acid pyrrolo[2,3-c]pyridin-1-ylamide,
4-Methyl-2-(4-methyl-thiazol-2-yl)-pyrimidine-5-carboxylic acid (3-isopropyl-pyrrolo[2,3-c]pyridin-1-yl)-amide,
4-Methyl-2-(4-methyl-thiazol-2-yl)-pyrimidine-5-carboxylic acid (3-difluoromethyl-pyrrolo[2,3-c]pyridin-1-yl)-amide,
4-Methyl-2-(4-methyl-thiazol-2-yl)-pyrimidine-5-carboxylic acid (3-trifluoromethyl-pyrrolo[2,3-c]pyridin-1-yl)-amide,
4-Methyl-2-(4-methyl-thiazol-2-yl)-pyrimidine-5-carboxylic acid (3-methyl-pyrrolo[3,2-c]pyridin-1-yl)-amide,
4-Methyl-2-(4-methyl-thiazol-2-yl)-pyrimidine-5-carboxylic acid pyrrolo[3,2-c]pyridin-1-ylamide,
4-Methyl-2-(4-methyl-thiazol-2-yl)-pyrimidine-5-carboxylic acid (3-isopropyl-pyrrolo[3,2-c]pyridin-1-yl)-amide,
4-Methyl-2-(4-methyl-thiazol-2-yl)-pyrimidine-5-carboxylic acid (3-difluoromethyl-pyrrolo[3,2-c]pyridin-1-yl)-amide,
4-Methyl-2-(4-methyl-thiazol-2-yl)-pyrimidine-5-carboxylic acid (3-trifluoromethyl-pyrrolo[3,2-c]pyridin-1-yl)-amide,
4-Methyl-2-thiazol-2-yl-pyrimidine-5-carboxylic acid pyrrolo[2,3-b]pyridin-1-ylamide,
4-Methyl-2-thiazol-2-yl-pyrimidine-5-carboxylic acid (3-methyl-pyrrolo[2,3-b]pyridin-1-yl)-amide,
4-Methyl-2-thiazol-2-yl-pyrimidine-5-carboxylic acid (3-isopropyl-pyrrolo[2,3-b]pyridin-1-yl)-amide,
4-Methyl-2-thiazol-2-yl-pyrimidine-5-carboxylic acid (3-difluoromethyl-pyrrolo[2,3-b]pyridin-1-yl)-amide,
4-Methyl-2-thiazol-2-yl-pyrimidine-5-carboxylic acid (3-trifluoromethyl-pyrrolo[2,3-b]pyridin-1-yl)-amide,
4-Methyl-2-thiazol-2-yl-pyrimidine-5-carboxylic acid pyrrolo[2,3-c]pyridin-1-ylamide,
4-Methyl-2-thiazol-2-yl-pyrimidine-5-carboxylic acid (3-methyl-pyrrolo[2,3-c]pyridin-1-yl)-amide,
4-Methyl-2-thiazol-2-yl-pyrimidine-5-carboxylic acid pyrrolo[2,3-c]pyridin-1-ylamide,
4-Methyl-2-thiazol-2-yl-pyrimidine-5-carboxylic acid (3-isopropyl-pyrrolo[2,3-c]pyridin-1-yl)-amide,
4-Methyl-2-thiazol-2-yl-pyrimidine-5-carboxylic acid (3-difluoromethyl-pyrrolo[2,3-c]pyridin-1-yl)-amide,
4-Methyl-2-thiazol-2-yl-pyrimidine-5-carboxylic acid (3-trifluoromethyl-pyrrolo[2,3-c]pyridin-1-yl)-amide,
4-Methyl-2-thiazol-2-yl-pyrimidine-5-carboxylic acid (3-methyl-pyrrolo[3,2-c]pyridin-1-yl)-amide,
4-Methyl-2-thiazol-2-yl-pyrimidine-5-carboxylic acid pyrrolo[3,2-c]pyridin-1-ylamide,
4-Methyl-2-thiazol-2-yl-pyrimidine-5-carboxylic acid (3-isopropyl-pyrrolo[3,2-c]pyridin-1-yl)-amide,
4-Methyl-2-thiazol-2-yl-pyrimidine-5-carboxylic acid (3-difluoromethyl-pyrrolo[3,2-c]pyridin-1-yl)-amide,
4-Methyl-2-thiazol-2-yl-pyrimidine-5-carboxylic acid (3-trifluoromethyl-pyrrolo[3,2-c]pyridin-1-yl)-amide,
4-Methyl-2-(4-chloro-thiazol-2-yl)-pyrimidine-5-carboxylic acid pyrrolo[2,3-b]pyridin-1-ylamide,
4-Methyl-2-(4-chloro-thiazol-2-yl)-pyrimidine-5-carboxylic acid (3-methyl-pyrrolo[2,3-b]pyridin-1-yl)-amide,
4-Methyl-2-(4-chloro-thiazol-2-yl)-pyrimidine-5-carboxylic acid (3-isopropyl-pyrrolo[2,3-b]pyridin-1-yl)-amide,
4-Methyl-2-(4-chloro-thiazol-2-yl)-pyrimidine-5-carboxylic acid (3-difluoromethyl-pyrrolo[2,3-b]pyridin-1-yl)-amide,
4-Methyl-2-(4-chloro-thiazol-2-yl)-pyrimidine-5-carboxylic acid (3-trifluoromethyl-pyrrolo[2,3-b]pyridin-1-yl)-amide,
4-Methyl-2-(4-chloro-thiazol-2-yl)-pyrimidine-5-carboxylic acid (3-methyl-pyrrolo[2,3-c]pyridin-1-yl)-amide,
4-Methyl-2-(4-chloro-thiazol-2-yl)-pyrimidine-5-carboxylic acid pyrrolo[2,3-c]pyridin-1-ylamide,
4-Methyl-2-(4-chloro-thiazol-2-yl)-pyrimidine-5-carboxylic acid (3-isopropyl-pyrrolo[2,3-c]pyridin-1-yl)-amide,
4-Methyl-2-(4-chloro-thiazol-2-yl)-pyrimidine-5-carboxylic acid (3-difluoromethyl-pyrrolo[2,3-c]pyridin-1-yl)-amide,
4-Methyl-2-(4-chloro-thiazol-2-yl)-pyrimidine-5-carboxylic acid (3-trifluoromethyl-pyrrolo[2,3-c]pyridin-1-yl)-amide,
4-Methyl-2-(4-chloro-thiazol-2-yl)-pyrimidine-5-carboxylic acid (3-methyl-pyrrolo[3,2-c]pyridin-1-yl)-amide,
4-Methyl-2-(4-chloro-thiazol-2-yl)-pyrimidine-5-carboxylic acid pyrrolo[3,2-c]pyridin-1-ylamide,
4-Methyl-2-(4-chloro-thiazol-2-yl)-pyrimidine-5-carboxylic acid (3-isopropyl-pyrrolo[3,2-c]pyridin-1-yl)-amide,
4-Methyl-2-(4-chloro-thiazol-2-yl)-pyrimidine-5-carboxylic acid (3-difluoromethyl-pyrrolo[3,2-c]pyridin-1-yl)-amide,
4-Methyl-2-(4-methyl-thiazol-2-yl)-pyrimidine-5-carboxylic acid (3-trifluoromethyl-pyrrolo[3,2-c]pyridin-1-yl)-amide,
2-(4-Chloro-thiazol-2-yl)-4-methyl-pyrimidine-5-carboxylic acid (5-fluoro-3-methyl-indol-1-yl)-amide,
2-(4-Methyl-thiazol-2-yl)-4-methyl-pyrimidine-5-carboxylic acid (5-fluoro-3-methyl-indol-1-yl)-amide,
2-(3-Fluoro-phenyl)-4-methyl-pyrimidine-5-carboxylic acid (2-methyl-3-oxo-2,3-dihydro-indazol-1-yl)amide,
2-(4-Chloro-thiazol-2-yl)-4-methyl-pyrimidine-5-carboxylic acid(5-fluoro-indol-1-yl)amide)amide,
6-(4-Chloro-thiazol-2-yl)-2-methyl-N-pyrrolo[2,3-c]pyridin-1-yl-nicotinamide,
2-(3-Fluoro-phenyl)-4-methyl-pyrimidine-5-carboxylic acid(5-methyl-4-oxo-4,5-dihydro-pyrrolo[3,2-c]pyridin-1-yl)amide,
4-Methyl-2-(4-methyl-thiazol-2-yl)-pyrimidine-5-carboxylic acid (5-trifluoromethyl-pyrrolo[3,2-b]pyridin-1-yl)-amide,
4-Methyl-2-(4-methyl-thiazol-2-yl)-pyrimidine-5-carboxylic acid (5-difluoromethyl-pyrrolo[3,2-b]pyridin-1-yl)-amide,
4-Methyl-2-(4-methyl-thiazol-2-yl)-pyrimidine-5-carboxylic acid (3-trifluoromethyl-pyrrolo[3,2-b]pyridin-1-yl)-amide,
4-Methyl-2-(4-methyl-thiazol-2-yl)-pyrimidine-5-carboxylic acid (3-difluoromethyl-pyrrolo[3,2-b]pyridin-1-yl)-amide,
4-Methyl-2-(4-methyl-thiazol-2-yl)-pyrimidine-5-carboxylic acid [3-(2,2,2-trifluoro-ethyl)-pyrrolo[3,2-b]pyridin-1-yl]-amide,
4-Methyl-2-(4-methyl-thiazol-2-yl)-pyrimidine-5-carboxylic acid [3-(2,2-difluoro-ethyl)-pyrrolo[3,2-b]pyridin-1-yl]-amide,
4-Methyl-2-(4-methyl-thiazol-2-yl)-pyrimidine-5-carboxylic acid [3-(2,2,2-trifluoro-ethyl)-pyrrolo[3,2-c]pyridin-1-yl]-amide,
4-Methyl-2-(4-methyl-thiazol-2-yl)-pyrimidine-5-carboxylic acid [3-(2,2-difluoro-ethyl)-pyrrolo[3,2-c]pyridin-1-yl]-amide, 4-Methyl-2-(4-methyl-thiazol-2-yl)-pyrimidine-5-carboxylic acid [3-(2,2,2-trifluoro-ethyl)-pyrrolo[2,3-c]pyridin-1-yl]-amide,
4-Methyl-2-(4-methyl-thiazol-2-yl)-pyrimidine-5-carboxylic acid [3-(2,2-difluoro-ethyl)-pyrrolo[2,3-c]pyridin-1-yl]-amide,
4-Methyl-2-(4-methyl-thiazol-2-yl)-pyrimidine-5-carboxylic acid [3-(2,2,2-trifluoro-ethyl)-pyrrolo[2,3-b]pyridin-1-yl]-amide,
4-Methyl-2-(4-methyl-thiazol-2-yl)-pyrimidine-5-carboxylic acid [3-(2,2-difluoro-ethyl)-pyrrolo[2,3-b]pyridin-1-yl]-amide,
4-Methyl-2-thiazol-2-yl-pyrimidine-5-carboxylic acid (5-trifluoromethyl-pyrrolo[3,2-b]pyridin-1-yl)-amide,
4-Methyl-2-thiazol-2-yl-pyrimidine-5-carboxylic acid (5-difluoromethyl-pyrrolo[3,2-b]pyridin-1-yl)-amide,
4-Methyl-2-thiazol-2-yl-pyrimidine-5-carboxylic acid (3-trifluoromethyl-pyrrolo[3,2-b]pyridin-1-yl)-amide,
4-Methyl-2-thiazol-2-yl-pyrimidine-5-carboxylic acid (3-difluoromethyl-pyrrolo[3,2-b]pyridin-1-yl)-amide,
4-Methyl-2-thiazol-2-yl-pyrimidine-5-carboxylic acid [3-(2,2,2-trifluoro-ethyl)-pyrrolo[3,2-b]pyridin-1-yl]-amide,
4-Methyl-2-thiazol-2-yl-pyrimidine-5-carboxylic acid [3-(2,2-difluoro-ethyl)-pyrrolo[3,2-b]pyridin-1-yl]-amide,
4-Methyl-2-thiazol-2-yl-pyrimidine-5-carboxylic acid [3-(2,2,2-trifluoro-ethyl)-pyrrolo[3,2-c]pyridin-1-yl]-amide,
4-Methyl-2-thiazol-2-yl-pyrimidine-5-carboxylic acid [3-(2,2-difluoro-ethyl)-pyrrolo[3,2-c]pyridin-1-yl]-amide,
4-Methyl-2-thiazol-2-yl-pyrimidine-5-carboxylic acid [3-(2,2,2-trifluoro-ethyl)-pyrrolo[2,3-c]pyridin-1-yl]-amide,
4-Methyl-2-thiazol-2-yl-pyrimidine-5-carboxylic acid [3-(2,2-difluoro-ethyl)-pyrrolo[2,3-c]pyridin-1-yl]-amide,
4-Methyl-2-thiazol-2-yl-pyrimidine-5-carboxylic acid [3-(2,2,2-trifluoro-ethyl)-pyrrolo[2,3-b]pyridin-1-yl]-amide,
4-Methyl-2-thiazol-2-yl-pyrimidine-5-carboxylic acid [3-(2,2-difluoro-ethyl)-pyrrolo[2,3-b]pyridin-1-yl]-amide,
2-(4-Chloro-thiazol-2-yl)-4-methyl-pyrimidine-5-carboxylic acid (5-trifluoromethyl-pyrrolo[3,2-b]pyridin-1-yl)-amide,
2-(4-Chloro-thiazol-2-yl)-4-methyl-pyrimidine-5-carboxylic acid (5-trifluoromethyl-pyrrolo[3,2-b]pyridin-1-yl)-amide,
2-(4-Chloro-thiazol-2-yl)-4-methyl-pyrimidine-5-carboxylic acid (3-trifluoromethyl-pyrrolo[3,2-b]pyridin-1-yl)-amide,
4-Methyl-2-(4-methyl-thiazol-2-yl)-pyrimidine-5-carboxylic acid (3-difluoromethyl-pyrrolo[3,2-b]pyridin-1-yl)-amide,
2-(4-Chloro-thiazol-2-yl)-4-methyl-pyrimidine-5-carboxylic acid [3-(2,2,2-trifluoro-ethyl)-pyrrolo[3,2-b]pyridin-1-yl]-amide,
2-(4-Chloro-thiazol-2-yl)-4-methyl-pyrimidine-5-carboxylic acid [3-(2,2-difluoro-ethyl)-pyrrolo[3,2-b]pyridin-1-yl]-amide,
2-(4-Chloro-thiazol-2-yl)-4-methyl-pyrimidine-5-carboxylic acid [3-(2,2,2-trifluoro-ethyl)-pyrrolo[3,2-c]pyridin-1-yl]-amide,
2-(4-Chloro-thiazol-2-yl)-4-methyl-pyrimidine-5-carboxylic acid [3-(2,2-difluoro-ethyl)-pyrrolo[3,2-c]pyridin-1-yl]-amide,
2-(4-Chloro-thiazol-2-yl)-4-methyl-pyrimidine-5-carboxylic acid [3-(2,2,2-trifluoro-ethyl)-pyrrolo[2,3-c]pyridin-1-yl]-amide,
2-(4-Chloro-thiazol-2-yl)-4-methyl-pyrimidine-5-carboxylic acid [3-(2,2-difluoro-ethyl)-pyrrolo[2,3-c]pyridin-1-yl]-amide,
2-(4-Chloro-thiazol-2-yl)-4-methyl-pyrimidine-5-carboxylic acid [3-(2,2,2-trifluoro-ethyl)-pyrrolo[2,3-b]pyridin-1-yl]-amide,
2-(4-Chloro-thiazol-2-yl)-4-methyl-pyrimidine-5-carboxylic acid [3-(2,2-difluoro-ethyl)-pyrrolo[2,3-b]pyridin-1-yl]-amide,
4-Methyl-[2,2']bipyrimidinyl-5-carboxylic acid (5-trifluoromethyl-pyrrolo[3,2-b]pyridin-1-yl)-amide,
4-Methyl-[2,2']bipyrimidinyl-5-carboxylic acid (5-difluoromethyl-pyrrolo[3,2-b]pyridin-1-yl)-amide,
4-Methyl-[2,2']bipyrimidinyl-5-carboxylic acid (3-trifluoromethyl-pyrrolo [3,2-b]pyridin-1-yl)-amide,
4-Methyl-[2,2']bipyrimidinyl-5-carboxylic acid (3-difluoromethyl-pyrrolo[3,2-b]pyridin-1-yl)-amide,
4-Methyl-[2,2']bipyrimidinyl-5-carboxylic acid [3-(2,2,2-trifluoro-ethyl)-pyrrolo [3,2-b]pyridin-1-yl]-amide,
4-Methyl-[2,2']bipyrimidinyl-5-carboxylic acid [3-(2,2-difluoro-ethyl)-pyrrolo [3,2-b]pyridin-1-yl]-amide,
4-Methyl-[2,2']bipyrimidinyl-5-carboxylic acid (3-trifluoromethyl-pyrrolo[3,2-c]pyridin-1-yl)-amide,
4-Methyl-[2,2']bipyrimidinyl-5-carboxylic acid (3-difluoromethyl-pyrrolo[3,2-c]pyridin-1-yl)-amide,
4-Methyl-[2,2']bipyrimidinyl-5-carboxylic acid [3-(2,2,2-trifluoro-ethyl)-pyrrolo[3,2-c]pyridin-1-yl]-amide,
4-Methyl-[2,2']bipyrimidinyl-5-carboxylic acid [3-2,2-difluoro-ethyl)-pyrrolo[3,2-c]pyridin-1-yl]-amide,
4-Methyl-[2,2']bipyrimidinyl-5-carboxylic acid (3-trifluoromethyl-pyrrolo[2,3-c]pyridin-1-yl)-amide,
4-Methyl-[2,2']bipyrimidinyl-5-carboxylic acid (3-difluoromethyl-pyrrolo [2,3-c]pyridin-1-yl)-amide,
4-Methyl-[2,2']bipyrimidinyl-5-carboxylic acid [3-(2,2,2-trifluoro-ethyl)-pyrrolo [2,3-c]pyridin-1-yl]-amide,
4-Methyl-[2,2']bipyrimidinyl-5-carboxylic acid [3-(2,2-difluoro-ethyl)-pyrrolo [2,3-c]pyridin-1-yl]-amide,
4-Methyl-[2,2']bipyrimidinyl-5-carboxylic acid (3-trifluoromethyl-pyrrolo[2,3-b]pyridin-1-yl)-amide,
4-Methyl-[2,2']bipyrimidinyl-5-carboxylic acid (3-difluoromethyl-pyrrolo[2,3-b]pyridin-1-yl)-amide,
4-Methyl-[2,2']bipyrimidinyl-5-carboxylic acid [3-(2,2,2-trifluoro-ethyl)-pyrrolo [2,3-b]pyridin-1-yl]-amide,
4-Methyl-[2,2']bipyrimidinyl-5-carboxylic acid [3-(2,2-difluoro-ethyl)-pyrrolo [2,3-b]pyridin-1-yl]-amide,
2-(3-Fluoro-phenyl)-4-methyl-pyrimidine-5-carboxylic acid (5-trifluoro methyl-pyrrolo[3,2-b]pyridin-1-yl)-amide,
2-(3-Fluoro-phenyl)-4-methyl-pyrimidine-5-carboxylic acid (5-difluorom ethyl-pyrrolo[3,2-b]pyridin-1-yl)-amide,
2-(3-Fluoro-phenyl)-4-methyl-pyrimidine-5-carboxylic acid (3-trifluoro methyl-pyrrolo[3,2-b]pyridin-1-yl)-amide,
2-(3-Fluoro-phenyl)-4-methyl-pyrimidine-5-carboxylic acid (3-trifluoro methyl-pyrrolo[3,2-c]pyridin-1-yl)-amide,
2-(3-Fluoro-phenyl)-4-methyl-pyrimidine-5-carboxylic acid (3-trifluoro methyl-pyrrolo[2,3-c]pyridin-1-yl)-amide,
2-(3-Fluoro-phenyl)-4-methyl-pyrimidine-5-carboxylic acid (3-trifluoromethyl-pyrrolo[2,3-b]pyridin-1-yl)-amide,
2-(3-Fluoro-phenyl)-4-methyl-pyrimidine-5-carboxylic acid [3-(2,2-difluoro-ethyl)-pyrrolo[3,2-b]pyridin-1-yl]-amide,
2-(3-Fluoro-phenyl)-4-methyl-pyrimidine-5-carboxylic acid [3-(2,2,2-trifluoro-ethyl)-pyrrolo[3,2-b]pyridin-1-yl]-amide,
2-(3-Fluoro-phenyl)-4-methyl-pyrimidine-5-carboxylic acid [3-(2,2,2-trifluoro-ethyl)-pyrrolo[3,2-c]pyridin-1-yl]-amide, 2-(3-Fluoro-phenyl)-4-methyl-pyrimidine-5-carboxylic acid [3-(2,2,2-trifluoro-ethyl)-pyrrolo[2,3-c]pyridin-1-yl]-amide, 4-Methyl-2-pyridin-2-yl-pyrimidine-5-carboxylic acid (3-difluoromethyl-indol-1-yl)-amide, 2-(4-Chloro-thiazol-2-yl)-4-methyl-pyrimidine-5-carboxylic acid (3-difluoromethyl-indol-1-yl)-amide, or 4-Methyl-2-thiazol-2-yl-pyrimidine-5-carboxylic acid (3-difluoromethyl-indol-1-yl)-amide, or an N-oxide thereof, or a pharmaceutically acceptable salt thereof.

20. A pharmaceutical composition comprising the compound according to claim 1, or an N-oxide thereof, or a pharmaceutically acceptable salt thereof, and a pharmaceutically acceptable carrier.

21. A method for treating an allergic or inflammatory disorder, selected from the group consisting of allergic rhinitis, asthma and chronic obstructive pulmonary disease, in a patient in need thereof, comprising administering to the patient a pharmaceutically effective amount of the compound according to claim 1, or an N-oxide thereof, or a pharmaceutically acceptable salt thereof.

22. The method according to claim 21, wherein the allergic or inflammatory disorder is allergic rhinitis.

23. The method according to claim 21, wherein the allergic or inflammatory disorder is asthma.

24. The method according to claim 21, wherein the allergic or inflammatory disorder is chronic obstructive pulmonary disease.

* * * * *